United States Patent
Hopper et al.

(10) Patent No.: US 7,585,882 B2
(45) Date of Patent: Sep. 8, 2009

(54) PHOSPHODIESTERASE 4 INHIBITORS

(75) Inventors: Allen Hopper, Glen Rock, NJ (US);
Robert Francis Dunn, Towaco, NJ (US); Erik Mikal Kuester, Rochester, MN (US); Richard Dennis Conticello, Ossining, NY (US); Ruiping Liu, Huntington, NY (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 0 days.

(21) Appl. No.: 11/253,812

(22) Filed: Oct. 20, 2005

(65) Prior Publication Data
US 2006/0135535 A1   Jun. 22, 2006

Related U.S. Application Data

(60) Provisional application No. 60/619,964, filed on Oct. 20, 2004.

(51) Int. Cl.
*A61K 31/4015* (2006.01)
*A61K 31/4025* (2006.01)
*A61K 31/433* (2006.01)
*C07D 207/12* (2006.01)
*C07D 285/08* (2006.01)
*C07D 403/12* (2006.01)
*A61K 31/341* (2006.01)
*C07D 407/10* (2006.01)
*C07D 407/14* (2006.01)

(52) U.S. Cl. ............ 514/340; 514/361; 514/424; 514/422; 514/363; 514/473; 548/128; 548/543; 548/517; 548/518; 548/524; 549/472

(58) Field of Classification Search ........... 514/424, 514/361, 340, 422, 363, 378, 473; 548/543, 548/128, 517, 518, 524, 246, 247; 546/268.7; 549/472
See application file for complete search history.

(56) References Cited

U.S. PATENT DOCUMENTS

| 4,012,495 | A | 3/1977 | Schmiechen et al. |
| 4,193,926 | A | 3/1980 | Schmiechen et al. |
| 4,219,551 | A | 8/1980 | Seidelmann et al. |
| 5,128,358 | A | 7/1992 | Saccomano et al. |
| 5,539,111 | A | 7/1996 | Petzoldt et al. |
| 5,814,651 | A | 9/1998 | Duplantier et al. |
| 5,846,514 | A | 12/1998 | Foster et al. |
| 5,935,978 | A | 8/1999 | Fenton et al. |
| 6,136,821 | A | 10/2000 | Hersperger |
| 6,258,833 | B1 | 7/2001 | Martins et al. |
| 6,334,997 | B1 | 1/2002 | Foster et al. |
| 6,372,777 | B1 | 4/2002 | Martins et al. |
| 6,403,597 | B1 | 6/2002 | Wilson et al. |
| 6,423,710 | B1 | 7/2002 | Martins et al. |
| 6,495,154 | B1 | 12/2002 | Tam et al. |
| 2003/0139406 | A1* | 7/2003 | Liu et al. .............. 514/227.8 |
| 2005/0026913 | A1* | 2/2005 | Tehim et al. .......... 514/227.5 |

FOREIGN PATENT DOCUMENTS

| WO | WO 91/16303 | 10/1991 |
| WO | WO 92/19594 | 11/1992 |
| WO | WO 93/07141 | 4/1993 |
| WO | WO 93/25517 | 12/1993 |
| WO | WO 94/14742 | 7/1994 |
| WO | WO 95/28926 | 11/1995 |
| WO | WO 95/35282 | 12/1995 |
| WO | WO 97/25312 | 7/1997 |
| WO | WO 01/62726 | 8/2001 |
| WO | WO 01/68600 | 9/2001 |
| WO | WO 02/45749 | 6/2002 |
| WO | WO 03/032981 | 4/2003 |
| WO | WO 2004/094375 | 11/2004 |

OTHER PUBLICATIONS

Barad et al. Proc. Natl. Acad. Sci. ,USA, vol. 95, pp. 15020-15025, Dec. 1998.
Christensen et al. J. Med. Chem, 1998, 41, 821-835.
Crossland, J. Drugs of the Future, vol. 13, No. 1 1988.
Demnitz et al. Molecules, 1998,3,107-119.
Egawa et al. Jpn J Pharmacol, 1997, Nov. 75 (3): 275-81.
Houslay et al. Advance in Pharmacology, vol. 44, pp. 225-342 (1988).
Keller et al. Chem. Pharm. Bull, 49 (8) 1009-1017 (2001).
Krause et al. Xenobiotica, 1988, vol. 18, No. 5, 561-571.
Langlois et al. Synthetic Communications, 27 (18), 3133-3144 (1997).
Lourenco et al. Nuclear Medicine and Biology, 28 (2001) 347-358.

(Continued)

*Primary Examiner*—Yong Chu
(74) *Attorney, Agent, or Firm*—Millen, White, Zelano, Branigan, P.C.

(57) ABSTRACT

Selective PDE4 inhibition is achieved by novel compounds, e.g., 4-(substituted-phenyl)-2-pyrrolidinone compounds. The compounds of the present invention are of formula I:

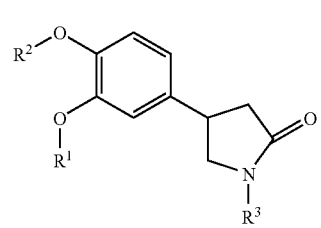

(I)

wherein $R^1$, $R^2$, and $R^3$ are as defined herein. The disclosure also relates to methods of preparing such compounds, compositions containing such compounds, and methods of use thereof.

35 Claims, No Drawings

OTHER PUBLICATIONS

Marivet et al. J. Med. Chem., 1989, 32, 1450-1457.
Martin, Idrugs, 2001 4 (3); 312-338.
Meyers et al. J. Org. Chem, 1993, 58 36-42.
Morgan et al. Biochemical Pharmacology, 1993, 45 (12) 2373-80 pp. 23-27.
Nakagura et al. British Journal of Pharmacology (2002) 135, 1783-1793.
Osby et al. Tetrahedron Letters, vol. 26, No. 52, pp. 6413-6416, 1985.
Robichaud et al. Neuropharmacology, 38 (1999), pp. 289-297.
Schmiechen et al. Psychopharmacology, (Berl) 1990; 102 (1) 17-20.
Wang et al. Biochemical and Biophysical Research Communications, 234, 320-324 (1997).
Zhang et al. Psychopharmacology DOI, 10.1007/s002130000414 (2000).
Zhang et al. Neuropsychopharmacology, 2000, 23, 198-204.
International Search Report for PCT/US04/011765.
Int'l Search Report and the Written Opinion of the Int'l. Searching Authority, issued Mar. 2, 2006 in PCT Application No. PCT/US 2005/037568.
JP Abstract No. 09 221 423 dated Aug. 26, 1997 (delphion .com).
JP Abstract 09 221 423 dated Aug. 26, 1997 (legal status).

* cited by examiner

PHOSPHODIESTERASE 4 INHIBITORS

This application claims the benefit of U.S. Provisional Application No. 60/619,964, filed Oct. 20, 2004, the entire disclosure of which is hereby incorporated by reference.

This application is related to copending U.S. application Ser. No. 10/270,724, filed Oct. 16, 2002, and U.S. application Ser. No. 11/186,958, filed Jul. 22, 2005, which claim the benefit of U.S. Provisional Application Ser. No. 60/329,314, filed Oct. 16, 2001, the entire disclosures of each of which are hereby incorporated by reference. This application is also related U.S. application Ser. No. 10/825,610, filed Apr. 16, 2004, which claims the benefit of U.S. Provisional Application Ser. No. 60/463,054, filed Apr. 16, 2003, the entire disclosures of each of which are hereby incorporated by reference.

FIELD OF THE INVENTION

The present invention relates generally to the field of phosphodiesterase 4 (PDE4) enzyme inhibition. More specifically this invention relates to selective PDE4 inhibition by novel compounds, e.g., 4-(substituted-phenyl)-2-pyrrolidinone compounds, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-inhibited, and inhibition of this enzyme creates positive inotropic activity. PDE 4 is cAMP specific, and its inhibition causes airway relaxation, anti-inflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, *Biochem. Biophys. Res. Comm.,* 234, 320-324, 1997]. In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful anti-inflammatory agents and therefore may be useful in treating diseases where inflammation is problematic such as asthma or arthritis. Further, rolipram improves the cognitive performance of rats and mice in learning paradigms.

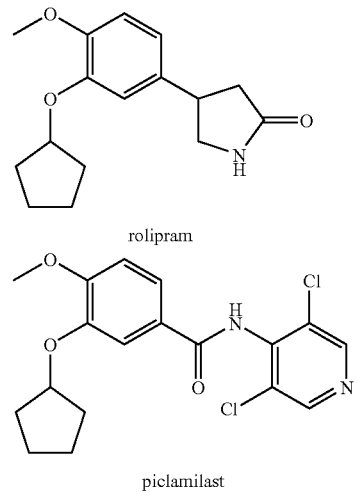

In addition to such compounds as rolipram, xanthine derivatives such as pentoxifylline, denbufylline, and theophylline inhibit PDE4 and have received attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an anti-depressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., *Drugs of the Future,* 17(9):799-807, 1992 for a general review]. Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotrophic effects, increased gastric acid secretion and stomach erosion. In humans, the primary side effect is nausea and emesis.

SUMMARY OF THE INVENTION

The present invention relates to novel compounds that inhibit, preferably selectively, PDE4 enzymes, and especially have improved side effect profiles, e.g., are relatively non-emetic (e.g., as compared to the previously discussed prior art compounds). In particular, the present invention relates to novel rolipram analogs. The compounds of this invention at the same time facilitate entry into cells, especially cells of the nervous system.

Still further, the present invention provides methods for synthesizing compounds with such activity and selectivity as well as methods of (and corresponding pharmaceutical compositions for) treating a patient, e.g., mammals, including humans, in need of PDE inhibition, especially PDE4 inhibition, for a disease state that involves elevated intracellular PDE4 levels or decreased cAMP levels, e.g., involving neurological syndromes, especially those states associated with memory impairment, most especially long term memory impairment, as where such memory impairment is due at least in part to catabolism of intracellular cAMP levels by PDE4 enzymes, or where such an impaired condition can be improved by increasing cAMP levels.

In a preferred aspect, the compounds of the invention improve such diseases by inhibiting PDE4 enzymes at doses that do not induce emesis or other side effects.

Upon further study of the specification and appended claims, further aspects, objects and advantages of this invention will become apparent to those skilled in the art.

The present invention includes compounds of Formula I:

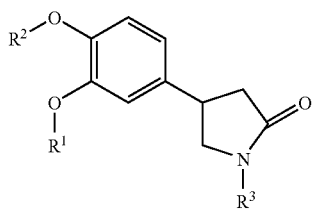

(I)

wherein
R$^1$ is alkyl having 1 to 8 carbon atoms wherein optionally one or more —CH$_2$CH$_2$— groups are replaced in each case by —CH═CH— or —C≡C— groups,
alkyl having 1 to 8 carbon atoms which is substituted one or more times by halogen, oxo or combinations thereof wherein optionally one or more —CH$_2$CH$_2$— groups are replaced in each case by —CH═CH— or —C≡C— groups,
cycloalkyl having 3 to 8 carbon atoms, which is unsubstituted or substituted one or more times by halogen, oxo, alkyl having 1 to 4 carbon atoms or combinations thereof,
a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, amino, alkylamino, dialkylamino, or combinations thereof,
aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
arylalkyl having 7 to 16 carbon atoms (e.g., 8 to 16 carbon atoms), which is unsubstituted or substituted preferably in the aryl portion, one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof,
arylalkenyl having 8 to 16 carbon atoms, wherein the alkenyl portion has up to 5 carbon atoms, which is unsubstituted or substituted preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof;
a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or
cycloalkylalkyl having 4 to 16 carbon atoms (e.g., cyclopentylethyl and cyclopropylmethyl), which is unsubstituted or substituted one or more times by halogen, oxo, alkyl or combinations thereof,
R$^2$ is alkyl having 1 to 4 carbon atoms, which is unsubstituted or substituted one or more times by halogen;
R$^3$ is H,
alkyl having 1 to 8 carbon atoms wherein optionally one or more —CH$_2$CH$_2$— groups are replaced in each case by —CH═CH— or —C≡C— groups,
alkyl having 1 to 8 carbon atoms which is substituted one or more times by halogen, oxo, or combinations thereof wherein optionally one or more —CH$_2$CH$_2$— groups are replaced in each case by —CH═CH— or —C≡C— groups,
cycloalkyl having 3 to 8 carbon atoms, which is unsubstituted or substituted one or more times by halogen, oxo, alkyl, or combinations thereof,
arylalkyl having 7 to 16 carbon atoms, which is unsubstituted or substituted preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenyl, phenoxy, and acyloxy (e.g., acetoxy), or combinations thereof,
heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, alkoxyalkyl having 3 to 8 carbon atoms, —C(O)R$^4$, —(CH$_2$)$_n$C(O)R$^4$, —(CH$_2$)$_n$OR$^5$, —(CH$_2$)$_n$SR$^5$, —(CH$_2$)$_n$SO$_2$R$^4$, —(CH$_2$)$_n$NR$^5$R$^6$, —CH$_2$CO$_2$R$^5$, —CH$_2$CONR$^6$R$^5$, —CH$_2$CONHR$^5$, —CHR$^7$CONR$^6$R$^5$, —CHR$^7$CONHR$^5$, —(CH$_2$)$_n$NR$^6$SO$_2$R$^4$, —(CH$_2$)$_n$NR$^6$COR$^4$, or —CH$_2$CONHSO$_2$R$^4$;

R$^4$ is alkyl having 1 to 12 carbon atoms which is unsubstituted or substituted one or more times by halogen, oxo, or combinations thereof wherein optionally one or more —CH$_2$CH$_2$— groups are replaced in each case by —CH═CH— or —C≡C— groups, alkoxyalkyl having 3 to 8 carbon atoms which is unsubstituted or substituted one or more times by halogen, oxo, or combinations thereof wherein optionally one or more —CH$_2$CH$_2$— groups are replaced in each case by —CH═CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, alkylsulphonamido (e.g., CH$_3$SO$_2$NH—, C$_2$H$_5$SO$_2$NH—), arylsulphonamido (e.g., C$_6$H$_5$SO$_2$NH—), halogenated arylsulphonamido (e.g., 4-F—C$_6$H$_5$SO$_2$NH—), phenoxy, acylamido (e.g., acetamido), and acyloxy (e.g., acetoxy), or combinations thereof, arylalkyl having 8 to 16 carbon atoms, which is unsubstituted or substituted preferably in the aryl portion, one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, aminosulphonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl, 1,3,4-thiadiazolyl), which is unsubstituted or substituted one or more times by halogen, aryl (e.g., phenyl, methylphenyl), alkyl, cycloalkyl (e.g., cyclopropyl), cycloalkylalkyl (e.g., cyclopropylmethyl), alkoxy, alkoxyalkyl (e.g., methoxymethyl), cyano, halogenated alkyl (e.g., trifluoromethyl), halogenated alkoxy (e.g., trifluoromethoxy), nitro, oxo, amino, alkylamino, dialkylamino, aminosulphonyl, heterocycle (e.g., pyridyl, piperidinyl, thienyl, tetrahydrofuranyl, pyrazinyl), heterocyclic-alkyl (e.g., thienylmethyl, piperidinylcarbonylmethyl), or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof; and R$^5$ is H, alkyl having 1 to 12 carbon atoms wherein optionally one or more —CH$_2$CH$_2$— groups are replaced in each case by —CH═CH— or —C≡C— groups, alkyl having 1 to 12 carbon atoms which is substituted one or more times by halogen, oxo, or combinations thereof wherein optionally one or more —CH$_2$CH$_2$— groups are replaced in each case by —CH═CH— or —C≡C— groups, alkoxyalkyl having 3 to 8 carbon atoms which is unsubstituted or substituted one or more times by halogen, oxo, or combinations thereof wherein optionally one or more —CH$_2$CH$_2$— groups are replaced in each case by —CH═CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, alkylsulphonamido (e.g., CH$_3$SO$_2$NH—, C$_2$H$_5$SO$_2$NH—), arylsulphonamido (e.g., C$_6$H$_5$SO$_2$NH—), halogenated arylsulphonamido (e.g., 4-F—C$_6$H$_5$SO$_2$NH—), phenoxy, acylamido (e.g., acetamido), and acyloxy (e.g., acetoxy), or combinations thereof, arylalkyl having 8 to 16 carbon atoms, which is unsubstituted or substituted preferably in the aryl portion, one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, aminosulphonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl, 1,3,4-thiadiazolyl, 1,2,4-thiadiazolyl, isoxazolyl, pyrazolyl, pyrazinyl, isothiazolyl, 1,3-thiazolyl, pyridyl, benzothiazolyl), which is unsubstituted or substituted one or more times by halogen, alkyl (e.g., methyl, ethyl, isopropyl), cycloalkyl (e.g., cyclopropyl), cycloalkylalkyl (e.g., cyclopropylmethyl), alkoxy, alkoxyalkyl (e.g., methoxymethyl), cyano, halogenated alkyl (e.g., trifluoromethyl), halogenated alkoxy (e.g., trifluoromethoxy), nitro, oxo, amino, alkylamino, dialkylamino, carboxamide, aminosulphonyl, aryl which is optionally substituted by alkyl or alkoxy (e.g., phenyl, methylphenyl, methoxyphenyl), arylalkyl which is optionally substituted by alkyl or alkoxy (e.g., benzyl), aryloxyalkyl wherein the aryl portion is optionally substituted by alkyl or alkoxy, arylsulfonyl (e.g., benzenesulfonyl), anilino, heterocycle (e.g., furyl, pyridyl, piperidinyl, thienyl, tetrahydrofuranyl, pyrazinyl), heterocyclic-alkyl wherein the alkyl portion is optionally substituted by oxo (e.g., thienylmethyl, piperidinylethyl, 2-oxo-2-piperidinyl-1-ylethyl or piperidinylcarbonylmethyl, 2-morpholin-4-yl-2-oxoethyl, 2-oxo-2-pyrrolidinyl-1-ylethyl), or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^6$ is H, alkyl having 1 to 12 carbon atoms wherein optionally one or more —$CH_2CH_2$— groups are replaced in each case by —CH=CH— or —C≡C— groups, alkyl having 1 to 12 carbon atoms which is substituted one or more times by halogen, oxo, or combinations thereof wherein optionally one or more —$CH_2CH_2$— groups are replaced in each case by —CH=CH— or —C≡C— groups, alkoxyalkyl having 3 to 8 carbon atoms which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 8 to 16 carbon atoms, which is unsubstituted or substituted preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof;

a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^7$ is alkyl having 1 to 8 carbon atoms (e.g., 1 to 4 carbon atoms) wherein optionally one or more —$CH_2CH_2$— groups are replaced in each case by —CH=CH— or —C≡C— groups (e.g., $CH_3$), alkyl having 1 to 8 carbon atoms which is substituted one or more times by halogen, oxo or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl having 1 to 4 carbon atoms or combinations thereof, or cycloalkylalkyl having 4 to 16 carbon atoms (e.g., cyclopropylmethyl), which is unsubstituted or substituted one or more times by halogen, oxo, alkyl or combinations thereof, n is 0 to 4 (e.g., 1 to 4 or 2 to 4);

and pharmaceutically acceptable salts or solvates (e.g., hydrates) thereof, or solvates of pharmaceutically acceptable salts thereof;

with the proviso that:

(a) when $R^2$ is $CH_3$ and $R^3$ is H, then $R^1$ is not methyl, ethyl, n-propyl, isopropyl, sec-butyl, n-butyl, isobutyl, neopentyl, 2-methylbutyl, isopentyl, n-hexyl, phenyl, cyclobutyl, cyclopentyl, cyclohexyl, cyclopentenyl, methylcyclopentyl, cyclopropylmethyl, cyclopentylmethyl, 2-propenyl, 2-propynyl, 3-methyl-2-butenyl, N-substituted 2-piperazinylethyl, norbornyl, 3-tetrahydrofuryl, 2-tetrahydrofuryl, 3-tetrahydrothienyl, 2-oxacyclopropyl, 2-oxacyclopenyl, 3-oxacyclopentyl, 2-chloroethyl, 2-bromoethyl, 2,2,2-trifluoroethyl, 3-bromopropyl, 3-chloropropyl, or 4-bromobutyl;

(b) when $R^1$ is cyclopentyl, and $R^2$ is methyl, then $R^3$ is not H, acetyl, benzyl, 4-hydroxybenzyl, 4-acetoxybenzyl, 4-bromobenzyl, 3,4-dimethoxybenzyl, 4-methylthiobenzyl, 4-cyanobenzyl, 2-aminobenzyl, 3-aminobenzyl, 4-aminobenzyl, 4-dimethylaminobenzyl, 2,4-diaminobenzyl, 4-amino-3,5-dimethoxybenzyl, 3-carboxybenzyl, 3-methoxycarbonylbenzyl, 4-methoxycarbonylbenzyl, 4-methylsulfinylbenzyl, 4-methylsufonylbenzyl, 2-nitrobenzyl, 3-nitrobenzyl, 4-nitrobenzyl, 2,4-dinitrobenzyl, 2-nitro-4-aminobenzyl, 2-amino-4-nitrobenzyl, morpholinoethyl, 2-pyridylmethyl, 3-pyridylmethyl, 4-pyridylmethyl, 4-(6-fluoroquinolyl)methyl, 2-(7-chloroquinolyl)methyl, 2-imidazoylmethyl, or substituted imidazoylmethyl;

(c) when $R^1$ is $CH_3$, and $R^3$ is H, then $R^2$ is not methyl, ethyl, or butyl;

(d) when $R^3$ is H, then $R^1$ and $R^2$ are not both ethyl or isobutyl; and (e) when R¹ and R² are both difluoromethyl, then R³ is not 4-aminobenzyl, or 4-amino-3,5-dimethoxybenzyl.

U.S. application Ser. No. 10/270,724, filed Oct. 16, 2002, and U.S. application Ser. No. 10/825,610, filed Apr. 16, 2004, also disclose compounds within the genus of formula I.

According to further compound aspect, the present invention includes solvates (e.g., hydrates) and solvates of pharmaceutically acceptable salts of compounds of Formula I in which R³ is H,
  alkyl having 1 to 8 carbon atoms wherein optionally one or more —CH₂CH₂— groups are replaced in each case by —CH═CH— or —C≡C— groups,
  alkyl having 1 to 8 carbon atoms which is substituted one or more times by halogen, oxo, or combinations thereof wherein optionally one or more —CH₂CH₂— groups are replaced in each case by —CH═CH— or —C≡C— groups,
  cycloalkyl having 3 to 8 carbon atoms, which is unsubstituted or substituted one or more times by halogen, oxo, alkyl, or combinations thereof,
  arylalkyl having 7 to 16 carbon atoms, which is unsubstituted or substituted preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenyl, phenoxy, and acyloxy (e.g., acetoxy), or combinations thereof,
  heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof,
  alkoxyalkyl having 3 to 8 carbon atoms,
  —C(O)R⁴, —(CH₂)ₙC(O)R⁴, —(CH₂)ₙOR⁵, —(CH₂)ₙSR⁵, —(CH₂)ₙSO₂R⁴, —(CH₂)ₙNR⁵R⁶, —CH₂CO₂R⁵, —CH₂CONR⁶R⁵, —CH₂CONHR⁵, —(CH₂)ₙNR⁶SO₂R⁴, —(CH₂)ₙNR⁶COR⁴, or —CH₂CONHSO₂R⁴.

In accordance with the method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound selected from the compounds according to formula I:

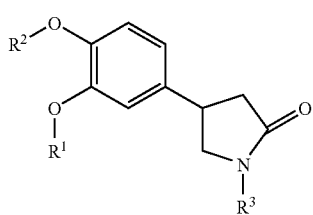

(I)

wherein
  R¹ is alkyl having 1 to 8 carbon atoms wherein optionally one or more —CH₂CH₂— groups are replaced in each case by —CH═CH— or —C≡C— groups,
  alkyl having 1 to 8 carbon atoms which is substituted one or more times by halogen, oxo or combinations thereof wherein optionally one or more —CH₂CH₂— groups are replaced in each case by —CH═CH— or —C≡C— groups,
  cycloalkyl having 3 to 8 carbon atoms, which is unsubstituted or substituted one or more times by halogen, oxo, alkyl having 1 to 4 carbon atoms or combinations thereof,
  a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, amino, alkylamino, dialkylamino, or combinations thereof,
  aryl having 6 to 14 carbon atoms, which is unsubstituted or substituted one or more times by halogen, CF₃, OCF₃, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
  arylalkyl having 7 to 16 carbon atoms (e.g., 8 to 16 carbon atoms), which is unsubstituted or substituted preferably in the aryl portion, one or more times by halogen, CF₃, OCF₃, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
  a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof,
  arylalkenyl having 8 to 16 carbon atoms, wherein the alkenyl portion has up to 5 carbon atoms, which is unsubstituted or substituted preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof;
  a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or
  cycloalkylalkyl having 4 to 16 carbon atoms (e.g., cyclopentylethyl and cyclopropylmethyl), which is unsubstituted or substituted one or more times by halogen, oxo, alkyl or combinations thereof, $R^2$ is alkyl having 1 to 4 carbon atoms, which is unsubstituted or substituted one or more times by halogen;

$R^3$ is H,
- alkyl having 1 to 8 carbon atoms wherein optionally one or more —CH$_2$CH$_2$— groups are replaced in each case by —CH=CH— or —C≡C— groups,
- alkyl having 1 to 8 carbon atoms which is substituted one or more times by halogen, oxo, or combinations thereof wherein optionally one or more —CH$_2$CH$_2$— groups are replaced in each case by —CH=CH— or —C≡C— groups,
- cycloalkyl having 3 to 8 carbon atoms, which is unsubstituted or substituted one or more times by halogen, oxo, alkyl, or combinations thereof,
- arylalkyl having 7 to 16 carbon atoms, which is unsubstituted or substituted preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenyl, phenoxy, and acyloxy (e.g., acetoxy), or combinations thereof,
- heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof,
- alkoxyalkyl having 3 to 8 carbon atoms,
- —C(O)R$^4$, —(CH$_2$)$_n$C(O)R$^4$, —(CH$_2$)$_n$OR$^5$, —(CH$_2$)$_n$SR$^5$, —(CH$_2$)$_n$SO$_2$R$^4$, —(CH$_2$)$_n$NR$^5$R$^6$, —CH$_2$CO$_2$R$^5$, —CH$_2$CONR$^6$R$^5$, —CH$_2$CONHR$^5$, —CHR$^7$CONR$^6$R$^5$, —CHR$^7$CONHR$^5$, —(CH$_2$)$_n$NR$^6$SO$_2$R, —(CH$_2$)$_n$NR$^6$COR$^4$, or —CH$_2$CONHSO$_2$R$^4$;

$R^4$ is alkyl having 1 to 12 carbon atoms which is unsubstituted or substituted one or more times by halogen, oxo, or combinations thereof wherein optionally one or more —CH$_2$CH$_2$— groups are replaced in each case by —CH=CH— or —C≡C— groups,
- alkoxyalkyl having 3 to 8 carbon atoms which is unsubstituted or substituted one or more times by halogen, oxo, or combinations thereof wherein optionally one or more —CH$_2$CH$_2$— groups are replaced in each case by —CH=CH— or —C≡C— groups,
- cycloalkyl having 3 to 8 carbon atoms, which is unsubstituted or substituted one or more times by halogen, oxo, alkyl, or combinations thereof,
- cycloalkylalkyl having 4 to 16 carbon atoms (e.g., cyclopentylethyl and cyclopropylmethyl), which is unsubstituted or substituted one or more times by halogen, oxo, alkyl or combinations thereof,
- aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, alkylsulphonamido (e.g., CH$_3$SO$_2$NH—, C$_2$H$_5$SO$_2$NH—), arylsulphonamido (e.g., C$_6$H$_5$SO$_2$NH—), halogenated arylsulphonamido (e.g., 4-F—C$_6$H$_5$SO$_2$NH—), phenoxy, acylamido (e.g., acetamido), and acyloxy (e.g., acetoxy), or combinations thereof,
- arylalkyl having 8 to 16 carbon atoms, which is unsubstituted or substituted preferably in the aryl portion, one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, aminosulphonyl, phenoxy, acylamido (e.g., acetamido), and acyloxy (e.g., acetoxy), or combinations thereof,
- a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl, 1,3,4-thiadiazolyl), which is unsubstituted or substituted one or more times by halogen, aryl (e.g., phenyl, methylphenyl), alkyl, cycloalkyl (e.g., cyclopropyl), cycloalkylalkyl (e.g., cyclopropylmethyl), alkoxy, alkoxyalkyl (e.g., methoxymethyl), cyano, halogenated alkyl (e.g., trifluoromethyl), halogenated alkoxy (e.g., trifluoromethoxy), nitro, oxo, amino, alkylamino, dialkylamino, aminosulphonyl, heterocycle (e.g., pyridyl, piperidinyl, thienyl, tetrahydrofuranyl, pyrazinyl), heterocyclic-alkyl (e.g., thienylmethyl, piperidinylcarbonylmethyl), or combinations thereof, or
- a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof; and $R^5$ is H,
- alkyl having 1 to 12 carbon atoms wherein optionally one or more —CH$_2$CH$_2$— groups are replaced in each case by —CH=CH— or —C≡C— groups,
- alkyl having 1 to 12 carbon atoms which is substituted one or more times by halogen, oxo, or combinations thereof wherein optionally one or more —CH$_2$CH$_2$— groups are replaced in each case by —CH=CH— or —C≡C— groups,
- alkoxyalkyl having 3 to 8 carbon atoms which is unsubstituted or substituted one or more times by halogen, oxo, or combinations thereof wherein optionally one or more —CH$_2$CH$_2$— groups are replaced in each case by —CH=CH— or —C≡C— groups,
- cycloalkyl having 3 to 8 carbon atoms, which is unsubstituted or substituted one or more times by halogen, oxo, alkyl, or combinations thereof,
- cycloalkylalkyl having 4 to 16 carbon atoms (e.g., cyclopentylethyl and cyclopropylmethyl), which is unsubstituted or substituted one or more times by halogen, oxo, alkyl or combinations thereof,
- aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, alkylsulphonamido (e.g., CH$_3$SO$_2$NH—, $C_2H_5SO_2NH-$), arylsulphonamido (e.g., $C_6H_5SO_2NH-$), halogenated arylsulphonamido (e.g., 4-F—$C_6H_5SO_2NH-$),phenoxy, acylamido (e.g., acetamido), and acyloxy (e.g., acetoxy), or combinations thereof, arylalkyl having 8 to 16 carbon atoms, which is unsubstituted or substituted preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, aminosulphonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl, 1,3,4-thiadiazolyl, 1,2,4-thiadiazolyl, isoxazolyl, pyrazolyl, pyrazinyl, isothiazolyl, 1,3-thiazolyl, pyridyl, benzothiazolyl), which is unsubstituted or substituted one or more times by halogen, alkyl (e.g., methyl, ethyl, isopropyl), cycloalkyl (e.g., cyclopropyl), cycloalkylalkyl (e.g., cyclopropylmethyl), alkoxy, alkoxyalkyl (e.g., methoxymethyl), cyano, halogenated alkyl (e.g., trifluoromethyl), halogenated alkoxy (e.g., trifluoromethoxy), nitro, oxo, amino, alkylamino, dialkylamino, carboxamide, aminosulphonyl, aryl which is optionally substituted by alkyl or alkoxy (e.g., phenyl, methylphenyl, methoxyphenyl), arylalkyl which is optionally substituted by alkyl or alkoxy (e.g., benzyl), aryloxyalkyl wherein the aryl portion is optionally substituted by alkyl or alkoxy, arylsulfonyl (e.g., benzenesulfonyl), anilino, heterocycle (e.g., furyl, pyridyl, piperidinyl, thienyl, tetrahydrofuranyl, pyrazinyl), heterocyclic-alkyl wherein the alkyl portion is optionally substituted by oxo (e.g., thienylmethyl, piperidinylethyl, 2-oxo-2-piperidinyl-1-ylethyl or piperidinylcarbonylmethyl, 2-morpholin-4-yl-2-oxoethyl, 2-oxo-2-pyrrolidinyl-1-ylethyl), or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, $R^6$ is H, alkyl having 1 to 12 carbon atoms wherein optionally one or more —$CH_2CH_2$— groups are replaced in each case by —CH=CH— or —C≡C— groups, alkyl having 1 to 12 carbon atoms which is substituted one or more times by halogen, oxo, or combinations thereof wherein optionally one or more —$CH_2CH_2$— groups are replaced in each case by —CH=CH— or —C≡C— groups, alkoxyalkyl having 3 to 8 carbon atoms which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 8 to 16 carbon atoms, which is unsubstituted or substituted preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof;

a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^7$ is alkyl having 1 to 8 carbon atoms (e.g., 1 to 4 carbon atoms) wherein optionally one or more —$CH_2CH_2$— groups are replaced in each case by —CH=CH— or —C≡C— groups (e.g., $CH_3$), alkyl having 1 to 8 carbon atoms which is substituted one or more times by halogen, oxo or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl having 1 to 4 carbon atoms or combinations thereof, or cycloalkylalkyl having 4 to 16 carbon atoms (e.g., cyclopentylethyl and cyclopropylmethyl), which is unsubstituted or substituted one or more times by halogen, oxo, alkyl or combinations thereof, n is 0 to 4 (e.g., 1 to 4 or 2 to 4);

and pharmaceutically acceptable salts or solvates (e.g., hydrates) thereof, or solvates of pharmaceutically acceptable salts thereof.

According to a further method aspect, in Formula I', when $R^2$ is $CH_3$ and $R^3$ is H, then $R^1$ is not cyclopentyl.

According to further method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a solvate (e.g., hydrate) or a solvate of pharmaceutically acceptable salt of a compound of Formula I in which $R^3$ is H, alkyl having 1 to 8 carbon atoms wherein optionally one or more —$CH_2CH_2$— groups are replaced in each case by —CH=CH— or —C≡C— groups, alkyl having 1 to 8 carbon atoms which is substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, arylalkyl having 7 to 16 carbon atoms, which is unsubstituted or substituted preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenyl, phenoxy, and acyloxy (e.g., acetoxy), or combinations thereof, heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, alkoxyalkyl having 3 to 8 carbon atoms, —C(O)$R^4$, —$(CH_2)_n$C(O)$R^4$, —$(CH_2)_n$O$R^5$, —$(CH_2)_n$S$R^5$, —$(CH_2)_n$SO$_2R^4$, —$(CH_2)_n$N$R^5R^6$, —$CH_2CO_2R^5$, —$CH_2CONR^6R^5$, —$CH_2CONHR^5$, —$(CH_2)_n$N$R^6$SO$_2R^4$, —$(CH_2)_n$N$R^6$CO$R^4$, or —$CH_2CONHSO_2R^4$.

According to a further compound and/or method aspect of the invention, when $R^1$ is benzyl, then $R^3$ is —$CH_2CONR^6R^5$.

In accordance with a further compound and/or method aspect of the invention, in formula I, $R^3$ is —$CH_2CONR^6R^5$ and $R^5$ is a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl, pyridyl, benzothiazolyl, 1,3,4-thiadiazolyl, 1,2,4-thiadiazolyl, isoxazolyl, pyrazolyl, pyrazinyl, isothiazolyl, 1,3-thiazolyl), which is unsubstituted or substituted one or more times by halogen, alkyl (e.g., methyl, ethyl, isopropyl), cycloalkyl (e.g., cyclopropyl), cycloalkylalkyl (e.g., cyclopropylmethyl), alkoxy, alkoxyalkyl (e.g., methoxymethyl), cyano, halogenated alkyl (e.g., trifluoromethyl), halogenated alkoxy (e.g., difluoromethoxy, trifluoromethoxy), nitro, oxo, amino, alkylamino, dialkylamino, carboxamide, aminosulphonyl, aryl which is optionally substituted by alkyl or alkoxy (e.g., phenyl, methylphenyl, methoxyphenyl), arylalkyl which is optionally substituted by alkyl or alkoxy (e.g., benzyl), aryloxyalkyl wherein the aryl portion is optionally substituted by alkyl or alkoxy, arylsulfonyl (e.g., benzenesulfonyl), anilino, heterocycle (e.g., furyl, pyridyl, piperidinyl, thienyl, tetrahydrofuranyl, pyrazinyl), heterocyclic-alkyl wherein the alkyl portion is optionally substituted by oxo (e.g., thienylmethyl, piperidinylethyl, 2-oxo-2-piperidinyl-1-ylethyl or piperidinylcarbonylmethyl, 2-morpholin-4-yl-2-oxoethyl, 2-oxo-2-pyrrolidinyl-1-ylethyl), or combinations thereof. In such a case, $R^6$ is, for example, H, alkyl (e.g., methyl, ethyl), or cycloalkylalkyl (e.g., cyclopropylmethyl).

In accordance with a further compound and/or method aspect of the invention, in formula I, $R^3$ is —$CH_2CONR^6R^5$ and $R^5$ is a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl, pyridyl, benzothiazolyl, 1,3,4-thiadiazolyl, 1,2,4-thiadiazolyl, isoxazolyl, pyrazolyl, pyrazinyl, isothiazolyl, 1,3-thiazolyl), which is unsubstituted or substituted one or more times by halogen, $C_{1-8}$-alkyl (e.g., methyl, ethyl, isopropyl), $C_{3-8}$-cycloalkyl (e.g., cyclopropyl), $C_{4-16}$-cycloalkylalkyl (e.g., cyclopropylmethyl), $C_{1-8}$-alkoxy, $C_{2-8}$-alkoxyalkyl (e.g., methoxymethyl), cyano, $C_{1-8}$-halogenated alkyl (e.g., trifluoromethyl), $C_{1-8}$-halogenated alkoxy (e.g., difluoromethoxy, trifluoromethoxy), nitro, oxo, amino, $C_{1-8}$-alkylamino, dialkylamino (each alkyl group having 1 to 8 carbon atoms), carboxamide, aminosulphonyl, $C_{6-14}$-aryl which is optionally substituted by $C_{1-8}$-alkyl or $C_{1-8}$-alkoxy (e.g., phenyl, methylphenyl, methoxyphenyl), $C_{6-14}$-aryl-$C_{1-8}$-alkyl which is optionally substituted by $C_{1-8}$-alkyl or $C_{1-8}$-alkoxy (e.g., benzyl), $C_{6-14}$-aryloxy-$C_{1-8}$-alkyl wherein the aryl portion is optionally substituted by $C_{1-8}$-alkyl or $C_{1-8}$-alkoxy, $C_{6-14}$-arylsulfonyl (e.g., benzenesulfonyl), anilino, heterocycle (e.g., furyl, pyridyl, piperidinyl, thienyl, tetrahydrofuranyl, pyrazinyl), heterocyclic-$C_{1-8}$-alkyl wherein the alkyl portion is optionally substituted by oxo (e.g., thienylmethyl, piperidinylethyl, 2-oxo-2-piperidinyl-1-ylethyl or piperidinylcarbonylmethyl, 2-morpholin-4-yl-2-oxoethyl, 2-oxo-2-pyrrolidinyl-1-ylethyl), or combinations thereof. In such a case, $R^6$ is, for example, H, $C_{1-8}$-alkyl (e.g., methyl, ethyl), or $C_{4-16}$-cycloalkylalkyl (e.g., cyclopropylmethyl).

In accordance with a further compound and/or method aspect of the invention, in formula I, $R^3$ is —$CH_2CONR^6R^5$ and $R^5$ is a heterocyclic group which is saturated, partially saturated or fully unsaturated, having 5 to 10 ring atoms in which at least 1 ring atom is a N, O or S atom (e.g., 3-thienyl, 2-thienyl, 3-tetrahydrofuranyl, pyridyl, benzothiazolyl, 1,3,4-thiadiazolyl, 1,2,4-thiadiazolyl, isoxazolyl, pyrazolyl, pyrazinyl, isothiazolyl, 1,3-thiazolyl), which is substituted one or more times by carboxamide, $C_{6-14}$-aryl-$C_{1-8}$-alkyl which is optionally substituted by $C_{1-8}$-alkyl or $C_{1-8}$-alkoxy (e.g., benzyl), $C_{6-14}$-aryloxy-$C_{1-8}$-alkyl wherein the aryl portion is optionally substituted by $C_{1-8}$-alkyl or $C_{1-8}$-alkoxy, $C_{6-14}$-arylsulfonyl (e.g., benzenesulfonyl), or anilino. In such a case, $R^6$ is, for example, H, $C_{1-8}$-alkyl (e.g., methyl, ethyl), or $C_{4-16}$-cycloalkylalkyl (e.g., cyclopropylmethyl).

In accordance with a further compound and/or method aspect of the invention, in formula I, $R^3$ is —$CH_2CONR^6R^5$ and $R^5$ is a heterocyclic group, which is saturated, partially saturated or fully unsaturated, having 5 to 10 ring atoms in which at least 1 ring atom is a N, O or S atom (e.g., 3-thienyl, 2-thienyl, 3-tetrahydrofuranyl, pyridyl, benzothiazolyl, 1,3,4-thiadiazolyl, 1,2,4-thiadiazolyl, isoxazolyl, pyrazolyl, pyrazinyl, isothiazolyl, 1,3-thiazolyl), which is substituted one or more times by carboxamide, arylalkyl which is optionally substituted by $C_{1-8}$-alkyl or $C_{1-8}$-alkoxy (e.g., benzyl), aryloxyalkyl wherein the aryl portion is optionally substituted by alkyl or alkoxy, arylsulfonyl (e.g., benzenesulfonyl), or anilino. In such a case, $R^6$ is, for example, H, $C_{1-8}$-alkyl (e.g., methyl, ethyl), or $C_{4-16}$-cycloalkylalkyl (e.g., cyclopropylmethyl).

In accordance with a further compound and/or method aspect of the invention, in formula I, $R^3$ is —$CH_2CONR^6R^5$ and $R^5$ is 1,2,4-thiadiazolyl, 1,3,4-thiadizaolyl, isoxazolyl, pyrazolyl, pyrazinyl, isothiazolyl, or 1,3-thiazolyl, which is unsubstituted or substituted one or more times by halogen, alkyl (e.g., methyl, ethyl, isopropyl), cycloalkyl (e.g., cyclopropyl), cycloalkylalkyl (e.g., cyclopropylmethyl), alkoxy, alkoxyalkyl (e.g., methoxymethyl), cyano, halogenated alkyl (e.g., trifluoromethyl), halogenated alkoxy, (e.g., trifluoromethoxy), nitro, oxo, amino, alkylamino, dialkylamino, carboxamide, aminosulphonyl, aryl which is optionally substituted by alkyl or alkoxy (e.g., phenyl, methylphenyl, methoxyphenyl), arylalkyl which is optionally substituted by alkyl or alkoxy, aryloxyalkyl wherein the aryl portion is optionally substituted by alkyl or alkoxy, arylsulfonyl (e.g., benzenesulfonyl), anilino, heterocycle (e.g., furyl, pyridyl, piperidinyl, thienyl, tetrahydrofuranyl, pyrazinyl), heterocyclic-alkyl wherein the alkyl portion is optionally substituted by oxo (e.g., thienylmethyl, piperidinylethyl, 2-oxo-2-piperidinyl-1-ylethyl or piperidinylcarbonylmethyl, 2-morpholin-4-yl-2-oxoethyl, 2-oxo-2-pyrrolidinyl-1-ylethyl), or combinations thereof. In such a case, $R^6$ is, for example, H, $C_{1-8}$-alkyl (e.g., methyl, ethyl), or $C_{4-16}$-cycloalkylalkyl (e.g., cyclopropylmethyl).

In accordance with a further compound and/or method aspect of the invention, in formula I, $R^3$ is —$CH_2CONR^6R^5$ and $R^5$ is 1,2,4-thiadiazolyl, 1,3,4-thiadizaolyl, isoxazolyl, pyrazolyl, pyrazinyl, isothiazolyl, or 1,3-thiazolyl, which is unsubstituted or substituted one or more times by halogen, $C_{1-8}$-alkyl (e.g., methyl, ethyl, isopropyl), $C_{3-8}$-cycloalkyl (e.g., cyclopropyl), $C_{4-16}$-cycloalkylalkyl (e.g., cyclopropylmethyl), $C_{1-8}$-alkoxy, $C_{2-8}$-alkoxyalkyl (e.g., methoxymethyl), cyano, $C_{1-8}$-halogenated alkyl (e.g., trifluoromethyl), $C_{1-8}$-halogenated alkoxy (e.g., trifluoromethoxy), nitro, oxo, amino, $C_{1-8}$-alkylamino, dialkylamino (each alkyl group having 1 to 8 carbon atoms), carboxamide, aminosulphonyl, $C_{6-14}$-aryl which is optionally substituted by $C_{1-8}$-alkyl or $C_{1-8}$-alkoxy (e.g., phenyl, methylphenyl, methoxyphenyl), $C_{6-14}$-aryl-$C_{1-8}$-alkyl which is optionally substituted by $C_{1-8}$-alkyl or $C_{1-8}$-alkoxy (e.g., benzyl), $C_{6-14}$-aryloxy-$C_{1-8}$-alkyl wherein the aryl portion is optionally substituted by $C_{1-8}$-alkyl or $C_{1-8}$-alkoxy, $C_{6-14}$-arylsulfonyl (e.g., benzenesulfonyl), anilino, heterocycle (e.g., furyl, pyridyl, piperidinyl, thienyl, tetrahydrofuranyl, pyrazinyl), heterocyclic-$C_{1-8}$-alkyl wherein the alkyl portion is optionally substituted by oxo (e.g., thienylmethyl, piperidinylethyl, 2-oxo-2-piperidinyl-1-ylethyl or piperidinylcarbonylmethyl, 2-morpholin-4-yl-2-oxoethyl, 2-oxo-2-pyrrolidinyl-1-ylethyl), or combinations thereof. In such a case, $R^6$ is, for example, H, $C_{1-8}$-alkyl (e.g., methyl, ethyl), or $C_{4-16}$-cycloalkylalkyl (e.g., cyclopropylmethyl).

In accordance with a further compound and/or method aspect of the invention, in formula I, $R^3$ is —$CHR^7CONR^6R^5$ or —$CHR^7CONHR^5$ wherein $R^5$ is not H.

In accordance with a further compound and/or method aspect of the invention, in formula I, $R^3$ is —$CH_2CONR^6R^5$, —$CH_2CONHR^5$, —$CHR^7CONR^6R^5$ or —$CHR^7CONHR^5$ in which $R^5$ is not H, and $R^1$ is ethyl, isopropyl, cyclopropylmethyl, cyclobutylmethyl, or benzyl. In this case, $R^2$ is preferably $CH_3$ or $CHF_2$.

In accordance with a further compound and/or method aspect of the invention, in formula I, $R^3$ is —$CH_2CONR^6R^5$, —$CH_2CONHR^5$, —$CHR^7CONR^6R^5$ or —$CHR^7CONHR^5$ wherein $R^5$ is isoxazolyl, pyrazolyl, or pyrazinyl, in each case substituted or unsubstituted. In this case, $R^1$ is preferably ethyl, isopropyl, cyclopropylmethyl, cyclobutylmethyl, benzyl, or tetrahydrofuranyl. Also, in this case, $R^2$ is preferably $CH_3$ or $CHF_2$.

In accordance with a further compound and/or method aspect of the invention, in formula I, $R^3$ is —$CH_2CONR^6R^5$, —$CH_2CONHR^5$, —$CHR^7CONR^6R^5$ or —$CHR^7CONHR^5$ wherein $R^5$ is 3-isopropyl-1,2,4-thiadiazol-5-yl, methylisothiazolyl (such as 3-methylisothiazol-5-yl), cyclopropylthiazolyl (such as 4-cyclopropyl-1,3-thiazol-2-yl), 5-cyclopropyl-1,3,4-thiadiazolyl, methylbenzothiazolyl (such as 4-methyl-1,3-benzothiazol-2-yl), or methylisoxazolyl (such as 5-methyl-isoxazol-3-yl). In this case, $R^1$ is preferably ethyl, isopropyl, cyclopropylmethyl, cyclobutylmethyl, benzyl, or tetrahydrofuranyl. Also, in this case, $R^2$ is preferably $CH_3$ or $CHF_2$.

In accordance with a further compound and/or method aspect of the invention, in formula I, $R^3$ is —$CHR^7CONR^6R^5$ or —$CHR^7CONHR^5$ wherein $R^7$ is alkyl (e.g., $CH_3$), $R^6$ is $C_{1-8}$ alkyl (e.g., $CH_3$), or $C_{4-16}$ cycloalkylalkyl (e.g., cyclopropylmethyl) and $R^5$ is a heterocyclic group, which is saturated, partially saturated or fully unsaturated, having 5 to 10 ring atoms in which at least 1 ring atom is a N, O or S atom (e.g., thiazolyl (e.g., 1,3-thiazol-2-yl), isothiazolyl (e.g., isothiazol-5-yl), thiadiazolyl (e.g., 1,2,4-thiadiazol-5-yl)), which is unsubstituted or substituted one or more times by $C_{1-8}$ alkyl.

In accordance with a further compound and/or method aspect of the invention, in formula I, $R^3$ is —$CHR^7CONHR^5$ wherein $R^7$ is alkyl (e.g., $CH_3$) and $R^5$ is a heterocyclic group, which is saturated, partially saturated or fully unsaturated, having 5 to 10 ring atoms in which at least 1 ring atom is a N, O or S atom (e.g., thiazolyl (e.g., 1,3-thiazol-2-yl), isothiazolyl (e.g., isothiazol-5-yl), thiadiazolyl (e.g., 1,2,4-thiadiazol-5-yl)), which is unsubstituted or substituted one or more times by $C_{1-8}$ alkyl.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes, but is not limited to, inflammatory diseases. These compounds may also function as antidepressants, or be useful in treating cognitive and negative symptoms of schizophrenia.

Assays for determining PDE 4 inhibiting activity, selectivity of PDE4 inhibiting activity, and selectivity of inhibiting PDE 4 isoenzymes are known within the art. See, e.g., U.S. Pat. No. 6,136,821, the disclosure of which is incorporated herein by reference.

Halogen herein refers to F, Cl, Br, and I. Preferred halogens are F and Cl.

Alkyl means a straight-chain or branched-chain aliphatic hydrocarbon radical. In the case of $R^1$ and $R^3$ suitable alkyl groups have preferably 1 to 8 carbon atoms, especially 1 to 4 carbon atoms. In the case of $R^2$, suitable alkyl groups have preferably 1 to 4 carbon atoms such as methyl, ethyl, propyl, isopropyl, and butyl. In the case of $R^4$, $R^5$, and $R^6$, suitable alkyl groups have preferably 1 to 12 carbon atoms, especially 1 to 8 carbon atoms, in particular 1 to 4 carbon atoms.

Suitable alkyl groups include methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

These alkyl radicals can optionally have one or more —$CH_2CH_2$— groups replaced in each case by —CH=CH— or —C≡C— groups. Suitable alkenyl or alkynyl groups are 1-propenyl, 2-propenyl, 1-propynyl, 1-butenyl, 2-butenyl, 3-butenyl, 1-butynyl, 1,3-butadienyl and 3-methyl-2-butenyl. Also, these alkyl radicals can optionally have one or more —$CH_2$— groups replaced in each case by O, S, or NH.

The substituted alkyl groups for $R^1$, $R^3$, $R^4$, $R^5$, and $R^6$ are alkyl groups as described above which are substituted in one or more positions by halogens and/or oxo. Halogens are preferred substituents, especially F and Cl. For $R^2$, the substituted alkyl groups have 1 to 4 carbon atoms and are substituted one or more times by halogen, especially F and Cl, e.g., $C_1$-$C_4$ alkyl substituted by up to five F atoms.

In the arylalkyl groups, heterocyclic-alkyl groups, cycloalkyl-alkyl groups and alkoxyalkyl groups, "alkyl" refers to a divalent alkylene group having in general up to about 13 carbon atoms. In the case of the arylalkyl group for $R^1$, the "alkyl" portion has preferably 2 to 10 carbon atoms. In the case of other arylalkyl groups, the "alkyl" portion has preferably 1 to 10. In the heterocyclic-alkyl groups, the "alkyl" portion preferably has 1 to 12 carbon atoms. In the alkoxyalkyl groups, the "alkyl" portion preferably has 2 to 7 carbon atoms. In the cycloalkylalkyl groups, the "alkyl" portion preferably has 1 to 13 carbon atoms.

In the cases where alkyl is a substituent (e.g., alkyl substituents on aryl and heterocyclic groups) or is part of a substituent (e.g., in the alkylamino, dialkylamino, hydroxyalkyl, hydroxyalkoxy, alkylthio, alkylsulphinyl, and alkylsulphonyl substituents for aryl), the alkyl portion preferably has 1 to 12 carbon atoms, especially 1 to 8 carbon atoms, in particular 1 to 4 carbon atoms. The alkyl groups, as described above, can be substituted in one or more positions by halogens and/or oxo. Halogens are preferred substituents, especially F and Cl.

Alkoxy means alkyl-O— groups in which the alkyl portion has 1 to 8 carbon atoms and which, for example, can be substituted by halogens. Suitable alkoxy groups include methoxy, ethoxy, propoxy, isopropoxy, isobutoxy, sec-butoxy, pentoxy, hexoxy, heptoxy, octoxy, and trifluoromethoxy. Preferred alkoxy groups are methoxy and ethoxy. The alkoxyalkyl group for $R^3$ preferably has 3 to 8 carbon atoms, e.g., methoxyethyl.

Similarly, alkoxycarbonyl means an alkyl-O—CO— group in which the alkyl portion has 1 to 8 carbon atoms.

Alkenyl refers to straight-chain or branched-chain aliphatic radicals containing 2 to 12 carbon atoms in which one or more —$CH_2$—$CH_2$— structures is replaced by —CH=CH—. Suitable alkenyl groups are ethenyl, 1-propenyl, 2-methylethenyl, 1-butene, 2-butene, 1-pentenyl, and 2-pentenyl. In the arylalkenyl groups, alkenyl refers to a divalent alkenylene group having preferably 2 to 5 carbon atoms.

Cycloalkyl means a monocyclic, bicyclic or tricyclic saturated hydrocarbon radical having 3 to 8 carbon atoms, preferably 4 to 6 carbon atoms, especially 5 carbon atoms. Suitable cycloalkyl groups include cyclopropyl, cyclobutyl, cyclopentyl, cyclohexyl, cycloheptyl, cyclooctyl, and norbornyl. Other suitable cycloalkyl groups include spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, and bicyclo[4.2.0]octyl. The preferred cycloalkyl group is cyclopentyl.

The cycloalkyl group can be substituted by halogens, oxo and/or alkyl. Halogens and/or alkyl groups are preferred substituents.

Cycloalkylalkyl refers to a cycloalkyl-alkyl-radical in which the cycloalkyl and alkyl portions are in accordance with the previous descriptions. Suitable examples include cyclopentylethyl and cyclopropylmethyl.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include phenyl, naphthyl and biphenyl. Substituted aryl groups include the above-described aryl groups which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenyl, phenoxy, and acyloxy (e.g., acetoxy).

Arylalkyl refers to an aryl-alkyl-radical in which the aryl and alkyl portions are in accordance with the previous descriptions. Suitable examples include 1-phenethyl, 2-phenethyl, phenpropyl, phenbutyl, phenpentyl, and naphthylenemethyl. Also, in the case of $R^3$, arylalkyl can be benzyl.

Arylalkenyl refers to an aryl-alkenyl-radical in which the aryl and alkenyl portions are in accordance with the previous descriptions of aryl and alkenyl. Suitable examples include 3-aryl-2-propenyl.

Heterocyclic groups refer to saturated, partially saturated and fully unsaturated heterocyclic groups having one or two rings and a total number of 5 to 10 ring atoms wherein at least one of the ring atoms is an N, O or S atom. Preferably, the heterocyclic group has one ring and has 5, 6, or 7 ring atoms or has two rings and is 5,6 fused or 6,6 fused. Preferably, the heterocyclic group contains 1 to 3, especially 1 or 2, hetero-ring atoms selected from N, O and S. Suitable saturated and partially saturated heterocyclic groups include, but are not limited to tetrahydrofuranyl, tetrahydrothienyl, pyrrolidinyl, isoxazolinyl and the like. Suitable heteroaryl groups include but are not limited to triazolyl (e.g., 1,2,4-triazolyl), thiadiazolyl (e.g., 1,3,4-thiadiazolyl, 1,2,4-thiadiazolyl), thiazolyl, oxazolyl, pyridyl, isoxazolyl, azatriazolyl, furyl, thienyl, pyrrolyl, pyrazolyl, imidazolyl, pyridyl, pyrimidinyl, indolyl, quinolinyl, naphthyridinyl, benzimidazolyl, benzthiazolyl, benzoxazolyl and the like. Preferred heterocyclic and heteroaryl groups include terahydrofuranyl, tetrahydropyranyl, 2-thienyl, 3-thienyl, 2-, 3- or 4-pyridyl, 1,3,4-thiadiazolyl, 1,2,4-thiadiazolyl, 1,3-thiazolyl, isothiazolyl, isoxazolyl, 2-, 3-, 4-, 5-, 6-, 7- or 8-quinolinyl, and 1-, 3-, 4-, 5-, 6-, 7- or 8-isoquinolinyl. In addition, heterocyclic groups include bicycloheterocyclic groups such as quinuclidinyl, 1-azabicyclo[2.2.1]heptyl, and 1-azabicyclo[3.2.1]octyl.

Substituted heterocyclic groups refer to the heterocyclic groups described above which are substituted in one or more places by halogen, aryl, alkyl, alkoxy, cyano, halogenated alkyl (e.g., trifluoromethyl), nitro, oxo, amino, alkylamino, dialkylamino, and carboxy.

Heterocyclic-alkyl refers to a heterocyclic-alkyl-group wherein the heterocyclic and alkyl portions are in accordance with the previous discussions. Suitable examples are pyridylmethyl, thienylmethyl, pyrimidinylmethyl, pyrazinylmethyl, isoquinolinylmethyl, pyridylethyl and thienylethyl.

Partially unsaturated carbocyclic structures are non-aromatic monocyclic or bicyclic structures containing 5 to 14 carbon atoms, preferably 6 to 10 carbon atoms, wherein the ring structure(s) contains at least one C=C bond. Suitable examples are cyclopentenyl, cyclohexenyl, tetrahydronaphthenyl and indan-2-yl.

Acyl refers to alkanoyl radicals having 1 to 13 carbon atoms in which the alkyl portion can be substituted by halogen, hydroxy, carboxy, alkyl, aryl and/or alkoxy; or aroyl radicals having 7 to 15 carbon atoms in which the aryl portion can be substituted by halogen, alkyl, alkoxy, nitro, carboxy and/or hydroxy. Suitable acyl groups include formyl, acetyl, propionyl, butanoyl and benzoyl.

Substituted radicals preferably have 1 to 3 substituents, especially 1 or 2 substituents.

Suitable $R^1$ groups include optionally substituted cycloalkyl, cycloalkylalkyl, aryl, heterocyclic, arylalkyl, or a partially unsaturated carbocyclic group, or $CHF_2$; for example, $CHF_2$, cyclopropyl, cyclobutyl, cyclopentyl, cyclohexyl, cyclopentylethyl, cyclopropylmethyl, cyclohexylpropyl, phenyl, napthyl, phenethyl, phenpropyl, furanyl, pyrazinyl, pyrimidinyl, pyridyl, quinolinyl, isoquinolinyl, thienyl, indanyl, tetrahydrofuranyl, phenylpropenyl, substituted phenyl, and substituted phenethyl. Suitable $R^1$ groups also include alkyl such as ethyl and isopropyl. Preferred $R^1$ groups include, for example, ethyl, isopropyl, cyclopropylmethyl, tetrahydrofuranyl, $CHF_2$, and cyclobutylmethyl.

$R^2$ is preferably substituted or unsubstituted alkyl having 1 to 4 carbon atoms, most preferably $CHF_2$ or $CH_3$.

Suitable $R^3$ groups include H and $CH_2CONR^6R^5$. Suitable $R^5$ groups include, but are not limited to, 3-thienyl, 2-thienyl, 3-tetrahydrofuranyl, 1,3,4-thiadiazolyl, 1,2,4-thiadiazolyl, isoxazolyl, pyrazolyl, pyrazinyl, isothiazolyl, 1,3-thiazolyl, and pyridyl, which in each case is unsubstituted or substituted.

Suitable $R^3$ groups also include $—CHR^7CONR^6R^5$ or $—CHR^7CONHR^5$. Suitable $R^5$ groups include, but are not limited to, 3-thienyl, 2-thienyl, 3-tetrahydrofuranyl, 1,3,4-thiadiazolyl, 1,2,4-thiadiazolyl, isoxazolyl, pyrazolyl, pyrazinyl, isothiazolyl, 1,3-thiazolyl, and pyridyl, which in each case is unsubstituted or substituted.

Preferred $R^5$ are aryl and heteroaryl groups, including, for example, fluorophenyl (such as 3-fluorophenyl), methylpyridinyl (such as 6-methyl-pyridin-2-yl), isopropylthiadiazolyl (such as 3-isopropyl-1,2,4-thiadiazol-5-yl), methylisothiazolyl (such as 3-methyl-isothiazol-5-yl), thiazolyl (such as 1,3-thiazol-2-yl), cyclopropylthiazolyl (such as 4-cyclopropyl-1,3-thiazol-2-yl), methylbenzothiazolyl (such as 4-methyl-1,3-benzothiazol-2-yl), methylpyrazolyl (such as 3-methyl-1H-pyrazol-5-yl), and methylisoxazolyl (such as 5-methyl-isoxazol-3-yl).

$R^6$ is preferably H, $C_1$-$C_5$ alkyl (such as $CH_3$ or 2-methylpropyl) or cycloalkylalkyl. More preferably, $R^6$ is cyclopropylmethyl. $R^6$ is also preferably H or $CH_3$.

$R^7$ is preferably H or $CH_3$.

In addition, preferred PDE4 inhibitors in accordance with the invention are compounds described by subformulas Ia-Iab, which correspond to formula I, but exhibit the following preferred groups:

Ia $R^2$ is $CH_3$ or $CHF_2$.

Ib $R^2$ is $CH_3$ or $CHF_2$, and
$R^3$ is H.

Ic $R^3$ is H; and
$R^1$ is optionally substituted cycloalkyl, heterocyclic group, heterocyclic alkyl group, arylalkyl or cycloalkylalkyl, or is $CHF_2$.

Id $R^2$ is $CH_3$ or $CHF_2$;
$R^1$ is cyclopentyl, tetrahydrofuranyl, or cyclopropylmethyl, as well as $CHF_2$ and phenethyl; and
$R^3$ is not H.

Ie $R^2$ is $CHF_2$ and
$R_3$ is H.

If $R^1$ is alkyl (e.g. ethyl), heterocyclic (e.g. tetrahydrofuranyl), cycloalkyl, or cycloalkylalkyl,
$R^2$ is $CHF_2$, and
$R^3$ is H.

Ig $R^3$ is $CH_2CONR^6R^5$.

Ih $R^1$ is tetrahydrofuranyl, ethyl, benzyl, cyclopropylmethyl, or cyclobutylmethyl;
$R^2$ is $CH_3$ or $CHF_2$; and
$R^3$ is $CH_2CONR^6R^5$.

Ii $R^1$ is tetrahydrofuranyl, ethyl, benzyl, cyclopropylmethyl, or cyclobutylmethyl;
$R^2$ is $CH_3$ or $CHF_2$;
$R^3$ is $CH_2CONR^6R^5$; and
$R^5$ is a heterocyclic group, which is saturated, partially saturated or fully unsaturated, and which is unsubstituted or substituted, or is phenyl which is unsubstituted or substituted.

Ij $R^1$ is tetrahydrofuranyl, ethyl, benzyl, cyclopropylmethyl, or cyclobutylmethyl;
$R^2$ is $CH_3$ or $CHF_2$;
$R^3$ is $CH_2CONR^6R^5$;
$R^5$ is a heterocyclic group, which is saturated, partially saturated or fully unsaturated, and which is unsubstituted or substituted, or is phenyl which is unsubstituted or substituted; and
$R^6$ is H, $C_{1-8}$-alkyl or $C_{4-16}$-cycloalkylalkyl.

Ik $R^1$ is tetrahydrofuranyl, ethyl, benzyl, cyclopropylmethyl, or cyclobutylmethyl;
$R^2$ is $CH_3$ or $CHF_2$;
$R^3$ is $CH_2CONR^6R^5$;
$R^5$ is thienyl, tetrahydrofuranyl, 1,3,4-thiadiazolyl, 1,2,4-thiadiazolyl, isoxazolyl, pyrazolyl, pyrazinyl, isothiazolyl, or 1,3-thiazolyl, which is unsubstituted or substituted, or phenyl which is unsubstituted or substituted; and
$R^6$ is H, $C_{1-8}$-alkyl or $C_{4-16}$-cycloalkylalkyl.

Il $R^1$ is tetrahydrofuranyl, ethyl, benzyl, cyclopropylmethyl, or cyclobutylmethyl;
$R^2$ is $CH_3$ or $CHF_2$;
$R^3$ is $CH_2CONR^6R^5$;
$R^6$ is H, $C_{1-8}$-alkyl or $C_{4-16}$-cycloalkylalkyl; and
$R^5$ is phenyl which is unsubstituted or substituted by halogen, or is thienyl, tetrahydrofuranyl, 1,3,4-thiadiazolyl, 1,2,4-thiadiazolyl, isoxazolyl, pyrazolyl, pyrazinyl, isothiazolyl, or 1,3-thiazolyl, which in each case is unsubstituted or substituted by methyl, ethyl, isopropyl, cyclopropyl, alkoxy (e.g., methoxy), trifluoromethyl, cyano, aminosulfonyl, carboxamide, benzyl, benzenesulfonyl, anilino, methoxyphenoxy, furyl, thienyl, pyridinyl, piperidinylethyl, 2-oxo-2-piperidinyl-1-ylethyl, 2-morpholin-4-yl-2-oxoethyl, or 2-oxo-2-pyrrolidinyl-1-ylethyl.

Im $R^1$ is tetrahydrofuranyl, cyclopropylmethyl, or cyclobutylmethyl;
$R^2$ is $CHF_2$; and
$R^3$ is H.

In $R^3$ is $—CH_2CONR^6R^5$, $—CH_2CONHR^5$, $—CHR^7CONR^6R^5$ or $—CHR^7CONHR^5$.

Io $R^3$ is $—CH_2CONR^6R^5$, $—CH_2CONHR^5$, $—CHR^7CONR^6R^5$ or $—CHR^7CONHR^5$; and
$R^7$ is $C_{1-4}$ alkyl.

Ip $R^3$ is $—CH_2CONR^6R^5$, $—CH_2CONHR^5$, $—CHR^7CONR^6R^5$ or $—CHR^7CONHR^5$;
$R^6$ is $C_{1-4}$ alkyl or $C_{4-16}$ cycloalkylalkyl; and
$R^7$ is $C_{1-4}$ alkyl.

Iq R³ is —CH₂CONR⁶R⁵, —CH₂CONHR⁵, —CHR⁷CONR⁶R⁵ or —CHR⁷CONHR⁵;
R⁵ is phenyl which is substituted or unsubstituted;
R⁶ is C₁₋₄ alkyl or C₄₋₁₆ cycloalkylalkyl; and
R⁷ is C₁₋₄ alkyl.

Ir R³ is —CH₂CONR⁶R⁵, —CH₂CONHR⁵, —CHR⁷CONR⁶R⁵ or —CHR⁷CONHR⁵;
R⁵ is a heterocyclic group which is substituted or unsubstituted;
R⁶ is C₁₋₄ alkyl or C₄₋₁₆ cycloalkylalkyl; and
R⁷ is C₁₋₄ alkyl.

Is R³ is —CH₂CONR⁶R⁵, —CH₂CONHR⁵, —CHR⁷CONR⁶R⁵ or —CHR⁷CONHR⁵;
R¹ is tetrahydrofuranyl, methyl, ethyl, benzyl, cyclopropylmethyl, or cyclobutylmethyl;
R² is CH₃ or CHF₂;
R⁵ is phenyl which is substituted or unsubstituted;
R⁶ is C₁₋₄ alkyl or C₄₋₁₆ cycloalkylalkyl; and
R⁷ is C₁₋₄ alkyl.

Iu R³ is —CH₂CONR⁶R⁵, —CH₂CONHR⁵, —CHR⁷CONR⁶R⁵ or —CHR⁷CONHR⁵;
R¹ is tetrahydrofuranyl, methyl, ethyl, benzyl, cyclopropylmethyl, or cyclobutylmethyl;
R² is CH₃ or CHF₂;
R⁵ is a heterocyclic group which is substituted or unsubstituted;
R⁶ is C₁₋₄ alkyl or C₄₋₁₆ cycloalkylalkyl; and
R⁷ is C₁₋₄ alkyl.

Iv R³ is —CHR⁷CONR⁶R⁵ or —CHR⁷CONHR⁵.

Iw R³ is —CHR⁷CONR⁶R⁵ or —CHR⁷CONHR⁵; and
R⁷ is C₁₋₄ alkyl.

Ix R³ is —CHR⁷CONR⁶R⁵ or —CHR⁷CONHR⁵
R⁶ is C₁₋₄ alkyl or C₄₋₁₆ cycloalkylalkyl; and
R⁷ is C₁₋₄ alkyl.

Iy R³ is —CHR⁷CONR⁶R⁵ or —CHR⁷CONHR⁵;
R⁵ is phenyl which is substituted or unsubstituted;
R⁶ is C₁₋₄ alkyl or C₄₋₁₆ cycloalkylalkyl; and
R⁷ is C₁₋₄ alkyl.

Iz R³ is —CHR⁷CONR⁶R⁵ or —CHR⁷CONHR⁵;
R⁵ is a heterocyclic group which is substituted or unsubstituted;
R⁶ is C₁₋₄ alkyl or C₄₋₁₆ cycloalkylalkyl; and
R⁷ is C₁₋₄ alkyl.

Iaa R³ is —CHR⁷CONR⁶R⁵ or —CHR⁷CONHR⁵;
R¹ is tetrahydrofuranyl, methyl, ethyl, benzyl, cyclopropylmethyl, or cyclobutylmethyl;
R² is CH₃ or CHF₂;
R⁵ is phenyl which is substituted or unsubstituted;
R⁶ is C₁₋₄ alkyl or C₄₋₁₆ cycloalkylalkyl; and
R⁷ is C₁₋₄ alkyl.

Iab R³ is —CHR⁷CONR⁶R⁵ or —CHR⁷CONHR⁵;
R¹ is tetrahydrofuranyl, methyl, ethyl, benzyl, cyclopropylmethyl, or cyclobutylmethyl;
R² is CH₃ or CHF₂;
R⁵ is a heterocyclic group which is substituted or unsubstituted;
R⁶ is C₁₋₄ alkyl or C₄₋₁₆ cycloalkylalkyl; and
R⁷ is C₁₋₄ alkyl.

Iac R¹ is ethyl, isopropyl, cyclopropylmethyl, tetrahydrofuranyl, CHF₂, or cyclobutylmethyl; and
R² is CH₃ or CHF₂.

Iad R¹ is ethyl, isopropyl, cyclopropylmethyl, tetrahydrofuranyl, CHF₂, or cyclobutylmethyl;
R² is CH₃ or CHF₂;
R³ is H, —CH₂CONR⁶R⁵, —CH₂CONHR⁵, or —CHR⁷CONHR⁵;
R⁵ is an aryl or heteroaryl group which is substituted or unsubstituted;
R⁶ is H or CH₃; and
R⁷ is H or CH₃.

Iae R¹ is ethyl, isopropyl, cyclopropylmethyl, tetrahydrofuranyl, CHF₂, or cyclobutylmethyl;
R² is CH₃ or CHF₂;
R³ is H, —CH₂CONR⁶R⁵, —CH₂CONHR⁵, or —CHR⁷CONHR⁵;
R⁵ is 3-fluorophenyl, 6-methyl-pyridin-2-yl, 3-isopropyl-1,2,4-thiadiazol-5-yl, 3-methyl-isothiazol-5-yl), 1,3-thiazol-2-yl, 4-cyclopropyl-1,3-thiazol-2-yl, 4-methyl-1,3-benzothiazol-2-yl, 3-methyl-1H-pyrazol-5-yl, or 5-methyl-isoxazol-3-yl;
R⁶ is H or CH₃; and
R⁷ is H or CH₃.

According to a further preferred compound and/or method aspect of the invention, the compound of formula I is selected from:

1) N-[5-(aminosulfonyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide,
2) N-[5-(4-methoxyphenyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide,
3) 2-((4S)-4-{4-methoxy-3-[(3R)-tetrahydrofuran-3-yloxy]phenyl}-2-oxopyrrolidin-1-yl)-N-1,3,4-thiadiazol-2-ylacetamide,
4) N-[5-(2-furyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide,
5) 2-((4S)-4-{4-methoxy-3-[(3R)-tetrahydrofuran-3-yloxy]phenyl}-2-oxopyrrolidin-1-yl)-N-[5-(2-oxo-2-piperidin-1-ylethyl)-1,3,4-thiadiazol-2-yl]acetamide,
6) 2-((4S)-4-{4-methoxy-3-[(3R)-tetrahydrofuran-3-yloxy]phenyl}-2-oxopyrrolidin-1-yl)-N-[5-(2-piperidin-1-ylethyl)-1,3,4-thiadiazol-2-yl]acetamide,
7) N-{5-[(4-methoxyphenoxy)methyl]-1,3,4-thiadiazol-2-yl}-2-((4S)-4-{4-methoxy-3-[(3R)-tetrahydrofuran-3-yloxy]phenyl}-2-oxopyrrolidin-1-yl)acetamide,
8) 2-((4S)-4-{4-methoxy-3-[(3R)-tetrahydrofuran-3-yloxy]phenyl}-2-oxopyrrolidin-1-yl)-N-[5-(2-morpholin-4-yl-2-oxoethyl)-1,3,4-thiadiazol-2-yl]acetamide,
9) 2-((4S)-4-{4-methoxy-3-[(3R)-tetrahydrofuran-3-yloxy]phenyl}-2-oxopyrrolidin-1-yl)-N-[5-(2-oxo-2-pyrrolidin-1-ylethyl)-1,3,4-thiadiazol-2-yl]acetamide,
10) 2-((4S)-4-{4-methoxy-3-[(3R)-tetrahydrofuran-3-yloxy]phenyl}-2-oxopyrrolidin-1-yl)-N-(3-phenyl-1,2,4-thiadiazol-5-yl)acetamide,
11) 2-((4S)-4-{4-methoxy-3-[(3R)-tetrahydrofuran-3-yloxy]phenyl}-2-oxopyrrolidin-1-yl)-N-(5-phenyl-1,3,4-thiadiazol-2-yl)acetamide,
12) N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
13) 2-((S)-4-{4-Methoxy-3-[(R)-(tetrahydrofuran-3-yl)oxy]-phenyl}-2-oxopyrrolidin-1-yl)-N-(5-(1-tert-butyloxycarbonylpiperidin)-4-yl-[1,3,4]thiadiazol-2-yl)-acetamide;
14) 2-((S)-4-{4-Methoxy-3-[(R)-(tetrahydrofuran-3-yl)oxy]-phenyl}-2-oxopyrrolidin-1-yl)-N-(5-piperidin-4-yl-[1,3,4]thiadiazol-2-yl)-acetamide hydroformate,
15) 2-((S)-4-{4-Methoxy-3-[(R)-(tetrahydrofuran-3-yl)oxy]-phenyl}-2-oxopyrrolidin-1-yl)-N-(3-methyl-isothiazol-5-yl)-acetamide, 16) 2-((4S)-4-{4-methoxy-3-[(3R)-tetrahydrofuran-3-yloxy]phenyl}-2-oxopyrrolidin-1-yl)-N-(5-methylisoxazol-3-yl)acetamide,
17) N-Isoxazol-3-yl-2-((S)-4-{4-methoxy-3-[(R)-(tetrahydrofuran-3-yl)oxy]-phenyl}-2-oxo-pyrrolidin-1-yl)-acetamide,
18) 2-((4S)-4-{4-methoxy-3-[(3R)-tetrahydrofuran-3-yloxy]phenyl}-2-oxopyrrolidin-1-yl)-N-(3-methyl-1H-pyrazol-5-yl)acetamide,
19) N-(4-Benzenesulfonyl-thiophen-3-yl)-2-((S)-4-{4-methoxy-3-[(R)-(tetrahydrofuran-3-yl)oxy]-phenyl}-2-oxo-pyrrolidin-1-yl)-acetamide,
20) 2-((S)-4-{4-Methoxy-3-[(R)-(tetrahydrofuran-3-yl)oxy]-phenyl}-2-oxo-pyrrolidin-1-yl)-N-(1H-pyrazol-3-yl)-acetamide,
21) 2-((4S)-4-{4-methoxy-3-[(3R)-tetrahydrofuran-3-yloxy]phenyl}-2-oxopyrrolidin-1-yl)-N-(5-methyl-1,3,4-thiadiazol-2-yl)acetamide,
22) 2-((4S)-4-{4-methoxy-3-[(3R)-tetrahydrofuran-3-yloxy]phenyl}-2-oxopyrrolidin-1-yl)-N-(3-methyl-1,2,4-thiadiazol-5-yl)acetamide,
23) 2-((4S)-4-{4-methoxy-3-[(3R)-tetrahydrofuran-3-yloxy]phenyl}-2-oxopyrrolidin-1-yl)-N-(3-methoxy-1,2,4-thiadiazol-5-yl)acetamide,
24) N-(3-ethyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
25) 5-{[((4S)-4-{4-methoxy-3-[(3R)-tetrahydrofuran-3-yloxy]phenyl}-2-oxopyrrolidin-1-yl)acetyl]amino}-3-methylisoxazole-4-carboxamide,
26) 2-((4S)-4-{4-methoxy-3-[(3R)-tetrahydrofuran-3-yloxy]phenyl}-2-oxopyrrolidin-1-yl)-N-(3-methylisoxazol-5-yl)acetamide,
27) 2-((4S)-4-{4-methoxy-3-[(3R)-tetrahydrofuran-3-yloxy]phenyl}-2-oxopyrrolidin-1-yl)-N-(5-methyl-3-phenylisoxazol-4-yl)acetamide,
28) N-(3,5-dimethylisoxazol-4-yl)-2-((4S)-4-{4-methoxy-3-[(3R)-tetrahydrofuran-3-yloxy]phenyl}-2-oxopyrrolidin-1-yl)acetamide,
29) 2-((4S)-4-{4-methoxy-3-[(3R)-tetrahydrofuran-3-yloxy]phenyl}-2-oxopyrrolidin-1-yl)-N-pyrazin-2-ylacetamide,
30) N-(2-Ethyl-2H-pyrazol-3-yl)-2-((S)-4-{4-methoxy-3-[(R)-(tetrahydrofuran-3-yl)oxy]-phenyl}-2-oxo-pyrrolidin-1-yl)-acetamide,
31) 2-((4S)-4-{4-methoxy-3-[(3R)-tetrahydrofuran-3-yloxy]phenyl}-2-oxopyrrolidin-1-yl)-N-(3-phenylisoxazol-5-yl)acetamide,
32) N-(3-anilino-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
33) 2-{(4R)-4-[3-(benzyloxy)-4-methoxyphenyl]-2-oxopyrrolidin-1-yl}-N-(3-methylisothiazol-5-yl)acetamide,
34) 2-{(4S)-4-[3-(benzyloxy)-4-methoxyphenyl]-2-oxopyrrolidin-1-yl}-N-(3-methylisothiazol-5-yl)acetamide,
35) N-(3-cyano-2-thienyl)-2-((4S)-4-{4-methoxy-3-[(3R)-tetrahydrofuran-3-yloxy]phenyl}-2-oxopyrrolidin-1-yl)acetamide,
36) 2-((4S)-4-{4-methoxy-3-[(3R)-tetrahydrofuran-3-yloxy]phenyl}-2-oxopyrrolidin-1-yl)-N-[4-(2-thienyl)-1,3-thiazol-2-yl]acetamide,
37) 2-((4S)-4-{4-methoxy-3-[(3R)-tetrahydrofuran-3-yloxy]phenyl}-2-oxopyrrolidin-1-yl)-N-[4-(trifluoromethyl)-1,3-thiazol-2-yl]acetamide,
38) 2-[4-(3-ethoxy-4-methoxyphenyl)-2-oxopyrrolidin-1-yl]-N-(3-fluorophenyl)acetamide,
39) 2-[4-(3-ethoxy-4-methoxyphenyl)-2-oxopyrrolidin-1-yl]-N-(3-methyl-1H-pyrazol-5-yl)acetamide,
40) 2-((4S)-4-{4-methoxy-3-[(3R)-tetrahydrofuran-3-yloxy]phenyl}-2-oxopyrrolidin-1-yl)-N-methyl-N-(3-methylisothiazol-5-yl)acetamide,
41) 2-((4S)-4-{4-methoxy-3-[(3R)-tetrahydrofuran-3-yloxy]phenyl}-2-oxopyrrolidin-1-yl)-N-methyl-N-(4-methyl-1,3-thiazol-2-yl)acetamide,
42) 2-[4-(3-ethoxy-4-methoxyphenyl)-2-oxopyrrolidin-1-yl]-N-(5-methylisoxazol-3-yl)acetamide,
43) 2-[4-(3-ethoxy-4-methoxyphenyl)-2-oxopyrrolidin-1-yl]-N-(4-methyl-1,3-thiazol-2-yl)acetamide,
44) 2-[4-(3-ethoxy-4-methoxyphenyl)-2-oxopyrrolidin-1-yl]-N-(3-methylisothiazol-5-yl)acetamide,
45) 2-[4-(3-ethoxy-4-methoxyphenyl)-2-oxopyrrolidin-1-yl]-N-(6-methylpyridin-2-yl)acetamide,
46) 2-{4-[3-(cyclopropylmethoxy)-4-methoxyphenyl]-2-oxopyrrolidin-1-yl}-N-(4-methyl-1,3-thiazol-2-yl)acetamide,
47) 2-{4-[3-(cyclopropylmethoxy)-4-methoxyphenyl]-2-oxopyrrolidin-1-yl}-N-(3-fluorophenyl)acetamide,
48) (4S)-4-[3-(cyclopropylmethoxy)-4-(difluoromethoxy)phenyl]pyrrolidin-2-one,
49) 2-{4-[3-(cyclopropylmethoxy)-4-methoxyphenyl]-2-oxopyrrolidin-1-yl}-N-(5-methyl-1H-pyrazol-3-yl)acetamide,
50) (4R)-4-[3-(cyclopropylmethoxy)-4-(difluoromethoxy)phenyl]pyrrolidin-2-one,
51) (4S)-4-{4-(difluoromethoxy)-3-[(3R)-tetrahydrofuran-3-yloxy]phenyl}pyrrolidin-2-one,
52) (4R)-4-{4-(difluoromethoxy)-3-[(3R)-tetrahydrofuran-3-yloxy]phenyl}pyrrolidin-2-one,
53) (4S)-4-[3-(cyclobutylmethoxy)-4-(difluoromethoxy)phenyl]pyrrolidin-2-one,
54) (4R)-4-[3-(cyclobutylmethoxy)-4-(difluoromethoxy)phenyl]pyrrolidin-2-one,
55) 2-{4-[3-(cyclopropylmethoxy)-4-methoxyphenyl]-2-oxopyrrolidin-1-yl}-N-(5-cyclopropyl-1,3,4-thiadiazol-2-yl)acetamide,
56) 2-{4-[3-(cyclopropylmethoxy)-4-methoxyphenyl]-2-oxopyrrolidin-1-yl}-N-(6-methylpyridin-2-yl)acetamide,
57) 2-{4-[3-(cyclopropylmethoxy)-4-methoxyphenyl]-2-oxopyrrolidin-1-yl}-N-(3-methylisoxazol-5-yl)acetamide,
58) 2-{4-[3-(cyclopropylmethoxy)-4-methoxyphenyl]-2-oxopyrrolidin-1-yl}-N-(3-isopropyl-1,2,4-thiadiazol-5-yl)acetamide,
59) 2-{4-[3-(cyclopropylmethoxy)-4-methoxyphenyl]-2-oxopyrrolidin-1-yl}-N-(3-methylisothiazol-5-yl)acetamide,
60) 2-((4S)-4-{4-Methoxy-3-[(3R)-tetrahydrofuran-3-yloxy]phenyl}-2-oxopyrrolidin-1-yl)-N-methyl-N-phenylacetamide,
61) 2-{4-[3-(cyclobutylmethoxy)-4-methoxyphenyl]-2-oxopyrrolidin-1-yl}-N-(3-fluorophenyl)acetamide,
62) 2-{4-[3-(cyclobutylmethoxy)-4-methoxyphenyl]-2-oxopyrrolidin-1-yl}-N-(5-methylisoxazol-3-yl)acetamide,
63) 2-{4-[3-(cyclobutylmethoxy)-4-methoxyphenyl]-2-oxopyrrolidin-1-yl}-N-(6-methylpyridin-2-yl)acetamide,
64) 2-((4S)-4-{4-methoxy-3-[(3R)-tetrahydrofuran-3-yloxy]phenyl}-2-oxopyrrolidin-1-yl)-N-methyl-N-(5-pyridin-4-yl-1,3,4-thiadiazol-2-yl)acetamide,
65) N-(5-cyclopropyl-1,3,4-thiadiazol-2-yl)-2-((4S)-4-{4-methoxy-3-[(3R)-tetrahydrofuran-3-yloxy]phenyl}-2-oxopyrrolidin-1-yl)-N-methylacetamide,
66) 2-{4-[3-(cyclobutylmethoxy)-4-methoxyphenyl]-2-oxopyrrolidin-1-yl}-N-(4-methyl-1,3-thiazol-2-yl)acetamide,
67) 2-{4-[3-(cyclopropylmethoxy)-4-methoxyphenyl]-2-oxopyrrolidin-1-yl}-N-(3-fluorophenyl)-N-methylacetamide, 68) N-(1-benzyl-3-methyl-1H-pyrazol-5-yl)-2-((4S)-4-{4-methoxy-3-[(3R)-tetrahydrofuran-3-yloxy]phenyl}-2-oxopyrrolidin-1-yl)-N-methylacetamide,
69) 2-{(4S)-4-[3-(cyclobutylmethoxy)-4-methoxyphenyl]-2-oxopyrrolidin-1-yl}-N-(5-methylisoxazol-3-yl)acetamide,
70) 2-{(4S)-4-[3-(cyclopropylmethoxy)-4-methoxyphenyl]-2-oxopyrrolidin-1-yl}-N-(3-fluorophenyl)acetamide,
71) 2-{(4R)-4-[3-(cyclobutylmethoxy)-4-methoxyphenyl]-2-oxopyrrolidin-1-yl}-N-(5-methylisoxazol-3-yl)acetamide,
72) 2-{(4R)-4-[3-(cyclopropylmethoxy)-4-methoxyphenyl]-2-oxopyrrolidin-1-yl}-N-(3-fluorophenyl)acetamide,
73) N-ethyl-2-((4S)-4-{4-methoxy-3-[(3R)-tetrahydrofuran-3-yloxy]phenyl}-2-oxopyrrolidin-1-yl)-N-(4-methyl-1,3-thiazol-2-yl)acetamide,
74) N-(cyclopropylmethyl)-2-((4S)-4-{4-methoxy-3-[(3R)-tetrahydrofuran-3-yloxy]phenyl}-2-oxopyrrolidin-1-yl)-N-(4-methyl-1,3-thiazol-2-yl)acetamide,
75) N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
76) 2-{(4R)-4-[3-(cyclopropylmethoxy)-4-methoxyphenyl]-2-oxopyrrolidin-1-yl}-N-(4-methyl-1,3-thiazol-2-yl)acetamide,
77) 2-{(4S)-4-[3-(cyclopropylmethoxy)-4-methoxyphenyl]-2-oxopyrrolidin-1-yl}-N-(4-methyl-1,3-thiazol-2-yl)acetamide,
78) 2-{(4R)-4-[3-(cyclopropylmethoxy)-4-methoxyphenyl]-2-oxopyrrolidin-1-yl}-N-(3-methylisothiazol-5-yl)acetamide,
79) 2-{(4S)-4-[3-(cyclopropylmethoxy)-4-methoxyphenyl]-2-oxopyrrolidin-1-yl}-N-(3-methylisothiazol-5-yl)acetamide, and
80) 2-{(4S)-4-[3-(cyclobutylmethoxy)-4-methoxyphenyl]-2-oxopyrrolidin-1-yl}-N-(3-fluorophenyl)acetamide, wherein salts listed above can also be in free base form or in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to a further preferred compound and/or method aspect of the invention, the compound of formula I is selected from:
1) N-[5-(aminosulfonyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide,
2) N-[5-(4-methoxyphenyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide,
3) 2-((4S)-4-{4-methoxy-3-[(3R)-tetrahydrofuran-3-yloxy]phenyl}-2-oxopyrrolidin-1-yl)-N-1,3,4-thiadiazol-2-ylacetamide,
4) N-[5-(2-furyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide,
5) 2-((4S)-4-{4-methoxy-3-[(3R)-tetrahydrofuran-3-yloxy]phenyl}-2-oxopyrrolidin-1-yl)-N-[5-(2-oxo-2-piperidin-1-ylethyl)-1,3,4-thiadiazol-2-yl]acetamide,
6) 2-((4S)-4-{4-methoxy-3-[(3R)-tetrahydrofuran-3-yloxy]phenyl}-2-oxopyrrolidin-1-yl)-N-[5-(2-piperidin-1-ylethyl)-1,3,4-thiadiazol-2-yl]acetamide,
7) N-{5-[(4-methoxyphenoxy)methyl]-1,3,4-thiadiazol-2-yl}-2-((4S)-4-{4-methoxy-3-[(3R)-tetrahydrofuran-3-yloxy]phenyl}-2-oxopyrrolidin-1-yl)acetamide,
8) 2-((4S)-4-{4-methoxy-3-[(3R)-tetrahydrofuran-3-yloxy]phenyl}-2-oxopyrrolidin-1-yl)-N-[5-(2-morpholin-4-yl-2-oxoethyl)-1,3,4-thiadiazol-2-yl]acetamide,
9) 2-((4S)-4-{4-methoxy-3-[(3R)-tetrahydrofuran-3-yloxy]phenyl}-2-oxopyrrolidin-1-yl)-N-[5-(2-oxo-2-pyrrolidin-1-ylethyl)-1,3,4-thiadiazol-2-yl]acetamide,
10) 2-((4S)-4-{4-methoxy-3-[(3R)-tetrahydrofuran-3-yloxy]phenyl}-2-oxopyrrolidin-1-yl)-N-(3-phenyl-1,2,4-thiadiazol-5-yl)acetamide,
11) 2-((4S)-4-{4-methoxy-3-[(3R)-tetrahydrofuran-3-yloxy]phenyl}-2-oxopyrrolidin-1-yl)-N-(5-phenyl-1,3,4-thiadiazol-2-yl)acetamide,
12) N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
14) 2-((S)-4-{4-Methoxy-3-[(R)-(tetrahydrofuran-3-yl)oxy]-phenyl}-2-oxopyrrolidin-1-yl)-N-(5-piperidin-4-yl-[1,3,4]thiadiazol-2-yl)-acetamide hydroformate,
15) 2-((S)-4-{4-Methoxy-3-[(R)-(tetrahydrofuran-3-yl)oxy]-phenyl}-2-oxopyrrolidin-1-yl)-N-(3-methyl-isothiazol-5-yl)-acetamide,
16) 2-((4S)-4-{4-methoxy-3-[(3R)-tetrahydrofuran-3-yloxy]phenyl}-2-oxopyrrolidin-1-yl)-N-(5-methylisoxazol-3-yl)acetamide,
17) N-Isoxazol-3-yl-2-((S)-4-{4-methoxy-3-[(R)-(tetrahydrofuran-3-yl)oxy]-phenyl}-2-oxo-pyrrolidin-1-yl)-acetamide,
18) 2-((4S)-4-{4-methoxy-3-[(3R)-tetrahydrofuran-3-yloxy]phenyl}-2-oxopyrrolidin-1-yl)-N-(3-methyl-1H-pyrazol-5-yl)acetamide,
19) N-(4-Benzenesulfonyl-thiophen-3-yl)-2-((S)-4-{4-methoxy-3-[(R)-(tetrahydrofuran-3-yl)oxy]-phenyl}-2-oxo-pyrrolidin-1-yl)-acetamide,
20) 2-((S)-4-{4-Methoxy-3-[(R)-(tetrahydrofuran-3-yl)oxy]-phenyl}-2-oxo-pyrrolidin-1-yl)-N-(1H-pyrazol-3-yl)-acetamide,
21) 2-((4S)-4-{4-methoxy-3-[(3R)-tetrahydrofuran-3-yloxy]phenyl}-2-oxopyrrolidin-1-yl)-N-(5-methyl-1,3,4-thiadiazol-2-yl)acetamide,
22) 2-((4S)-4-{4-methoxy-3-[(3R)-tetrahydrofuran-3-yloxy]phenyl}-2-oxopyrrolidin-1-yl)-N-(3-methyl-1,2,4-thiadiazol-5-yl)acetamide,
23) 2-((4S)-4-{4-methoxy-3-[(3R)-tetrahydrofuran-3-yloxy]phenyl}-2-oxopyrrolidin-1-yl)-N-(3-methoxy-1,2,4-thiadiazol-5-yl)acetamide,
24) N-(3-ethyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
25) 5-{[((4S)-4-{4-methoxy-3-[(3R)-tetrahydrofuran-3-yloxy]phenyl}-2-oxopyrrolidin-1-yl)acetyl]amino}-3-methylisoxazole-4-carboxamide,
26) 2-((4S)-4-{4-methoxy-3-[(3R)-tetrahydrofuran-3-yloxy]phenyl}-2-oxopyrrolidin-1-yl)-N-(3-methylisoxazol-5-yl)acetamide,
27) 2-((4S)-4-{4-methoxy-3-[(3R)-tetrahydrofuran-3-yloxy]phenyl}-2-oxopyrrolidin-1-yl)-N-(5-methyl-3-phenylisoxazol-4-yl)acetamide, 28) N-(3,5-dimethylisoxazol-4-yl)-2-((4S)-4-{4-methoxy-3-[(3R)-tetrahydrofuran-3-yloxy]phenyl}-2-oxopyrrolidin-1-yl)acetamide,
29) 2-((4S)-4-{4-methoxy-3-[(3R)-tetrahydrofuran-3-yloxy]phenyl}-2-oxopyrrolidin-1-yl)-N-pyrazin-2-ylacetamide,
30) N-(2-Ethyl-2H-pyrazol-3-yl)-2-((S)-4-{4-methoxy-3-[(R)-(tetrahydrofuran-3-yl)oxy]-phenyl}-2-oxo-pyrrolidin-1-yl)-acetamide,
31) 2-((4S)-4-{4-methoxy-3-[(3R)-tetrahydrofuran-3-yloxy]phenyl}-2-oxopyrrolidin-1-yl)-N-(3-phenylisoxazol-5-yl)acetamide,
32) N-(3-anilino-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
33) 2-{(4R)-4-[3-(benzyloxy)-4-methoxyphenyl]-2-oxopyrrolidin-1-yl}-N-(3-methylisothiazol-5-yl)acetamide,
34) 2-{(4S)-4-[3-(benzyloxy)-4-methoxyphenyl]-2-oxopyrrolidin-1-yl}-N-(3-methylisothiazol-5-yl)acetamide,
35) N-(3-cyano-2-thienyl)-2-((4S)-4-{4-methoxy-3-[(3R)-tetrahydrofuran-3-yloxy]phenyl}-2-oxopyrrolidin-1-yl)acetamide,
36) 2-((4S)-4-{4-methoxy-3-[(3R)-tetrahydrofuran-3-yloxy]phenyl}-2-oxopyrrolidin-1-yl)-N-[4-(2-thienyl)-1,3-thiazol-2-yl]acetamide,
37) 2-((4S)-4-{4-methoxy-3-[(3R)-tetrahydrofuran-3-yloxy]phenyl}-2-oxopyrrolidin-1-yl)-N-[4-(trifluoromethyl)-1,3-thiazol-2-yl]acetamide,
38) 2-[4-(3-ethoxy-4-methoxyphenyl)-2-oxopyrrolidin-1-yl]-N-(3-fluorophenyl)acetamide,
39) 2-[4-(3-ethoxy-4-methoxyphenyl)-2-oxopyrrolidin-1-yl]-N-(3-methyl-1H-pyrazol-5-yl)acetamide,
40) 2-((4S)-4-{4-methoxy-3-[(3R)-tetrahydrofuran-3-yloxy]phenyl}-2-oxopyrrolidin-1-yl)-N-methyl-N-(3-methylisothiazol-5-yl)acetamide,
41) 2-((4S)-4-{4-methoxy-3-[(3R)-tetrahydrofuran-3-yloxy]phenyl}-2-oxopyrrolidin-1-yl)-N-methyl-N-(4-methyl-1,3-thiazol-2-yl)acetamide,
42) 2-[4-(3-ethoxy-4-methoxyphenyl)-2-oxopyrrolidin-1-yl]-N-(5-methylisoxazol-3-yl)acetamide,
43) 2-[4-(3-ethoxy-4-methoxyphenyl)-2-oxopyrrolidin-1-yl]-N-(4-methyl-1,3-thiazol-2-yl)acetamide,
44) 2-[4-(3-ethoxy-4-methoxyphenyl)-2-oxopyrrolidin-1-yl]-N-(3-methylisothiazol-5-yl)acetamide,
45) 2-[4-(3-ethoxy-4-methoxyphenyl)-2-oxopyrrolidin-1-yl]-N-(6-methylpyridin-2-yl)acetamide,
46) 2-{4-[3-(cyclopropylmethoxy)-4-methoxyphenyl]-2-oxopyrrolidin-1-yl}-N-(4-methyl-1,3-thiazol-2-yl)acetamide,
47) 2-{4-[3-(cyclopropylmethoxy)-4-methoxyphenyl]-2-oxopyrrolidin-1-yl}-N-(3-fluorophenyl)acetamide,
48) (4S)-4-[3-(cyclopropylmethoxy)-4-(difluoromethoxy)phenyl]pyrrolidin-2-one,
49) 2-{4-[3-(cyclopropylmethoxy)-4-methoxyphenyl]-2-oxopyrrolidin-1-yl}-N-(5-methyl-1H-pyrazol-3-yl)acetamide,
50) (4R)-4-[3-(cyclopropylmethoxy)-4-(difluoromethoxy)phenyl]pyrrolidin-2-one,
51) (4S)-4-{4-(difluoromethoxy)-3-[(3R)-tetrahydrofuran-3-yloxy]phenyl}pyrrolidin-2-one,
52) (4R)-4-{4-(difluoromethoxy)-3-[(3R)-tetrahydrofuran-3-yloxy]phenyl}pyrrolidin-2-one,
53) (4S)-4-[3-(cyclobutylmethoxy)-4-(difluoromethoxy)phenyl]pyrrolidin-2-one,
54) (4R)-4-[3-(cyclobutylmethoxy)-4-(difluoromethoxy)phenyl]pyrrolidin-2-one,
55) 2-{4-[3-(cyclopropylmethoxy)-4-methoxyphenyl]-2-oxopyrrolidin-1-yl}-N-(5-cyclopropyl-1,3,4-thiadiazol-2-yl)acetamide,
56) 2-{4-[3-(cyclopropylmethoxy)-4-methoxyphenyl]-2-oxopyrrolidin-1-yl}-N-(6-methylpyridin-2-yl)acetamide,
57) 2-{4-[3-(cyclopropylmethoxy)-4-methoxyphenyl]-2-oxopyrrolidin-1-yl}-N-(3-methylisoxazol-5-yl)acetamide,
58) 2-{4-[3-(cyclopropylmethoxy)-4-methoxyphenyl]-2-oxopyrrolidin-1-yl}-N-(3-isopropyl-1,2,4-thiadiazol-5-yl)acetamide,
59) 2-{4-[3-(cyclopropylmethoxy)-4-methoxyphenyl]-2-oxopyrrolidin-1-yl}-N-(3-methylisothiazol-5-yl)acetamide,
60) 2-((4S)-4-{4-Methoxy-3-[(3R)-tetrahydrofuran-3-yloxy]phenyl}-2-oxopyrrolidin-1-yl)-N-methyl-N-phenylacetamide,
61) 2-{4-[3-(cyclobutylmethoxy)-4-methoxyphenyl]-2-oxopyrrolidin-1-yl}-N-(3-fluorophenyl)acetamide,
62) 2-{4-[3-(cyclobutylmethoxy)-4-methoxyphenyl]-2-oxopyrrolidin-1-yl}-N-(5-methylisoxazol-3-yl)acetamide,
63) 2-{4-[3-(cyclobutylmethoxy)-4-methoxyphenyl]-2-oxopyrrolidin-1-yl}-N-(6-methylpyridin-2-yl)acetamide,
64) 2-((4S)-4-{4-methoxy-3-[(3R)-tetrahydrofuran-3-yloxy]phenyl}-2-oxopyrrolidin-1-yl)-N-methyl-N-(5-pyridin-4-yl-1,3,4-thiadiazol-2-yl)acetamide,
65) N-(5-cyclopropyl-1,3,4-thiadiazol-2-yl)-2-((4S)-4-{4-methoxy-3-[(3R)-tetrahydrofuran-3-yloxy]phenyl}-2-oxopyrrolidin-1-yl)-N-methylacetamide,
66) 2-{4-[3-(cyclobutylmethoxy)-4-methoxyphenyl]-2-oxopyrrolidin-1-yl}-N-(4-methyl-1,3-thiazol-2-yl)acetamide,
67) 2-{4-[3-(cyclopropylmethoxy)-4-methoxyphenyl]-2-oxopyrrolidin-1-yl}-N-(3-fluorophenyl)-N-methylacetamide,
68) N-(1-benzyl-3-methyl-1H-pyrazol-5-yl)-2-((4S)-4-{4-methoxy-3-[(3R)-tetrahydrofuran-3-yloxy]phenyl}-2-oxopyrrolidin-1-yl)-N-methylacetamide,
73) N-ethyl-2-((4S)-4-{4-methoxy-3-[(3R)-tetrahydrofuran-3-yloxy]phenyl}-2-oxopyrrolidin-1-yl)-N-(4-methyl-1,3-thiazol-2-yl)acetamide,
74) N-(cyclopropylmethyl)-2-((4S)-4-{4-methoxy-3-[(3R)-tetrahydrofuran-3-yloxy]phenyl}-2-oxopyrrolidin-1-yl)-N-(4-methyl-1,3-thiazol-2-yl)acetamide, and
75) N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, wherein salts listed above can also be in free base form or in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

The following table presents the structures for selected compounds of formula I in accordance with the present invention:

| Compound | Structure |
|---|---|
| 1) | 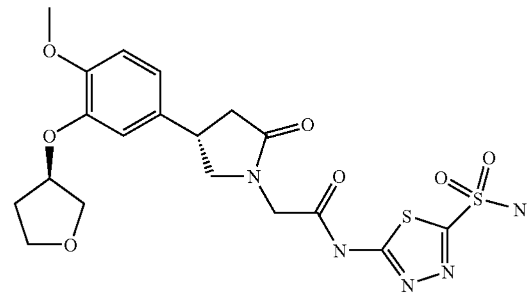 |
| 2) | 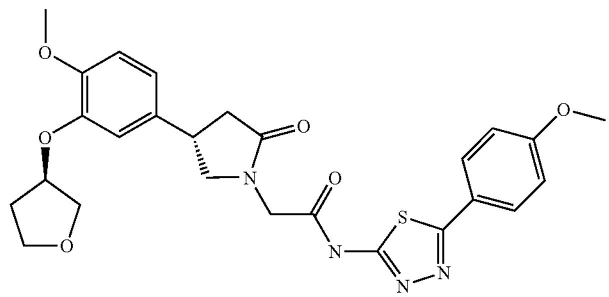 |
| 3) | 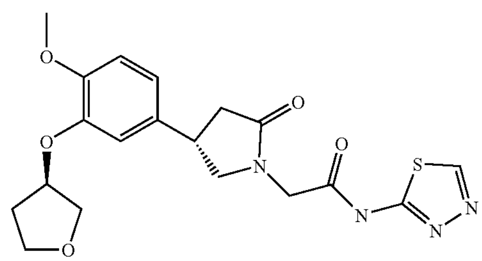 |
| 4) | 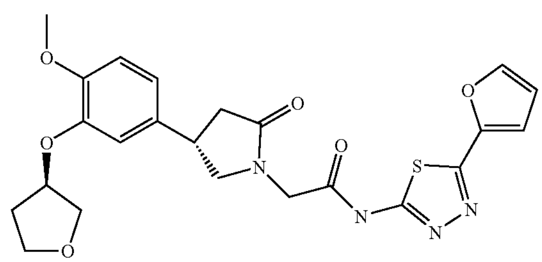 |
| 5) | 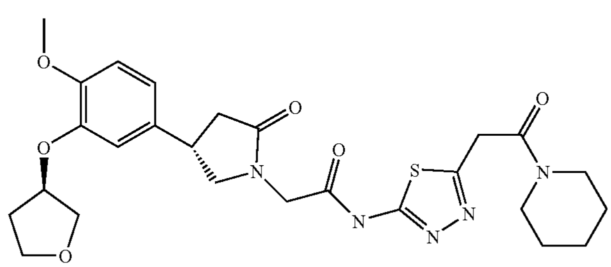 |

-continued

| Compound | Structure |
|---|---|
| 6) | 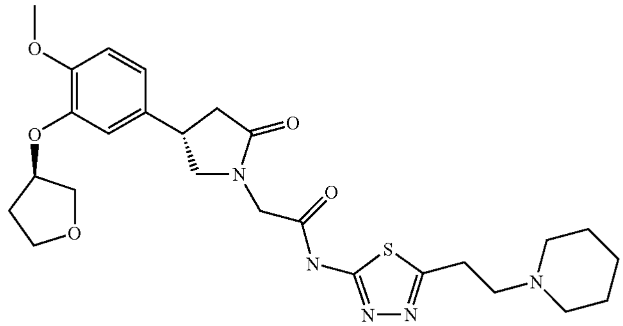 |
| 7) | 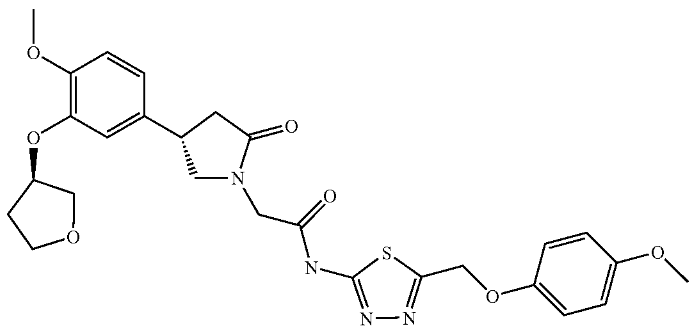 |
| 8) | 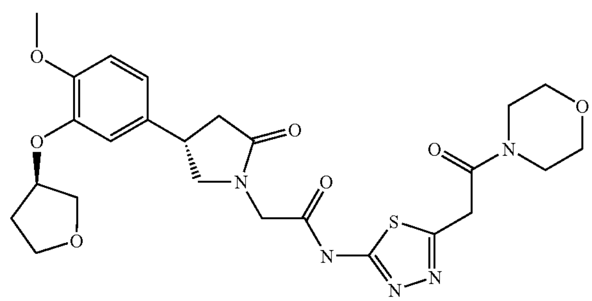 |
| 9) | 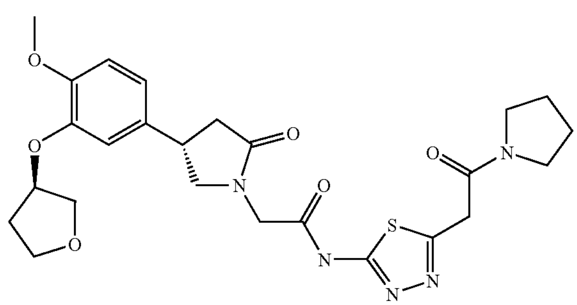 |
| 10) | 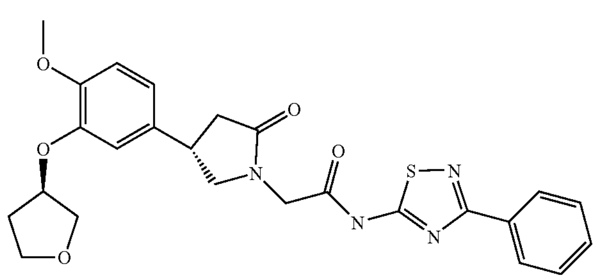 |

-continued

| Compound | Structure |
|---|---|
| 11) | 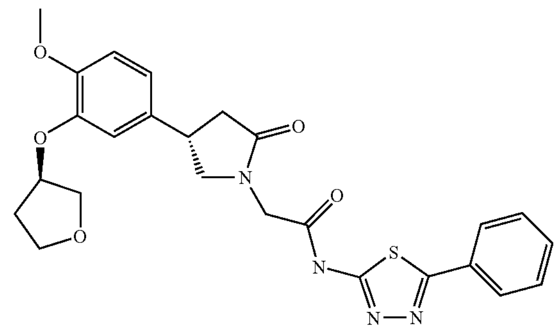 |
| 12) | 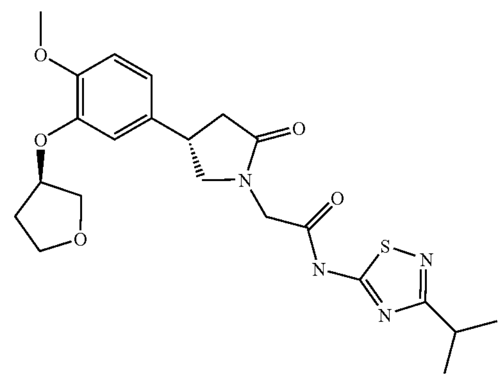 |
| 13) | 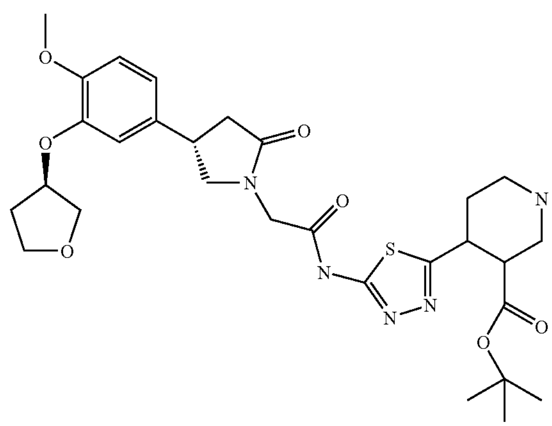 |
| 14) | 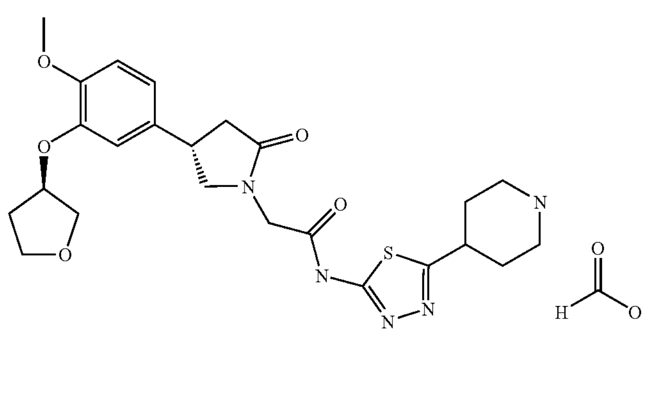 |

-continued

| Compound | Structure |
|---|---|
| 15) | 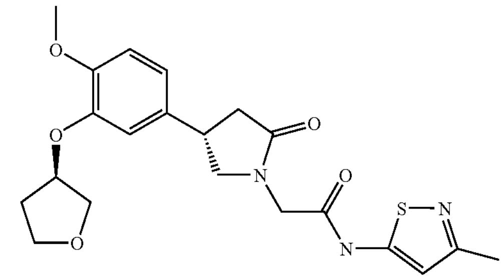 |
| 16) | 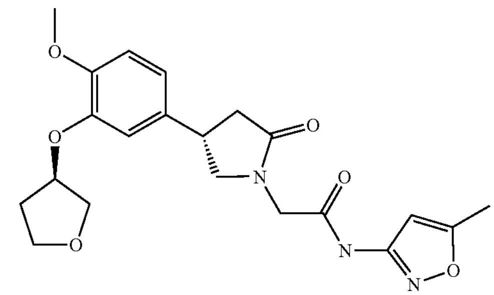 |
| 17) | 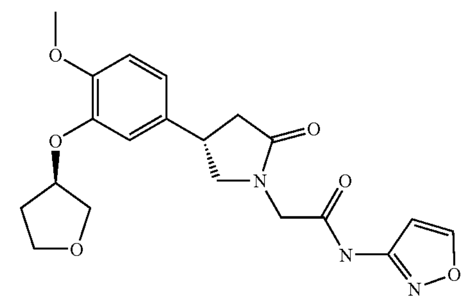 |
| 18) | 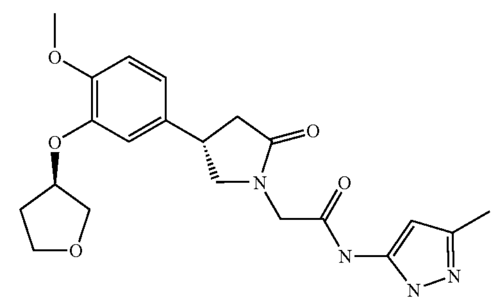 |
| 19) | 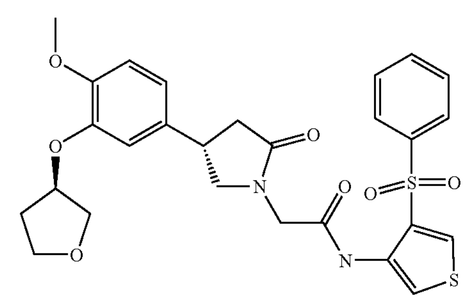 |

| Compound | Structure |
|---|---|
| 20) | 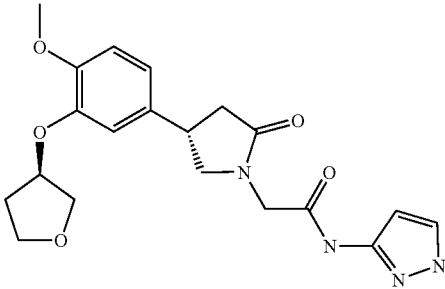 |
| 21) | 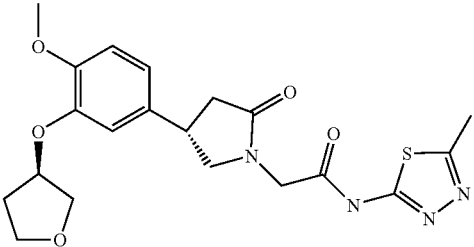 |
| 22) | 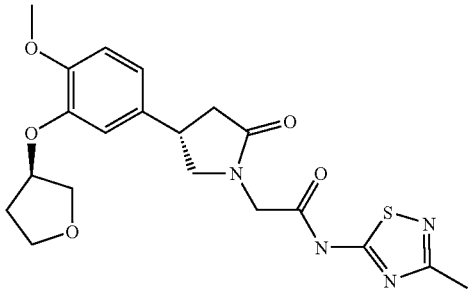 |
| 23) | 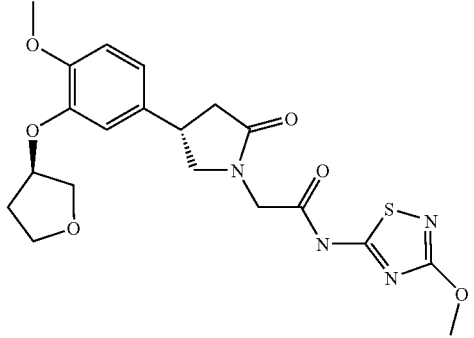 |
| 24) | 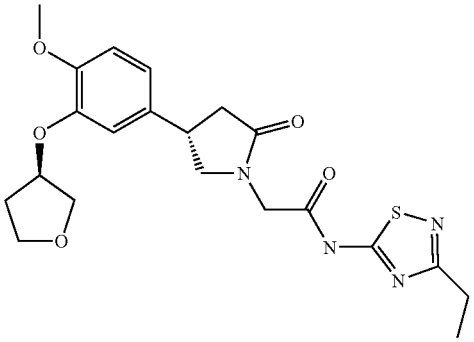 |

| Compound | Structure |
|---|---|
| 25) | 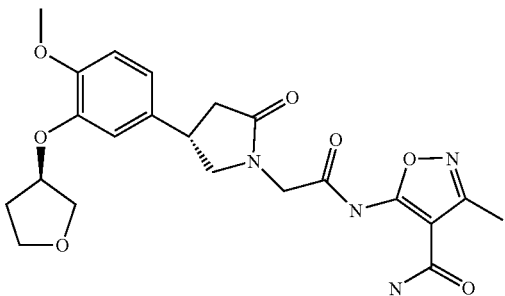 |
| 26) | 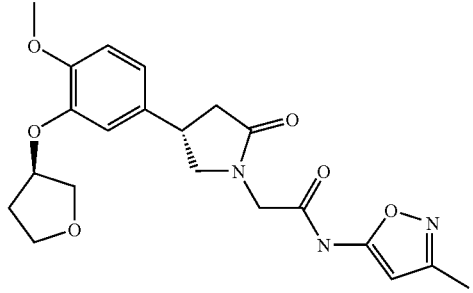 |
| 27) | 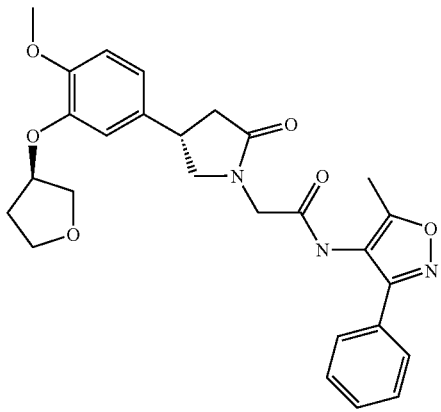 |
| 28) | 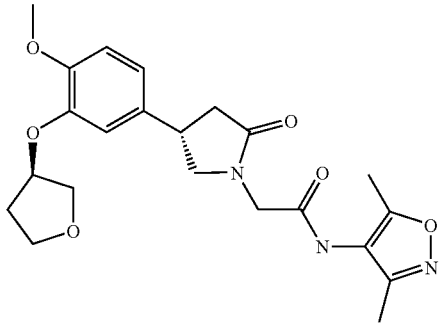 |

-continued

| Compound | Structure |
|---|---|
| 29) | 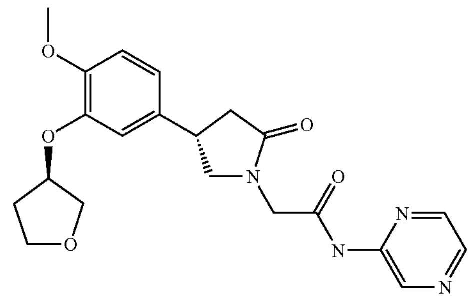 |
| 30) | 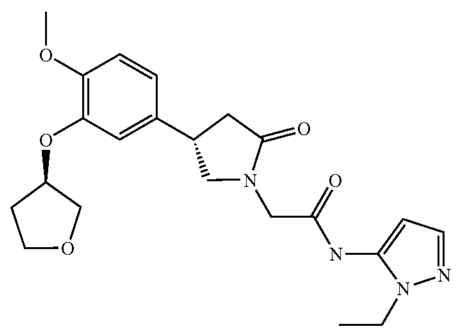 |
| 31) | 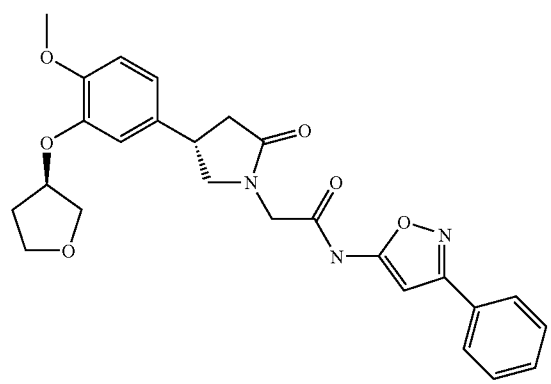 |
| 32) | 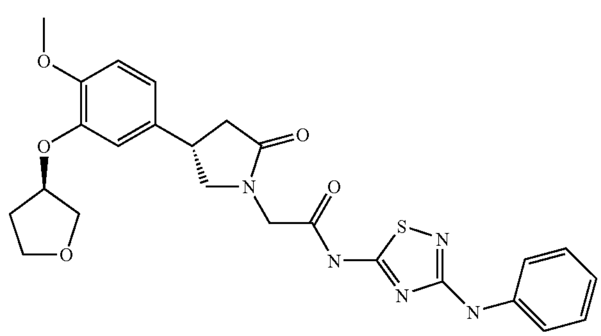 |

| Compound | Structure |
|---|---|
| 33) | 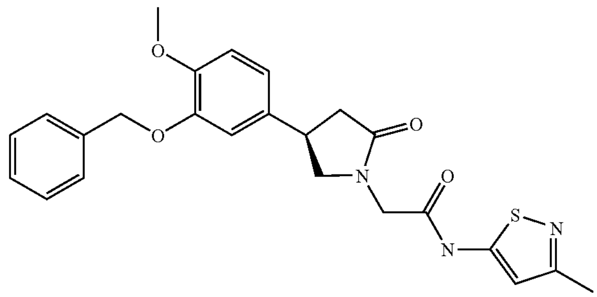 |
| 34) | 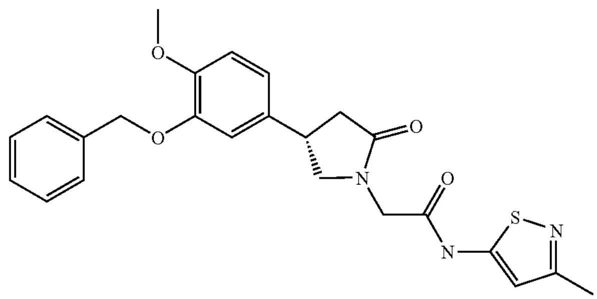 |
| 35) | 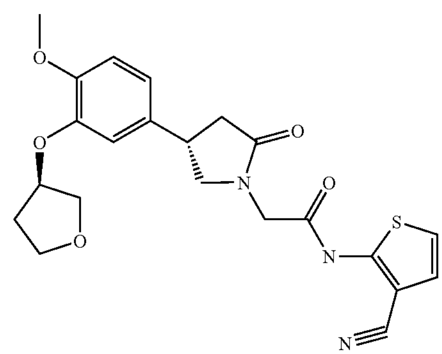 |
| 36) | 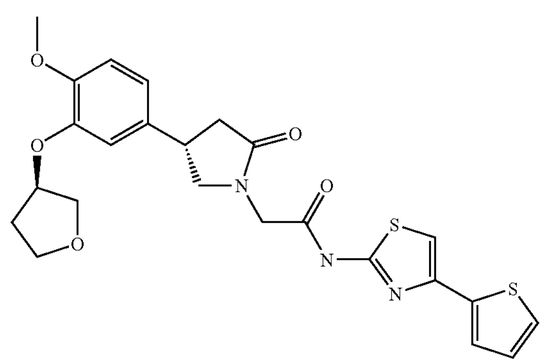 |

-continued

| Compound | Structure |
|---|---|
| 37) | (structure: 4-(4-methoxy-3-((tetrahydrofuran-3-yl)oxy)phenyl)-2-oxopyrrolidin-1-yl acetamide with 4-(trifluoromethyl)thiazol-2-yl) |
| 38) | (structure: 4-(3-ethoxy-4-methoxyphenyl)-2-oxopyrrolidin-1-yl acetamide with 3-fluorophenyl) |
| 39) | (structure: 4-(3-ethoxy-4-methoxyphenyl)-2-oxopyrrolidin-1-yl acetamide with 3-methyl-1H-pyrazol-5-yl) |
| 40) | (structure: 4-(4-methoxy-3-((tetrahydrofuran-3-yl)oxy)phenyl)-2-oxopyrrolidin-1-yl acetamide with N-methyl-N-(3-methylisothiazol-5-yl)) |
| 41) | (structure: 4-(4-methoxy-3-((tetrahydrofuran-3-yl)oxy)phenyl)-2-oxopyrrolidin-1-yl acetamide with N-methyl-N-(4-methylthiazol-2-yl)) |

-continued
| Compound | Structure |
|---|---|
| 42) | 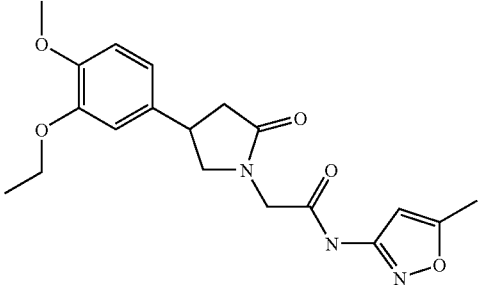 |
| 43) | 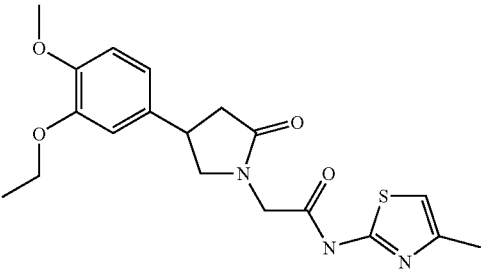 |
| 44) | 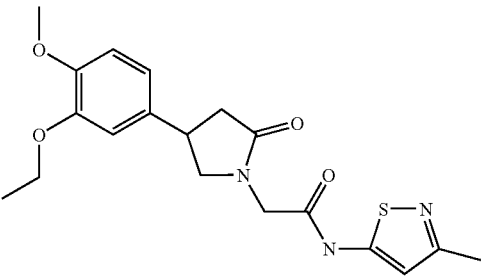 |
| 45) | 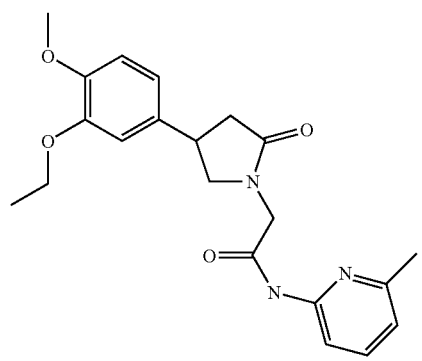 |

| Compound | Structure |
|---|---|
| 46) | 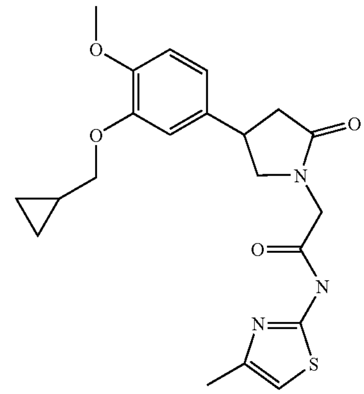 |
| 47) | 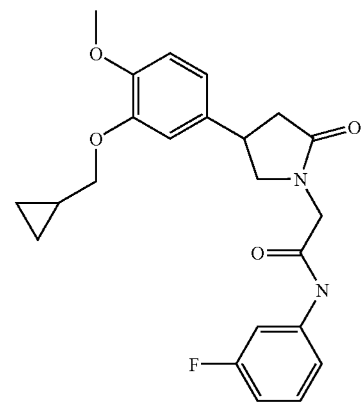 |
| 48) | 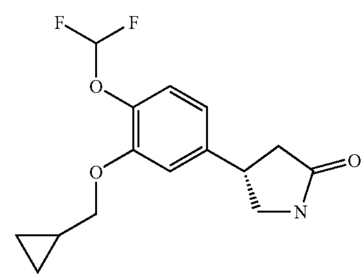 |
| 49) | 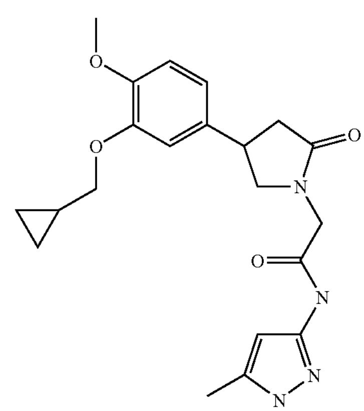 |

-continued

| Compound | Structure |
|---|---|
| 50) | 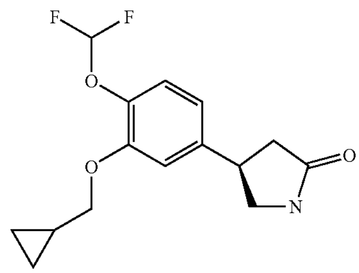 |
| 51) | 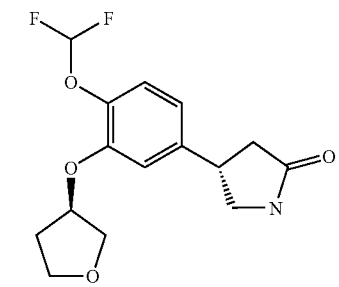 |
| 52) | 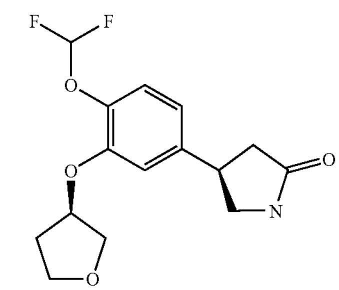 |
| 53) | 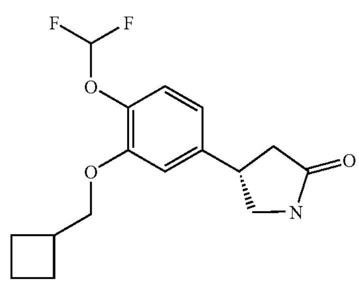 |
| 54) | 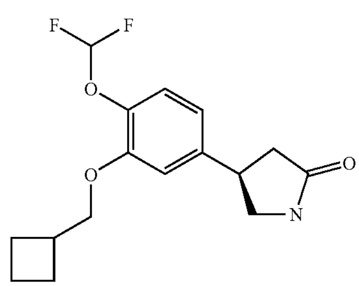 |

-continued
| Compound | Structure |
|---|---|
| 55) | 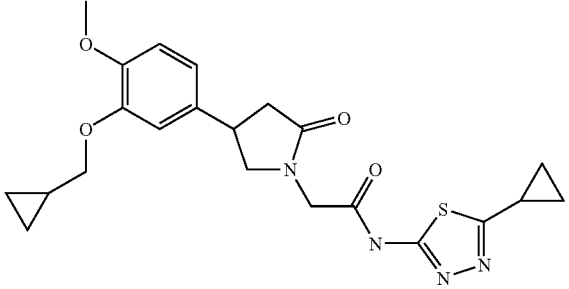 |
| 56) | 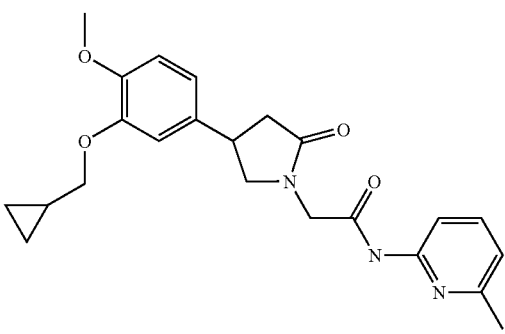 |
| 57) | 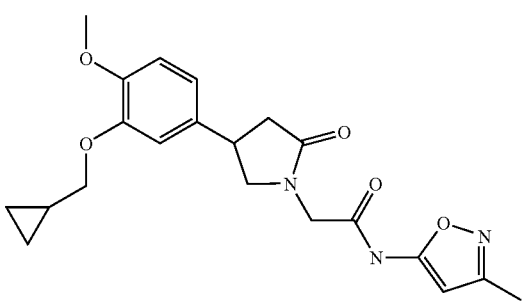 |
| 58) | 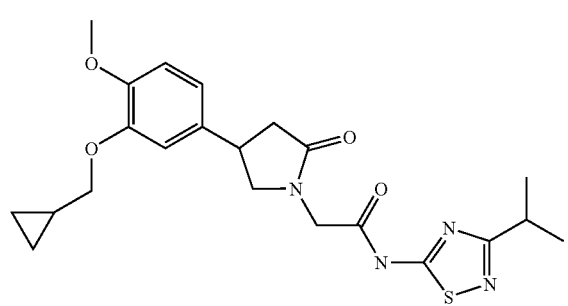 |
| 59) | 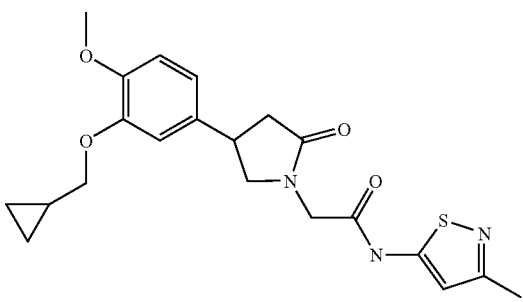 |

-continued

| Compound | Structure |
|---|---|
| 60) | 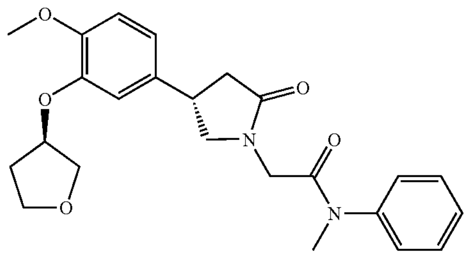 |
| 61) | 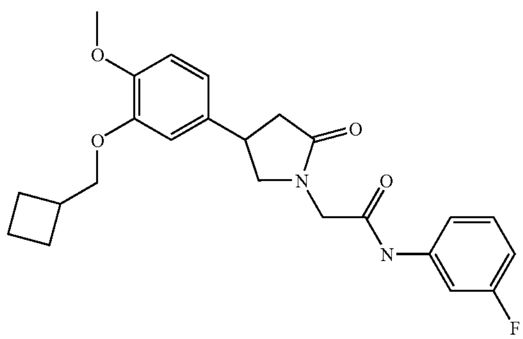 |
| 62) | 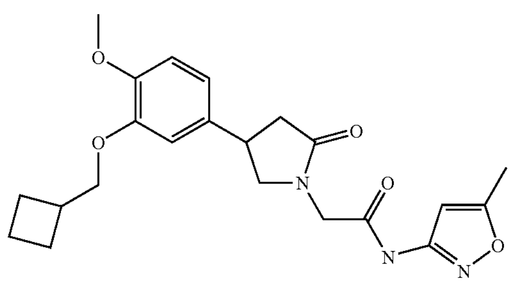 |
| 63) | 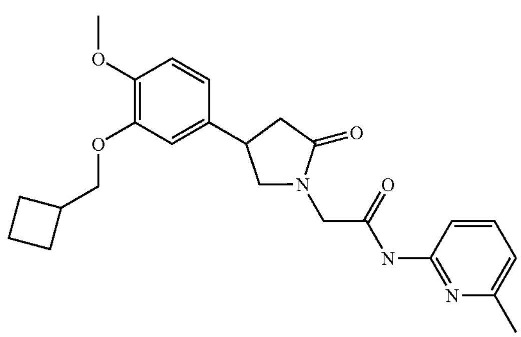 |
| 64) | 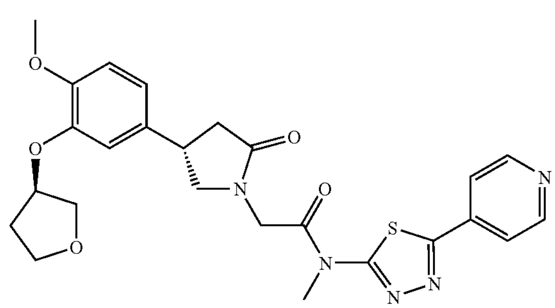 |

| Compound | Structure |
|---|---|
| 65) | 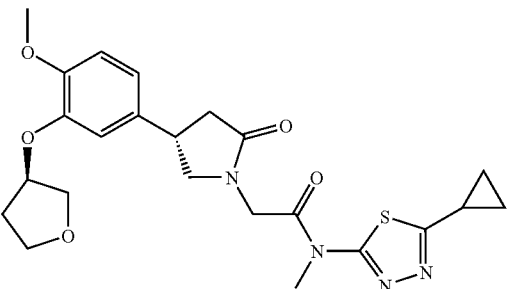 |
| 66) | 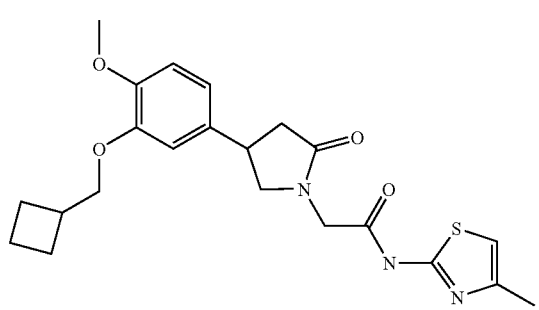 |
| 67) | 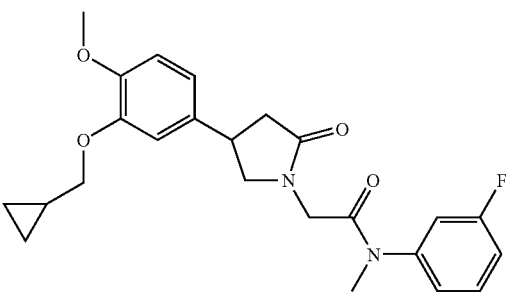 |
| 68) | 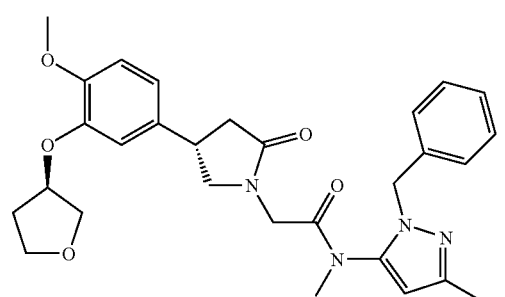 |
| 69) | 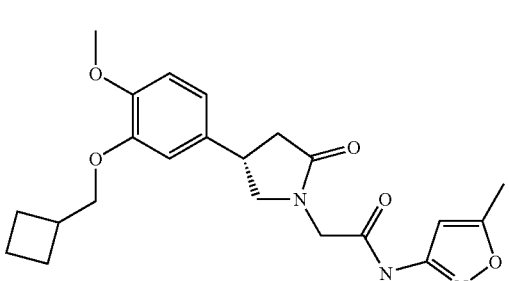 |

-continued

| Compound | Structure |
|---|---|
| 70) | 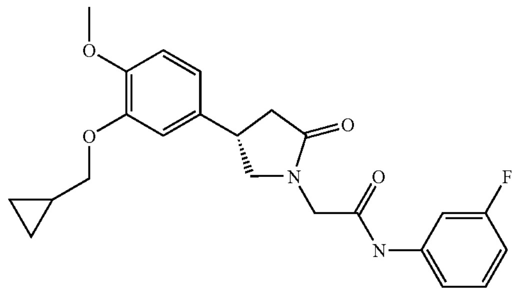 |
| 71) | 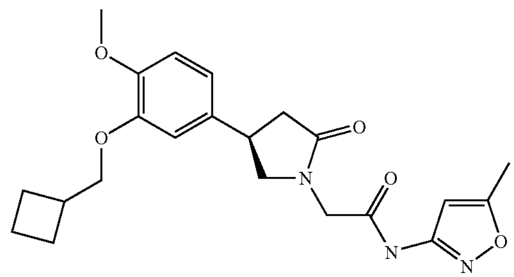 |
| 72) | 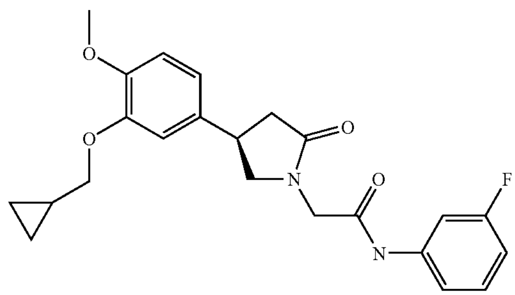 |
| 73) | 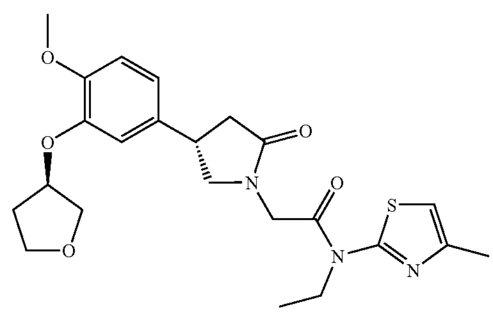 |
| 74) | 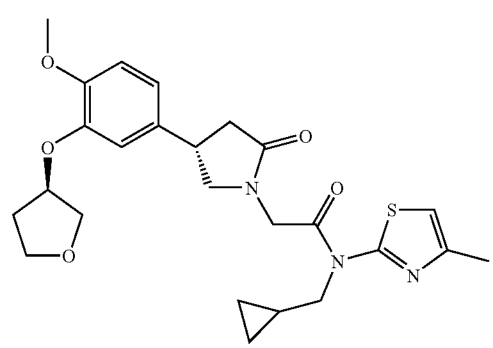 |

| Compound | Structure |
|---|---|
| 75) | 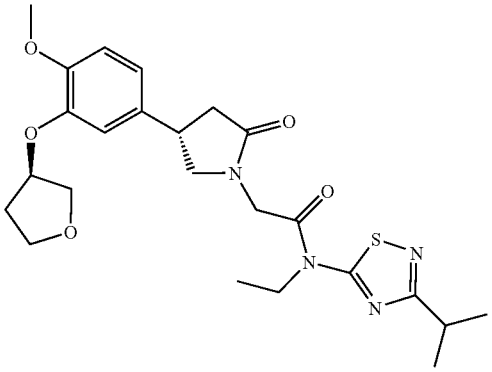 |
| 76) | 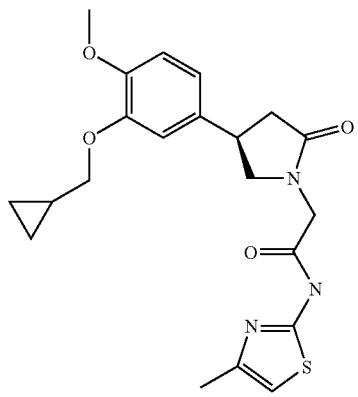 |
| 77) | 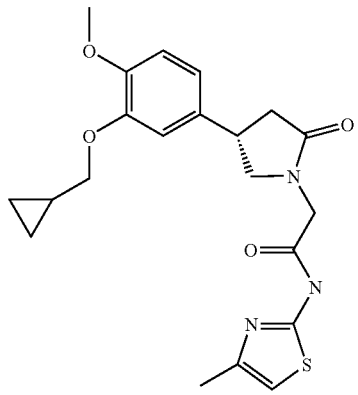 |
| 78) | 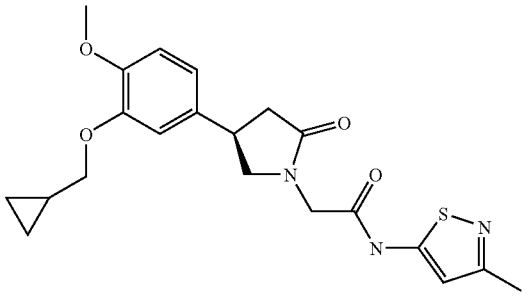 |

| Compound | Structure |
|---|---|
| 79) | 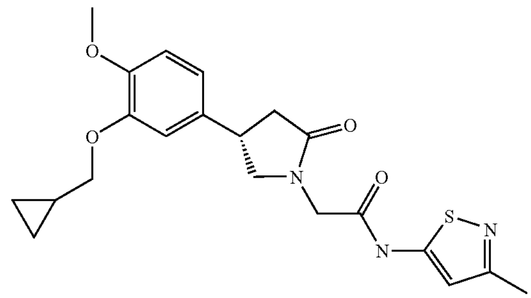 |
| 80) | 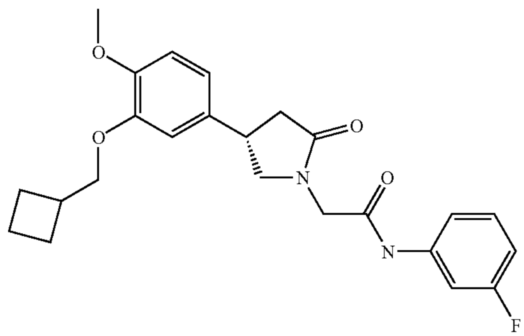 |

According to an additional preferred compound and/or method aspect of the invention, the compound of formula I is selected from:

81) N-(cyclopropylmethyl)-N-(5-cyclopropyl-1,3,4-thiadiazol-2-yl)-2-((4S)-4-{4-methoxy-3-[(3R)-tetrahydrofuran-3-yloxy]phenyl}-2-oxopyrrolidin-1-yl)acetamide,
82) 2-{4-[3-(cyclopropylmethoxy)-4-methoxyphenyl]-2-oxopyrrolidin-1-yl}-N-(5-cyclopropyl-1,3,4-thiadiazol-2-yl)-N-methylacetamide,
83) 2-{4-[3-(cyclopropylmethoxy)-4-methoxyphenyl]-2-oxopyrrolidin-1-yl}-N-(cyclopropylmethyl)-N-(5-cyclopropyl-1,3,4-thiadiazol-2-yl)acetamide,
84) 2-{4-[3-(cyclopropylmethoxy)-4-methoxyphenyl]-2-oxopyrrolidin-1-yl}-N-(cyclopropylmethyl)-N-(4-methyl-1,3-thiazol-2-yl)acetamide,
85) 2-{4-[3-(cyclopropylmethoxy)-4-methoxyphenyl]-2-oxopyrrolidin-1-yl}-N-methyl-N-(4-methyl-1,3-thiazol-2-yl)acetamide,
86) 2-{4-[3-(cyclopropylmethoxy)-4-(difluoromethoxy)phenyl]-2-oxopyrrolidin-1-yl}-N-methyl-N-(4-methyl-1,3-thiazol-2-yl)acetamide,
87) 2-{4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide,
88) 2-[(4S)-4-(3-ethoxy-4-methoxyphenyl)-2-oxopyrrolidin-1-yl]-N-(3-fluorophenyl)acetamide,
89) 2-[(4R)-4-(3-ethoxy-4-methoxyphenyl)-2-oxopyrrolidin-1-yl]-N-(3-fluorophenyl)acetamide,
90) 2-[(4S)-4-(3-ethoxy-4-methoxyphenyl)-2-oxopyrrolidin-1-yl]-N-methyl-N-(4-methyl-1,3-thiazol-2-yl)acetamide,
91) 2-[(4S)-4-(3-ethoxy-4-methoxyphenyl)-2-oxopyrrolidin-1-yl]-N-(3-isopropyl-1,2,4-thiadiazol-5-yl)-N-methylacetamide,
92) N-(5-cyclopropyl-1,3,4-thiadiazol-2-yl)-2-[(4S)-4-(3-ethoxy-4-methoxyphenyl)-2-oxopyrrolidin-1-yl]-N-methylacetamide,
93) N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide,
94) 2-[(4R)-4-(3-ethoxy-4-methoxyphenyl)-2-oxopyrrolidin-1-yl]-N-(3-isopropyl-1,2,4-thiadiazol-5-yl)-N-methylacetamide,
95) N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide,
96) N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide,
97) N-(4-cyclopropyl-1,3-thiazol-2-yl)-2-((4S)-4-{4-methoxy-3-[(3R)-tetrahydrofuran-3-yloxy]phenyl}-2-oxopyrrolidin-1-yl)acetamide,
98) 2-{(4R)-4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide,
99) 2-{(4S)-4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide,
100) 2-[(4S)-4-(3-ethoxy-4-methoxyphenyl)-2-oxopyrrolidin-1-yl]-N-(3-methylisothiazol-5-yl)acetamide,
101) 2-[(4R)-4-(3-ethoxy-4-methoxyphenyl)-2-oxopyrrolidin-1-yl]-N-(3-methylisothiazol-5-yl)acetamide,
102) (4R)-4-[3-(benzyloxy)-4-(difluoromethoxy)phenyl]pyrrolidin-2-one,
103) (4S)-4-[3-(benzyloxy)-4-(difluoromethoxy)phenyl]pyrrolidin-2-one,
104) (4R)-4-[4-(difluoromethoxy)-3-ethoxyphenyl]pyrrolidin-2-one, 105) (2R)-2-{(4S)-4-[3-(benzyloxy)-4-methoxyphenyl]-2-oxopyrrolidin-1-yl}-N-(3-methylisothiazol-5-yl)propanamide,
106) 2-[(4S)-4-(3-ethoxy-4-methoxyphenyl)-2-oxopyrrolidin-1-yl]-N-(3-isopropyl-1,2,4-thiadiazol-5-yl)acetamide,
107) N-(5-cyclopropyl-1,3,4-thiadiazol-2-yl)-2-[(4S)-4-(3-ethoxy-4-methoxyphenyl)-2-oxopyrrolidin-1-yl]acetamide,
108) N-(4-cyclopropyl-1,3-thiazol-2-yl)-2-[(4S)-4-(3-ethoxy-4-methoxyphenyl)-2-oxopyrrolidin-1-yl]acetamide,
109) 2-{(4S)-4-[3-(cyclopropylmethoxy)-4-methoxyphenyl]-2-oxopyrrolidin-1-yl}-N-(3-isopropyl-1,2,4-thiadiazol-5-yl)acetamide,
110) 2-{(4S)-4-[3-(cyclopropylmethoxy)-4-methoxyphenyl]-2-oxopyrrolidin-1-yl}-N-(3-isopropyl-1,2,4-thiadiazol-5-yl)-N-methylacetamide,
111) 2-[(4S)-4-(3-ethoxy-4-methoxyphenyl)-2-oxopyrrolidin-1-yl]-N-(5-pyridin-4-yl-1,3,4-thiadiazol-2-yl)acetamide,
112) 2-[(4S)-4-(3-ethoxy-4-methoxyphenyl)-2-oxopyrrolidin-1-yl]-N-(4-methyl-1,3-benzothiazol-2-yl)acetamide,
113) 2-[(4S)-4-(3-isopropoxy-4-methoxyphenyl)-2-oxopyrrolidin-1-yl]-N-(3-isopropyl-1,2,4-thiadiazol-5-yl)-N-methylacetamide,
114) 2-{(4S)-4-[3-(cyclopropylmethoxy)-4-methoxyphenyl]-2-oxopyrrolidin-1-yl}-N-(5-cyclopropyl-1,3,4-thiadiazol-2-yl)acetamide,
115) 2-{(4S)-4-[3-(cyclopropylmethoxy)-4-methoxyphenyl]-2-oxopyrrolidin-1-yl}-N-(5-cyclopropyl-1,3,4-thiadiazol-2-yl)-N-methylacetamide,
116) N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide,
117) N-(5-cyclopropyl-1,3,4-thiadiazol-2-yl)-2-[(4S)-4-(3-isopropoxy-4-methoxyphenyl)-2-oxopyrrolidin-1-yl]acetamide,
118) N-(3-fluorophenyl)-2-[(4S)-4-(3-isopropoxy-4-methoxyphenyl)-2-oxopyrrolidin-1-yl]-N-methylacetamide,
119) 2-[(4S)-4-(3-ethoxy-4-methoxyphenyl)-2-oxopyrrolidin-1-yl]-N-(3-methyl-1H-pyrazol-5-yl)acetamide,
120) 2-[(4S)-4-(3-isopropoxy-4-methoxyphenyl)-2-oxopyrrolidin-1-yl]-N-(3-isopropyl-1,2,4-thiadiazol-5-yl)acetamide,
121) 2-[(4S)-4-(3-ethoxy-4-methoxyphenyl)-2-oxopyrrolidin-1-yl]-N-(3-fluorophenyl)-N-methylacetamide,
122) 2-{(4S)-4-[4-(difluoromethoxy)-3-ethoxyphenyl]-2-oxopyrrolidin-1-yl}-N-(3-isopropyl-1,2,4-thiadiazol-5-yl)acetamide,
123) 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide,
124) N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide,
125) N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide,
126) 2-{(4S)-4-[4-(difluoromethoxy)-3-ethoxyphenyl]-2-oxopyrrolidin-1-yl}-N-(3-fluorophenyl)acetamide,
127) 2-{(4S)-4-[4-(difluoromethoxy)-3-ethoxyphenyl]-2-oxopyrrolidin-1-yl}-N-(3-fluorophenyl)-N-methylacetamide,
128) N-(4-cyclopropyl-1,3-thiazol-2-yl)-2-{(4S)-4-[4-(difluoromethoxy)-3-ethoxyphenyl]-2-oxopyrrolidin-1-yl}acetamide,
129) 2-{(4S)-4-[3-(cyclopropylmethoxy)-4-methoxyphenyl]-2-oxopyrrolidin-1-yl}-N-(3-fluorophenyl)-N-methylacetamide,
130) 2-{(4S)-4-[3-(cyclopropylmethoxy)-4-methoxyphenyl]-2-oxopyrrolidin-1-yl}-N-(4-cyclopropyl-1,3-thiazol-2-yl)acetamide,
131) 2-[(4S)-4-(3-ethoxy-4-methoxyphenyl)-2-oxopyrrolidin-1-yl]-N-[4-(trifluoromethyl)-1,3-thiazol-2-yl]acetamide,
132) 2-[(4S)-4-(3-ethoxy-4-methoxyphenyl)-2-oxopyrrolidin-1-yl]-N-(4-methoxy-1,3-benzothiazol-2-yl)acetamide,
133) 2-[(4S)-4-(3-ethoxy-4-methoxyphenyl)-2-oxopyrrolidin-1-yl]-N-(4-methyl-1,3-thiazol-2-yl)acetamide,
134) 2-[(4S)-4-(3-ethoxy-4-methoxyphenyl)-2-oxopyrrolidin-1-yl]-N-methyl-N-(3-methylisothiazol-5-yl)acetamide,
135) 2-[(4S)-4-(3-ethoxy-4-methoxyphenyl)-2-oxopyrrolidin-1-yl]-N-(5-methylisoxazol-3-yl)acetamide,
136) (2S)-2-[(4S)-4-(3-ethoxy-4-methoxyphenyl)-2-oxopyrrolidin-1-yl]-N-(3-isopropyl-1,2,4-thiadiazol-5-yl)propanamide,
137) (2R)-2-[(4S)-4-(3-ethoxy-4-methoxyphenyl)-2-oxopyrrolidin-1-yl]-N-(3-isopropyl-1,2,4-thiadiazol-5-yl)propanamide,
138) (2S)-2-[(4R)-4-(3-ethoxy-4-methoxyphenyl)-2-oxopyrrolidin-1-yl]-N-(3-isopropyl-1,2,4-thiadiazol-5-yl)propanamide,
139) (2R)-2-[(4R)-4-(3-ethoxy-4-methoxyphenyl)-2-oxopyrrolidin-1-yl]-N-(3-isopropyl-1,2,4-thiadiazol-5-yl)propanamide,
140) (2R)-2-[(4S)-4-(3-ethoxy-4-methoxyphenyl)-2-oxopyrrolidin-1-yl]-N-(4-methyl-1,3-thiazol-2-yl)propanamide,
141) (2S)-2-[(4S)-4-(3-ethoxy-4-methoxyphenyl)-2-oxopyrrolidin-1-yl]-N-(4-methyl-1,3-thiazol-2-yl)propanamide,
142) 2-{(4S)-4-[3-(cyclopropylmethoxy)-4-methoxyphenyl]-2-oxopyrrolidin-1-yl}-N-(6-methylpyridin-2-yl)acetamide,
143) 2-{(4S)-4-[3-(cyclopropylmethoxy)-4-methoxyphenyl]-2-oxopyrrolidin-1-yl}-N-1,3-thiazol-2-ylacetamide,
144) N-(4-cyclopropyl-1,3-thiazol-2-yl)-2-[(4S)-4-(3-isopropoxy-4-methoxyphenyl)-2-oxopyrrolidin-1-yl]acetamide,
145) N-(3-fluorophenyl)-2-[(4S)-4-(3-isopropoxy-4-methoxyphenyl)-2-oxopyrrolidin-1-yl]acetamide,
146) 2-{(4S)-4-[3-(cyclopropylmethoxy)-4-methoxyphenyl]-2-oxopyrrolidin-1-yl}-N-(5-methylisoxazol-3-yl)acetamide,
147) N-(4-cyclopropyl-1,3-thiazol-2-yl)-2-[(4S)-4-(3-isopropoxy-4-methoxyphenyl)-2-oxopyrrolidin-1-yl]-N-methylacetamide,
148) N-(4-cyclopropyl-1,3-thiazol-2-yl)-2-[(4S)-4-(3-ethoxy-4-methoxyphenyl)-2-oxopyrrolidin-1-yl]-N-methylacetamide,
149) 2-{(4S)-4-[3-(cyclopropylmethoxy)-4-methoxyphenyl]-2-oxopyrrolidin-1-yl}-N-(4-cyclopropyl-1,3-thiazol-2-yl)-N-methylacetamide,
150) 2-{(4S)-4-[3-(cyclopropylmethoxy)-4-methoxyphenyl]-2-oxopyrrolidin-1-yl}-N-methyl-N-(5-methylisoxazol-3-yl)acetamide,
151) 2-{(4S)-4-[4-(difluoromethoxy)-3-isopropoxyphenyl]-2-oxopyrrolidin-1-yl}-N-(3-fluorophenyl)acetamide,
152) 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 153) 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide,
154) N-(4-cyclopropyl-1,3-thiazol-2-yl)-2-{(4S)-4-[4-(difluoromethoxy)-3-isopropoxyphenyl]-2-oxopyrrolidin-1-yl}acetamide,
155) N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide,
156) 2-{(4S)-4-[4-(difluoromethoxy)-3-isopropoxyphenyl]-2-oxopyrrolidin-1-yl}-N-(3-fluorophenyl)-N-methylacetamide,
157) N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide,
158) (4R)-4-[4-(difluoromethoxy)-3-methoxyphenyl]pyrrolidin-2-one,
159) (4R)-4-[4-(difluoromethoxy)-3-isopropoxyphenyl]pyrrolidin-2-one,
160) (4R)-4-[4-(difluoromethoxy)-3-isopropoxyphenyl]-1-isopropylpyrrolidin-2-one,
161) N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide,
162) N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide,
163) 2-{(4S)-4-[3-(cyclopropylmethoxy)-4-(difluoromethoxy)phenyl]-2-oxopyrrolidin-1-yl}-N-(5-cyclopropyl-1,3,4-thiadiazol-2-yl)acetamide,
164) 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)-N-methylacetamide,
165) 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)acetamide,
166) 2-{(4S)-4-[3-(cyclopropylmethoxy)-4-(difluoromethoxy)phenyl]-2-oxopyrrolidin-1-yl}-N-(3-fluorophenyl)-N-methylacetamide,
167) 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)acetamide,
168) 2-{(4S)-4-[3-(cyclopropylmethoxy)-4-(difluoromethoxy)phenyl]-2-oxopyrrolidin-1-yl}-N-(3-fluorophenyl)acetamide,
169) 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)-N-methylacetamide,
170) 2-{(4S)-4-[4-(difluoromethoxy)-3-ethoxyphenyl]-2-oxopyrrolidin-1-yl}-N-(3-methylisothiazol-5-yl)acetamide,
171) (2S)-2-{(4S)-4-[4-(difluoromethoxy)-3-ethoxyphenyl]-2-oxopyrrolidin-1-yl}-N-(3-fluorophenyl)propanamide
172) (2R)-2-{(4S)-4-[4-(difluoromethoxy)-3-ethoxyphenyl]-2-oxopyrrolidin-1-yl}-N-(3-fluorophenyl)propanamide
173) (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide
174) (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide
175) 2-{(4S)-4-[4-(difluoromethoxy)-3-ethoxyphenyl]-2-oxopyrrolidin-1-yl}-N-(6-methylpyridin-2-yl)acetamide
176) (2S)-2-{(4S)-4-[4-(difluoromethoxy)-3-ethoxyphenyl]-2-oxopyrrolidin-1-yl}-N-(6-methylpyridin-2-yl)propanamide
177) (2R)-2-{(4S)-4-[4-(difluoromethoxy)-3-ethoxyphenyl]-2-oxopyrrolidin-1-yl}-N-(6-methylpyridin-2-yl)propanamide wherein a compound listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to an additional preferred compound and/or method aspect of the invention, the compound of formula I is selected from:

81. N-(cyclopropylmethyl)-N-(5-cyclopropyl-1,3,4-thiadiazol-2-yl)-2-((4S)-4-{4-methoxy-3-[(3R)-tetrahydrofuran-3-yloxy]phenyl}-2-oxopyrrolidin-1-yl)acetamide,
82. 2-{4-[3-(cyclopropylmethoxy)-4-methoxyphenyl]-2-oxopyrrolidin-1-yl}-N-(5-cyclopropyl-1,3,4-thiadiazol-2-yl)-N-methylacetamide,
83. 2-{4-[3-(cyclopropylmethoxy)-4-methoxyphenyl]-2-oxopyrrolidin-1-yl}-N-(cyclopropylmethyl)-N-(5-cyclopropyl-1,3,4-thiadiazol-2-yl)acetamide,
84. 2-{4-[3-(cyclopropylmethoxy)-4-methoxyphenyl]-2-oxopyrrolidin-1-yl}-N-(cyclopropylmethyl)-N-(4-methyl-1,3-thiazol-2-yl)acetamide,
85. 2-{4-[3-(cyclopropylmethoxy)-4-methoxyphenyl]-2-oxopyrrolidin-1-yl}-N-methyl-N-(4-methyl-1,3-thiazol-2-yl)acetamide,
86. 2-{4-[3-(cyclopropylmethoxy)-4-(difluoromethoxy)phenyl]-2-oxopyrrolidin-1-yl}-N-methyl-N-(4-methyl-1,3-thiazol-2-yl)acetamide,
87. 2-{4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide,
88. 2-[(4S)-4-(3-ethoxy-4-methoxyphenyl)-2-oxopyrrolidin-1-yl]-N-(3-fluorophenyl)acetamide,
89. 2-[(4R)-4-(3-ethoxy-4-methoxyphenyl)-2-oxopyrrolidin-1-yl]-N-(3-fluorophenyl)acetamide,
90. 2-[(4S)-4-(3-ethoxy-4-methoxyphenyl)-2-oxopyrrolidin-1-yl]-N-methyl-N-(4-methyl-1,3-thiazol-2-yl)acetamide,
91. 2-[(4S)-4-(3-ethoxy-4-methoxyphenyl)-2-oxopyrrolidin-1-yl]-N-(3-isopropyl-1,2,4-thiadiazol-5-yl)-N-methylacetamide,
92. N-(5-cyclopropyl-1,3,4-thiadiazol-2-yl)-2-[(4S)-4-(3-ethoxy-4-methoxyphenyl)-2-oxopyrrolidin-1-yl]-N-methylacetamide,
93. N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide,
94. 2-[(4R)-4-(3-ethoxy-4-methoxyphenyl)-2-oxopyrrolidin-1-yl]-N-(3-isopropyl-1,2,4-thiadiazol-5-yl)-N-methylacetamide,
95. N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, 96. N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide,
97. N-(4-cyclopropyl-1,3-thiazol-2-yl)-2-((4S)-4-{4-methoxy-3-[(3R)-tetrahydrofuran-3-yloxy]phenyl}-2-oxopyrrolidin-1-yl)acetamide,
98. 2-{(4R)-4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide,
99. 2-{(4S)-4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide,
100. 2-[(4S)-4-(3-ethoxy-4-methoxyphenyl)-2-oxopyrrolidin-1-yl]-N-(3-methylisothiazol-5-yl)acetamide,
101. 2-[(4R)-4-(3-ethoxy-4-methoxyphenyl)-2-oxopyrrolidin-1-yl]-N-(3-methylisothiazol-5-yl)acetamide,
102. (4R)-4-[3-(benzyloxy)-4-(difluoromethoxy)phenyl]pyrrolidin-2-one,
103. (4S)-4-[3-(benzyloxy)-4-(difluoromethoxy)phenyl]pyrrolidin-2-one,
104. (4R)-4-[4-(difluoromethoxy)-3-ethoxyphenyl]pyrrolidin-2-one,
105. (2R)-2-{(4S)-4-[3-(benzyloxy)-4-methoxyphenyl]-2-oxopyrrolidin-1-yl}-N-(3-methylisothiazol-5-yl)propanamide,
106. 2-[(4S)-4-(3-ethoxy-4-methoxyphenyl)-2-oxopyrrolidin-1-yl]-N-(3-isopropyl-1,2,4-thiadiazol-5-yl)acetamide,
107. N-(5-cyclopropyl-1,3,4-thiadiazol-2-yl)-2-[(4S)-4-(3-ethoxy-4-methoxyphenyl)-2-oxopyrrolidin-1-yl]acetamide,
108. N-(4-cyclopropyl-1,3-thiazol-2-yl)-2-[(4S)-4-(3-ethoxy-4-methoxyphenyl)-2-oxopyrrolidin-1-yl]acetamide,
109. 2-{(4S)-4-[3-(cyclopropylmethoxy)-4-methoxyphenyl]-2-oxopyrrolidin-1-yl}-N-(3-isopropyl-1,2,4-thiadiazol-5-yl)acetamide,
110. 2-{(4S)-4-[3-(cyclopropylmethoxy)-4-methoxyphenyl]-2-oxopyrrolidin-1-yl}-N-(3-isopropyl-1,2,4-thiadiazol-5-yl)-N-methylacetamide,
111. 2-[(4S)-4-(3-ethoxy-4-methoxyphenyl)-2-oxopyrrolidin-1-yl]-N-(5-pyridin-4-yl-1,3,4-thiadiazol-2-yl)acetamide,
112. 2-[(4S)-4-(3-ethoxy-4-methoxyphenyl)-2-oxopyrrolidin-1-yl]-N-(4-methyl-1,3-benzothiazol-2-yl)acetamide,
113. 2-[(4S)-4-(3-isopropoxy-4-methoxyphenyl)-2-oxopyrrolidin-1-yl]-N-(3-isopropyl-1,2,4-thiadiazol-5-yl)-N-methylacetamide,
114. 2-{(4S)-4-[3-(cyclopropylmethoxy)-4-methoxyphenyl]-2-oxopyrrolidin-1-yl}-N-(5-cyclopropyl-1,3,4-thiadiazol-2-yl)acetamide,
115. 2-{(4S)-4-[3-(cyclopropylmethoxy)-4-methoxyphenyl]-2-oxopyrrolidin-1-yl}-N-(5-cyclopropyl-1,3,4-thiadiazol-2-yl)-N-methylacetamide,
116. N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide,
117. N-(5-cyclopropyl-1,3,4-thiadiazol-2-yl)-2-[(4S)-4-(3-isopropoxy-4-methoxyphenyl)-2-oxopyrrolidin-1-yl]acetamide,
118. N-(3-fluorophenyl)-2-[(4S)-4-(3-isopropoxy-4-methoxyphenyl)-2-oxopyrrolidin-1-yl]-N-methylacetamide,
119. 2-[(4S)-4-(3-ethoxy-4-methoxyphenyl)-2-oxopyrrolidin-1-yl]-N-(3-methyl-1H-pyrazol-5-yl)acetamide,
120. 2-[(4S)-4-(3-isopropoxy-4-methoxyphenyl)-2-oxopyrrolidin-1-yl]-N-(3-isopropyl-1,2,4-thiadiazol-5-yl)acetamide,
121. 2-[(4S)-4-(3-ethoxy-4-methoxyphenyl)-2-oxopyrrolidin-1-yl]-N-(3-fluorophenyl)-N-methylacetamide,
122. 2-{(4S)-4-[4-(difluoromethoxy)-3-ethoxyphenyl]-2-oxopyrrolidin-1-yl}-N-(3-isopropyl-1,2,4-thiadiazol-5-yl)acetamide,
123. 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide,
124. N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide,
125. N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide,
126. 2-{(4S)-4-[4-(difluoromethoxy)-3-ethoxyphenyl]-2-oxopyrrolidin-1-yl}-N-(3-fluorophenyl)acetamide,
127. 2-{(4S)-4-[4-(difluoromethoxy)-3-ethoxyphenyl]-2-oxopyrrolidin-1-yl}-N-(3-fluorophenyl)-N-methylacetamide,
128. N-(4-cyclopropyl-1,3-thiazol-2-yl)-2-{(4S)-4-[4-(difluoromethoxy)-3-ethoxyphenyl]-2-oxopyrrolidin-1-yl}acetamide,
129. 2-{(4S)-4-[3-(cyclopropylmethoxy)-4-methoxyphenyl]-2-oxopyrrolidin-1-yl}-N-(3-fluorophenyl)-N-methylacetamide,
130. 2-{(4S)-4-[3-(cyclopropylmethoxy)-4-methoxyphenyl]-2-oxopyrrolidin-1-yl}-N-(4-cyclopropyl-1,3-thiazol-2-yl)acetamide,
131. 2-[(4S)-4-(3-ethoxy-4-methoxyphenyl)-2-oxopyrrolidin-1-yl]-N-[4-(trifluoromethyl)-1,3-thiazol-2-yl]acetamide,
132. 2-[(4S)-4-(3-ethoxy-4-methoxyphenyl)-2-oxopyrrolidin-1-yl]-N-(4-methoxy-1,3-benzothiazol-2-yl)acetamide,
133. 2-[(4S)-4-(3-ethoxy-4-methoxyphenyl)-2-oxopyrrolidin-1-yl]-N-(4-methyl-1,3-thiazol-2-yl)acetamide,
134. 2-[(4S)-4-(3-ethoxy-4-methoxyphenyl)-2-oxopyrrolidin-1-yl]-N-methyl-N-(3-methylisothiazol-5-yl)acetamide,
135. 2-[(4S)-4-(3-ethoxy-4-methoxyphenyl)-2-oxopyrrolidin-1-yl]-N-(5-methylisoxazol-3-yl)acetamide,
136. (2S)-2-[(4S)-4-(3-ethoxy-4-methoxyphenyl)-2-oxopyrrolidin-1-yl]-N-(3-isopropyl-1,2,4-thiadiazol-5-yl)propanamide,
137. (2R)-2-[(4S)-4-(3-ethoxy-4-methoxyphenyl)-2-oxopyrrolidin-1-yl]-N-(3-isopropyl-1,2,4-thiadiazol-5-yl)propanamide,
138. (2S)-2-[(4R)-4-(3-ethoxy-4-methoxyphenyl)-2-oxopyrrolidin-1-yl]-N-(3-isopropyl-1,2,4-thiadiazol-5-yl)propanamide,
139. (2R)-2-[(4R)-4-(3-ethoxy-4-methoxyphenyl)-2-oxopyrrolidin-1-yl]-N-(3-isopropyl-1,2,4-thiadiazol-5-yl)propanamide,
140. (2R)-2-[(4S)-4-(3-ethoxy-4-methoxyphenyl)-2-oxopyrrolidin-1-yl]-N-(4-methyl-1,3-thiazol-2-yl)propanamide,
141. (2S)-2-[(4S)-4-(3-ethoxy-4-methoxyphenyl)-2-oxopyrrolidin-1-yl]-N-(4-methyl-1,3-thiazol-2-yl)propanamide,
142. 2-{(4S)-4-[3-(cyclopropylmethoxy)-4-methoxyphenyl]-2-oxopyrrolidin-1-yl}-N-(6-methylpyridin-2-yl)acetamide,
143. 2-{(4S)-4-[3-(cyclopropylmethoxy)-4-methoxyphenyl]-2-oxopyrrolidin-1-yl}-N-1,3-thiazol-2-ylacetamide,
144. N-(4-cyclopropyl-1,3-thiazol-2-yl)-2-[(4S)-4-(3-isopropoxy-4-methoxyphenyl)-2-oxopyrrolidin-1-yl]acetamide,
145. N-(3-fluorophenyl)-2-[(4S)-4-(3-isopropoxy-4-methoxyphenyl)-2-oxopyrrolidin-1-yl]acetamide, 146. 2-{(4S)-4-[3-(cyclopropylmethoxy)-4-methoxyphenyl]-2-oxopyrrolidin-1-yl}-N-(5-methylisoxazol-3-yl)acetamide,
147. N-(4-cyclopropyl-1,3-thiazol-2-yl)-2-[(4S)-4-(3-isopropoxy-4-methoxyphenyl)-2-oxopyrrolidin-1-yl]-N-methylacetamide,
148. N-(4-cyclopropyl-1,3-thiazol-2-yl)-2-[(4S)-4-(3-ethoxy-4-methoxyphenyl)-2-oxopyrrolidin-1-yl]-N-methylacetamide,
149. 2-{(4S)-4-[3-(cyclopropylmethoxy)-4-methoxyphenyl]-2-oxopyrrolidin-1-yl}-N-(4-cyclopropyl-1,3-thiazol-2-yl)-N-methylacetamide,
150. 2-{(4S)-4-[3-(cyclopropylmethoxy)-4-methoxyphenyl]-2-oxopyrrolidin-1-yl}-N-methyl-N-(5-methylisoxazol-3-yl)acetamide,
151. 2-{(4S)-4-[4-(difluoromethoxy)-3-isopropoxyphenyl]-2-oxopyrrolidin-1-yl}-N-(3-fluorophenyl)acetamide,
152. 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide,
153. 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide,
154. N-(4-cyclopropyl-1,3-thiazol-2-yl)-2-{(4S)-4-[4-(difluoromethoxy)-3-isopropoxyphenyl]-2-oxopyrrolidin-1-yl}acetamide,
155. N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide,
156. 2-{(4S)-4-[4-(difluoromethoxy)-3-isopropoxyphenyl]-2-oxopyrrolidin-1-yl}-N-(3-fluorophenyl)-N-methylacetamide,
157. N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide,
158. (4R)-4-[4-(difluoromethoxy)-3-methoxyphenyl]pyrrolidin-2-one,
159. (4R)-4-[4-(difluoromethoxy)-3-isopropoxyphenyl]pyrrolidin-2-one,
160. (4R)-4-[4-(difluoromethoxy)-3-isopropoxyphenyl]-1-isopropylpyrrolidin-2-one,
161. N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide,
162. N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide,
163. 2-{(4S)-4-[3-(cyclopropylmethoxy)-4-(difluoromethoxy)phenyl]-2-oxopyrrolidin-1-yl}-N-(5-cyclopropyl-1,3,4-thiadiazol-2-yl)acetamide,
164. 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)-N-methylacetamide,
165. 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)acetamide,
166. 2-{(4S)-4-[3-(cyclopropylmethoxy)-4-(difluoromethoxy)phenyl]-2-oxopyrrolidin-1-yl}-N-(3-fluorophenyl)-N-methylacetamide,
167. 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)acetamide,
168. 2-{(4S)-4-[3-(cyclopropylmethoxy)-4-(difluoromethoxy)phenyl]-2-oxopyrrolidin-1-yl}-N-(3-fluorophenyl)acetamide,
169. 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)-N-methylacetamide,
170. 2-{(4S)-4-[4-(difluoromethoxy)-3-ethoxyphenyl]-2-oxopyrrolidin-1-yl}-N-(3-methylisothiazol-5-yl)acetamide, wherein a compound listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to a further preferred compound and/or method aspect of the invention, the compound of formula I is selected from:

81) N-(cyclopropylmethyl)-N-(5-cyclopropyl-1,3,4-thiadiazol-2-yl)-2-((4S)-4-{4-methoxy-3-[(3R)-tetrahydrofuran-3-yloxy]phenyl}-2-oxopyrrolidin-1-yl)acetamide,
82) 2-{4-[3-(cyclopropylmethoxy)-4-methoxyphenyl]-2-oxopyrrolidin-1-yl}-N-(5-cyclopropyl-1,3,4-thiadiazol-2-yl)-N-methylacetamide,
83) 2-{4-[3-(cyclopropylmethoxy)-4-methoxyphenyl]-2-oxopyrrolidin-1-yl}-N-(cyclopropylmethyl)-N-(5-cyclopropyl-1,3,4-thiadiazol-2-yl)acetamide,
84) 2-{4-[3-(cyclopropylmethoxy)-4-methoxyphenyl]-2-oxopyrrolidin-1-yl}-N-(cyclopropylmethyl)-N-(4-methyl-1,3-thiazol-2-yl)acetamide,
85) 2-{4-[3-(cyclopropylmethoxy)-4-methoxyphenyl]-2-oxopyrrolidin-1-yl}-N-methyl-N-(4-methyl-1,3-thiazol-2-yl)acetamide,
86) 2-{4-[3-(cyclopropylmethoxy)-4-(difluoromethoxy)phenyl]-2-oxopyrrolidin-1-yl}-N-methyl-N-(4-methyl-1,3-thiazol-2-yl)acetamide,
87) 2-{4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide,
88) 2-[(4S)-4-(3-ethoxy-4-methoxyphenyl)-2-oxopyrrolidin-1-yl]-N-(3-fluorophenyl)acetamide,
89) 2-[(4R)-4-(3-ethoxy-4-methoxyphenyl)-2-oxopyrrolidin-1-yl]-N-(3-fluorophenyl)acetamide,
90) 2-[(4S)-4-(3-ethoxy-4-methoxyphenyl)-2-oxopyrrolidin-1-yl]-N-methyl-N-(4-methyl-1,3-thiazol-2-yl)acetamide,
91) 2-[(4S)-4-(3-ethoxy-4-methoxyphenyl)-2-oxopyrrolidin-1-yl]-N-(3-isopropyl-1,2,4-thiadiazol-5-yl)-N-methylacetamide,
92) N-(5-cyclopropyl-1,3,4-thiadiazol-2-yl)-2-[(4S)-4-(3-ethoxy-4-methoxyphenyl)-2-oxopyrrolidin-1-yl]-N-methylacetamide,
93) N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide,
94) 2-[(4R)-4-(3-ethoxy-4-methoxyphenyl)-2-oxopyrrolidin-1-yl]-N-(3-isopropyl-1,2,4-thiadiazol-5-yl)-N-methylacetamide,
95) N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, 96) N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide,
97) N-(4-cyclopropyl-1,3-thiazol-2-yl)-2-((4S)-4-{4-methoxy-3-[(3R)-tetrahydrofuran-3-yloxy]phenyl}-2-oxopyrrolidin-1-yl)acetamide,
100) 2-[(4S)-4-(3-ethoxy-4-methoxyphenyl)-2-oxopyrrolidin-1-yl]-N-(3-methylisothiazol-5-yl)acetamide,
104) (4R)-4-[4-(difluoromethoxy)-3-ethoxyphenyl]pyrrolidin-2-one,
105) (2R)-2-{(4S)-4-[3-(benzyloxy)-4-methoxyphenyl]-2-oxopyrrolidin-1-yl}-N-(3-methylisothiazol-5-yl)propanamide,
106) 2-[(4S)-4-(3-ethoxy-4-methoxyphenyl)-2-oxopyrrolidin-1-yl]-N-(3-isopropyl-1,2,4-thiadiazol-5-yl)acetamide,
107) N-(5-cyclopropyl-1,3,4-thiadiazol-2-yl)-2-[(4S)-4-(3-ethoxy-4-methoxyphenyl)-2-oxopyrrolidin-1-yl]acetamide,
108) N-(4-cyclopropyl-1,3-thiazol-2-yl)-2-[(4S)-4-(3-ethoxy-4-methoxyphenyl)-2-oxopyrrolidin-1-yl]acetamide,
109) 2-{(4S)-4-[3-(cyclopropylmethoxy)-4-methoxyphenyl]-2-oxopyrrolidin-1-yl}-N-(3-isopropyl-1,2,4-thiadiazol-5-yl)acetamide,
110) 2-{(4S)-4-[3-(cyclopropylmethoxy)-4-methoxyphenyl]-2-oxopyrrolidin-1-yl}-N-(3-isopropyl-1,2,4-thiadiazol-5-yl)-N-methylacetamide,
111) 2-[(4S)-4-(3-ethoxy-4-methoxyphenyl)-2-oxopyrrolidin-1-yl]-N-(5-pyridin-4-yl-1,3,4-thiadiazol-2-yl)acetamide,
112) 2-[(4S)-4-(3-ethoxy-4-methoxyphenyl)-2-oxopyrrolidin-1-yl]-N-(4-methyl-1,3-benzothiazol-2-yl)acetamide,
113) 2-[(4S)-4-(3-isopropoxy-4-methoxyphenyl)-2-oxopyrrolidin-1-yl]-N-(3-isopropyl-1,2,4-thiadiazol-5-yl)-N-methylacetamide,
114) 2-{(4S)-4-[3-(cyclopropylmethoxy)-4-methoxyphenyl]-2-oxopyrrolidin-1-yl}-N-(5-cyclopropyl-1,3,4-thiadiazol-2-yl)acetamide,
115) 2-{(4S)-4-[3-(cyclopropylmethoxy)-4-methoxyphenyl]-2-oxopyrrolidin-1-yl}-N-(5-cyclopropyl-1,3,4-thiadiazol-2-yl)-N-methylacetamide,
116) N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide,
117) N-(5-cyclopropyl-1,3,4-thiadiazol-2-yl)-2-[(4S)-4-(3-isopropoxy-4-methoxyphenyl)-2-oxopyrrolidin-1-yl]acetamide,
118) N-(3-fluorophenyl)-2-[(4S)-4-(3-isopropoxy-4-methoxyphenyl)-2-oxopyrrolidin-1-yl]-N-methylacetamide,
119) 2-[(4S)-4-(3-ethoxy-4-methoxyphenyl)-2-oxopyrrolidin-1-yl]-N-(3-methyl-1H-pyrazol-5-yl)acetamide,
120) 2-[(4S)-4-(3-isopropoxy-4-methoxyphenyl)-2-oxopyrrolidin-1-yl]-N-(3-isopropyl-1,2,4-thiadiazol-5-yl)acetamide,
121) 2-[(4S)-4-(3-ethoxy-4-methoxyphenyl)-2-oxopyrrolidin-1-yl]-N-(3-fluorophenyl)-N-methylacetamide,
122) 2-{(4S)-4-[4-(difluoromethoxy)-3-ethoxyphenyl]-2-oxopyrrolidin-1-yl}-N-(3-isopropyl-1,2,4-thiadiazol-5-yl)acetamide,
123) 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide,
124) N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide,
125) N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide,
126) 2-{(4S)-4-[4-(difluoromethoxy)-3-ethoxyphenyl]-2-oxopyrrolidin-1-yl}-N-(3-fluorophenyl)acetamide,
127) 2-{(4S)-4-[4-(difluoromethoxy)-3-ethoxyphenyl]-2-oxopyrrolidin-1-yl}-N-(3-fluorophenyl)-N-methylacetamide,
128) N-(4-cyclopropyl-1,3-thiazol-2-yl)-2-{(4S)-4-[4-(difluoromethoxy)-3-ethoxyphenyl]-2-oxopyrrolidin-1-yl}acetamide,
129) 2-{(4S)-4-[3-(cyclopropylmethoxy)-4-methoxyphenyl]-2-oxopyrrolidin-1-yl}-N-(3-fluorophenyl)-N-methylacetamide,
130) 2-{(4S)-4-[3-(cyclopropylmethoxy)-4-methoxyphenyl]-2-oxopyrrolidin-1-yl}-N-(4-cyclopropyl-1,3-thiazol-2-yl)acetamide,
131) 2-[(4S)-4-(3-ethoxy-4-methoxyphenyl)-2-oxopyrrolidin-1-yl]-N-[4-(trifluoromethyl)-1,3-thiazol-2-yl]acetamide,
132) 2-[(4S)-4-(3-ethoxy-4-methoxyphenyl)-2-oxopyrrolidin-1-yl]-N-(4-methoxy-1,3-benzothiazol-2-yl)acetamide,
133) 2-[(4S)-4-(3-ethoxy-4-methoxyphenyl)-2-oxopyrrolidin-1-yl]-N-(4-methyl-1,3-thiazol-2-yl)acetamide,
134) 2-[(4S)-4-(3-ethoxy-4-methoxyphenyl)-2-oxopyrrolidin-1-yl]-N-methyl-N-(3-methylisothiazol-5-yl)acetamide,
135) 2-[(4S)-4-(3-ethoxy-4-methoxyphenyl)-2-oxopyrrolidin-1-yl]-N-(5-methylisoxazol-3-yl)acetamide,
136) (2S)-2-[(4S)-4-(3-ethoxy-4-methoxyphenyl)-2-oxopyrrolidin-1-yl]-N-(3-isopropyl-1,2,4-thiadiazol-5-yl)propanamide,
137) (2R)-2-[(4S)-4-(3-ethoxy-4-methoxyphenyl)-2-oxopyrrolidin-1-yl]-N-(3-isopropyl-1,2,4-thiadiazol-5-yl)propanamide,
138) (2S)-2-[(4R)-4-(3-ethoxy-4-methoxyphenyl)-2-oxopyrrolidin-1-yl]-N-(3-isopropyl-1,2,4-thiadiazol-5-yl)propanamide,
139) (2R)-2-[(4R)-4-(3-ethoxy-4-methoxyphenyl)-2-oxopyrrolidin-1-yl]-N-(3-isopropyl-1,2,4-thiadiazol-5-yl)propanamide,
140) (2R)-2-[(4S)-4-(3-ethoxy-4-methoxyphenyl)-2-oxopyrrolidin-1-yl]-N-(4-methyl-1,3-thiazol-2-yl)propanamide,
141) (2S)-2-[(4S)-4-(3-ethoxy-4-methoxyphenyl)-2-oxopyrrolidin-1-yl]-N-(4-methyl-1,3-thiazol-2-yl)propanamide,
142) 2-{(4S)-4-[3-(cyclopropylmethoxy)-4-methoxyphenyl]-2-oxopyrrolidin-1-yl}-N-(6-methylpyridin-2-yl)acetamide,
143) 2-{(4S)-4-[3-(cyclopropylmethoxy)-4-methoxyphenyl]-2-oxopyrrolidin-1-yl}-N-1,3-thiazol-2-ylacetamide,
144) N-(4-cyclopropyl-1,3-thiazol-2-yl)-2-[(4S)-4-(3-isopropoxy-4-methoxyphenyl)-2-oxopyrrolidin-1-yl]acetamide,
145) N-(3-fluorophenyl)-2-[(4S)-4-(3-isopropoxy-4-methoxyphenyl)-2-oxopyrrolidin-1-yl]acetamide,
146) 2-{(4S)-4-[3-(cyclopropylmethoxy)-4-methoxyphenyl]-2-oxopyrrolidin-1-yl}-N-(5-methylisoxazol-3-yl)acetamide,
147) N-(4-cyclopropyl-1,3-thiazol-2-yl)-2-[(4S)-4-(3-isopropoxy-4-methoxyphenyl)-2-oxopyrrolidin-1-yl]-N-methylacetamide,
148) N-(4-cyclopropyl-1,3-thiazol-2-yl)-2-[(4S)-4-(3-ethoxy-4-methoxyphenyl)-2-oxopyrrolidin-1-yl]-N-methylacetamide, 149) 2-{(4S)-4-[3-(cyclopropylmethoxy)-4-methoxyphenyl]-2-oxopyrrolidin-1-yl}-N-(4-cyclopropyl-1,3-thiazol-2-yl)-N-methylacetamide, 150) 2-{(4S)-4-[3-(cyclopropylmethoxy)-4-methoxyphenyl]-2-oxopyrrolidin-1-yl}-N-methyl-N-(5-methylisoxazol-3-yl)acetamide, 151) 2-{(4S)-4-[4-(difluoromethoxy)-3-isopropoxyphenyl]-2-oxopyrrolidin-1-yl}-N-(3-fluorophenyl)acetamide, 152) 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 153) 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, 154) N-(4-cyclopropyl-1,3-thiazol-2-yl)-2-{(4S)-4-[4-(difluoromethoxy)-3-isopropoxyphenyl]-2-oxopyrrolidin-1-yl}acetamide, 155) N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, 156) 2-{(4S)-4-[4-(difluoromethoxy)-3-isopropoxyphenyl]-2-oxopyrrolidin-1-yl}-N-(3-fluorophenyl)-N-methylacetamide, 157) N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, 158) (4R)-4-[4-(difluoromethoxy)-3-methoxyphenyl]pyrrolidin-2-one, 159) (4R)-4-[4-(difluoromethoxy)-3-isopropoxyphenyl]pyrrolidin-2-one, 160) (4R)-4-[4-(difluoromethoxy)-3-isopropoxyphenyl]-1-isopropylpyrrolidin-2-one, 161) N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, 162) N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, 163) 2-{(4S)-4-[3-(cyclopropylmethoxy)-4-(difluoromethoxy)phenyl]-2-oxopyrrolidin-1-yl}-N-(5-cyclopropyl-1,3,4-thiadiazol-2-yl)acetamide, 164) 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)-N-methylacetamide, 165) 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)acetamide, 166) 2-{(4S)-4-[3-(cyclopropylmethoxy)-4-(difluoromethoxy)phenyl]-2-oxopyrrolidin-1-yl}-N-(3-fluorophenyl)-N-methylacetamide, 167) 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)acetamide, 168) 2-{(4S)-4-[3-(cyclopropylmethoxy)-4-(difluoromethoxy)phenyl]-2-oxopyrrolidin-1-yl}-N-(3-fluorophenyl)acetamide, 169) 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)-N-methylacetamide, 170) 2-{(4S)-4-[4-(difluoromethoxy)-3-ethoxyphenyl]-2-oxopyrrolidin-1-yl}-N-(3-methylisothiazol-5-yl)acetamide, wherein a compound listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to a further preferred compound and/or method aspect of the invention, the compound of formula I is selected from:

171) (2S)-2-{(4S)-4-[4-(difluoromethoxy)-3-ethoxyphenyl]-2-oxopyrrolidin-1-yl}-N-(3-fluorophenyl)propanamide, 172) (2R)-2-{(4S)-4-[4-(difluoromethoxy)-3-ethoxyphenyl]-2-oxopyrrolidin-1-yl}-N-(3-fluorophenyl)propanamide, 173) (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, 174) (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, 175) 2-{(4S)-4-[4-(difluoromethoxy)-3-ethoxyphenyl]-2-oxopyrrolidin-1-yl}-N-(6-methylpyridin-2-yl)acetamide, 176) (2S)-2-{(4S)-4-[4-(difluoromethoxy)-3-ethoxyphenyl]-2-oxopyrrolidin-1-yl}-N-(6-methylpyridin-2-yl)propanamide, and 177) (2R)-2-{(4S)-4-[4-(difluoromethoxy)-3-ethoxyphenyl]-2-oxopyrrolidin-1-yl}-N-(6-methylpyridin-2-yl)propanamide, wherein a compound listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

The following table also presents structures for selected compounds of Formula I in accordance with the present invention:

| Compound | Structure |
|---|---|
| 81) | 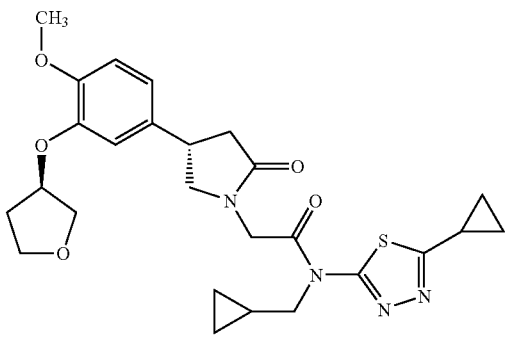 |
| 82) | 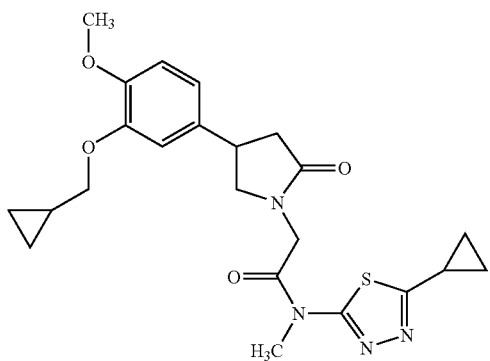 |
| 83) | 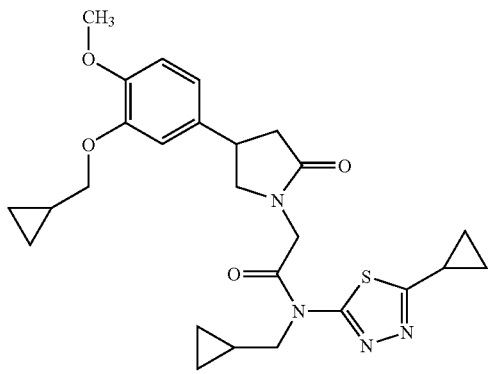 |
| 84) | 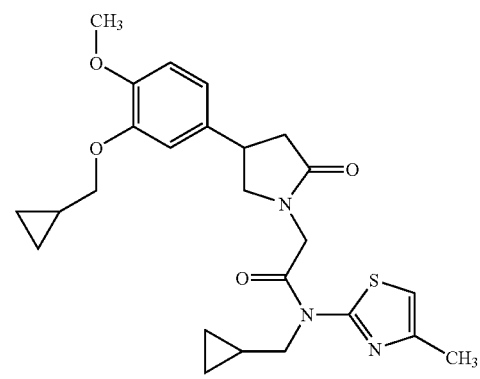 |

-continued
| Compound | Structure |
|---|---|
| 85) | 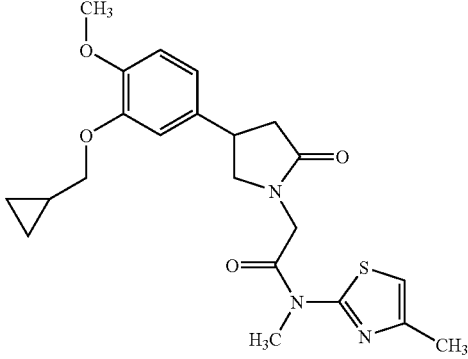 |
| 86) | 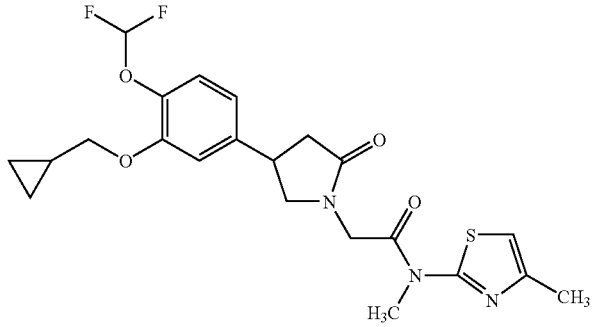 |
| 87) | 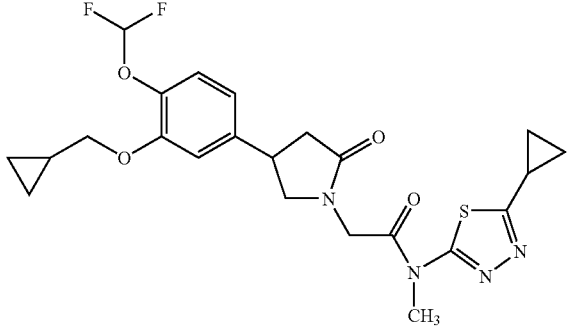 |
| 88) | 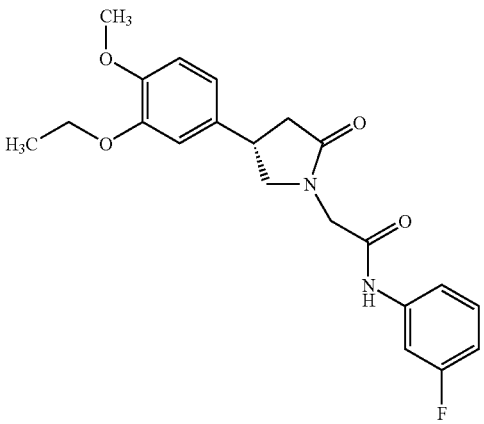 |

-continued
| Compound | Structure |
|---|---|
| 89) | 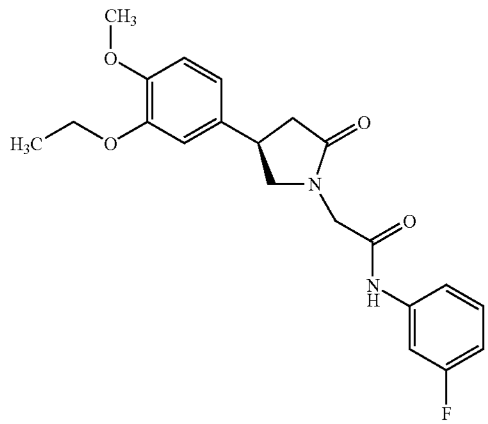 |
| 90) | 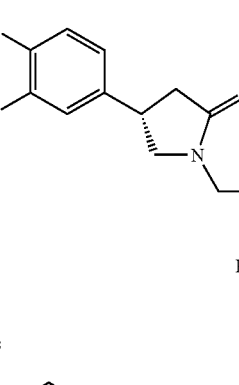 |
| 91) | 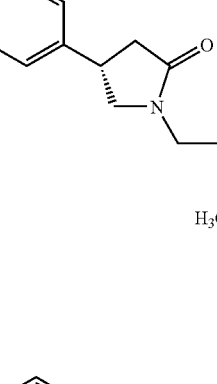 |
| 92) | 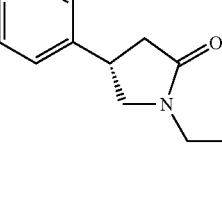 |

-continued

| Compound | Structure |
|---|---|
| 93) | 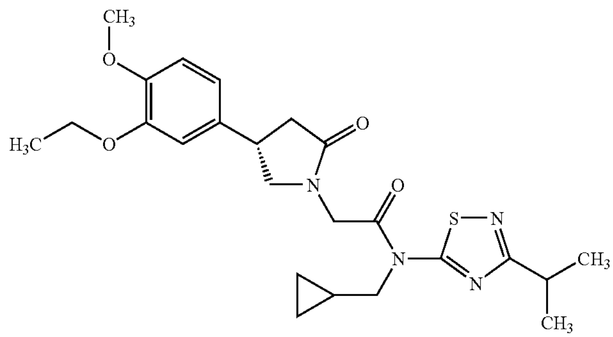 |
| 94) | 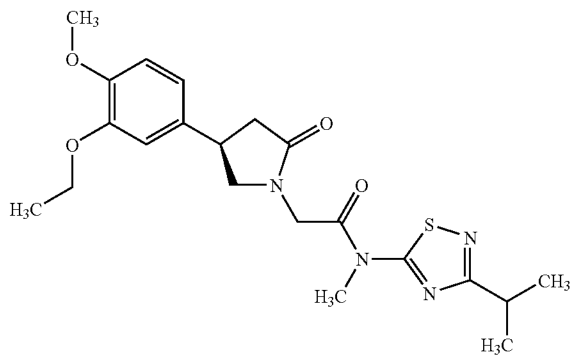 |
| 95) | 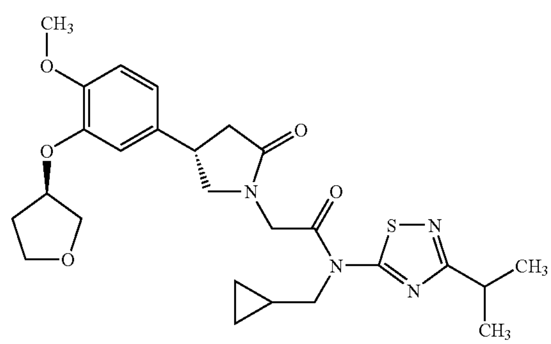 |
| 96) | 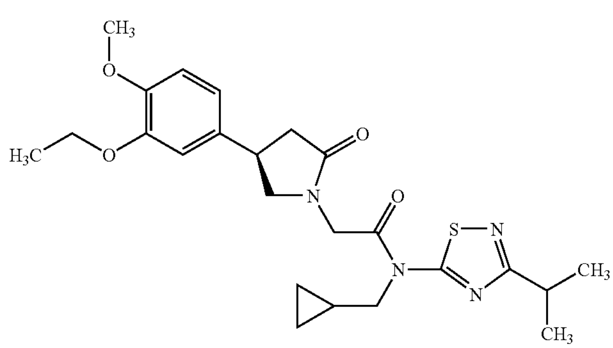 |

-continued
| Compound | Structure |
|---|---|
| 97) | 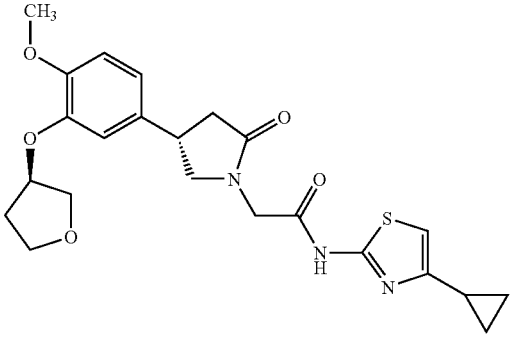 |
| 98) | 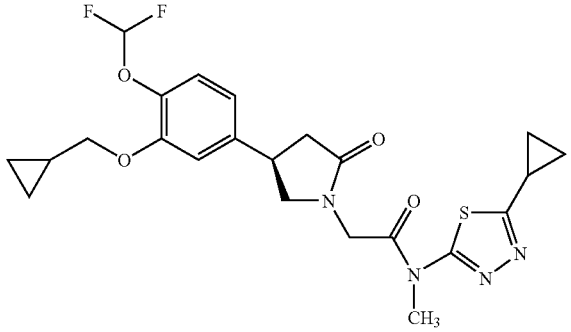 |
| 99) | 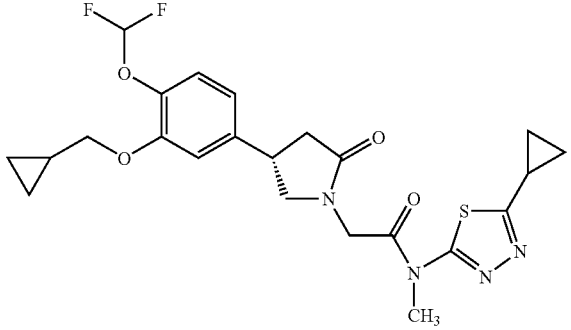 |
| 100) | 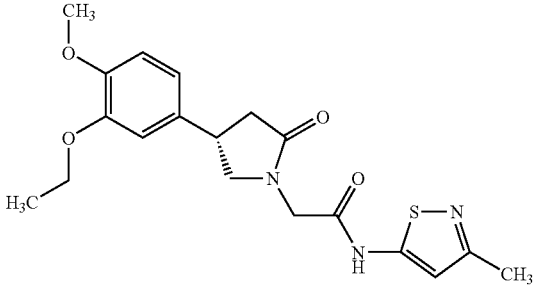 |

| Compound | Structure |
|---|---|
| 101) | 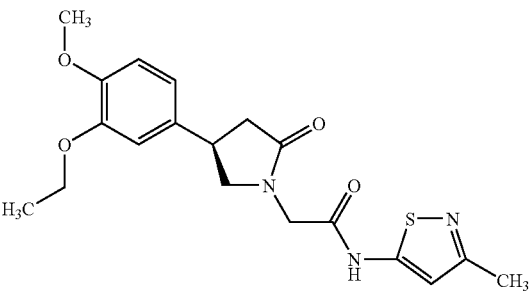 |
| 102) | 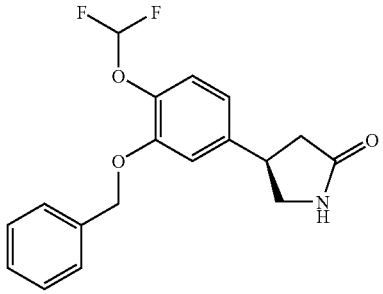 |
| 103) | 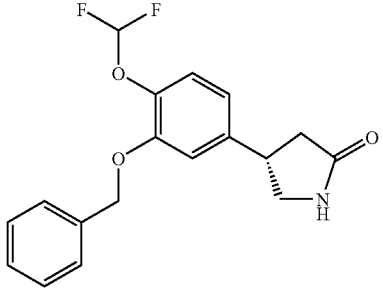 |
| 104) | 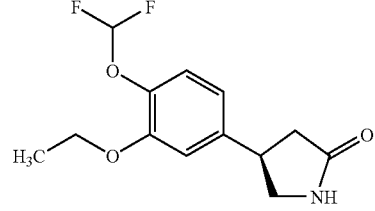 |
| 105) | 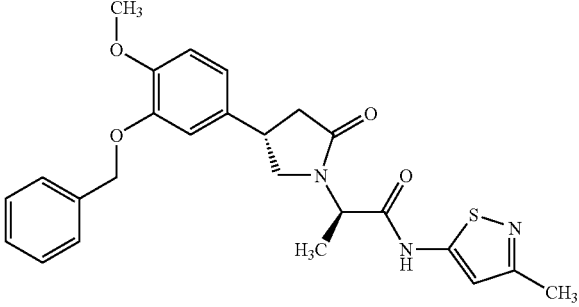 |

-continued
| Compound | Structure |
|---|---|
| 106) | 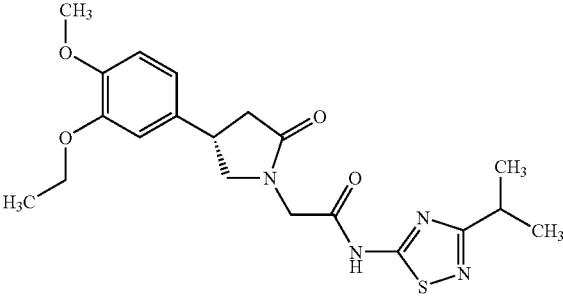 |
| 107) | 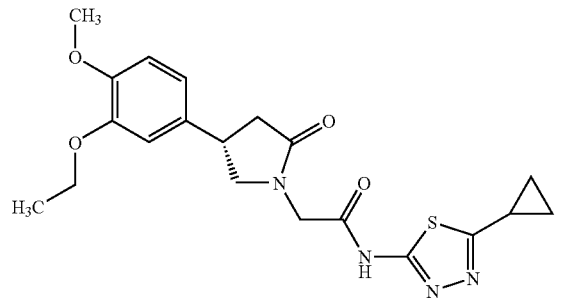 |
| 108) | 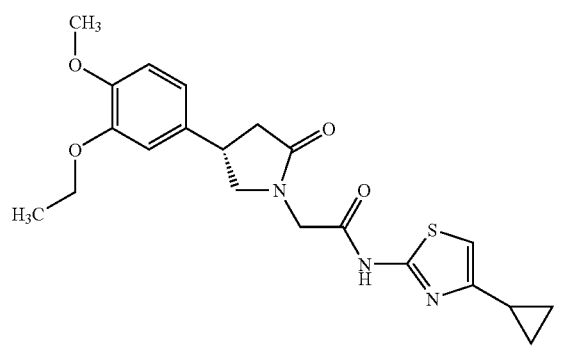 |
| 109) | 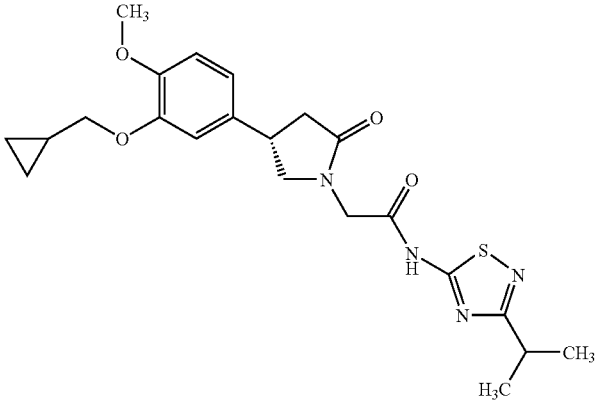 |

-continued

| Compound | Structure |
|---|---|
| 110) | 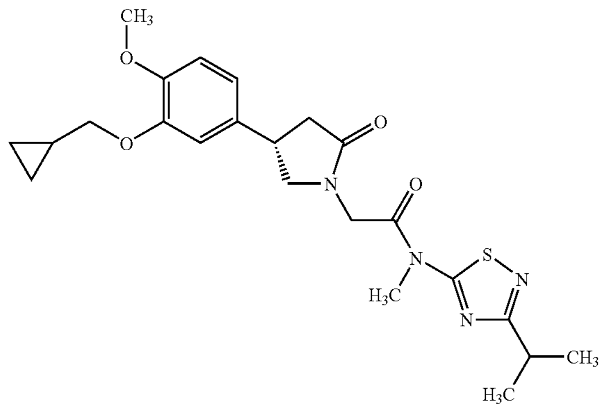 |
| 111) | 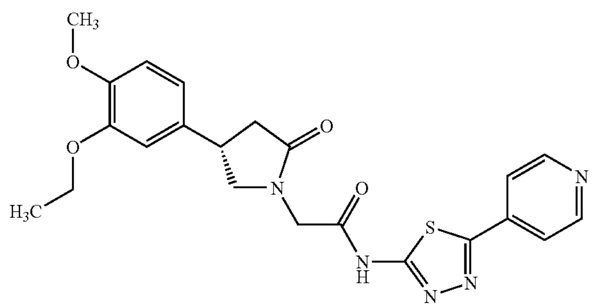 |
| 112) | 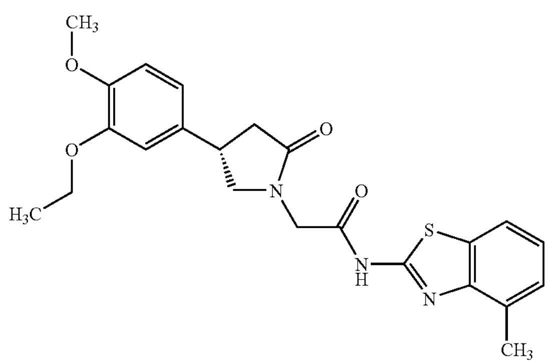 |
| 113) | 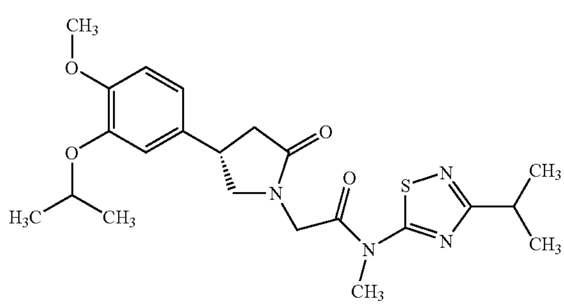 |

-continued

| Compound | Structure |
|---|---|
| 114) | 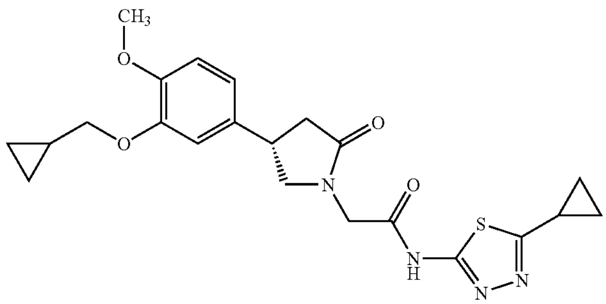 |
| 115) | 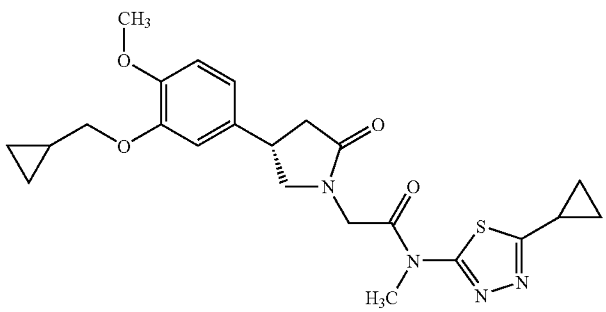 |
| 116) | 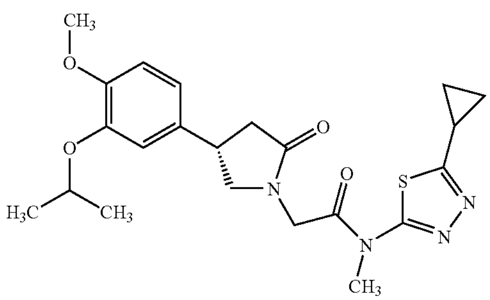 |
| 117) | 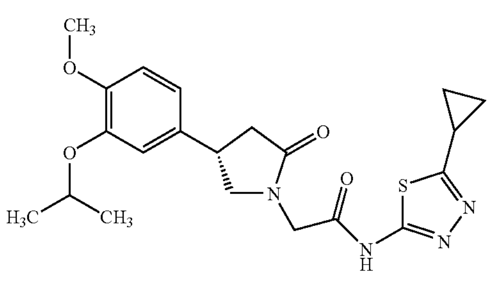 |
| 118) | 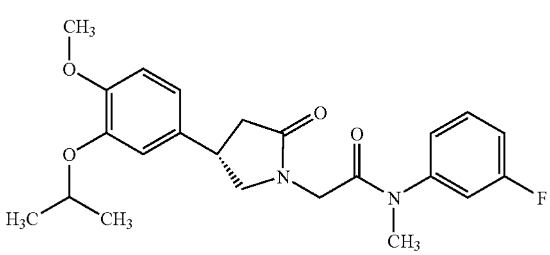 |

-continued
| Compound | Structure |
|---|---|
| 119) | 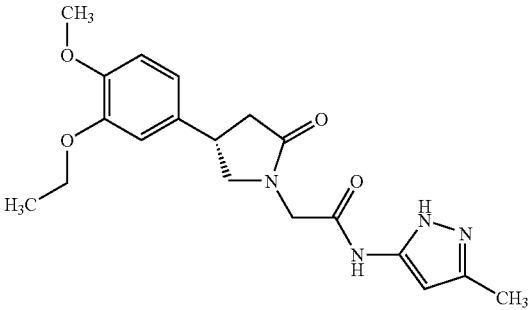 |
| 120) | 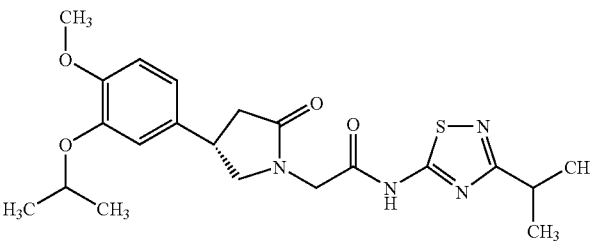 |
| 121) | 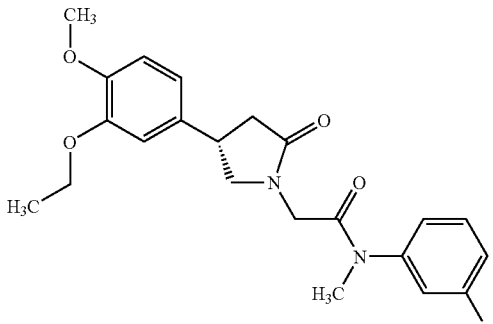 |
| 122) | 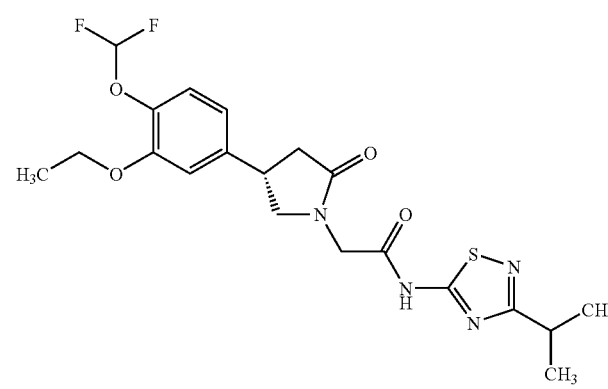 |

-continued
| Compound | Structure |
|---|---|
| 123) | 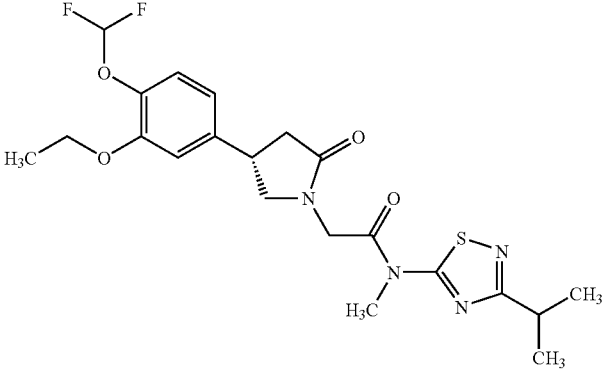 |
| 124) | 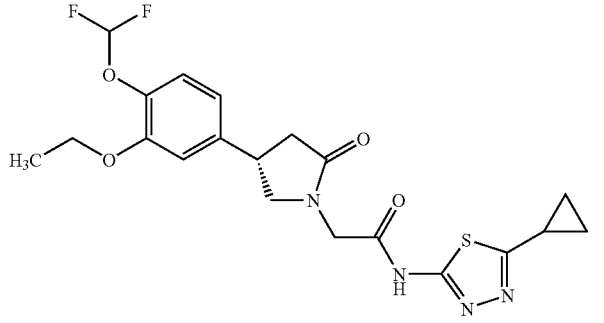 |
| 125) | 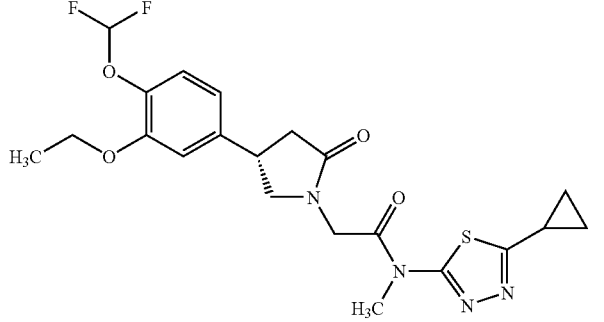 |
| 126) | 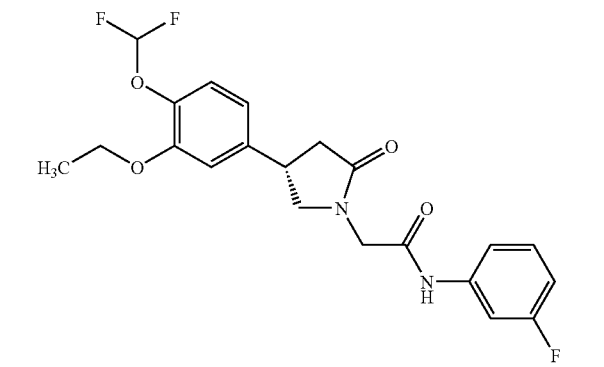 |

-continued
| Compound | Structure |
|---|---|
| 127) | 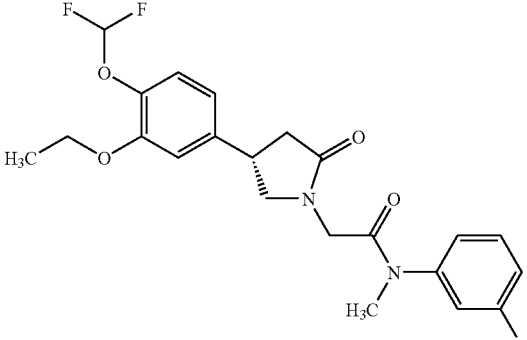 |
| 128) | 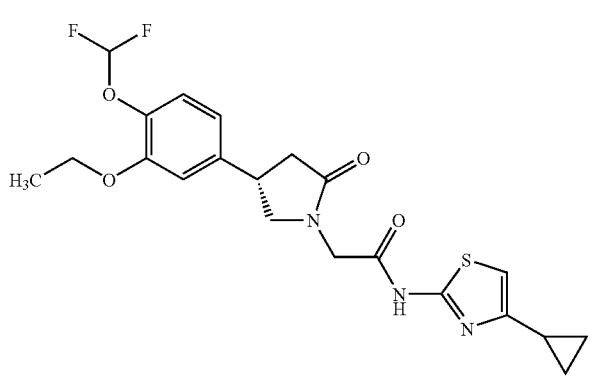 |
| 129) | 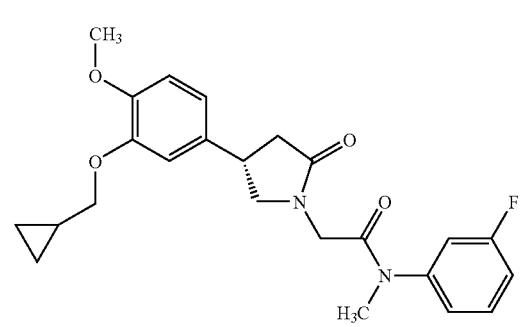 |
| 130) | 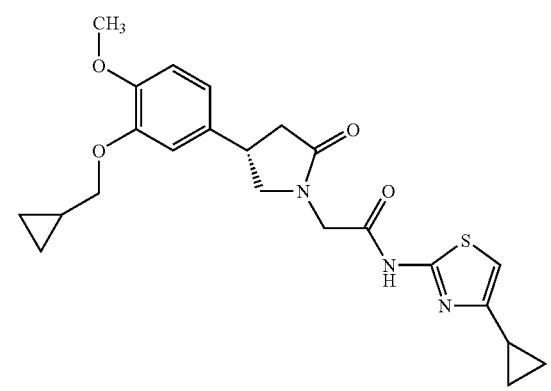 |

-continued

| Compound | Structure |
|---|---|
| 131) | 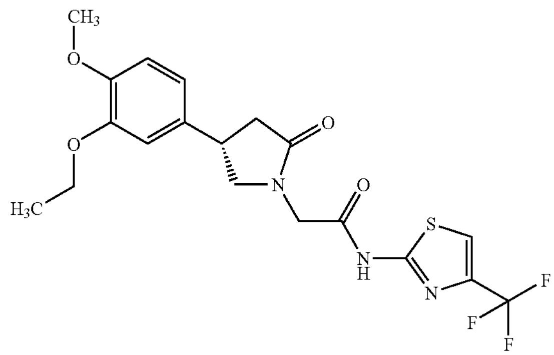 |
| 132) | 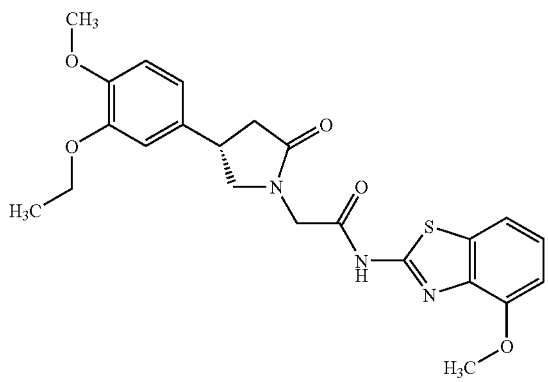 |
| 133) | 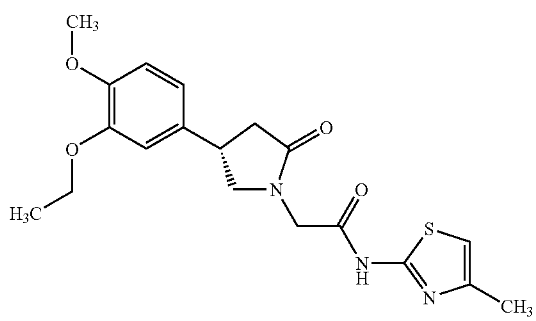 |
| 134) | 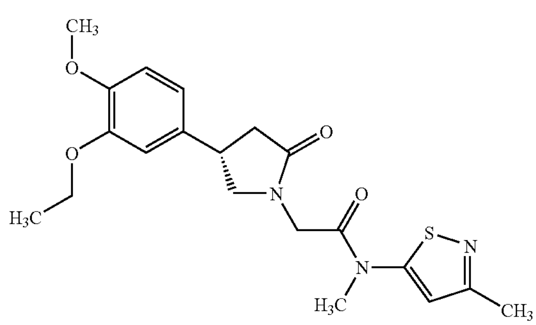 |

-continued

| Compound | Structure |
|---|---|
| 135) | 4-(3-ethoxy-4-methoxyphenyl)-1-[2-((5-methylisoxazol-3-yl)amino)-2-oxoethyl]pyrrolidin-2-one |
| 136) | (S)-2-[(S)-3-(3-ethoxy-4-methoxyphenyl)-5-oxopyrrolidin-1-yl]-N-(3-isopropyl-1,2,4-thiadiazol-5-yl)propanamide |
| 137) | (R)-2-[(S)-3-(3-ethoxy-4-methoxyphenyl)-5-oxopyrrolidin-1-yl]-N-(3-isopropyl-1,2,4-thiadiazol-5-yl)propanamide |
| 138) | (S)-2-[(R)-3-(3-ethoxy-4-methoxyphenyl)-5-oxopyrrolidin-1-yl]-N-(3-isopropyl-1,2,4-thiadiazol-5-yl)propanamide |
| 139) | (R)-2-[(R)-3-(3-ethoxy-4-methoxyphenyl)-5-oxopyrrolidin-1-yl]-N-(3-isopropyl-1,2,4-thiadiazol-5-yl)propanamide |

-continued
| Compound | Structure |
|---|---|
| 140) | 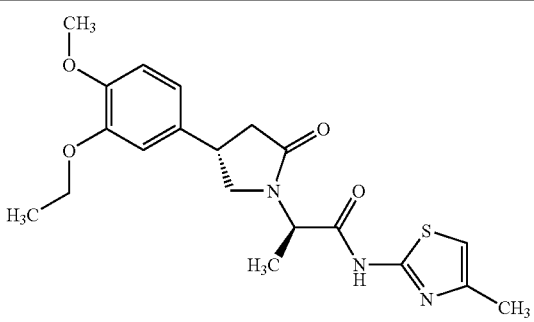 |
| 141) | 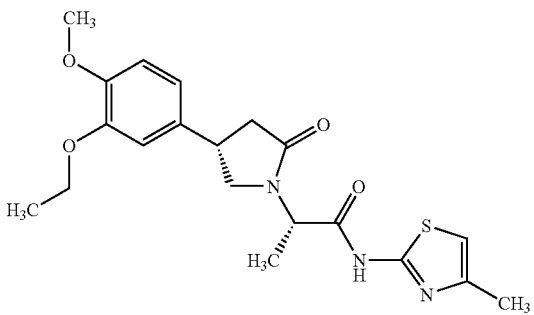 |
| 142) | 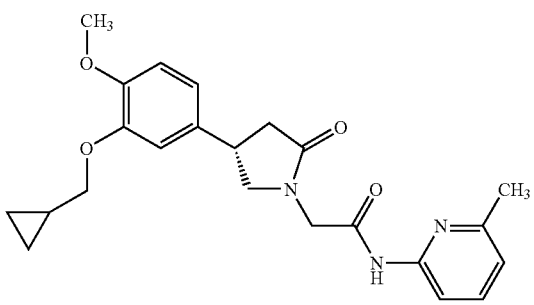 |
| 143) | 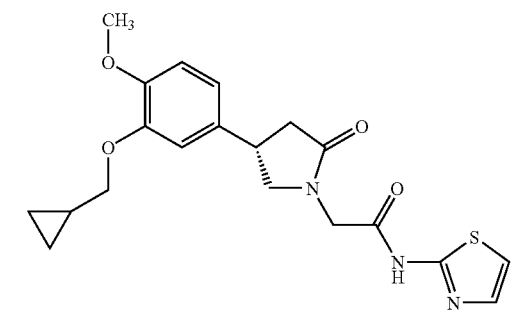 |

-continued
| Compound | Structure |
|---|---|
| 144) | 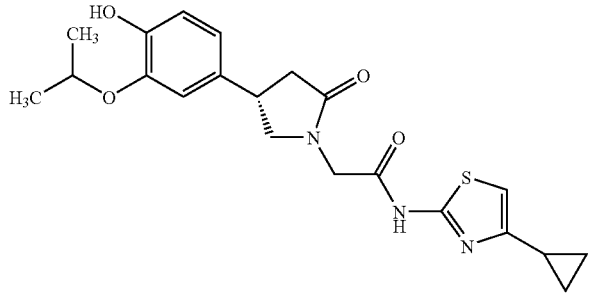 |
| 145) | 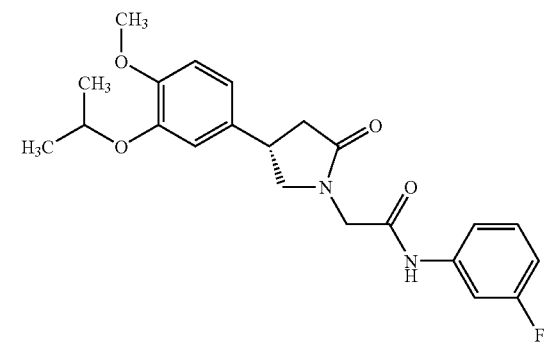 |
| 146) | 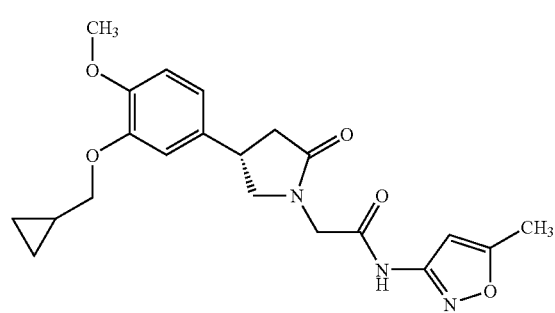 |
| 147) | 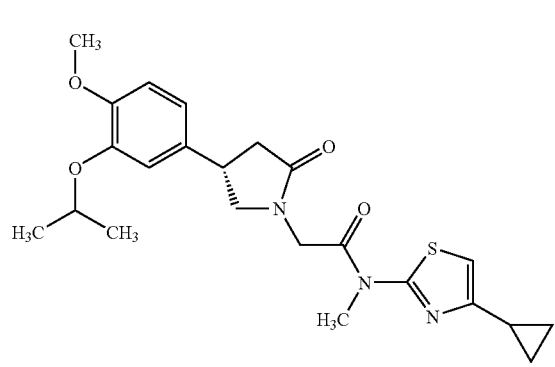 |

-continued
| Compound | Structure |
|---|---|
| 148) | 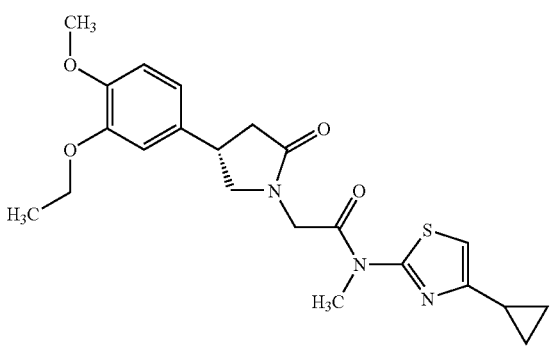 |
| 149) | 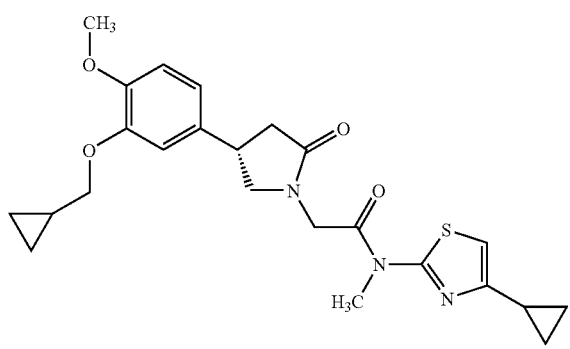 |
| 150) | 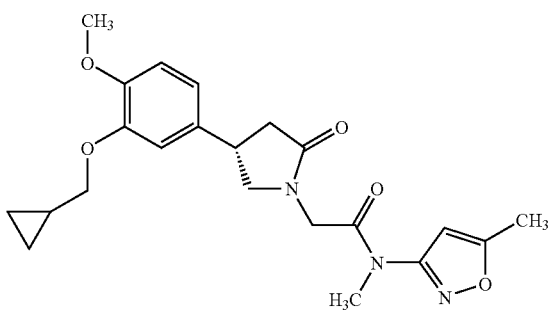 |
| 151) | 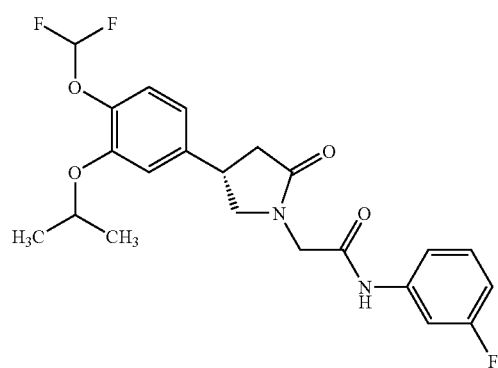 |

-continued
| Compound | Structure |
|---|---|
| 152) | 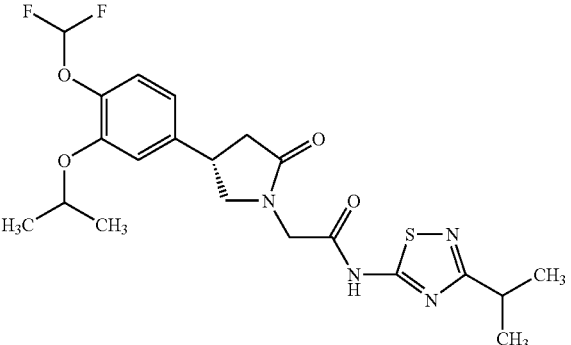 |
| 153) | 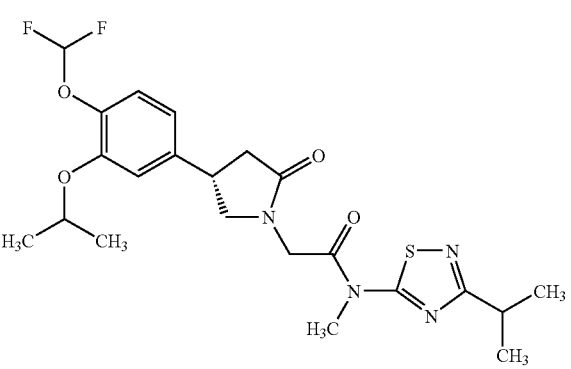 |
| 154) | 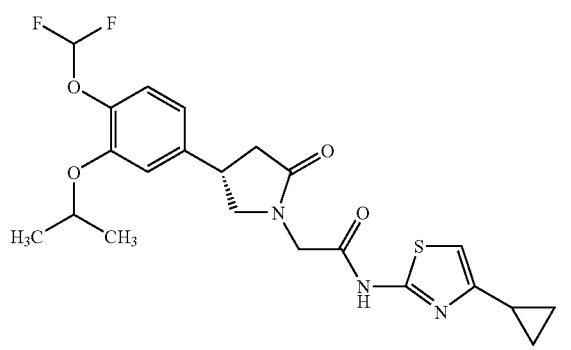 |
| 155) | 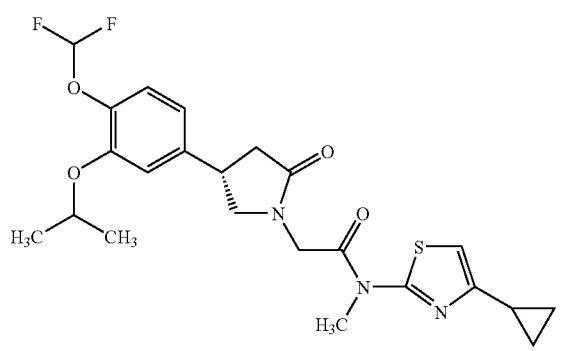 |

-continued
| Compound | Structure |
|---|---|
| 156) | 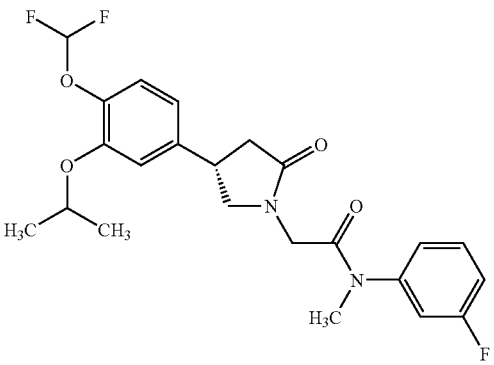 |
| 157) | 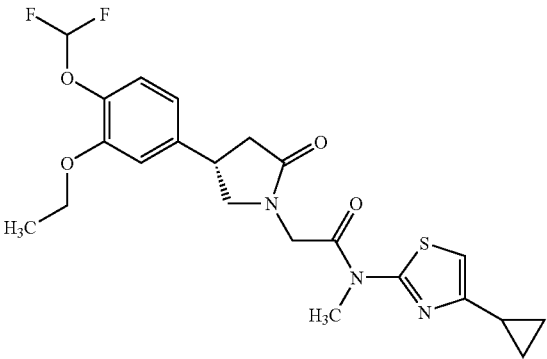 |
| 158) | 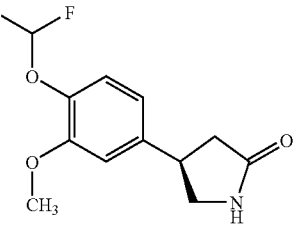 |
| 159) | 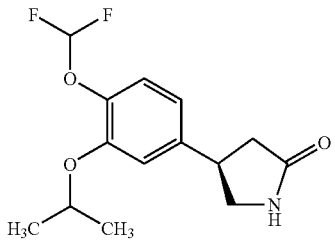 |
| 160) | 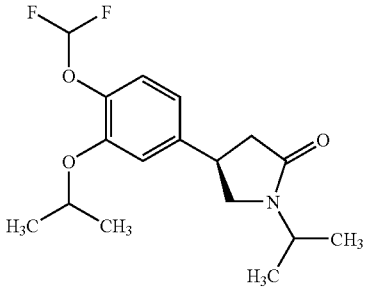 |

-continued
| Compound | Structure |
|---|---|
| 161) | 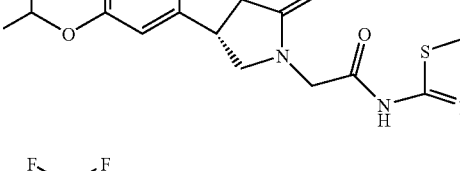 |
| 162) | 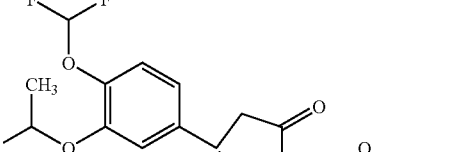 |
| 163) | 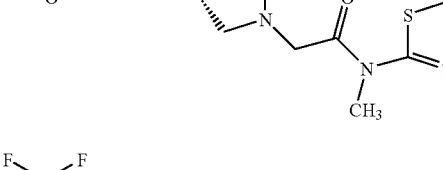 |
| 164) | 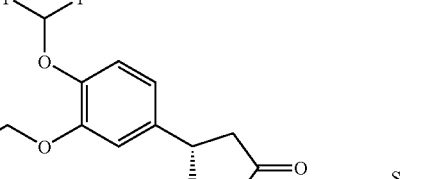 |
| 165) | 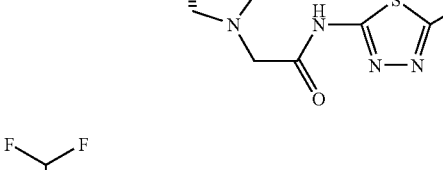 |

-continued
| Compound | Structure |
|---|---|
| 166) | 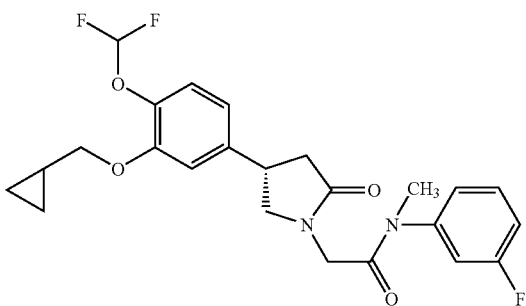 |
| 167) | 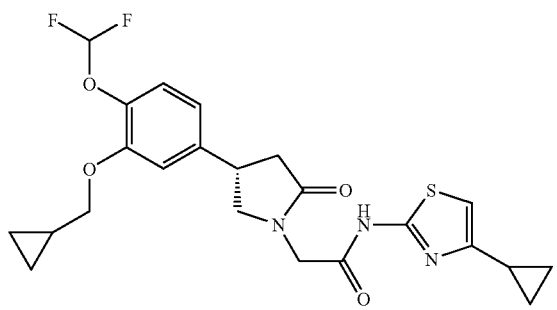 |
| 168) | 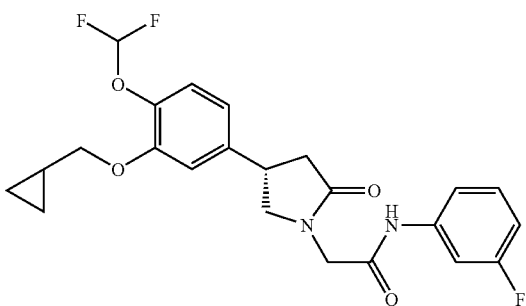 |
| 169) | 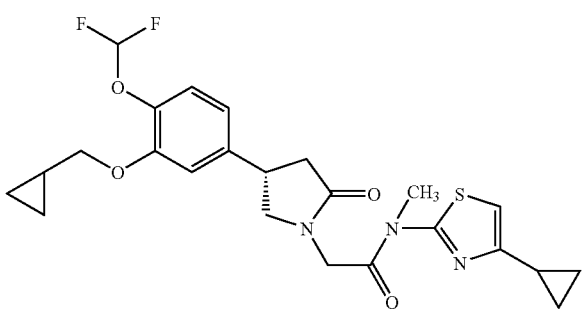 |

-continued
| Compound | Structure |
|---|---|
| 170) | 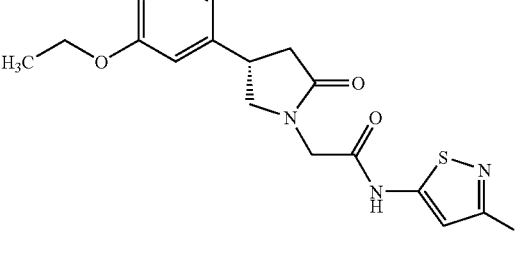 |
| 171) | 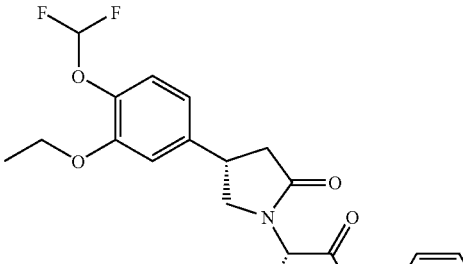 |
| 172) | 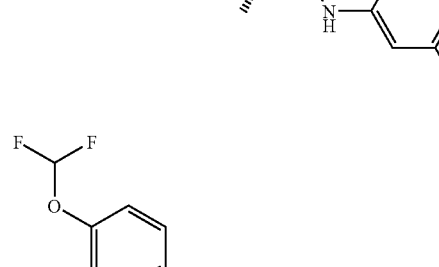 |
| 173) | 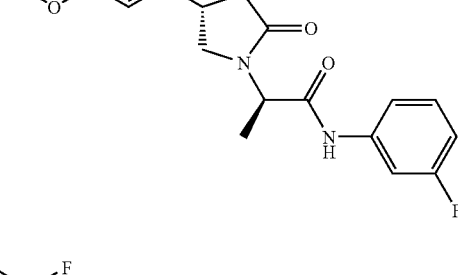 |

-continued
| Compound | Structure |
|---|---|
| 174) | 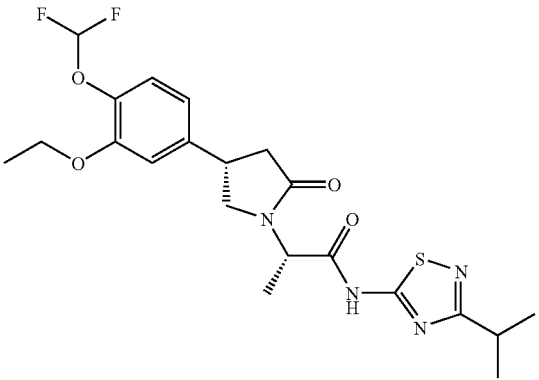 |
| 175) | 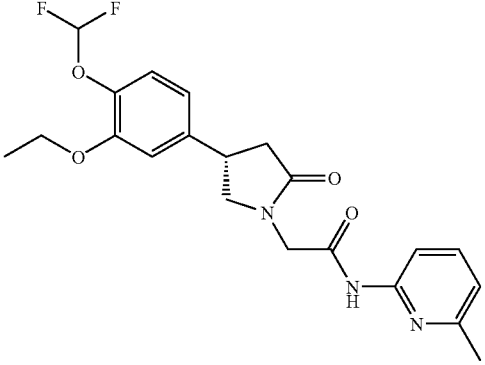 |
| 176) | 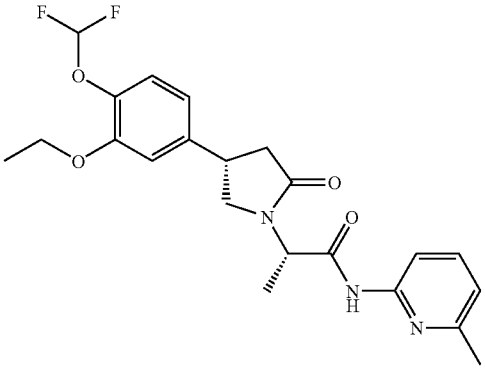 |
| 177) | 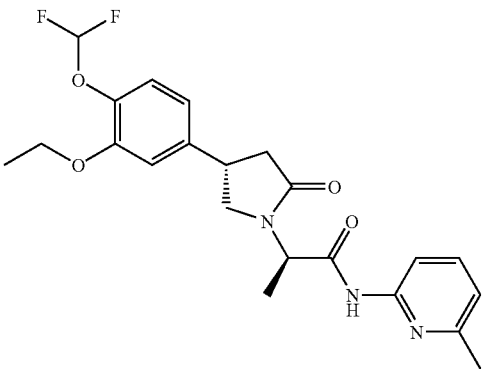 |

Other preferred aspects include pharmaceutical compositions comprising a compound of this invention and a pharmaceutically acceptable carrier and, optionally, another active agent as discussed below; a method of inhibiting a PDE4 enzyme, especially an isoenzyme, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc.; a method of treating a disease state modulated by PDE4 activity, in a patient, e.g., in a mammal, e.g., a human, e.g., those disease states mentioned herein.

The compounds of the present invention may be prepared conventionally. Some of the known processes that can be used are described below. All starting materials are known or can be conventionally prepared from known starting materials by one of ordinary skill.

Preparation of Starting Material

Enantiomerically pure rolipram, 4-(3-cyclopentyloxy-4-methoxyphenyl)-2-pyrrolidone, and the starting material 4-(3-benzyloxy-4-methoxyphenyl)-2-pyrrolidone were prepared as shown in scheme I and in a similar fashion as described previously (see, e.g., J. Demnitz, et. al., Enantiodivergent synthesis of (R)- and (S)-Rolipram, *Molecules,* 3, 107-119, 1998) (Other compounds of formula I can be similarly prepared using alternate $R^2$ groups in place $CH_3$ and/or alternate $R^1$ groups in place of benzyl and cyclopentyl).

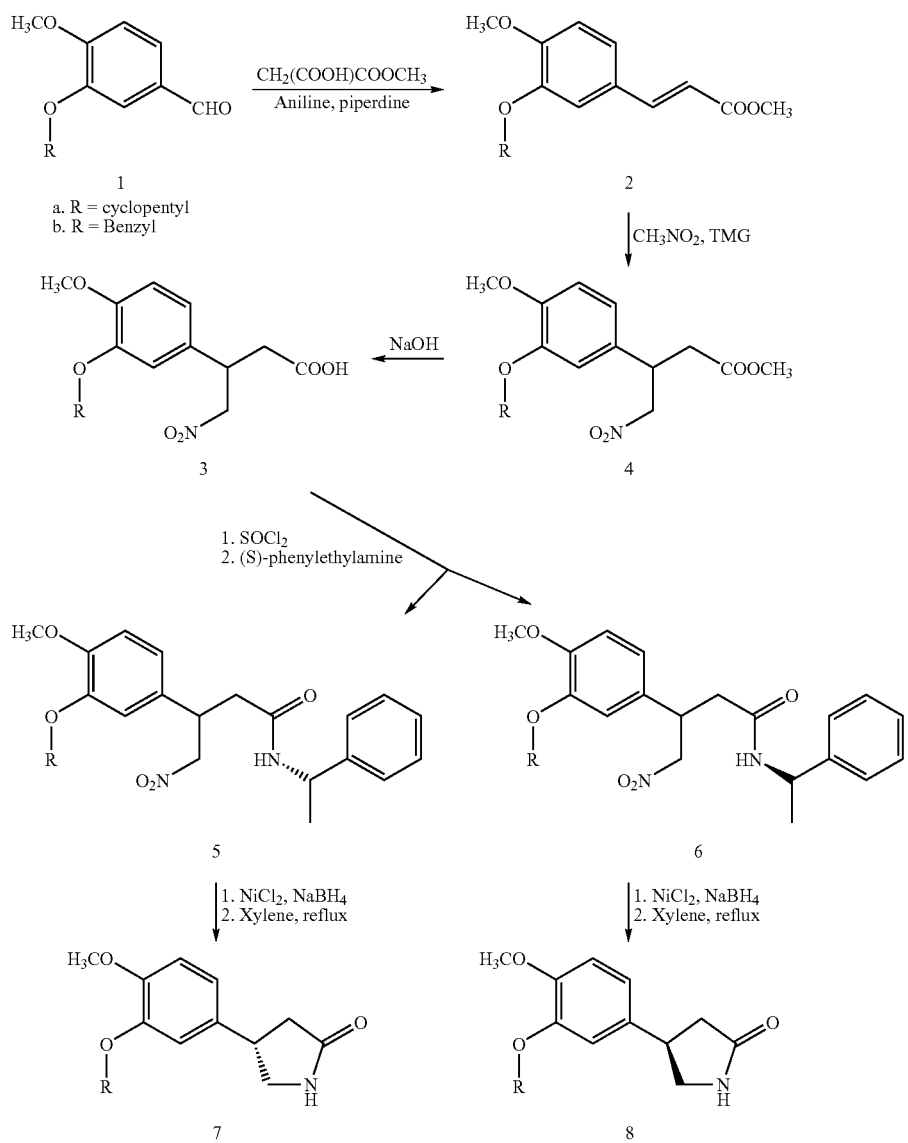

Thus, appropriately substituted benzaldehydes may be condensed with monomethyl malonate to provide the corresponding methyl cinnamyl esters after decarboxylation. Conjugate addition of nitromethane using tetramethyl guanidine as base provides methyl 4-nitro-3-(substituted-phenyl)butyrate. Racemic 4-(3-benzyloxy-4-methoxyphenyl)-2-pyrrolidone is produced in 85% yield by selective reduction of the nitro group to the corresponding amine using $NiCl_2$ and $NaBH_4$ (see, e.g., Osby, J. O.; Ganem, B., Rapid and efficient reduction of aliphatic nitro compounds to amines, *Tetrahedron Lett.*, 26, 6413-6416, 1985) and subsequent treatment with $K_2CO_3$.

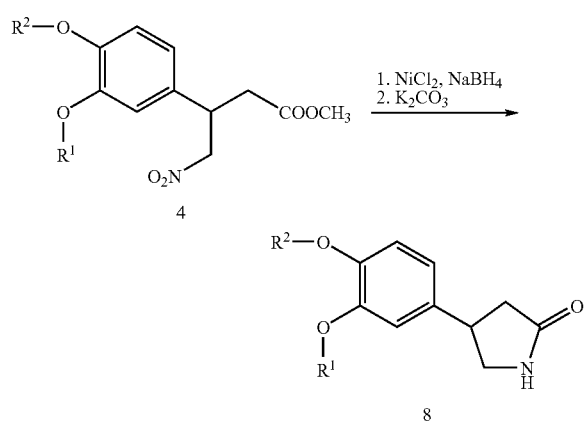

Methyl 4-nitro-3-(substituted-phenyl)butyrate may be enantiomerically resolved by synthesizing diastereomeric phenethylamine amides as shown in scheme I. Nitro group reduction by catalytic hydrogenation as described by Demnitz, J. *Molecules*, 1998, 3, 107-119 was not successful. Reduction of the diastereomerically pure nitro amides using $NiCl_2$ and $NaBH_4$ produces 90% yield of the corresponding diastereomerically pure amines. Cyclization by warming to reflux in xylene yields 51% of (S)-(+)-rolipram and 24% of (R)-(−)-rolipram, both in greater than 99% ee as determined by chiral HPLC (Kusters, E.; Spondlin, C.; Influence of temperature on the enantioseparation of rolipram and structurally related racemates on Chiralcel-OD, *J. Chromatograpmy A*, 737, 333-337, 1996). Enantiomerically pure 3-benzyloxy derivatives 8 (R=benzyl) may be produced in similar yield and purity after cyclization.

Alternatively, enantiomerically pure pyrrolidones 7 and 8 can be prepared according to the methods of D. M. Barnes et. al. (see, e.g., D. M. Barnes, et. al., *J. Am. Chem. Soc.*, 124, 13097-13105, 2002).

3-Aryloxy rolipram derivatives may be prepared by cross coupling reactions with aryl boronic acids using a copper catalyst in the presence of an amine base. Suitable copper catalysts include copper diacetate, copper (II) chloride, etc. Generally, halogenated solvents are utilized, such as chloroform, dichloromethane, 1,2-dichloroethane, and the like. Commonly used bases include triethylamine, diisopropylamine, and pyrrolidine. Alternatively, 3-phenyloxyrolipram can be prepared by Ullman type coupling reaction starting with iodobenzene and 3-hydroxyrolipram as described previously (see, e.g., U.S. Pat. No. 4,193,926). Compounds substituted at the 3-position with arylalkyl, alkyl, cycloalkyl, heteroalkyl or cycloalkylalkyl groups can be prepared by either Mitsunobu reaction between phenol 9 ($R^1$=H) and alcohol or by an alkylation reaction between phenol 9 ($R^1$=H) and $R^1X$, where X is a suitable leaving group, such as Cl, Br, methanesulphonyl, tosyloxy, etc.

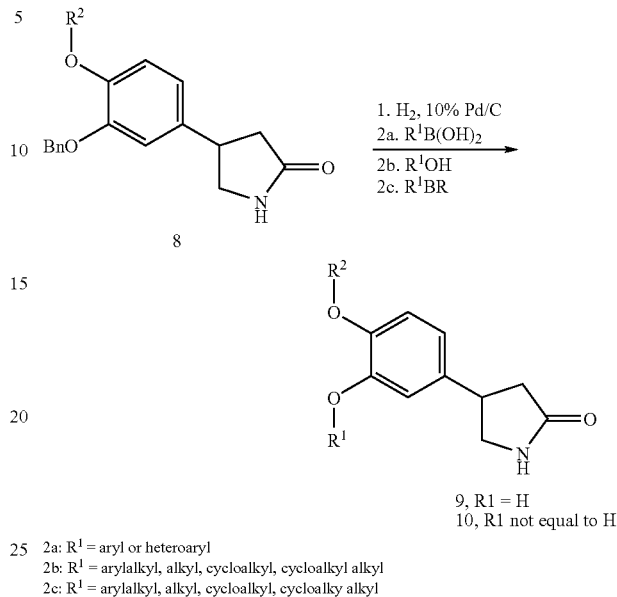

2a: $R^1$ = aryl or heteroaryl
2b: $R^1$ = arylalkyl, alkyl, cycloalkyl, cycloalkyl alkyl
2c: $R^1$ = arylalkyl, alkyl, cycloalkyl, cycloalky alkyl A series of enantiomerically pure N-substituted rolipram derivatives were synthesized by methods common to the art (Christensen, S. B., et. al., *J. Med. Chem.*, 41, 821-835, 1998). Thus, the target compounds may be obtained by alkylation reaction with alkyl halides, cycloalkyl halides, arylacyl chlorides, alpha bromoacetates, appropriately substituted alpha-bromides, and arylalkyl halides (i.e., benzylbromides) in polar aprotic solvents (i.e., DMF, THF, DMSO) using a non-nucleophilic base such as NaH or LDA, and a phase transfer catalyst such as 15-crown-5 ether.

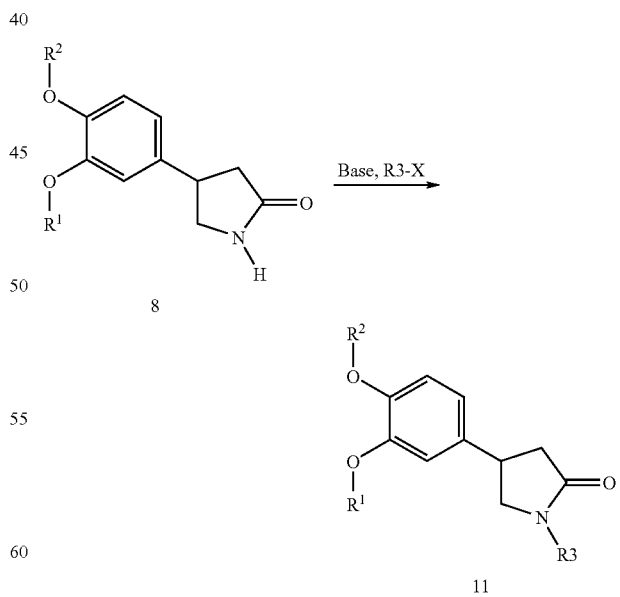

Reaction of methyl alpha-bromoacetate (e.g., $BrCHR^7CO_2R$) with a rolipram derivative as described above produces methyl N-acetates 12 (R=$CH_3$), which can be saponified to the acid 12 (R=H) by treatment with a base, such as NaOH or KOH, and then converted to the acid chloride 13 by use of any number of reagents, such as thionyl chloride or oxalyl chloride. Such acid chlorides undergo reaction with a number of nucleophiles including anilines to provide compounds of type 14.

Alternatively, the acid 12 (R=H) undergoes coupling reactions with amines and a suitable coupling reagent such as DCC or HBTU in the presence of an aprotic solvent such as dichloromethane or THF to produce amides of the type 14. In certain instances where $R^1$ is a protecting group such as benzyl this group can be selectively removed from 14 to give the corresponding compound in which $R^1$=H. This phenol can then be substituted by methods common in the art, such as by reaction with cyclopentyl bromide in the presence of a suitable base or by a Mitsunobu reaction with 3(S)-hydroxytetrahydrofuran, to generate desired target compounds.

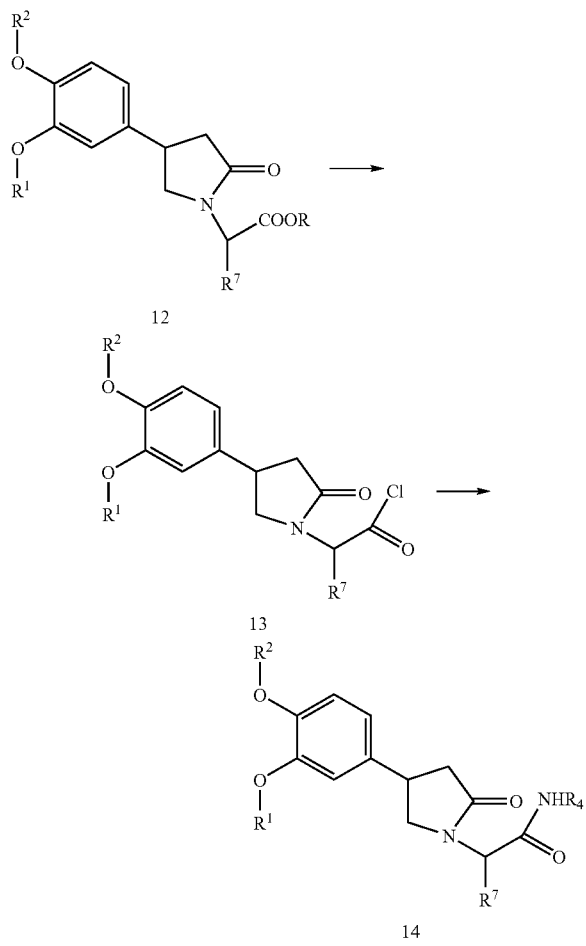

R = H, $C_{1-4}$ alkyl

One of ordinary skill in the art will recognize that some of the compounds of formula I can exist in different geometrical isomeric forms. In addition, some of the compounds of the present invention possess one or more asymmetric carbon atoms and are thus capable of existing in the form of optical isomers, as well as in the form of racemic or nonracemic mixtures thereof, and in the form of diastereomers and diastereomeric mixtures inter alia. For example, in the pyrrolidone structure, the carbon atom at the 4-ring position will be chiral. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

In the compounds of formula I, when $R^3$ is H, the 4(R) enantiomers are preferred, and when $R^3$ is other than H, the 4(S)-enantiomers are preferred. When $R^1$ is 3-tetrahydrofuran, the 3(R) enantiomers are preferred over the 3(S) enantiomers.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I-II can likewise be obtained by utilizing optically active starting materials in chiral syntheses processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 6(10), 110, 2000, CAN 133: 68895 AN 2000:473538 CAPLUS; Kabalka, George W.; Varma, Rajender S. The synthesis of radiolabeled compounds VIA organometallic intermediates, Tetrahedron, 45(21), 6601-21, 1989, CODEN: TETRAB ISSN:0040-4020. CAN 112:20527 AN 1990:20527 CAPLUS; and Evans, E. Anthony. Synthesis of radiolabeled compounds, J. Radioanal. Chem., 64(1-2), 9-32, 1981, CODEN: JRACBN ISSN:0022-4081, CAN 95:76229 AN 1981:476229 CAPLUS.

The present invention also relates to useful forms of the compounds as disclosed herein, such as free base forms, and pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydroformate, hydrobromide, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of formula I can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of formula I can exist in different solvate forms. Solvates of the compounds of the invention may also form when solvent molecules are incorporated into the crystalline lattice structure of the compound molecule during the crystallization process. For example, suitable solvates include hydrates, e.g., monohydrates, dihydrates, sesquihydrates, and hemihydrates.

The compounds of the invention can be administered alone or as an active ingredient of a formulation. Thus, the present invention also includes pharmaceutical compositions of compounds of formula I containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their high degree of selective PDE4 inhibition, the compounds of the present invention can be administered to anyone requiring PDE4 inhibition. Administration may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The present invention further includes methods of treatment that involve inhibition of PDE4 enzymes. Thus, the present invention includes methods of selective inhibition of PDE4 enzymes in patients, e.g., mammals, especially humans, wherein such inhibition has a therapeutic effect, such as where such inhibition may relieve conditions involving neurological syndromes, such as the loss of memory, especially long-term memory. Such methods comprise administering to a patient in need thereof, especially a mammal, most especially a human, an inhibitory amount of a compound, alone or as part of a formulation, as disclosed herein.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (Alzheimer's, Parkinson's disease, Pick's disease), vascular (Infarcts, Hemorrhage, Cardiac Disorders), mixed vascular and Alzheimer's, bacterial meningitis, Creutzfeld-Jacob Disease, and multiple sclerosis), traumatic (subdural hematoma or traumatic brain injury), infectious (HIV), toxic (heavy metals, alcohol, medications), metabolic (Vitamin $B_{12}$ or folate deficiency), CNS hypoxia, Cushing's disease, psychiatric (depression and schizophrenia) and hydrocephalus.

The present invention also includes methods for treating memory loss separate from dementias, including mild cognitive impairment (MCI) and age-related cognitive decline. The present invention includes methods of treatment for memory impairment as a result of disease including Huntington's disease and Down's syndrome. According to another aspect, the invention includes methods for treating memory loss from anesthetics, chemotherapy, radiation treatment, and post-surgical trauma.

The compounds of the invention can also be used to treat schizophrenia, bipolar or manic depression, major depression, and drug addiction. PDE4 inhibitors can be used to raise cAMP levels and prevent neurons from undergoing apoptosis. PDE4 inhibitors are also known to be anti-inflammatory. The combination of preventing neuronal apoptosis and inhibiting inflammatory responses make these compounds useful to treat neurodegeneration resulting from any disease or injury, including stroke, Alzheimer's disease, multiple sclerosis, amyolaterosclerosis (ALS), and multiple systems atrophy (MSA).

Thus, in accordance with a preferred embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to formula I or a pharmaceutically acceptable salt or solvate (e.g., hydrate) thereof, or a solvate of a pharmaceutically acceptable salt thereof.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a further embodiment of the invention, there is provided a method of treating allergic and inflammatory disease states, comprising administering an effective amount of a compound according to formula I or a pharmaceutically acceptable salt or solvate (e.g., hydrate) thereof, or a solvate of a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia areata, hypertrophic scars, discoid lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases, osteoporosis, and the like. The compounds can also be used in a method of treating patients suffering from disease states characterized by decreased NMDA function, such as schizophrenia. The compounds can also be used to treat psychosis characterized by elevated levels of PDE 4, for example, various forms of depression, such as manic depression, major depression, and depression associated with psychiatric and neurological disorders.

The use of trisubstituted phenyl derivatives for treating asthma, chronic bronchitis, psoriasis, allergic rhinitis, and other inflammatory diseases, and for inhibiting tumor necrosis factor is known within the art. See, e.g., WO 98/58901, JP 11-189577, JP 10-072415, WO 93/25517, WO 94/14742, U.S. Pat. No. 5,814,651, and U.S. Pat. No. 5,935,978. These references describe 1,3,4-trisubstituted phenyl compounds said to exhibit PDE4 inhibition activity. They also describe assays for determining PDE4 inhibition activity, and methods for synthesizing such compounds. The entire disclosures of these documents are hereby incorporated by reference.

The invention is also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins are: dentatorubral-pallidoluysian atrophy, DRPLA (atrophin-1);

spinocerebellar ataxia type-1 (ataxin-1); spinocerebellar ataxia type-2 (ataxin-2); spinocerebellar ataxia type-3 also called Machado-Joseph disease, MJD (ataxin-3); spinocerebellar ataxia type-6 (alpha 1a-voltage dependent calcium channel); spinocerebellar ataxia type-7 (ataxin-7); and spinal and bulbar muscular atrophy, SBMA, also known as Kennedy disease (androgen receptor).

Thus, in accordance with a further aspect of the invention, there is provided a method of treating a polyglutamine-repeat disease or CAG repeat expansion disease comprising administering to a patient, especially a human, a therapeutically effective amount of a compound according to formula I or a pharmaceutically acceptable salt or solvate (e.g., hydrate) thereof, or a solvate of a pharmaceutically acceptable salt thereof.

In accordance with a further embodiment, there is provided a method of treating Huntington's disease (HD), dentatorubral-pallidoluysian atrophy (DRPLA), spinocerebellar ataxia type-1, spinocerebellar ataxia type-2, spinocerebellar ataxia type-3 (Machado-Joseph disease), spinocerebellar ataxia type-6, spinocerebellar ataxia type-7, or spinal and bulbar muscular atrophy, comprising administering to a patient, especially a human, a therapeutically effective amount of a compound according to formula I or a pharmaceutically acceptable salt or solvate (e.g., hydrate) thereof, or a solvate of a pharmaceutically acceptable salt thereof.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury (IRI), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The compounds of the present invention can be administered as the sole active agent or in combination with other pharmaceutical agents such as other agents used in the treatment of cognitive impairment and/or in the treatment of psychosis, e.g., other PDE4 inhibitors, PDE10 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below their usual dosage range.

The compounds of the present invention can be administered as the sole active agent or in combination with other pharmaceutical agents used in the treatment of allergic and/or inflammatory conditions, e.g. respiratory conditions. Suitable examples of other pharmaceutical agents used in the treatment of allergic and/or inflammatory conditions, e.g. respiratory conditions which may be used in combination with the compounds of the present invention include, but are not limited to, other PDE-4 inhibitors, 5-lipoxygenase (5-LO) inhibitors or 5-lipoxygenase activating protein (FLAP) antagonists (e.g., zileuton, fenleuton), leukotriene antagonists (LTRAs) including antagonists of $LTB_4$, $LTC_4$, $LTD_4$, and $LTE_4$ (e.g., ontazolast, ablukast, pranlukast, verlukast, zariflukast, montelukast, zileuton), histaminic receptor antagonists, including H1 and H3 antagonists (e.g., cetirizine, loratidine, desloratidine, fexofenadine, astemizole, azelastine, chlorpheniramine, cimetidine, ranitidine, famotidine, nizatidine), $\alpha_1$ and $\alpha_2$ adrenoceptor agonist vasoconstrictor sympathomimetic agents for decongestant use (e.g., propylhexedrine, phenylephrine, phenylpropanolamine, pseudoephedrine, naphazoline hydrochloride), muscarinic receptor (M1, M2, and M3) antagonists (e.g., ipratropium salts, namely bromide, tiotropium salts, namely bromide, oxitropium salts, namely bromide, perenzepine, and telenzepine), anticholinergic agents, $\beta_1$ to $\beta_4$ (e.g. $\beta_2$) adrenoceptor agonists (e.g., isoprenaline, albuterol, salbutamol, formoterol, salmeterol), COX-1 inhibitors (NSAIDs), COX-2 selective inhibitors, nitric oxide NSAIDs, oral or inhaled glucocorticosteroids (e.g., prednisone, prednisolone, flunisolide, triamcinolone acetonide, beclomethasone diprionate), and adenosine A2a receptor agonists. Further examples of suitable other pharmaceutical agents which may be used in combination with the compounds of the present invention are disclosed in U.S. Pat. Nos. 6,559,168 and 6,756,392, which are hereby incorporated by reference in their entireties. In such combinations, each active ingredient can be administered either in accordance with their usual dosage range or a dose below its usual dosage range.

The compounds of the invention are also suitable for use in the treatment of asbestos-related diseases or disorders. See, for example, U.S. Published Application No. 2005/0142104, which is hereby incorporated by reference in its entirety.

Thus, in accordance with a further aspect of the invention, there is provided a method of treating asbestos-related diseases or disorders comprising administering to a patient, such as a mammal, e.g., a human, a therapeutically effective amount of a compound of the invention (e.g., in the form of a pharmaceutically acceptable salt or solvate (e.g., hydrate) thereof). In accordance with a further embodiment, there is provided a method of treating, for example, mesothelioma, asbestosis, pleural effusion, pleural plaque, pleural calcification, diffuse pleural thickening, round atelectasis, and bronchogenic carcinoma, comprising administering to a patient, such as a mammal, e.g., a human, a therapeutically effective amount of a compound of the invention (e.g., in the form of a pharmaceutically acceptable salt or solvate (e.g., hydrate) thereof).

The compounds of the present invention may also be administered in combination with other known therapeutics for the treatment of asbestos-related diseases or disorders including, but not limited to, other PDE-4 inhibitors, anticancer agents, antibiotics, anti-inflammatory agents, cytokines, steroids, immunomodulatory agents, immunosuppressive agents, and combinations thereof. In addition, the compounds of the present invention can be used in combination with conventional therapies used to treat, prevent, or manage asbestos-related diseases or disorders, including, but not limited to, chemotherapy, surgery, radiation therapy, photodynamic therapy, and combinations thereof.

When used in combination with one or more additional pharmaceutical agent or agents for the treatment of asbestos-related diseases or disorders, the compounds of the present invention may be administered prior to, concurrently with, or following administration of the additional pharmaceutical agent or agents. When used in combination with one or more conventional therapies for the treatment of asbestos-related diseases or disorders, the compounds of the present invention may be administered prior to, concurrently with, or following the conventional therapy.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of generally 0.001-100 mg/ky/day, for example, 0.01-100 mg/kg/day, preferably 0.1-70 mg/kg/day, especially 0.5-10 mg/kg/day. Unit dosage forms can contain generally 0.01-1000 mg of active compound, for example, 0.1-50 mg of active compound. For intravenous administration, the compounds can be administered, in single or multiple dosages, at a dosage level of, for example, 0.001-50 mg/kg/day, preferably 0.001-10 mg/kg/day, especially 0.01-1 mg/kg/day. Unit dosage forms can contain, for example, 0.1-10 mg of active compound.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

U.S. application Ser. No. 10/270,724, filed Oct. 16, 2002, and U.S. application Ser. No. 10/825,610, filed Apr. 16, 2004, also describes the synthesis of compounds within the genus of formula I.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

EXAMPLES

All spectra were recorded at 300 MHz on a Bruker Instruments NMR unless otherwise stated. Coupling constants (J) are in Hertz (Hz) and peaks are listed relative to TMS ($\delta$ 0.00 ppm). Sulfonic acid ion exchange resins (SCX) were purchased from Varian Technologies. Analytical HPLC was performed on 4.6 mm×100 mm Waters Sunfire RP C18 5 μm column using (i) a gradient of 20/80 to 80/20 acetonitrile (0.1% formic acid)/water (0.1% formic acid) over 6 min (Method A), (ii) a gradient of 20/80 to 80/20 acetonitrile (0.1% formic acid)/water (0.1% formic acid) over 8 min (Method B), (iii) a gradient of 40/60 to 80/20 acetonitrile (0.1% formic acid)/water (0.1% formic acid) over 6 min (Method C), (iv) a gradient of 40/60 to 80/20 acetonitrile (0.1% formic acid)/water (0.1% formic acid) over 8 min (Method D), (v) an isocratic eluent of 80/20 acetonitrile/water (0.1% formic acid) over 8 minutes (Method E), (vi) a gradient of 10/90 to 90/10 acetonitrile (0.1% formic acid)/water (0.1% formic acid) over 6 min (Method F), or (vii) a gradient of 5/95 to 60/40 acetonitrile (0.1% formic acid)/water (0.1% formic acid) over 6 min (Method G). Preparative HPLC was performed on 30 mm×100 mm Xtera Prep $RP_{18}$ 5μ columns using an 8 min gradient of 95/5 to 20/80 water (0.1% formic acid)/acetonitrile (0.1% formic acid).

Intermediate A 4-(3-Benzyloxy-4-methoxyphenyl)-2-pyrrolidone $NaBH_4$ (14 g, 104.5 mmol) was slowly added to a mixture of $NiCl_2 \cdot 6H_2O$ (8.3 g, 34.8 mmol) in MeOH (750 mL). The mixture was stirred for 30 minutes at 0° C. and then a solution of methyl 3-(3-benzyloxy-4-methoxyphenyl)-4-nitrobutanoate (25 g) in 500 mL of MeOH was added. An additional 8.3 g (34.8 mmol) of $NiCl_2 \cdot 6H_2O$ was then added, followed by the slow portion-wise addition of $NaBH_4$ (9.2 g, 243 mmol). The resulting mixture stirred at 0° C. for 1 hour and then $K_2CO_3$ (150 g) was added in one portion. The mixture was allowed to warm to room temperature and stirred for 18 hours. The suspension was then filtered through celite, washed with MeOH (2×1000 mL) and concentrated. The residue was dissolved in EtOAc (2000 mL) and the organic fraction was successively washed with $H_2O$ (200 mL) and brine (250 mL), dried ($Na_2SO_4$) and concentrated to a solid. Trituration with hexanes/EtOAc provided 13 g of 4-(3-benzyloxy-4-methoxyphenyl)-2-pyrrolidone. An additional 2.3 g of product was obtained by extracting the aqueous fractions with EtOAc and combining this with the trituration solvent, concentrating and triturating with EtOAc/hexanes. Total yield was 15.3 g (74%). $^1$H NMR (400 MHz, $CDCl_3$) $\delta$ 7.44-7.26 (m, 5H), 6.87-6.70 (m, 3H), 5.75 (bs, 1H), 5.14 (s, 2H), 3.87 (s, 3H), 3.70-3.50 (m, 2H), 3.28 (t, 1H), 2.70-2.63 (m, 1H), 2.42-2.35 (m, 1H).

4-(3-Benzyloxy-4-difluoromethoxyphenyl)-2-pyrrolidone was prepared in a similar manner starting with methyl 3-(3-benzyloxy-4-difluoromethoxyphenyl)-4-nitrobutanoate.

The separate enantiomers of the racemic compounds listed above can be obtained through the use of optically active starting materials or by conventional resolution techniques such as chiral HPLC.

Intermediate B 4-(3-Hydroxy-4-methoxyphenyl)-2-pyrrolidone

A mixture of 4-(3-Benzyloxy-4-methoxyphenyl)-2-pyrrolidone (3.5 g, 11.6 mmol) and 350 mg of 10% Pd/C in 50 mL of MeOH and 10 mL of $CH_2Cl_2$ was shaken on a Paar apparatus under a 20 psi atmosphere of hydrogen for 8 hours. The mixture was filtered through celite and concentrated to afford 2.4 g (99%) of 4-(3-Hydroxy-4-methoxyphenyl)-2-pyrrolidone that was used without further purification for the syntheses described in Examples 1-3. $^1$H NMR (300 MHz, $CDCl_3$) $\delta$ 6.82 (s, 1H), 6.79 (d, J=7.6 Hz, 1H), 6.70 (d, J=7.6 Hz, 1H), 6.50 (s, 1H), 3.87 (s, 3H), 3.77 (t, J=8.4 Hz, 1H), 3.62 (t, J=8.0 Hz, 1H), 3.40 (t, J=8.4 Hz, 1H), 2.71 (dd, J=16.8, 8.8 Hz, 1H), 2.49 (dd, J=16.8, 9.0 Hz, 1H).

4-(4-Difluoromethoxy-3-hydroxyphenyl)-2-pyrrolidone was prepared in a similar manner starting with 4-(3-benzyloxy-4-difluoromethoxyphenyl)-2-pyrrolidone.

The separate enantiomers of the racemic compounds listed above can be obtained through the use of optically active starting materials or by conventional resolution techniques such as chiral HPLC. For example, the following have been prepared:

(4S)-4-(4-Difluoromethoxy-3-hydroxyphenyl)-2-pyrrolidone (4R)-4-(4-Difluoromethoxy-3-hydroxyphenyl)-2-pyrrolidone

Example 1

4-[3-(4-Chlorophenoxy)-4-methoxyphenyl]-2-pyrrolidone

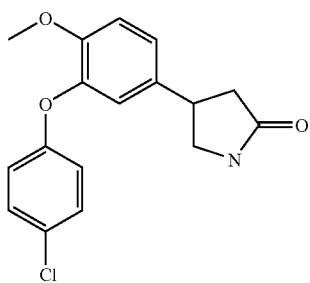

A mixture of 4-(3-hydroxy-4-methoxyphenyl)-2-pyrrolidone (63 mg, 0.3 mmol), 4-chlorophenylboronic acid (61 mg, 0.45 mmol), copper (II) acetate (54 mg, 0.3 mmol), triethylamine (152 mg, 1.5 mmol), dichloromethane (3 mL) and small amount of molecular sieves was allowed to stir at ambient temperature. After 18 hours, the mixture was filtered over celite and the filtrate was concentrated in vacuo. The resulting residue was dissolved in 30 mL of ethyl acetate and washed successively with saturated aqueous sodium bicarbonate solution and brine. Purification by flash column chromatography (ethyl acetate/hexane 1:1 to methanol/dichloromethane 3:97) gave 26 mg (27%) of 4-(3-(4-chlorophenyloxy)-4-methoxyphenyl)-2-pyrrolidone: $^1$H NMR (300 MHz, CDCl$_3$) δ 7.24 (d, J=9.2 Hz, 2H), 7.03 (d, J=8.4 Hz, 1H), 6.95 (d, J=8.4 Hz, 1H), 6.87 (s, 1H), 6.83 (d, J=9.2 Hz, 2H), 5.83 (b, 1H), 3.80 (s, 3H), 3.72 (t, J=8.4 Hz, 1H), 3.65-3.62 (m, 1H), 3.34 (t, J=8.4 Hz, 1H), 2.68 (dd, J=16.8, 8.8 Hz, 1H), 2.41 (dd, J=16.8, 9.2 Hz, 1H).

The following compounds were prepared in a similar manner using different starting material arylboronic acids and aryl vinyl boronic acids:

4-(4-Methoxy-3-phenoxyphenyl)-2-pyrrolidone

4-[4-Methoxy-3-(4-methoxyphenoxy)phenyl]-2-pyrrolidone

4-[4-Methoxy-3-(3-thienyloxy)phenyl]-2-pyrrolidone

4-[3-(4-Fluorophenoxy)-4-methoxyphenyl]-2-pyrrolidone

4-[3-Cyanophenoxy-4-methoxyphenyl]-2-pyrrolidone

4-[4-Methoxy-3-naphthyloxyphenyl]-2-pyrrolidone

4-[4-Methoxy-3-((2-phenyl)ethenyloxy)phenyl]-2-pyrrolidone

4-[4-Methoxy-3-((2-(4-chlorophenyl)ethenyloxy)phenyl]-2-pyrrolidone

The separate enantiomers of racemic compounds listed above can be obtained through the use of optically active starting materials or by conventional resolution techniques such as chiral HPLC.

Example 2

4-(3-Cinnamyloxy-4-methoxyphenyl)-2-pyrrolidone

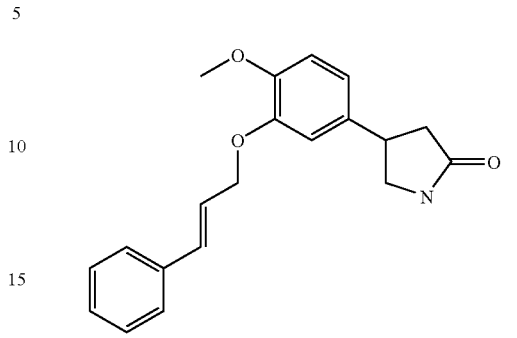

Diisopropylazodicarboxylate (61 mg, 0.6 mmol) was added to a solution of 4-(3-hydroxy-4-methoxyphenyl)-2-pyrrolidone (63 mg, 0.3 mmol), cinnamyl alcohol (43 mg, 0.3 mmol) and triphenyl phosphine (157 mg, 0.6 mmol) in 3 mL of tetrahydrofuran and the reaction mixture was stirred at 70° C. After 12 hours, the same work-up procedure as described in Example 1 gave 70 mg (70%) of 4-(3-cinnamyloxy-4-methoxyphenyl)-2-pyrrolidone: $^1$H NMR (300 MHz, CDCl$_3$) δ 7.40 (d, J=6.8 Hz, 2H), 7.31 (t, J=6.8 Hz, 2H), 7.25 (d, J=7.2 Hz, 1H), 6.86-6.81 (m, 2H), 6.71 (d, J=15.6 Hz, 1H), 6.42 (m, 1H), 5.92 (b, 1H), 4.76 (dd, J=6.0, 1.2 Hz, 2H), 3.87 (s, 3H), 3.71 (t, J=8.8 Hz, 1H), 3.64-3.56 (m, 1H), 3.35 (t, J=8.8 Hz, 1H).

The following compounds were prepared in a similar manner using different starting material alcohols:

4-(3-(3-Cyclohexyl-1-propyloxy)-4-methoxyphenyl)-2-pyrrolidone 4-(4-Methoxy-3-(3-phenyl-1-butyloxy)phenyl)-2-pyrrolidone 4-[4-Methoxy-3-indanyloxyphenyl]-2-pyrrolidone 4-[4-Methoxy-3-(2-(4-chlorophenethyl)ethoxy)phenyl]-2-pyrrolidone 4-[4-Methoxy-3-(2-(4-methylphenyl)ethoxy)phenyl]-2-pyrrolidone 4-[4-Methoxy-3-(2-(2-thienyl)ethoxy)phenyl]-2-pyrrolidone 4-[4-Methoxy-3-(2-(3-chlorophenyl)ethoxy)phenyl]-2-pyrrolidone 4-[4-Methoxy-3-(2-(4-fluorophenyl)ethoxy)phenyl]-2-pyrrolidone 4-[4-Methoxy-3-(2-(4-pyridyl)ethoxy)phenyl-2-pyrrolidone 4-[4-Methoxy-3-(3-(R)-tetrahydrofuranyloxy)phenyl]-2-pyrrolidone 4-[4-Methoxy-3-(3-(S)-tetrahydrofuranyloxy)phenyl]-2-pyrrolidone 4-[4-Methoxy-3-(2-(4-cyanophenyl)ethoxy)phenyl]-2-pyrrolidone 4-[4-Methoxy-3-(3-(4-chlorophenyl)propoxy)phenyl]-2-pyrrolidone 4-[4-Methoxy-3-(2-(3-methylphenyl)ethoxy)phenyl]-2-pyrrolidone 4-(R)-[4-Methoxy-3-(3-(R)-tetrahydrofuranyloxy)phenyl]-2-pyrrolidone 4-(S)-[4-Methoxy-3-(3-(R)-tetrahydrofuranyloxy)phenyl]-2-pyrrolidone 4-(R)-[4-Methoxy-3-(3-(S)-tetrahydrofuranyloxy)phenyl]-2-pyrrolidone 4-(S)-[4-Methoxy-3-(3-(S)-tetrahydrofuranyloxy)phenyl]-2-pyrrolidone 4-[4-Methoxy-3-cyclopropylmethoxyphenyl]-2-pyrrolidone 4-[4-Methoxy-3-cyclobutylmethoxyphenyl]-2-pyrrolidone 4-[4-Methoxy-3-cycloheptyloxyphenyl]-2-pyrrolidone
4-[4-Methoxy-3-cyclohexylmethoxyphenyl]-2-pyrrolidone
4-[4-Methoxy-3-(2-cyclohexyl)ethoxyphenyl]-2-pyrrolidone
4-[4-Methoxy-3-cyclopentylmethoxyphenyl]-2-pyrrolidone
4-[4-Methoxy-3-cyclohexyloxyphenyl]-2-pyrrolidone
4-[4-Methoxy-3-(3-cyclopentyl)propoxyphenyl]-2-pyrrolidone
4-[4-Difluoromethoxy-3-(3-(R)-tetrahydrofuranyloxy)phenyl]-2-pyrrolidone
4-[4-Difluoromethoxy-3-(2-cyclohexylethoxy)phenyl]-2-pyrrolidone
4-[4-Difluoromethoxy-3-(2-phenylethoxy)phenyl]-2-pyrrolidone
4-[4-Difluoromethoxy-3-(cyclopropylmethoxy)phenyl]-2-pyrrolidone The separate enantiomers of racemic compounds listed above can be obtained through the use of optically active starting materials or by conventional resolution techniques such as chiral HPLC. For example, the following have been prepared:
48) (4S)-4-[3-(cyclopropylmethoxy)-4-(difluoromethoxy)phenyl]pyrrolidin-2-one, LC/MS (EI) $t_R$ 3.21 (Method C), m/z 298.1 ($M^+$+1)
50) (4R)-4-[3-(cyclopropylmethoxy)-4-(difluoromethoxy)phenyl]pyrrolidin-2-one, LC/MS (EI) $t_R$ 3.21 (Method C), m/z 298.1 ($M^+$+1)
51) (4S)-4-{4-(difluoromethoxy)-3-[(3R)-tetrahydrofuran-3-yloxy]phenyl}pyrrolidin-2-one, LC/MS (EI) $t_R$ 3.05 (Method C), m/z 314.1 ($M^+$+1)
52) (4R)-4-{4-(difluoromethoxy)-3-[(3R)-tetrahydrofuran-3-yloxy]phenyl}pyrrolidin-2-one, LC/MS (EI) $t_R$ 3.05 (Method C), m/z 314.1 ($M^+$+1)

Example 3

4-(4-Methoxy-3-phenpropyloxyphenyl)-2-pyrrolidone

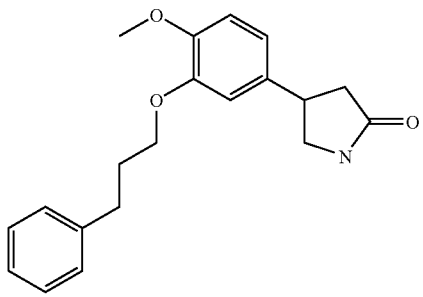

A mixture of 4-(3-hydroxy-4-methoxyphenyl)-2-pyrrolidone (42 mg, 0.2 mmol), 3-phenylpropyl bromide (44 mg, 0.22 mmol), potassium carbonate (83 mg, 0.6 mmol) and N,N-dimethylformamide (3 mL) was allowed stirred at 100° C. for 18 hours, then cooled to 25° C. The solid was removed by filtration, and the filtrate was concentrated in vacuo. The same work up procedure as described in Example 1 gave 47 mg (72%) of 4-(3-(3-phenylpropoxy)-4-methoxyphenyl)-2-pyrrolidone: $^1$H NMR (300 MHz, CDCl$_3$) δ 7.34-7.17 (m, 5H), 6.82 (d, J=8.4 Hz, 1H), 6.78 (d, J=12 Hz, 1H), 6.70 (s, 1H), 6.02 (b, 1H), 4.03 (t, J=7.2 Hz, 2H), 3.84 (s, 3H), 3.75 (t, J=8.8 Hz, 1H), 3.63-3.55 (m, 1H), 3.36 (t, J=8.8 Hz, 1H), 2.82 (t, J=8.0 Hz, 2H), 2.71 (dd, J=16.8, 8.8 Hz, 2H), 2.47 (dd, J=16.6, 8.8 Hz), 2.20-2.13 (m, 2H).

The following compound was prepared in a similar manner using different starting material arylalkyl bromides and alkyl bromides (unless otherwise stated):
4-(4-Methoxy-3-(2-phenylethoxy)phenyl)-2-pyrrolidone
4-(4-Methoxy-3-(3-phenyl-1-propoxy)phenyl)-2-pyrrolidone
4-[4-methoxy-3-[1-(3-phenyl-2-propenyl)oxyphenyl]-2-pyrrolidone
4-[4-methoxy-3-(2-cyclopropylethoxy)phenyl]-2-pyrrolidone
4-[4-methoxy-3-(2-cyclopentylethoxy)phenyl]-2-pyrrolidone
4-[4-Difluoromethoxy-3-cyclopentoxyphenyl]-2-pyrrolidone
4-[4-Difluoromethoxy-3-cyclobutylmethoxyphenyl]-2-pyrrolidone The separate enantiomers of racemic compounds listed above can be obtained through the use of optically active starting materials or by conventional resolution techniques such as chiral HPLC. For example, the following have been prepared:
53) (4S)-4-[3-(cyclobutylmethoxy)-4-(difluoromethoxy)phenyl]pyrrolidin-2-one, LC/MS (EI) $t_R$ 312.1 (Method C), m/z 3.99 ($M^+$+1)
54) (4R)-4-[3-(cyclobutylmethoxy)-4-(difluoromethoxy)phenyl]pyrrolidin-2-one, LC/MS (EI) $t_R$ 312.1 (Method C), m/z 3.99 ($M^+$+1)
102) (4R)-4-[3-(benzyloxy)-4-(difluoromethoxy)phenyl]pyrrolidin-2-one,
103) (4S)-4-[3-(benzyloxy)-4-(difluoromethoxy)phenyl]pyrrolidin-2-one,
104) (4R)-4-[4-(difluoromethoxy)-3-ethoxyphenyl]pyrrolidin-2-one (prepared using iodoethane), LC/MS (EI) $t_R$ 3.23 (Method C), m/z 272.1 ($M^+$+1)
158) (4R)-4-[4-(difluoromethoxy)-3-methoxyphenyl]pyrrolidin-2-one (prepared using methyl iodide), LC/MS (EI) $t_R$ 3.15 (Method C), m/z 258.1 ($M^+$+1)
159) (4R)-4-[4-(difluoromethoxy)-3-isopropoxyphenyl]pyrrolidin-2-one, LC/MS (EI) $t_R$ 3.47 (Method C), m/z 286.2 ($M^+$+1)

Example 4

(4S)-4-(3-Cyclopentyloxy-4-methoxyphenyl)-1-(2,3-difluorobenzyl)-2-pyrrolidone

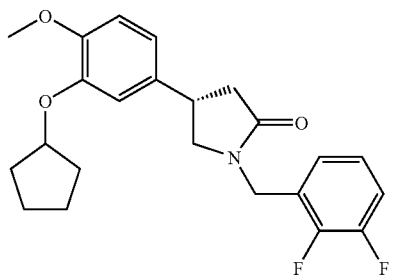

Sodium hydride (20 mg, 0.5 mmol) was added, under an atmosphere of nitrogen at room temperature, to a mixture of 4-(3-cyclopentyloxy-4-methoxyphenyl)-2-pyrrolidone (110 mg, 0.4 mmol) and 110 μL of 15-crown-5 in 2 mL of N,N-dimethylformamide. After 3 hours, the mixture was cooled to 0° C. and 2,3-difluorobenzyl bromide (166 mg, 0.8 mmol) in 2 mL of tetrahydrofuran was added. The resulting mixture was allowed to stir at room temperature for 6 hours. 100 mL of ethyl acetate was added, followed by the addition of 100 mL of ice cold water. After standard aqueous work up, the crude product was purified by flash column chromatography (ethyl acetate/hexane 2:1) to afford 112 mg (70%) of 1-(2,3-difluorobenzyl)-4-(3-cyclopentyloxy-4-methoxyphenyl)-2-pyrrolidone: $^1$H NMR (300 MHz, CDCl$_3$) δ 7.18-6.98 (m, 3H), 6.79 (d, J=8.1 Hz, 1H), 6.90 (d, J=8.1 Hz, 1H), 6.68 (s, 1H) 4.71-4.69 (m, 1H), 4.60 (s, 2H), 3.81 (s, 3H), 3.68 (t, J=9.0 Hz, 1H), 3.66-3.54 (m, 1H), 3.29 (dd, J=9.6, 7.2 Hz, 1H), 2.84 (dd, J=16.8, 9.0 Hz, 1H), 2.57 (dd, J=16.8, 8.4 Hz, 1H), 2.00-1.75 (b, 6H), 1.70-1.52 (b, 2H).

The following compounds were prepared in a similar manner by reaction of different 4-(3-Substituted)-oxy-4-methoxyphenyl)-2-pyrrolidones with different arylalkyl bromides and alkyl bromides:

(4S)-4-(3-Cyclopentyloxy-4-methoxyphenyl)-1-(2-methylbenzyl)-2-pyrrolidone
(4S)-1-(2-Chlorobenzyl)-4-(3-cyclopentyloxy-4-methoxyphenyl)-2-pyrrolidone
(4S)-1-(4-Chlorobenzyl)-4-(3-cyclopentyloxy-4-methoxyphenyl)-2-pyrrolidone
(4S)-1-(3-Chlorobenzyl)-4-(3-cyclopentyloxy-4-methoxyphenyl)-2-pyrrolidone
(4S)-4-(3-Cyclopentyloxy-4-methoxyphenyl)-1-(3-methoxybenzyl)-2-pyrrolidone
(4S)-4-(3-Cyclopentyloxy-4-methoxyphenyl)-1-(2-nitrobenzyl)-2-pyrrolidone
(4S)-4-(3-Cyclopentyloxy-4-methoxyphenyl)-1-(3-nitrobenzyl)-2-pyrrolidone
(4S)-4-(3-Cyclopentyloxy-4-methoxyphenyl)-1-(2-fluorobenzyl)-2-pyrrolidone
(4S)-4-(3-Cyclopentyloxy-4-methoxyphenyl)-1-(3-fluorobenzyl)-2-pyrrolidone
(4S)-4-(3-Cyclopentyloxy-4-methoxyphenyl)-1-(4-fluorobenzyl)-2-pyrrolidone
(4S)-4-(3-Cyclopentyloxy-4-methoxyphenyl)-1-benzyl-2-pyrrolidone
(4S)-1-(4-Cyanobenzyl)-4-(3-cyclopentyloxy-4-methoxyphenyl)-2-pyrrolidone
(4S)-4-(3-Cyclopentyloxy-4-methoxyphenyl)-1-(2-trifluoromethylbenzyl)-2-pyrrolidone
(4S)-4-(3-Cyclopentyloxy-4-methoxyphenyl)-1-(3-trifluoromethylbenzyl)-2-pyrrolidone
(4S)-4-(3-Cyclopentyloxy-4-methoxyphenyl)-1-(4-trifluoromethylbenzyl)-2-pyrrolidone
(4S)-1-(3,5-Bistrifluoromethylbenzyl)-4-(3-cyclopentyloxy-4-methoxyphenyl)-2-pyrrolidone
(4S)-4-(3-Cyclopentyloxy-4-methoxyphenyl)-1-(3,4-difluorobenzyl)-2-pyrrolidone
(4S)-4-(3-Cyclopentyloxy-4-methoxyphenyl)-1-(3,5-difluorobenzyl)-2-pyrrolidone
(4S)-4-(3-Cyclopentyloxy-4-methoxyphenyl)-1-(2,4-difluorobenzyl)-2-pyrrolidone
(4S)-4-(3-Cyclopentyloxy-4-methoxyphenyl)-1-(2,6-difluorobenzyl)-2-pyrrolidone
(4S)-1-(2-Chloro-4-fluorobenzyl)-4-(3-cyclopentyloxy-4-methoxyphenyl)-2-pyrrolidone
(4S)-4-(3-Cyclopentyloxy-4-methoxyphenyl)-1-(3,4-dichlorobenzyl)-2-pyrrolidone
(4S)-1-(4-tert-Butylbenzyl)-4-(3-cyclopentyloxy-4-methoxyphenyl)-2-pyrrolidone
(4S)-4-(3-Cyclopentyloxy-4-methoxyphenyl)-1-ethyl-2-pyrrolidone
(4S)-4-(3-Cyclopentyloxy-4-methoxyphenyl)-1-propyl-2-pyrrolidone
(4S)-4-(3-Cyclopentyloxy-4-methoxyphenyl)-1-butyl-2-pyrrolidone
(4S)-4-(3-Cyclopentyloxy-4-methoxyphenyl)-1-(2-methoxyethyl)-2-pyrrolidone
(4S)-4-(3-Cyclopentyloxy-4-methoxyphenyl)-1-(2-phenylbenzyl)-2-pyrrolidone
(4R)-4-(3-Cyclopentyloxy-4-methoxyphenyl)-1-(2-methylbenzyl)-2-pyrrolidone
(4R)-1-(2-Chlorobenzyl)-4-(3-cyclopentyloxy-4-methoxyphenyl)-2-pyrrolidone
(4R)-1-(4-Chlorobenzyl)-4-(3-cyclopentyloxy-4-methoxyphenyl)-2-pyrrolidone
(4R)-1-(3-Chlorobenzyl)-4-(3-cyclopentyloxy-4-methoxyphenyl)-2-pyrrolidone
(4R)-4-(3-Cyclopentyloxy-4-methoxyphenyl)-1-(3-methoxybenzyl)-2-pyrrolidone
(4R)-4-(3-Cyclopentyloxy-4-methoxyphenyl)-1-(2-nitrobenzyl)-2-pyrrolidone
(4R)-4-(3-Cyclopentyloxy-4-methoxyphenyl)-1-(3-nitrobenzyl)-2-pyrrolidone
(4R)-4-(3-Cyclopentyloxy-4-methoxyphenyl)-1-(2-fluorobenzyl)-2-pyrrolidone
(4R)-4-(3-Cyclopentyloxy-4-methoxyphenyl)-1-(3-fluorobenzyl)-2-pyrrolidone
(4R)-4-(3-Cyclopentyloxy-4-methoxyphenyl)-1-(4-fluorobenzyl)-2-pyrrolidone
(4R)-4-(3-Cyclopentyloxy-4-methoxyphenyl)-1-benzyl-2-pyrrolidone
(4R)-1-(4-Cyanobenzyl)-4-(3-cyclopentyloxy-4-methoxyphenyl)-2-pyrrolidone
(4R)-4-(3-Cyclopentyloxy-4-methoxyphenyl)-1-(2-trifluoromethylbenzyl)-2-pyrrolidone
(4R)-4-(3-Cyclopentyloxy-4-methoxyphenyl)-1-(3-trifluoromethylbenzyl)-2-pyrrolidone
(4R)-4-(3-Cyclopentyloxy-4-methoxyphenyl)-1-(4-trifluoromethylbenzyl)-2-pyrrolidone
(4R)-1-(3,5-bistrifluoromethylbenzyl)-4-(3-cyclopentyloxy-4-methoxyphenyl)-2-pyrrolidone
(4R)-4-(3-Cyclopentyloxy-4-methoxyphenyl)-1-(3,4-difluorobenzyl)-2-pyrrolidone
(4R)-4-(3-Cyclopentyloxy-4-methoxyphenyl)-1-(3,5-difluorobenzyl)-2-pyrrolidone
(4R)-4-(3-Cyclopentyloxy-4-methoxyphenyl)-1-(2,4-difluorobenzyl)-2-pyrrolidone
(4R)-4-(3-Cyclopentyloxy-4-methoxyphenyl)-1-(2,6-difluorobenzyl)-2-pyrrolidone
(4R)-4-(3-Cyclopentyloxy-4-methoxyphenyl)-1-(2,3-difluorobenzyl)-2-pyrrolidone
(4R)-1-(2-Chloro-4-fluorobenzyl)-4-(3-cyclopentyloxy-4-methoxyphenyl)-2-pyrrolidone
(4R)-4-(3-Cyclopentyloxy-4-methoxyphenyl)-1-(3,4-dichlorobenzyl)-2-pyrrolidone
(4R)-1-(4-tert-Butylbenzyl)-4-(3-cyclopentyloxy-4-methoxyphenyl)-2-pyrrolidone
(4R)-4-(3-Cyclopentyloxy-4-methoxyphenyl)-1-ethyl-2-pyrrolidone
(4R)-4-(3-Cyclopentyloxy-4-methoxyphenyl)-1-propyl-2-pyrrolidone
(4R)-4-(3-Cyclopentyloxy-4-methoxyphenyl)-1-butyl-2-pyrrolidone
(4R)-4-(3-Cyclopentyloxy-4-methoxyphenyl)-1-(2-methoxyethyl)-2-pyrrolidone
(4R)-4-(3-Cyclopentyloxy-4-methoxyphenyl)-1-(2-phenylbenzyl)-2-pyrrolidone
4-(3-Cyclopentyloxy-4-methoxyphenyl)-1-(2-chloro-4-fluorobenzyl)-2-pyrrolidone
(4R)-(3-cyclopentyloxy-4-methoxyphenyl)-1-methoxycarbonylmethyl-2-pyrrolidone
(4S)-(3-cyclopentyloxy-4-methoxyphenyl)-1-methoxycarbonylmethyl-2-pyrrolidone
2-[4-(3-benzyloxy-4-methoxyphenyl)-2-oxopyrrolidin-1-yl] propanoic acid
2-[4-(3-ethoxy-4-methoxyphenyl)-2-oxopyrrolidin-1-yl] propanoic acid
4-(3-Cyclopentyloxy-4-methoxyphenyl)-1-cyanomethyl-2-pyrrolidone
4-(3-Cyclopentyloxy-4-methoxyphenyl)-1-cyclopentyl-2-pyrrolidone
4-(3-Cyclopentyloxy-4-methoxyphenyl)-1-(4-methoxybenzoyl)-2-pyrrolidone 4-(3-Cyclopentyloxy-4-methoxyphenyl)-1-(4-chlorobenzoyl)-2-pyrrolidone 4-(3-Cyclopentyloxy-4-methoxyphenyl)-1-(4-nitrobenzoyl)-2-pyrrolidone 4-(3-Cyclopentyloxy-4-methoxyphenyl)-1-benzoyl-2-pyrrolidone (4R)-1-(2,3-Difluorobenzyl)-4-(3-(3-(S)-tetrahydrofuryl)oxy-4-methoxyphenyl)-2-pyrrolidone (4S)-1-(2,3-Difluorobenzyl)-4-(3-(3-(S)-tetrahydrofuryl)oxy-4-methoxyphenyl)-2-pyrrolidone (4R)-1-(2,3-Difluorobenzyl)-4-(3-(3-(R)-tetrahydrofuryl)oxy-4-methoxyphenyl)-2-pyrrolidone (4S)-1-(2,3-Difluorobenzyl)-4-(3-(3-(R)-tetrahydrofuryl)oxy-4-methoxyphenyl)-2-pyrrolidone (4S)-1-[2-(3-Chlorophenoxy)ethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-(2-oxo-2-phenylethyl)-2-pyrrolidone (4S)-4-[4-Methoxy-3-(3R)-tetrahydrofuranyloxyphenyl]-1-(2-oxo-2-(4-methoxyphenyl)ethyl)-2-pyrrolidone, 160) (4R)-4-[4-(difluoromethoxy)-3-isopropoxyphenyl]-1-isopropylpyrrolidin-2-one, LC/MS (EI) $t_R$ 4.11 (Method C), m/z 328.2 (M$^+$+1)

The separate enantiomers of racemic compounds listed above can be obtained through the use of optically active starting materials or by conventional resolution techniques such as chiral HPLC.

Example 5 (Intermediate)

(4S)-4-(3-cyclopentyloxy-4-methoxyphenyl)-2-pyrrolidone-1-acetic acid

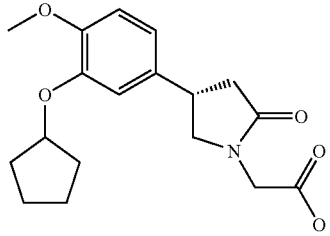

Methyl (4S)-4-(3-cyclopentyloxy-4-methoxyphenyl)-2-pyrrolidone-1-acetate (250 mg, 0.72 mmol) was treated with 8 mL of a 1M solution of potassium hydroxide in 95% methanol. After 10 hours, the reaction solution was acidified with 2N HCl to pH 3, and 30 mL of water was added. The resulting mixture was then extracted with ethyl acetate (2×60 mL) and the organic layer was concentrated. Chromatographic purification (methanol/dichloromethane 5:100) afforded 242 mg (quantitative yield) of 4-(3-cyclopentyloxy-4-methoxyphenyl)-2-pyrrolidone-1-acetic acid: $^1$H NMR (300 MHz, CDCl$_3$) δ 6.85-73 (m, 3H), 4.84-4.74 (m, 1H), 4.20 (d, J=12.0 Hz, 1H), 4.12 (d, J=12.0, 1H), 3.82 (s, 4H), 3.66-3.46 (m, 2H), 2.89 (dd, J=16.8, 8.7 Hz, 1H), 2.58 (dd, J=16.8, 8.4 Hz, 1H), 2.00-1.72 (b, 6H), 1.70-1.50 (b, 2H).

The following compound was prepared in a similar manner using different starting materials:
(4S)-4-(4-Methoxy-3-(3R)-tetrahydrofuranyloxyphenyl)-2-pyrrolidone-1-acetic acid Example 6

(4S)-4-(3-Cyclopentyloxy-4-methoxyphenyl)-2-pyrrolidone-1-acetyl chloride

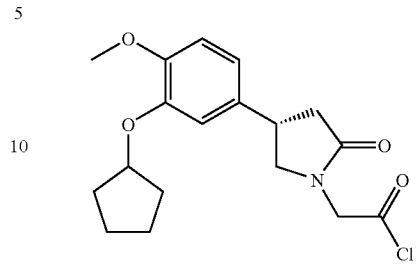

(4S)-4-(3-Cyclopentyloxy-4-methoxyphenyl)-2-pyrrolidone-1-acetic acid (50 mg, 0.15 mmol) was dissolved in 3 mL of CH$_2$Cl$_2$ and treated with oxalylchloride (0.17 mmol) at 4° C. The reaction mixture was stirred at ambient temperature for 2 hours and concentrated in vacuo to give (4S)-4-(3-Cyclopentyloxy-4-methoxyphenyl)-2-pyrrolidone-1-acetyl chloride.

The following compounds were prepared in a similar manner using different starting materials:
4-(3-Cyclopentyloxy-4-methoxyphenyl)-2-pyrrolidone-1-acetyl chloride,
(4R)-4-(3-Cyclopentyloxy-4-methoxyphenyl)-2-pyrrolidone-1-acetyl chloride.

Example 7

4-(3-Cyclopentyloxy-4-methoxyphenyl)-1-(N-(2,6-dimethylphenyl)-aminocarbonylmethyl)-2-pyrrolidone

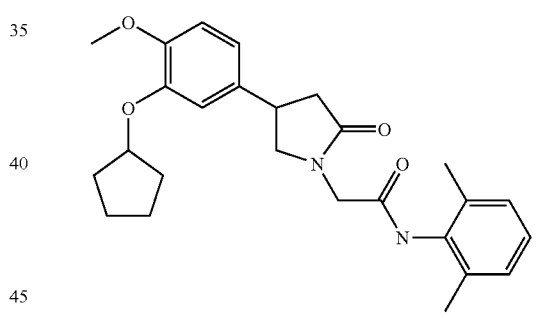

4-(3-Cyclopentyloxy-4-methoxyphenyl)-2-pyrrolidone-1-acetyl chloride was dissolved in 3 mL of CH$_2$Cl$_2$ and added to a solution of 1,6-dimethylaniline (39 mg, 0.3 mmol) in tetrahydrofuran (2 mL) containing diisopropylethylamine (39 mg, 0.3 mmol). After 3 hours, the mixture was concentrated in vacuo, and the residue was dissolved in EtOAc (50 mL), washed with 1 N HCl (50 mL), water (50 mL), and aqueous saturated sodium bicarbonate solution (50 mL). The organic phase was concentrated and the resulting product purified by column chromatography over SiO$_2$ to give 49 mg (75%) of 4-(3-cyclopentyloxy-4-methoxyphenyl)-1-(N-(2,6-dimethylphenyl)-aminocarbonylmethyl)-2-pyrrolidone. $^1$H NMR (300 MHz, CDCl$_3$) δ 7.68 (s, 1H), 7.18-7.03 (m, 3H), 6.84-6.73 (m, 3H), 4.84-4.70 (m, 1H), 4.16 (d, J=11.4 Hz, 1H), 4.13 (d, J=11.4 Hz, 1H), 3.94 (t, J=8.0 Hz, 1H), 3.85-3.75 (m, 4H), 3.68-3.46 (m, 2H), 2.86 (dd, J=16.8, 8.4 Hz, 1H), 2.61 (dd, J=16.8, 8.4 Hz, 1H), 2.19 (s, 6H), 1.98-1.72 (b, 6H), 1.70-1.53 (b, 2H).

The following compounds were formed in a similar manner using different starting materials:
(4S)-4-(3-Cyclopentyloxy-4-methoxyphenyl)-1-(N-(2,6-dimethylphenyl)-aminocarbonylmethyl)-2-pyrrolidone (4R)-4-(3-Cyclopentyloxy-4-methoxyphenyl)-1-(N-(2,6-dimethylphenyl)-aminocarbonylmethyl)-2-pyrrolidone
4-(3-Cyclopentyloxy-4-methoxyphenyl)-1-(N-(2-methylphenyl)-aminocarbonylmethyl)-2-pyrrolidone
(4R)-4-(3-Cyclopentyloxy-4-methoxyphenyl)-1-(N-(2-methylphenyl)-aminocarbonylmethyl)-2-pyrrolidone
(4S)-4-(3-Cyclopentyloxy-4-methoxyphenyl)-1-(N-(2-methylphenyl)-aminocarbonylmethyl)-2-pyrrolidone
4-(3-Cyclopentyloxy-4-methoxyphenyl)-1-(N-(2,3-difluorophenyl)-aminocarbonylmethyl)-2-pyrrolidone
4-(3-Cyclopentyloxy-4-methoxyphenyl)-1-(N-(3-chlorophenyl)-aminocarbonylmethyl)-2-pyrrolidone
4-(3-Cyclopentyloxy-4-methoxyphenyl)-1-(N-(4-pyridyl)-aminocarbonylmethyl)-2-pyrrolidone
4-(3-Cyclopentyloxy-4-methoxyphenyl)-1-(N-(4-methoxyphenyl)-aminocarbonylmethyl)-2-pyrrolidone
4-(3-Cyclopentyloxy-4-methoxyphenyl)-1-(N-(4-chloro-2-fluorophenyl)-aminocarbonylmethyl)-2-pyrrolidone
4-(3-Cyclopentyloxy-4-methoxyphenyl)-1-(N-(3-methylphenyl)-aminocarbonylmethyl)-2-pyrrolidone
4-(3-Cyclopentyloxy-4-methoxyphenyl)-1-(N-(4-methylphenyl)-aminocarbonylmethyl)-2-pyrrolidone
4-(3-Cyclopentyloxy-4-methoxyphenyl)-1-(N-(4-nitrophenyl)-aminocarbonylmethyl)-2-pyrrolidone
(4S)-(3-Cyclopentyloxy-4-methoxyphenyl)-1-(N-(2,3-difluorophenyl)-aminocarbonylmethyl)-2-pyrrolidone
(4R)-(3-Cyclopentyloxy-4-methoxyphenyl)-1-(N-(2,3-difluorophenyl)-aminocarbonylmethyl)-2-pyrrolidone
4-(3-Cyclopentyloxy-4-methoxyphenyl)-1-(N-(3-(2-chloropyridinyl))-aminocarbonylmethyl)-2-pyrrolidone
4-(3-Cyclopentyloxy-4-methoxyphenyl)-1-(N-(2-(2-pyridylethyl))-aminocarbonylmethyl)-2-pyrrolidone
4-(3-Cyclopentyloxy-4-methoxyphenyl)-1-(N-(2-(2-(N-methylpyrrolidinyl)ethyl))-aminocarbonylmethyl)-2-pyrrolidone
4-(3-Cyclopentyloxy-4-methoxyphenyl)-1-(N-(4-pyridylmethyl)-aminocarbonylmethyl)-2-pyrrolidone
4-(3-Cyclopentyloxy-4-methoxyphenyl)-1-(N-(1-imidazoylpropyl)-aminocarbonylmethyl)-2-pyrrolidone
4-(3-Cyclopentyloxy-4-methoxyphenyl)-1-(N-(4-(4-methylpiperazinyl))-hydrazinocarbonylmethyl)-2-pyrrolidone
4-(3-Cyclopentyloxy-4-methoxyphenyl)-1-(N-(2-(N-methylpyrrolidinyl)methyl)-aminocarbonylmethyl)-2-pyrrolidone
4-(3-Cyclopentyloxy-4-methoxyphenyl)-1-(N-(4-pyrimidinyl)-aminocarbonylmethyl)-2-pyrrolidone
4-(3-Cyclopentyloxy-4-methoxyphenyl)-1-(N-(3-(5-methylisoxazolyl))-aminocarbonylmethyl)-2-pyrrolidone
4-(3-Cyclopentyloxy-4-methoxyphenyl)-1-(N-(2,6-dimethylpiperazinyl)-hydrazinocarbonylmethyl)-2-pyrrolidone
4-(3-Cyclopentyloxy-4-methoxyphenyl)-1-(N-(2-(4,5-dimethylthiazolyl))-aminocarbonylmethyl)-2-pyrrolidone
4-(3-Cyclopentyloxy-4-methoxyphenyl)-1-(N-(2-(2-methylpiperidinyl)ethyl)-aminocarbonylmethyl)-2-pyrrolidone
4-(3-Cyclopentyloxy-4-methoxyphenyl)-1-(N-(3,4-dimethoxyphenethyl)-aminocarbonylmethyl)-2-pyrrolidone
4-(3-Cyclopentyloxy-4-methoxyphenyl)-1-(N-(2-pyridinyl)-aminocarbonylmethyl)-2-pyrrolidone
4-(3-Cyclopentyloxy-4-methoxyphenyl)-1-(N-(3-pyridinyl)-aminocarbonylmethyl)-2-pyrrolidone
4-(3-Cyclopentyloxy-4-methoxyphenyl)-1-(N-(3-(2,4-dimethoxypyridinyl))-aminocarbonylmethyl)-2-pyrrolidone
4-(3-Cyclopentyloxy-4-methoxyphenyl)-1-(N-(3-(4-methoxypyridinyl))-aminocarbonylmethyl)-2-pyrrolidone
4-(3-Cyclopentyloxy-4-methoxyphenyl)-1-(N-(4-tert-butyloxycarbonylaminophenyl)-aminocarbonylmethyl)-2-pyrrolidone The separate enantiomers of racemic compounds listed above can be obtained through the use of optically active starting materials or by conventional resolution techniques such as chiral HPLC.

Example 8

4-(3-Cyclopentyloxy-4-methoxyphenyl)-1-(N-(4-anilino)-aminocarbonylmethyl)-2-pyrrolidone

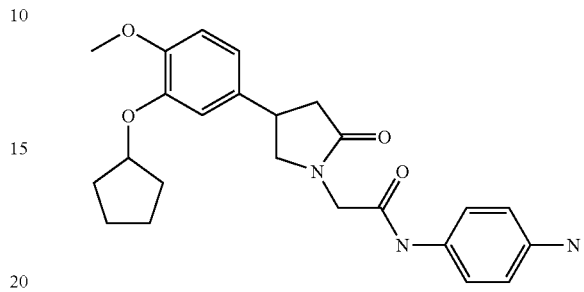

A mixture of 4-(3-cyclopentyloxy-4-methoxyphenyl)-1-(N-(4-tert-butyloxycarbonylaminophenyl)-aminocarbonylmethyl)-2-pyrrolidone (see application Ser. No. 10/270,724, filed Oct. 16, 2002) was stirred in a 1:2 mixture of TFA and dichloromethane for 2 hours at room temperature. The material was concentrated in vacuo and purified by column chromatography over $SiO_2$ to provide 4-(3-cyclopentyloxy-4-methoxyphenyl)-1-(N-(4-anilino)-aminocarbonylmethyl)-2-pyrrolidone. $^1$H NMR (300 MHz, $CDCl_3$) δ7.90 (s, 1H), 7.24 (d, J=6.3 Hz, 2H), 6.83-6.75 (m, 2H), 6.64 (d, J=6.3 Hz, 2H), 4.74 (m, 1H), 4.13 (d, J=15.6 Hz, 1H), 4.03 (d, J=15.6 Hz, 1H), 3.92 (m, 1H), 3.83 (s, 3H), 3.70-3.50 (m, 3H), 2.84 (dd, J=16.5, 7.8 Hz, 1H), 2.61 (dd, J=16.5, 7.8 Hz, 1H), 1.95-1.80 (m 6H), 1.59 (m, 2H).

The following compounds were formed in a similar fashion with different starting materials:
(4S)-4-[4-Methoxy-3-(3R)-tetrahydrofuranyloxyphenyl]-1-[N-(5-(4-piperidinyl)-1,3,4-thiadiazol-2-yl)aminocarbonylmethyl]-2-pyrrolidone,
14) 2-((S)-4-{4-Methoxy-3-[(R)-(tetrahydrofuran-3-yl)oxy]-phenyl}-2-oxopyrrolidin-1-yl)-N-(5-piperidin-4-yl-[1,3,4]thiadiazol-2-yl)-acetamide, LC/MS (EI) $t_R$ 5.17 (Method G), m/z 502.1 ($M^+$+1)

Example 9

(4S)-1-[N-(2,3-Difluorophenyl-(N-methyl)aminocarbonylmethyl)]-4-(4-methoxy-3-(3R)-tetrahydrofuranyloxyphenyl)-2-pyrrolidone

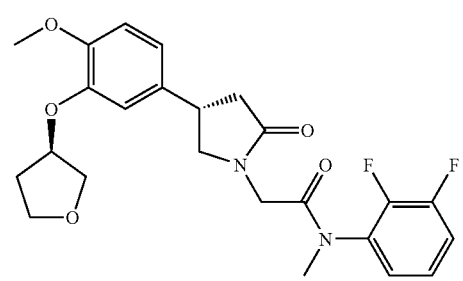

NaH (4.9 mg, 0.12 mmol) was added to a solution of (4S)-1-[N-(2,3-Difluorophenylaminocarbonylmethyl]-4-(4-methoxy-3-(3R)-tetrahydrofuranyloxyphenyl)-2-pyrrolidone (50 mg, 0.112 mmol) in 2 mL of DMF in a in a nitrogen purged flask, cooled to 0° C. The reaction mixture was stirred at 0° C. for 1 hour and then iodomethane (10.5 μL, 0.168 mmol) was added. The resulting mixture was warmed to room temperature and stirred for 16 hours. Concentration, followed by purification by preparative TLC using MeOH/EtOAc/Hexanes (7/46/46) as eluant provided 34.5 mg (67%) of (4S)-1-[N-(2,3-Difluorophenyl-(N-methyl)aminocarbonylmethyl]-4-(4-methoxy-3-(3R)-tetrahydrofuranyloxyphenyl)-2-pyrrolidone. $^1$H NMR (CDCl$_3$) δ 7.25-7.17 (m, 3H), 6.90-6.78 (m, 3H), 5.02 (broad d, 1H), 4.05-4.02 (m, 3H), 3.97-3.89 (m, 2H), 3.83 (s, 3H), 3.73-3.39 (m, 4H), 3.27 (s, 3H), 2.83-2.78 (m, 1H), 2.52-2.48 (m, 1H), 2.17 (broad s, 2H).

The following compounds were made using a similar procedure with different starting materials:

(4S)-4-(4-Methoxy-3-(3R)-tetrahydrofuranyloxyphenyl)-1-[N-(2-methylphenyl-(N-methyl)aminocarbonylmethyl)]-2-pyrrolidone (4S)-4-(4-Methoxy-3-(3R)-tetrahydrofuranyloxyphenyl)-1-[N-(2-(6-methylpyridyl)-(N-methyl)aminocarbonylmethyl)]-2-pyrrolidone (4S)-1-[N-(2,3-Difluorophenyl-(N-ethyl)aminocarbonylmethyl)]-4-(4-methoxy-3-(3R)-tetrahydrofuranyloxyphenyl)-2-pyrrolidone (4S)-1-[N-(2,3-Difluorophenyl-(N-isopropyl)aminocarbonylmethyl)]-4-(4-methoxy-3-(3R)-tetrahydrofuranyloxyphenyl)-2-pyrrolidone (4S)-1-[N-(2,3-Difluorophenyl-(N-cyclopropylmethyl)aminocarbonylmethyl)]-4-(4-methoxy-3-(3R)-tetrahydrofuranyloxyphenyl)-2-pyrrolidone (4S)-1-[N-(2,3-Difluorophenyl)-N-(2-methylpropyl)aminocarbonylmethyl]-4-[4-methoxy-3-(3R)-tetrahydrofuranyloxyphenyl]-2-pyrrolidone (4S)-1-[N-(6-Fluorobenzothiazol-2-yl)-N-(methyl)aminocarbonylmethyl]-4-[4-methoxy-3-(3R)-tetrahydrofuranyloxyphenyl]-2-pyrrolidone (4S)-1-[N-(3-Fluorophenyl)-N-(methyl)aminocarbonylmethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-[N-(4-methoxyphenyl)-N-(methyl)aminocarbonylmethyl]-2-pyrrolidone (4S)-1-[N-(4-Isopropylphenyl)-N-(methyl)aminocarbonylmethyl]-4-[4-methoxy-3-(3R)-tetrahydrofuranyloxyphenyl]-2-pyrrolidone (4S)-1-[N-(3,4-Methylenedioxyphenyl)-N-(methyl)aminocarbonylmethyl]-4-[4-methoxy-3-(3R)-tetrahydrofuranyloxyphenyl]-2-pyrrolidone 4S)-4-[4-Methoxy-3-(3R)-tetrahydrofuranyloxyphenyl]-1-[N-methyl-N-(thiazol-2-yl)aminocarbonylmethyl]-2-pyrrolidone (4S)-1-[N-(Benzothiazol-2-yl)-N-(cyclopropylmethyl)aminocarbonylmethyl]-4-[4-methoxy-3-(3R)-tetrahydrofuranyloxyphenyl]-2-pyrrolidone (4S)-1-[N-Cyclopropylmethyl-N-(6-fluorobenzothiazol-2-yl)aminocarbonylmethyl]-4-[4-methoxy-3-(3R)-tetrahydrofuranyloxyphenyl]-2-pyrrolidone 40) 2-((4S)-4-{4-methoxy-3-[(3R)-tetrahydrofuran-3-yloxy]phenyl}-2-oxopyrrolidin-1-yl)-N-methyl-N-(3-methylisothiazol-5-yl)acetamide, LC/MS (EI) $t_R$ 2.6 (Method C), m/z 446.1 (M$^+$+1)

41) 2-((4S)-4-{4-methoxy-3-[(3R)-tetrahydrofuran-3-yloxy]phenyl}-2-oxopyrrolidin-1-yl)-N-methyl-N-(4-methyl-1,3-thiazol-2-yl)acetamide, LC/MS (EI) $t_R$ 3.02 (Method C), m/z 446.1 (M$^+$+1)

60)  2-((4S)-4-{4-Methoxy-3-[(3R)-tetrahydrofuran-3-yloxy]phenyl}-2-oxopyrrolidin-1-yl)-N-methyl-N-phenylacetamide, LC/MS (EI) $t_R$ 2.91 (Method C), m/z 425.2 (M$^+$+1)

64) 2-((4S)-4-{4-methoxy-3-[(3R)-tetrahydrofuran-3-yloxy]phenyl}-2-oxopyrrolidin-1-yl)-N-methyl-N-(5-pyridin-4-yl-1,3,4-thiadiazol-2-yl)acetamide, LC/MS (EI) $t_R$ 2.9 (Method C), m/z 510.0 (M$^+$+1)

65)  N-(5-cyclopropyl-1,3,4-thiadiazol-2-yl)-2-((4S)-4-{4-methoxy-3-[(3R)-tetrahydrofuran-3-yloxy]phenyl}-2-oxopyrrolidin-1-yl)-N-methylacetamide, LC/MS (EI) $t_R$ 3.1 (Method C), m/z 473.0 (M$^+$+1)

67) 2-{4-[3-(cyclopropylmethoxy)-4-methoxyphenyl]-2-oxopyrrolidin-1-yl}-N-(3-fluorophenyl)-N-methylacetamide, LC/MS (EI) $t_R$ 3.94 (Method C), m/z 427.1 (M$^+$+1)

68)  N-(1-benzyl-3-methyl-1H-pyrazol-5-yl)-2-((4S)-4-{4-methoxy-3-[(3R)-tetrahydrofuran-3-yloxy]phenyl}-2-oxopyrrolidin-1-yl)-N-methylacetamide, LC/MS (EI) $t_R$ 2.97 (Method C), m/z 519.3 (M$^+$+1)

73) N-ethyl-2-((4S)-4-{4-methoxy-3-[(3R)-tetrahydrofuran-3-yloxy]phenyl}-2-oxopyrrolidin-1-yl)-N-(4-methyl-1,3-thiazol-2-yl)acetamide, LC/MS (EI) $t_R$ 3.16 (Method C), m/z 460.0 (M$^+$+1)

74)  N-(cyclopropylmethyl)-2-((4S)-4-{4-methoxy-3-[(3R)-tetrahydrofuran-3-yloxy]phenyl}-2-oxopyrrolidin-1-yl)-N-(4-methyl-1,3-thiazol-2-yl)acetamide, LC/MS (EI) $t_R$ 3.53 (Method C), m/z 486.0 (M$^+$+1)

75) N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 4.1 (Method C), m/z 489.2 (M$^+$+1)

81)  N-(cyclopropylmethyl)-N-(5-cyclopropyl-1,3,4-thiadiazol-2-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 3.34 (Method C), m/z 513.2 (M$^+$+1)

82) 2-{4-[3-(cyclopropylmethoxy)-4-methoxyphenyl]-2-oxopyrrolidin-1-yl}-N-(5-cyclopropyl-1,3,4-thiadiazol-2-yl)-N-methylacetamide, LC/MS (EI) $t_R$ 3.3 (Method C), m/z 457.2 (M$^+$+1)

83) 2-{4-[3-(cyclopropylmethoxy)-4-methoxyphenyl]-2-oxopyrrolidin-1-yl}-N-(cyclopropylmethyl)-N-(5-cyclopropyl-1,3,4-thiadiazol-2-yl)acetamide, LC/MS (EI) $t_R$ 3.93 (Method C), m/z 497.2 (M$^+$+1)

84) 2-{4-[3-(cyclopropylmethoxy)-4-methoxyphenyl]-2-oxopyrrolidin-1-yl}-N-(cyclopropylmethyl)-N-(4-methyl-1,3-thiazol-2-yl)acetamide, LC/MS (EI) $t_R$ 4.32 (Method C), m/z 470.2 (M$^+$+1)

85) 2-{4-[3-(cyclopropylmethoxy)-4-methoxyphenyl]-2-oxopyrrolidin-1-yl}-N-methyl-N-(4-methyl-1,3-thiazol-2-yl)acetamide LC/MS (EI) $t_R$ 3.61 (Method C), m/z 430.1 (M$^+$+1)

86)  2-{4-[3-(cyclopropylmethoxy)-4-(difluoromethoxy)phenyl]-2-oxopyrrolidin-1-yl}-N-methyl-N-(4-methyl-1,3-thiazol-2-yl)acetamide, LC/MS (EI) $t_R$ 4.41 (Method D), m/z 466.2 (M$^+$+1)

87)  2-{4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide, LC/MS (EI) $t_R$ 4.11 (Method D), m/z 493.1 (M$^+$+1)

90)  2-[(4S)-4-(3-ethoxy-4-methoxyphenyl)-2-oxopyrrolidin-1-yl]-N-methyl-N-(4-methyl-1,3-thiazol-2-yl)acetamide, LC/MS (EI) $t_R$ 3.62 (Method C), m/z 404.2 (M$^+$+1)

91)  2-[(4S)-4-(3-ethoxy-4-methoxyphenyl)-2-oxopyrrolidin-1-yl]-N-(3-isopropyl-1,2,4-thiadiazol-5-yl)-N-methylacetamide LC/MS (EI) $t_R$ 3.88 (Method C), m/z 433.1 (M$^+$+1)

92)  N-(5-cyclopropyl-1,3,4-thiadiazol-2-yl)-2-[(4S)-4-(3-ethoxy-4-methoxyphenyl)-2-oxopyrrolidin-1-yl]-N-methylacetamide, LC/MS (EI) $t_R$ 3.36 (Method C), m/z 431.3 (M$^+$+1)

93) N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide LC/MS (EI) $t_R$ 4.56 (Method D), m/z 473.2 (M$^+$+1)

94) 2-[(4R)-4-(3-ethoxy-4-methoxyphenyl)-2-oxopyrrolidin-1-yl]-N-(3-isopropyl-1,2,4-thiadiazol-5-yl)-N-methylacetamide, LC/MS (EI) $t_R$ 3.89 (Method C), m/z 433.1 (M$^+$+1)

95) N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 4.24 (Method C), m/z 515.2 (M$^+$+1)

96) N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide, LC/MS (EI) $t_R$ 4.58 (Method C), m/z 473.2 (M$^+$+1)

98) 2-{(4R)-4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide, 99) 2-{(4S)-4-[3-(cyclopropylmethoxy)-4-(difluoromethoxy)phenyl]-2-oxopyrrolidin-1-yl}-N-(5-cyclopropyl-1,3,4-thiadiazol-2-yl)-N-methylacetamide, 110) 2-{(4S)-4-[3-(cyclopropylmethoxy)-4-methoxyphenyl]-2-oxopyrrolidin-1-yl}-N-(3-isopropyl-1,2,4-thiadiazol-5-yl)-N-methylacetamide, LC/MS (EI) $t_R$ 6.2 (Method A), m/z 459.2 (M$^+$+1)

113) 2-[(4S)-4-(3-isopropoxy-4-methoxyphenyl)-2-oxopyrrolidin-1-yl]-N-(3-isopropyl-1,2,4-thiadiazol-5-yl)-N-methylacetamide, LC/MS (EI) $t_R$ 2.03 (Method C), m/z 447.2 (M$^+$+1)

115) 2-{(4S)-4-[3-(cyclopropylmethoxy)-4-methoxyphenyl]-2-oxopyrrolidin-1-yl}-N-(5-cyclopropyl-1,3,4-thiadiazol-2-yl)-N-methylacetamide, LC/MS (EI) $t_R$ 5.6 (Method A), m/z 457.2 (M$^+$+1)

116) N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide, LC/MS (EI) $t_R$ 1.91 (Method C), m/z 445.1 (M$^+$+1)

118) N-(3-fluorophenyl)-2-[(4S)-4-(3-isopropoxy-4-methoxyphenyl)-2-oxopyrrolidin-1-yl]-N-methylacetamide, LC/MS (EI) $t_R$ 2.21 (Method C), m/z 415.2 (M$^+$+1)

121) 2-[(4S)-4-(3-ethoxy-4-methoxyphenyl)-2-oxopyrrolidin-1-yl]-N-(3-fluorophenyl)-N-methylacetamide, LC/MS (EI) $t_R$ 3.5 (Method C), m/z 401.2 (M$^+$+1)

123) 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide, LC/MS (EI) $t_R$ 4.35 (Method C), m/z 419.1 (M$^+$+1)

125) N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide, LC/MS (EI) $t_R$ 3.69 (Method C), m/z 467.2 (M$^+$+1)

127) 2-{(4S)-4-[4-(difluoromethoxy)-3-ethoxyphenyl]-2-oxopyrrolidin-1-yl}-N-(3-fluorophenyl)-N-methylacetamide, LC/MS (EI) $t_R$ 3.92 (Method C), m/z 432.1 (M$^+$+1)

129) 2-{(4S)-4-[3-(cyclopropylmethoxy)-4-methoxyphenyl]-2-oxopyrrolidin-1-yl}-N-(3-fluorophenyl)-N-methylacetamide, LC/MS (EI) $t_R$ 3.7 (Method C), m/z 427.2 (M$^+$+1)

134) 2-[(4S)-4-(3-ethoxy-4-methoxyphenyl)-2-oxopyrrolidin-1-yl]-N-methyl-N-(3-methylisothiazol-5-yl)acetamide, LC/MS (EI) $t_R$ 3.18 (Method C), m/z 404.1 (M$^+$+1)

147) N-(4-cyclopropyl-1,3-thiazol-2-yl)-2-[(4S)-4-(3-isopropoxy-4-methoxyphenyl)-2-oxopyrrolidin-1-yl]-N-methylacetamide, LC/MS (EI) $t_R$ 3.42 (Method C), m/z 444.1 (M$^+$+1)

148) N-(4-cyclopropyl-1,3-thiazol-2-yl)-2-[(4S)-4-(3-ethoxy-4-methoxyphenyl)-2-oxopyrrolidin-1-yl]-N-methylacetamide, LC/MS (EI) $t_R$ 3.99 (Method C), m/z 430.1 (M$^+$+1)

149) 2-{(4S)-4-[3-(cyclopropylmethoxy)-4-methoxyphenyl]-2-oxopyrrolidin-1-yl}-N-(4-cyclopropyl-1,3-thiazol-2-yl)-N-methylacetamide, LC/MS (EI) $t_R$ 4.3 (Method C), m/z 456.2 (M$^+$+1)

150) 2-{(4S)-4-[3-(cyclopropylmethoxy)-4-methoxyphenyl]-2-oxopyrrolidin-1-yl}-N-methyl-N-(5-methylisoxazol-3-yl)acetamide, LC/MS (EI) $t_R$ 3.7 (Method C), m/z 414.2 (M$^+$+1)

153) 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, LC/MS (EI) $t_R$ 4.65 (Method C), m/z 483.1 (M$^+$+1)

155) N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, LC/MS (EI) $t_R$ 4.79 (Method C), m/z 480.2 (M$^+$+1)

156) 2-{(4S)-4-[4-(difluoromethoxy)-3-isopropoxyphenyl]-2-oxopyrrolidin-1-yl}-N-(3-fluorophenyl)-N-methylacetamide, LC/MS (EI) $t_R$ 4.18 (Method C), m/z 451.1 (M$^+$+1)

157) N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, LC/MS (EI) $t_R$ 4.51 (Method C), m/z 466.1 (M$^+$+1)

162) N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, LC/MS (EI) $t_R$ 3.88 (Method C), m/z 481.1 (M$^+$+1)

164) 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)-N-methylacetamide, LC/MS (EI) $t_R$ 4.64 (Method C), m/z 495.1 (M$^+$+1)

166) 2-{(4S)-4-[3-(cyclopropylmethoxy)-4-(difluoromethoxy)phenyl]-2-oxopyrrolidin-1-yl}-N-(3-fluorophenyl)-N-methylacetamide, LC/MS (EI) $t_R$ 4.23 (Method C), m/z 463.2 (M$^+$+1)

169) 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)-N-methylacetamide, LC/MS (EI) $t_R$ 4.77 (Method C), m/z 492.2 (M$^+$+1)

Example 10A (4S)-4-(4-Methoxy-3-(3R)-tetrahydrofuranyloxyphenyl)-1-[N-(phenylaminocarbonylmethyl)]-2-pyrrolidone

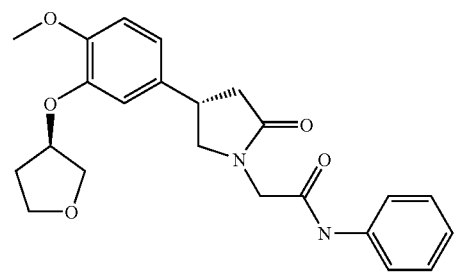

1-Hydroxybenzotriazole (54 mg; 0.35 mmol) was added to a flask containing (4S)-4-(4-methoxy-3-(3R)-tetrahydrofuranyloxyphenyl)-2-pyrrolidone-1-acetic acid (108 mg; 0.32 mmol) in 5 mL of dichloromethane. After 5 minutes, N,N-diisopropylethylamine (61 uL, 0.35 mmol), aniline (32 uL, 0.35 mmol) and O-benzotriazol-1-yl-N,N,N',N'-tetramethyluronium hexafluorophosphate (HBTU) (132 mg; 0.35 mmol) were added. The reaction was stirred at room temperature for 16 hours, then diluted with ethyl acetate (50 mL) and washed with water (25 mL), 1M HCl (25 mL), saturated $K_2CO_3$ (25 mL) and brine (25 mL). After drying over sodium sulfate the solvent was removed under reduced pressure to afford 132 mg (100%) of (4S)-4-(4-methoxy-3-(3R)-tetrahydrofuranyloxyphenyl)-1-[N-(phenylaminocarbonylmethyl)]-2-pyrrolidone as an off white solid. $^1$H NMR (CDCl$_3$; 300 MHz) 8.2 (br s, 1H); 7.5 (d, 2H); 7.3 (t, 2H); 7.1 (t, 2H); 6.9 (s, 2H); 6.7 (s, 1H); 4.9 (br s, 1H); 3.8-4.2 (m, 7H); 3.8 (s, 3H); 3.6 (m, 2H), 2.9 (m, 2H); 2.5 (m, 1H) 2.1 (m, 2H) ppm; MS [M+H]=411; [M+Na]=433.

The following compounds were made using a similar procedure with different starting materials:

(4S)-1-[N-(4,5-Dimethylthiazol)-2-yl)aminocarbonylmethyl]-4-(4-methoxy-3-(3R)-tetrahydrofuranyloxyphenyl)-2-pyrrolidone (4S)-1-[N-(3-Chlorophenyl)aminocarbonylmethyl]-4-(4-methoxy-3-(3R)-tetrahydrofuranyloxyphenyl)-2-pyrrolidone (4S)-4-(4-Methoxy-3-(3R)-tetrahydrofuranyloxyphenyl)-1-[N-(3-methoxycarbonylphenyl)aminocarbonylmethyl)]-2-pyrrolidone (4S)-1-[N-(3-Fluorophenyl)aminocarbonylmethyl]-4-(4-methoxy-3-(3R)-tetrahydrofuranyloxyphenyl)-2-pyrrolidone (4S)-4-(4-Methoxy-3-(3R)-tetrahydrofuranyloxyphenyl)-1-[N-(2-thiazolyl)aminocarbonylmethyl]-2-pyrrolidone (4S)-1-[N-(4-Methoxyphenyl)aminocarbonylmethyl]-4-(4-methoxy-3-(3R)-tetrahydrofuranyloxyphenyl)-2-pyrrolidone (4S)-1-[N-(2,6-Dimethylphenyl)aminocarbonylmethyl]-4-(4-methoxy-3-(3R)-tetrahydrofuranyloxyphenyl)-2-pyrrolidone (4S)-1-[N-(4-Isopropylphenyl)aminocarbonylmethyl]-4-(4-methoxy-3-(3R)-tetrahydrofuranyloxyphenyl)-2-pyrrolidone (4S)-4-(4-Methoxy-3-(3R)-tetrahydrofuranyloxyphenyl)-1-[N-(3,4-methylenedioxyphenyl)aminocarbonylmethyl]-2-pyrrolidone (4S)-4-(4-Methoxy-3-(3R)-tetrahydrofuranyloxyphenyl)-1-[N-(2-(4-trifluoromethyl)pyridyl)aminocarbonylmethyl]-2-pyrrolidone (4S)-1-[N-(2-(5-Chlorobenzoxazolyl)aminocarbonylmethyl)]-4-(4-methoxy-3-(3R)-tetrahydrofuranyloxyphenyl)-2-pyrrolidone (4S)-1-[N-(2-(Benzthiazolyl)aminocarbonylmethyl)]-4-(4-methoxy-3-(3R)-tetrahydrofuranyloxyphenyl)-2-pyrrolidone (4S)-1-[N-(2-(6-Fluorobenzthiazolyl)aminocarbonylmethyl)]-4-(4-methoxy-3-(3R)-tetrahydrofuranyloxyphenyl)-2-pyrrolidone (4S)-1-[N-(2-(Benzimidazolyl)aminocarbonylmethyl)]-4-(4-methoxy-3-(3R)-tetrahydrofuranyloxyphenyl)-2-pyrrolidone (4S)-1-[N-(2,3-Difluorophenylaminocarbonylmethyl]-4-(4-methoxy-3-(3R)-tetrahydrofuranyloxyphenyl)-2-pyrrolidone (4S)-4-(4-Methoxy-3-(3R)-tetrahydrofuranyloxyphenyl)-1-[N-(4-ethoxycarbonylphenyl)aminocarbonylmethyl)]-2-pyrrolidone Example 10B (4S)-4-[4-Methoxy-3-(3R)-tetrahydrofuranyloxyphenyl]-1-[N-(4-methylbenzothiazol-2-yl)aminocarbonylmethyl]-2-pyrrolidone

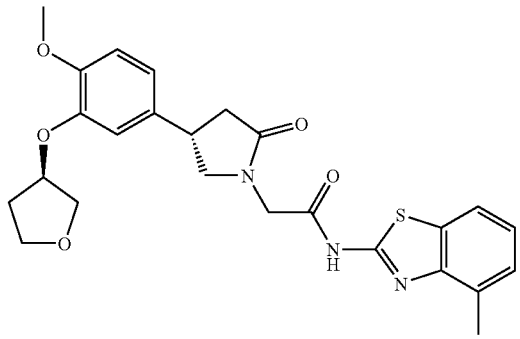

(4S)-4-[4-Methoxy-3-(3R)-tetrahydrofuranyloxyphenyl]-2-pyrrolidone-1-acetic acid (700 mg; 2.09 mmol) was stirred in dichloromethane (35 mL) and HOBT (543 mg; 3.55 mmol) was added in one portion, followed by addition of N,N-diisopropylethylamine (0.62 mL, 3.55 mmol), 2-amino-4-methylbenzothiazole (583 mg, 3.55 mmol) and EDCI HCl (680 mg, 3.55 mmol). The mixture was stirred at room temperature for 48 hours during which time a precipitate formed. The solvent was then evaporated under reduced pressure and the residue was partitioned between ethyl acetate (100 mL) and 1M HCl (50 mL). The organic layer was washed with aqueous sodium bicarbonate (50 mL), brine (25 mL), and dried over sodium sulfate. Evaporation of the solvent afforded 360 mg (36%) of (4S)-4-[4-Methoxy-3-(3R)-tetrahydrofuranyloxyphenyl]-1-[N-(4-methylbenzothiazol-2-yl)aminocarbonylmethyl]-2-pyrrolidone as a white solid. $^1$H NMR (CDCl$_3$; 300 MHz) δ 2.2 (m, 2H); 2.6 (s, 3H); 2.7 (m, 1H); 3.0 (m, 1H); 3.6 (m, 2H); 3.8 (s, 3H); 3.9-4.1 (m, 5H); 4.3 (s, 2H); 5.0 (m, 1H); 6.8 (s, 1H); 6.9 (s, 2H); 7.3 (m, 3H) 7.7 (m, 1H). ES-MS [M+H]+=482.2 Elemental analysis: Calculated for $C_{25}H_{27}N_3O_5S$; % C, 62.35; % H, 5.65; % N, 8.73. Found % C, 62.08; % H, 5.89; % N, 8.65.

The following compounds were made using a similar procedure with different starting materials:

(4S)-4-[4-Methoxy-3-(3R)-tetrahydrofuranyloxyphenyl]-1-[N-(4-methylbenzothiazol-2-yl)aminocarbonylmethyl]-2-pyrrolidone (4S)-4-[4-Methoxy-3-(3R)-tetrahydrofuranyloxyphenyl]-1-[N-(5-methylthiazol-2-yl)aminocarbonylmethyl]-2-pyrrolidone (4S)-4-[4-Methoxy-3-(3R)-tetrahydrofuranyloxyphenyl]-1-[N-(6-methylbenzothiazol-2-yl)aminocarbonylmethyl]-2-pyrrolidone (4S)-4-[4-Methoxy-3-(3R)-tetrahydrofuranyloxyphenyl]-1-[N-(4-methoxybenzothiazol-2-yl)aminocarbonylmethyl]-2-pyrrolidone (4S)-1-[N-(6-Ethoxycarbonylbenzothiazol-2-yl)aminocarbonylmethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-[N-(6-trifluoromethoxylbenzothiazol-2-yl)aminocarbonylmethyl]-2-pyrrolidone (4S)-1-[N-(4-tert-Butylthiazol-2-yl)aminocarbonylmethyl]-4-[4-methoxy-3-(3R)-tetrahydrofuranyloxyphenyl]-2-pyrrolidone (4S)-1-[N-(4-Isopropyloxyphenyl)aminocarbonylmethyl]-4-[4-methoxy-3-(3R)-tetrahydrofuranyloxyphenyl]-2-pyrrolidone (4S)-1-[N-(4-Fluorophenyl)aminocarbonylmethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-[2-(1,2,3,4-tetrahydroisoquinolinyl)carbonylmethyl]-2-pyrrolidone (4S)-4-[4-Methoxy-3-(3R)-tetrahydrofuranyloxyphenyl]-1-[1-(1,2,3,4-tetrahydroquinolinyl)carbonylmethyl]-2-pyrrolidone (4S)-4-[4-Methoxy-3-(3R)-tetrahydrofuranyloxyphenyl]-1-[N-(4-trifluoromethoxyphenyl)aminocarbonylmethyl]-2-pyrrolidone (4S)-4-[4-Methoxy-3-(3R)-tetrahydrofuranyloxyphenyl]-1-[N-(4-methylthiazol-2-yl)aminocarbonylmethyl]-2-pyrrolidone (4S)-1-[N-(4-tert-Butylphenyl)aminocarbonylmethyl]-4-[4-methoxy-3-(3R)-tetrahydrofuranyloxyphenyl]-2-pyrrolidone (4S)-1-[N-(6-Chlorobenzothiazol-2-yl)aminocarbonylmethyl]-4-[4-methoxy-3-(3R)-tetrahydrofuranyloxyphenyl]-2-pyrrolidone (4S)-1-[N-(Indan-2-yl)aminocarbonylmethyl]-4-[4-methoxy-3-(3R)-tetrahydrofuranyloxyphenyl]-2-pyrrolidone (4S)-1-[N-(5-Chlorothiazol-2-yl)aminocarbonylmethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-[N-(4-phenylthiazol-2-yl)aminocarbonylmethyl]-2-pyrrolidone (4S)-4-[4-Methoxy-3-(3R)-tetrahydrofuranyloxyphenyl]-1-[N-(6-methoxybenzothiazol-2-yl)aminocarbonylmethyl]-2-pyrrolidone (4S)-1-[N-(5-Cyclopropyl-1,3,4-thiadiazol-2-yl)aminocarbonylmethyl]-4-[4-methoxy-3-(3R)-tetrahydrofuranyloxyphenyl]-2-pyrrolidone (4S)-1-[N-(Benzothiazol-6-yl)aminocarbonylmethyl]-4-[4-methoxy-3-(3R)-tetrahydrofuranyloxyphenyl]-2-pyrrolidone (4S)-1-[N-(4-Ethoxycarbonylthiazol-2-yl)aminocarbonylmethyl]-4-[4-methoxy-3-(3R)-tetrahydrofuranyloxyphenyl]-2-pyrrolidone (4S)-1-[N-(5-tert-Butyl-1,3,4-thiadiazol-2-yl)aminocarbonylmethyl]-4-[4-methoxy-3-(3R)-tetrahydrofuranyloxyphenyl]-2-pyrrolidone (4S)-1-[N-(2,4-Dimethoxyphenyl)aminocarbonylmethyl]-4-[4-methoxy-3-(3R)-tetrahydrofuranyloxyphenyl]-2-pyrrolidone (4S)-1-[N-(3,5-Dimethoxyphenyl)aminocarbonylmethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-[N-(2,2,3,3-tetrafluorobenzo-1,4-dioxan-6-yl)aminocarbonylmethyl]-2-pyrrolidone (4S)-1-[N-(3,4-(Difluoromethylene)dioxyphenyl)-N-methylaminocarbonylmethyl]-4-[4-methoxy-3-(3R)-tetrahydrofuranyloxyphenyl]-2-pyrrolidone (4S)-1-[N-(3-Fluoro-4-methoxyphenyl)aminocarbonylmethyl]-4-[4-methoxy-3-(3R)-tetrahydrofuranyloxyphenyl]-2-pyrrolidone (4S)-1-[N-(1,4-Benzodioxan-6-yl)aminocarbonylmethyl]-4-[4-methoxy-3-(3R)-tetrahydrofuranyloxyphenyl]-2-pyrrolidone (4S)-1-[N-(2-Fluorophenyl)aminocarbonylmethyl]-4-[4-methoxy-3-(3R)-tetrahydrofuranyloxyphenyl]-2-pyrrolidone (4S)-1-[N-(3,4-Dimethoxyphenyl)aminocarbonylmethyl]-4-[4-methoxy-3-(3R)-tetrahydrofuranyloxyphenyl]-2-pyrrolidone (4S)-1-[N-(3,4-Difluorophenyl)aminocarbonylmethyl]-4-[4-methoxy-3-(3R)-tetrahydrofuranyloxyphenyl]-2-pyrrolidone (4S)-1-[N-(4-Methanesulfonamidophenyl)aminocarbonylmethyl]-4-[4-methoxy-3-(3R)-tetrahydrofuranyloxyphenyl]-2-pyrrolidone (4S)-1-[N-(4-(4-Fluorophenyl)thiazol-2-yl)aminocarbonylmethyl]-4-[4-methoxy-3-(3R)-tetrahydrofuranyloxyphenyl]-2-pyrrolidone (4S)-1-[N-(3-Fluoro-4-methylphenyl)aminocarbonylmethyl]-4-[4-methoxy-3-(3R)-tetrahydrofuranyloxyphenyl]-2-pyrrolidone (4S)-1-[N-(4,6-Difluorobenzothiazol-2-yl)aminocarbonylmethyl]-4-[4-methoxy-3-(3R)-tetrahydrofuranyloxyphenyl]-2-pyrrolidone (4R)-1-[N-(3-Fluorophenyl)aminocarbonylmethyl]-4-[4-methoxy-3-(3S)-tetrahydrofuranyloxyphenyl]-2-pyrrolidone (4S)-1-[N-(4-tert-Butyloxycarbonyl-3-fluorophenyl)aminocarbonylmethyl]-4-[4-methoxy-3-(3R)-tetrahydrofuranyloxyphenyl]-2-pyrrolidone (4S)-1-[N-(4-Ethanesulfonamidophenyl)aminocarbonylmethyl]-4-[4-methoxy-3-(3R)-tetrahydrofuranyloxyphenyl]-2-pyrrolidone (4S)-1-[N-(4-Benzenesulfonamidophenyl)aminocarbonylmethyl]-4-[4-methoxy-3-(3R)-tetrahydrofuranyloxyphenyl]-2-pyrrolidone (4S)-1-[N-(4-(4-Fluorobenzene)sulfonamidophenyl)aminocarbonylmethyl]-4-[4-methoxy-3-(3R)-tetrahydrofuranyloxyphenyl]-2-pyrrolidone (4S)-1-[N-(2,3-Difluorobenzyl)aminocarbonylmethyl]-4-[4-methoxy-3-(3R)-tetrahydrofuranyloxyphenyl]-2-pyrrolidone (4S)-1-[N-(5-Cyclopropylmethyl-1,3,4-thiadiazol-2-yl)aminocarbonylmethyl]-4-[4-methoxy-3-(3R)-tetrahydrofuranyloxyphenyl]-2-pyrrolidone (4S)-1-[N-(6-Ethylpyridin-2-yl)aminocarbonylmethyl]-4-[4-methoxy-3-(3R)-tetrahydrofuranyloxyphenyl]-2-pyrrolidone (4S)-1-[N-(3-Fluorobenzyl)aminocarbonylmethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-[N-(2-methylbenzyl)aminocarbonylmethyl]-2-pyrrolidone (4S)-1-[N-(4-Methanesulfonylbenzyl)aminocarbonylmethyl]-4-[4-Methoxy-3-(3R)-tetrahydrofuranyloxyphenyl]-2-pyrrolidone (4S)-1-[N-(4-Aminosufonylbenzyl)aminocarbonylmethyl]-4-[4-methoxy-3-(3R)-tetrahydrofuranyloxyphenyl]-2-pyrrolidone (4S)-1-[N-(Benzothiazol-2-yl)methylaminocarbonylmethyl]-4-[4-methoxy-3-(3R)-tetrahydrofuranyloxyphenyl]-2-pyrrolidone (4S)-4-[4-Methoxy-3-(3R)-tetrahydrofuranyloxyphenyl]-1-[N-(3-methylpyridin-2-yl)methylaminocarbonylmethyl]-2-pyrrolidone (4S)-4-[4-Methoxy-3-(3R)-tetrahydrofuranyloxyphenyl]-1-[N-(5-trifluoromethyl-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(4-pyridyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(4-(3-pyridyl)thiazol-2-yl)aminocarbonylmethyl]-2-pyrrolidone (4S)-4-[4-Methoxy-3-(3R)-tetrahydrofuranyloxyphenyl]-1-[N-(4-(2-pyridyl)thiazol-2-yl)aminocarbonylmethyl]-2-pyrrolidone (4S)-4-[4-Methoxy-3-(3R)-tetrahydrofuranyloxyphenyl]-1-[N-(4-(4-pyridyl)thiazol-2-yl)aminocarbonylmethyl]-2-pyrrolidone (4S)-4-[4-Methoxy-3-(3R)-tetrahydrofuranyloxyphenyl]-1-[N-(5-(4-pyridyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-ethoxycarbonyl-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-methoxycarbonyl-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(3,4-methylenedioxyphenyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(2-thienyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(2-thienylmethyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(2-propyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(2-pyrazinyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-methoxymethyl-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(2-tetrahydrofuranyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-aminosulfonyl-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(4-methoxyphenyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(4-methoxyphenyloxymethyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(4-morpholinylcarbonylmethyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(1-piperidinylcarbonylmethyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(1-pyrrolidinylcarbonylmethyl)-1,3,4-thiadiazol-2-yl)aminocarbonylmethyl]-2-pyrrolidone (4S)-4-[4-Methoxy-3-(3R)-tetrahydrofuranyloxyphenyl]-1-[N-(5-(4-(N-tertbutyloxycarbonyl)piperidinyl)-1,3,4-thiadiazol-2-yl)aminocarbonylmethyl]-2-pyrrolidone (4S)-1-[N-(4-Ethoxycarbonylthiazol-2-yl)aminocarbonylmethyl]-4-[4-methoxy-3-(3R)-tetrahydrofuranyloxyphenyl]-2-pyrrolidone (4S)-1-[N-(4-tert-butyloxycarbonyl-3-fluorophenyl)aminocarbonylmethyl]-4-[4-methoxy-3-(3R)-tetrahydrofuranyloxyphenyl]-2-pyrrolidone 1) N-[5-(aminosulfonyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide, LC/MS (EI) $t_R$ 2.68 (Method C), m/z 498.2 (M$^+$+1)

2) N-[5-(4-methoxyphenyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide, LC/MS (EI) $t_R$ 3.2 (Method C), m/z 525.2 (M$^+$+1)

3) 2-((4S)-4-{4-methoxy-3-[(3R)-tetrahydrofuran-3-yloxy]phenyl}-2-oxopyrrolidin-1-yl)-N-1,3,4-thiadiazol-2-ylacetamide, LC/MS (EI) $t_R$ 2.31 (Method C), m/z 419.1 (M$^+$+1)

4) N-[5-(2-furyl)-1,3,4-thiadiazol-2-yl]-2-((4S)-4-{4-methoxy-3-[(3R)-tetrahydrofuran-3-yloxy]phenyl}-2-oxopyrrolidin-1-yl)acetamide, LC/MS (EI) $t_R$ 3.12 (Method C), m/z 485.1 (M$^+$+1)

5) 2-((4S)-4-{4-methoxy-3-[(3R)-tetrahydrofuran-3-yloxy]phenyl}-2-oxopyrrolidin-1-yl)-N-[5-(2-oxo-2-piperidin-1-ylethyl)-1,3,4-thiadiazol-2-yl]acetamide, LC/MS (EI) $t_R$ 2.8 (Method C), m/z 544.3 (M$^+$+1)

6) 2-((4S)-4-{4-methoxy-3-[(3R)-tetrahydrofuran-3-yloxy]phenyl}-2-oxopyrrolidin-1-yl)-N-[5-(2-piperidin-1-ylethyl)-1,3,4-thiadiazol-2-yl]acetamide, LC/MS (EI) $t_R$ 2.2 (Method C), m/z 530.2 (M$^+$+1)

7) N-{5-[(4-methoxyphenoxy)methyl]-1,3,4-thiadiazol-2-yl}-2-((4S)-4-{4-methoxy-3-[(3R)-tetrahydrofuran-3-yloxy]phenyl}-2-oxopyrrolidin-1-yl)acetamide, LC/MS (EI) $t_R$ 3.35 (Method C), m/z 555.2 (M$^+$+1)

8) 2-((4S)-4-{4-methoxy-3-[(3R)-tetrahydrofuran-3-yloxy]phenyl}-2-oxopyrrolidin-1-yl)-N-[5-(2-morpholin-4-yl-2-oxoethyl)-1,3,4-thiadiazol-2-yl]acetamide, LC/MS (EI) $t_R$ 2.48 (Method C), m/z 546.2 (M$^+$+1)

9) 2-((4S)-4-{4-methoxy-3-[(3R)-tetrahydrofuran-3-yloxy]phenyl}-2-oxopyrrolidin-1-yl)-N-[5-(2-oxo-2-pyrrolidin-1-ylethyl)-1,3,4-thiadiazol-2-yl]acetamide, LC/MS (EI) $t_R$ 2.61 (Method C), m/z 530.3 (M$^+$+1)

10) 2-((4S)-4-{4-methoxy-3-[(3R)-tetrahydrofuran-3-yloxy]phenyl}-2-oxopyrrolidin-1-yl)-N-(3-phenyl-1,2,4-thiadiazol-5-yl)acetamide, LC/MS (EI) $t_R$ 3.83 (Method C), m/z 495.1 (M$^+$+1)

11) 2-((4S)-4-{4-methoxy-3-[(3R)-tetrahydrofuran-3-yloxy]phenyl}-2-oxopyrrolidin-1-yl)-N-(5-phenyl-1,3,4-thiadiazol-2-yl)acetamide, LC/MS (EI) $t_R$ 3.21 (Method C), m/z 495.1 (M$^+$+1)

12) N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 3.42 (Method C), m/z 461.1 (M$^+$+1)

13) 2-((S)-4-{4-Methoxy-3-[(R)-(tetrahydrofuran-3-yl)oxy]-phenyl}-2-oxopyrrolidin-1-yl)-N-(5-(1-tert-butyloxycarbonylpiperidin)-4-yl-[1,3,4]thiadiazol-2-yl)-acetamide, 15) 2-((S)-4-{4-Methoxy-3-[(R)-(tetrahydrofuran-3-yl)oxy]-phenyl}-2-oxopyrrolidin-1-yl)-N-(3-methyl-isothiazol-5-yl)-acetamide, LC/MS (EI) $t_R$ 2.89 (Method C), m/z 432.1 (M$^+$+1)

16) 2-((4S)-4-{4-methoxy-3-[(3R)-tetrahydrofuran-3-yloxy]phenyl}-2-oxopyrrolidin-1-yl)-N-(5-methylisoxazol-3-yl)acetamide, LC/MS (EI) $t_R$ 2.91 (Method C), m/z 416.2 (M$^+$+1)

17) N-Isoxazol-3-yl-2-((S)-4-{4-methoxy-3-[(R)-(tetrahydrofuran-3-yl)oxy]-phenyl}-2-oxo-pyrrolidin-1-yl)-acetamide, LC/MS (EI) $t_R$ 2.77 (Method C), m/z 402.1 (M$^+$+1)

18) 2-((4S)-4-{4-methoxy-3-[(3R)-tetrahydrofuran-3-yloxy]phenyl}-2-oxopyrrolidin-1-yl)-N-(3-methyl-1H-pyrazol-5-yl)acetamide, LC/MS (EI) $t_R$ 3.05 (Method C), m/z 415.2 ($M^+$+1)

19) N-(4-Benzenesulfonyl-thiophen-3-yl)-2-((S)-4-{4-methoxy-3-[(R)-(tetrahydrofuran-3-yl)oxy]-phenyl}-2-oxo-pyrrolidin-1-yl)-acetamide, LC/MS (EI) $t_R$ 3.73 (Method C), m/z 557.1 ($M^+$+1)

20) 2-((S)-4-{4-Methoxy-3-[(R)-(tetrahydrofuran-3-yl)oxy]-phenyl}-2-oxopyrrolidin-1-yl)-N-(1H-pyrazol-3-yl)-acetamide, LC/MS (EI) $t_R$ 2.3 (Method X), m/z 401.0 ($M^+$+1)

21) 2-((4S)-4-{4-methoxy-3-[(3R)-tetrahydrofuran-3-yloxy]phenyl}-2-oxopyrrolidin-1-yl)-N-(5-methyl-1,3,4-thiadiazol-2-yl)acetamide, LC/MS (EI) $t_R$ 2.49 (Method C), m/z 433.0 ($M^+$+1)

22) 2-((4S)-4-{4-methoxy-3-[(3R)-tetrahydrofuran-3-yloxy]phenyl}-2-oxopyrrolidin-1-yl)-N-(3-methyl-1,2,4-thiadiazol-5-yl)acetamide, LC/MS (EI) $t_R$ 2.8 (Method C), m/z 433.1 ($M^+$+1)

23) 2-((4S)-4-{4-methoxy-3-[(3R)-tetrahydrofuran-3-yloxy]phenyl}-2-oxopyrrolidin-1-yl)-N-(3-methoxy-1,2,4-thiadiazol-5-yl)acetamide, LC/MS (EI) $t_R$ 2.96 (Method C), m/z 449.1 ($M^+$+1)

24) N-(3-ethyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 3.09 (Method C), m/z 447.2 ($M^+$+1)

25) 5-{[(((4S)-4-{4-methoxy-3-[(3R)-tetrahydrofuran-3-yloxy]phenyl}-2-oxopyrrolidin-1-yl)acetyl]amino}-3-methylisoxazole-4-carboxamide, LC/MS (EI) $t_R$ 2.57 (Method C), m/z 459.0 ($M^+$+1)

26) 2-((4S)-4-{4-methoxy-3-[(3R)-tetrahydrofuran-3-yloxy]phenyl}-2-oxopyrrolidin-1-yl)-N-(3-methylisoxazol-5-yl)acetamide, LC/MS (EI) $t_R$ 2.9 (Method C), m/z 416.2 ($M^+$+1)

27) 2-((4S)-4-{4-methoxy-3-[(3R)-tetrahydrofuran-3-yloxy]phenyl}-2-oxopyrrolidin-1-yl)-N-(5-methyl-3-phenylisoxazol-4-yl)acetamide, LC/MS (EI) $t_R$ 3.24 (Method C), m/z 492.2 ($M^+$+1)

28) N-(3,5-dimethylisoxazol-4-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 2.7 (Method C), m/z 430.0 ($M^+$+1)

29) 2-((4S)-4-{4-methoxy-3-[(3R)-tetrahydrofuran-3-yloxy]phenyl}-2-oxopyrrolidin-1-yl)-N-pyrazin-2-ylacetamide, LC/MS (EI) $t_R$ 2.7 (Method B), m/z 413.1 ($M^+$+1)

30) N-(2-Ethyl-2H-pyrazol-3-yl)-2-((S)-4-{4-methoxy-3-[(R)-(tetrahydrofuran-3-yl)oxy]-phenyl}-2-oxo-pyrrolidin-1-yl)-acetamide, LC/MS (EI) $t_R$ 2.66 (Method C), m/z 429.0 ($M^+$+1)

31) 2-((4S)-4-{4-methoxy-3-[(3R)-tetrahydrofuran-3-yloxy]phenyl}-2-oxopyrrolidin-1-yl)-N-(3-phenylisoxazol-5-yl)acetamide, LC/MS (EI) $t_R$ 3.63 (Method C), m/z 478.2 ($M^+$+1)

32) N-(3-anilino-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 3.16 (Method C), m/z 510.1 ($M^+$+1)

33) 2-{(4R)-4-[3-(benzyloxy)-4-methoxyphenyl]-2-oxopyrrolidin-1-yl}-N-(3-methylisothiazol-5-yl)acetamide, LC/MS (EI) $t_R$ 3.8 (Method C), m/z 452.0 ($M^+$+1)

34) 2-{(4S)-4-[3-(benzyloxy)-4-methoxyphenyl]-2-oxopyrrolidin-1-yl}-N-(3-methylisothiazol-5-yl)acetamide, LC/MS (EI) $t_R$ 3.8 (Method C), m/z 452.0 ($M^+$+1)

35) N-(3-cyano-2-thienyl)-2-((4S)-4-{4-methoxy-3-[(3R)-tetrahydrofuran-3-yloxy]phenyl}-2-oxopyrrolidin-1-yl)acetamide, LC/MS (EI) $t_R$ 3.22 (Method C), m/z 442.2 ($M^+$+1)

36) 2-((4S)-4-{4-methoxy-3-[(3R)-tetrahydrofuran-3-yloxy]phenyl}-2-oxopyrrolidin-1-yl)-N-[4-(2-thienyl)-1,3-thiazol-2-yl]acetamide LC/MS (EI) $t_R$ 3.79 (Method C), m/z 500.0 ($M^+$+1)

37) 2-((4S)-4-{4-methoxy-3-[(3R)-tetrahydrofuran-3-yloxy]phenyl}-2-oxopyrrolidin-1-yl)-N-[4-(trifluoromethyl)-1,3-thiazol-2-yl]acetamide, LC/MS (EI) $t_R$ 3.51 (Method C), m/z 486.0 ($M^+$+1)

38) 2-[4-(3-ethoxy-4-methoxyphenyl)-2-oxopyrrolidin-1-yl]-N-(3-fluorophenyl)acetamide, LC/MS (EI) $t_R$ 3.4 (Method C), m/z 387.1 ($M^+$+1X)

39) 2-[4-(3-ethoxy-4-methoxyphenyl)-2-oxopyrrolidin-1-yl]-N-(3-methyl-1H-pyrazol-5-yl)acetamide, LC/MS (EI) $t_R$ 2.45 (Method C), m/z 373.2 ($M^+$+1)

42) 2-[4-(3-ethoxy-4-methoxyphenyl)-2-oxopyrrolidin-1-yl]-N-(5-methylisoxazol-3-yl)acetamide, LC/MS (EI) $t_R$ 3.17 (Method C), m/z 374.0 ($M^+$+1)

43) 2-[4-(3-ethoxy-4-methoxyphenyl)-2-oxopyrrolidin-1-yl]-N-(4-methyl-1,3-thiazol-2-yl)acetamide, LC/MS (EI) $t_R$ 3.42 (Method C), m/z 390.0 ($M^+$+1)

44) 2-[4-(3-ethoxy-4-methoxyphenyl)-2-oxopyrrolidin-1-yl]-N-(3-methylisothiazol-5-yl)acetamide, LC/MS (EI) $t_R$ 2.76 (Method C), m/z 390.0 ($M^+$+1)

45) 2-[4-(3-ethoxy-4-methoxyphenyl)-2-oxopyrrolidin-1-yl]-N-(6-methylpyridin-2-yl)acetamide, LC/MS (EI) $t_R$ 3.15 (Method C), m/z 384.1 ($M^+$+1)

46) 2-{4-[3-(cyclopropylmethoxy)-4-methoxyphenyl]-2-oxopyrrolidin-1-yl}-N-(4-methyl-1,3-thiazol-2-yl)acetamide, LC/MS (EI) $t_R$ 3.27 (Method C), m/z 416.2 ($M^+$+1)

47) 2-{4-[3-(cyclopropylmethoxy)-4-methoxyphenyl]-2-oxopyrrolidin-1-yl}-N-(3-fluorophenyl)acetamide, LC/MS (EI) $t_R$ 3.67 (Method C), m/z 298.1 ($M^+$+1)

49) 2-{4-[3-(cyclopropylmethoxy)-4-methoxyphenyl]-2-oxopyrrolidin-1-yl}-N-(5-methyl-1H-pyrazol-3-yl)acetamide, LC/MS (EI) $t_R$ 3.15 (Method C), m/z 399.2 ($M^+$+1)

55) 2-{4-[3-(cyclopropylmethoxy)-4-methoxyphenyl]-2-oxopyrrolidin-1-yl}-N-(5-cyclopropyl-1,3,4-thiadiazol-2-yl)acetamide, LC/MS (EI) $t_R$ 3.12 (Method C), m/z 443.1 ($M^+$+1)

56) 2-{4-[3-(cyclopropylmethoxy)-4-methoxyphenyl]-2-oxopyrrolidin-1-yl}-N-(6-methylpyridin-2-yl)acetamide, LC/MS (EI) $t_R$ 3.19 (Method C), m/z 410.2 ($M^+$+1)

57) 2-{4-[3-(cyclopropylmethoxy)-4-methoxyphenyl]-2-oxopyrrolidin-1-yl}-N-(3-methylisoxazol-5-yl)acetamide, LC/MS (EI) $t_R$ 3.15 (Method C), m/z 400.2 ($M^+$+1)

58) 2-{4-[3-(cyclopropylmethoxy)-4-methoxyphenyl]-2-oxopyrrolidin-1-yl}-N-(3-isopropyl-1,2,4-thiadiazol-5-yl)acetamide, LC/MS (EI) $t_R$ 3.69 (Method C), m/z 445.2 ($M^+$+1)

59) 2-{4-[3-(cyclopropylmethoxy)-4-methoxyphenyl]-2-oxopyrrolidin-1-yl}-N-(3-methylisothiazol-5-yl)acetamide, LC/MS (EI) $t_R$ 2.91 (Method C), m/z 425.2 ($M^+$+1)

61) 2-{4-[3-(cyclobutylmethoxy)-4-methoxyphenyl]-2-oxopyrrolidin-1-yl}-N-(3-fluorophenyl)acetamide, LC/MS (EI) $t_R$ 4.5 (Method C), m/z 427.2 ($M^+$+1)

62) 2-{4-[3-(cyclobutylmethoxy)-4-methoxyphenyl]-2-oxopyrrolidin-1-yl}-N-(5-methylisoxazol-3-yl)acetamide, LC/MS (EI) $t_R$ 3.9 (Method C), m/z 414.2 ($M^+$+1)

63) 2-{4-[3-(cyclobutylmethoxy)-4-methoxyphenyl]-2-oxopyrrolidin-1-yl}-N-(6-methylpyridin-2-yl)acetamide, LC/MS (EI) $t_R$ 4.0 (Method C), m/z 424.2 ($M^+$+1)

66) 2-{4-[3-(cyclobutylmethoxy)-4-methoxyphenyl]-2-oxopyrrolidin-1-yl}-N-(4-methyl-1,3-thiazol-2-yl)acetamide, LC/MS (EI) $t_R$ 4.1 (Method C), m/z 430.1 (M$^+$+1) NO DATA 69) 2-{(4S)-4-[3-(cyclobutylmethoxy)-4-methoxyphenyl]-2-oxopyrrolidin-1-yl}-N-(5-methylisoxazol-3-yl)acetamide, LC/MS (EI) $t_R$ 3.8 (Method C), m/z 414.2 (M$^+$+1)

70) 2-{(4S)-4-[3-(cyclopropylmethoxy)-4-methoxyphenyl]-2-oxopyrrolidin-1-yl}-N-(3-fluorophenyl)acetamide, 71) 2-{(4R)-4-[3-(cyclobutylmethoxy)-4-methoxyphenyl]-2-oxopyrrolidin-1-yl}-N-(5-methylisoxazol-3-yl)acetamide, 72) 2-{(4R)-4-[3-(cyclopropylmethoxy)-4-methoxyphenyl]-2-oxopyrrolidin-1-yl}-N-(3-fluorophenyl)acetamide, 76) 2-{(4R)-4-[3-(cyclopropylmethoxy)-4-methoxyphenyl]-2-oxopyrrolidin-1-yl}-N-(4-methyl-1,3-thiazol-2-yl)acetamide, 77) 2-{(4S)-4-[3-(cyclopropylmethoxy)-4-methoxyphenyl]-2-oxopyrrolidin-1-yl}-N-(4-methyl-1,3-thiazol-2-yl)acetamide 78) 2-{(4R)-4-[3-(cyclopropylmethoxy)-4-methoxyphenyl]-2-oxopyrrolidin-1-yl}-N-(3-methylisothiazol-5-yl)acetamide, 79) 2-{(4S)-4-[3-(cyclopropylmethoxy)-4-methoxyphenyl]-2-oxopyrrolidin-1-yl}-N-(3-methylisothiazol-5-yl)acetamide, 80) 2-{(4S)-4-[3-(cyclobutylmethoxy)-4-methoxyphenyl]-2-oxopyrrolidin-1-yl}-N-(3-fluorophenyl)acetamide, 88) 2-[(4S)-4-(3-ethoxy-4-methoxyphenyl)-2-oxopyrrolidin-1-yl]-N-(3-fluorophenyl)acetamide, LC/MS (EI) $t_R$ 3.43 (Method C), m/z 387.1 (m++1)

89) 2-[(4R)-4-(3-ethoxy-4-methoxyphenyl)-2-oxopyrrolidin-1-yl]-N-(3-fluorophenyl)acetamide, LC/MS (EI) $t_R$ 3.43 (Method C), m/z 387.1 (M$^+$+1)

97) N-(4-cyclopropyl-1,3-thiazol-2-yl)-2-((4S)-4-{4-methoxy-3-[(3R)-tetrahydrofuran-3-yloxy]phenyl}-2-oxopyrrolidin-1-yl)acetamide, LC/MS (EI) $t_R$ 3.41 (Method C), m/z 458 (M$^+$+1)

100) 2-[(4S)-4-(3-ethoxy-4-methoxyphenyl)-2-oxopyrrolidin-1-yl]-N-(3-methylisothiazol-5-yl)acetamide, LC/MS (EI) $t_R$ 3.16 (Method C), m/z 390.2 (M$^+$+1)

101) 2-[(4R)-4-(3-ethoxy-4-methoxyphenyl)-2-oxopyrrolidin-1-yl]-N-(3-methylisothiazol-5-yl)acetamide, 105) (2R)-2-{(4S)-4-[3-(benzyloxy)-4-methoxyphenyl]-2-oxopyrrolidin-1-yl}-N-(3-methylisothiazol-5-yl)propanamide, LC/MS (EI) $t_R$ 3.86 (Method C), m/z 466.1 (M$^+$+1)

106) 2-[(4S)-4-(3-ethoxy-4-methoxyphenyl)-2-oxopyrrolidin-1-yl]-N-(3-isopropyl-1,2,4-thiadiazol-5-yl)acetamide, LC/MS (EI) $t_R$ 3.68 (Method C), m/z 419.2 (M$^+$+1)

107) N-(5-cyclopropyl-1,3,4-thiadiazol-2-yl)-2-[(4S)-4-(3-ethoxy-4-methoxyphenyl)-2-oxopyrrolidin-1-yl]acetamide, LC/MS (EI) $t_R$ 3.19 (Method C), m/z 417.2 (M$^+$+1)

108) N-(4-cyclopropyl-1,3-thiazol-2-yl)-2-[(4S)-4-(3-ethoxy-4-methoxyphenyl)-2-oxopyrrolidin-1-yl]acetamide, LC/MS (EI) $t_R$ 3.67 (Method C), m/z 416.1 (M$^+$+1)

109) 2-{(4S)-4-[3-(cyclopropylmethoxy)-4-methoxyphenyl]-2-oxopyrrolidin-1-yl}-N-(3-isopropyl-1,2,4-thiadiazol-5-yl)acetamide, LC/MS (EI) $t_R$ 5.94 (Method A), m/z 445.2 (M$^+$+1)

111) 2-[(4S)-4-(3-ethoxy-4-methoxyphenyl)-2-oxopyrrolidin-1-yl]-N-(5-pyridin-4-yl-1,3,4-thiadiazol-2-yl)acetamide, LC/MS (EI) $t_R$ 1.99 (Method C), m/z 454.1 (M$^+$+1)

112) 2-[(4S)-4-(3-ethoxy-4-methoxyphenyl)-2-oxopyrrolidin-1-yl]-N-(4-methyl-1,3-benzothiazol-2-yl)acetamide, LC/MS (EI) $t_R$ 2.05 (Method C), m/z 440.1 (M$^+$+1)

114) 2-{(4S)-4-[3-(cyclopropylmethoxy)-4-methoxyphenyl]-2-oxopyrrolidin-1-yl}-N-(5-cyclopropyl-1,3,4-thiadiazol-2-yl)acetamide, LC/MS (EI) $t_R$ 5.2 (Method A), m/z 443.2 (M$^+$+1)

117) N-(5-cyclopropyl-1,3,4-thiadiazol-2-yl)-2-[(4S)-4-(3-isopropoxy-4-methoxyphenyl)-2-oxopyrrolidin-1-yl]acetamide, LC/MS (EI) $t_R$ 1.91 (Method C), m/z 431.2 (M$^+$+1)

119) 2-[(4S)-4-(3-ethoxy-4-methoxyphenyl)-2-oxopyrrolidin-1-yl]-N-(3-methyl-1H-pyrazol-5-yl)acetamide, LC/MS (EI) $t_R$ 1.98 (Method C), m/z 373.2 (M$^+$+1)

120) 2-[(4S)-4-(3-isopropoxy-4-methoxyphenyl)-2-oxopyrrolidin-1-yl]-N-(3-isopropyl-1,2,4-thiadiazol-5-yl)acetamide, LC/MS (EI) $t_R$ 2.08 (Method C), m/z 433.2 (M$^+$+1)

122) 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, LC/MS (EI) $t_R$ 4.08 (Method C), m/z 455.1 (M$^+$+1)

124) N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide, LC/MS (EI) $t_R$ 3.72 (Method C), m/z 453.1 (M$^+$+1)

126) 2-{(4S)-4-[4-(difluoromethoxy)-3-ethoxyphenyl]-2-oxopyrrolidin-1-yl}-N-(3-fluorophenyl)acetamide, LC/MS (EI) $t_R$ 4.03 (Method C), m/z 423.2 (M$^+$+1)

128) N-(4-cyclopropyl-1,3-thiazol-2-yl)-2-{(4S)-4-[4-(difluoromethoxy)-3-ethoxyphenyl]-2-oxopyrrolidin-1-yl}acetamide, LC/MS (EI) $t_R$ 4.07 (Method C), m/z 452.2 (M$^+$+1)

130) 2-{(4S)-4-[3-(cyclopropylmethoxy)-4-methoxyphenyl]-2-oxopyrrolidin-1-yl}-N-(4-cyclopropyl-1,3-thiazol-2-yl)acetamide, LC/MS (EI) $t_R$ 3.8 (Method C), m/z 442.2 (M$^+$+1)

131) 2-[(4S)-4-(3-ethoxy-4-methoxyphenyl)-2-oxopyrrolidin-1-yl]-N-[4-(trifluoromethyl)-1,3-thiazol-2-yl]acetamide, LC/MS (EI) $t_R$ 3.76 (Method C), m/z 444.1 (M$^+$+1)

132) 2-[(4S)-4-(3-ethoxy-4-methoxyphenyl)-2-oxopyrrolidin-1-yl]-N-(4-methoxy-1,3-benzothiazol-2-yl)acetamide, LC/MS (EI) $t_R$ 3.7 (Method C), m/z 456.1 (M$^+$+1)

133) 2-[(4S)-4-(3-ethoxy-4-methoxyphenyl)-2-oxopyrrolidin-1-yl]-N-(4-methyl-1,3-thiazol-2-yl)acetamide, LC/MS (EI) $t_R$ 3.26 (Method C), n/z 390.1 (M$^+$+1)

135) 2-[(4S)-4-(3-ethoxy-4-methoxyphenyl)-2-oxopyrrolidin-1-yl]-N-(5-methylisoxazol-3-yl)acetamide, LC/MS (EI) $t_R$ 3.13 (Method C), m/z 374.2 (M$^+$+1)

136) (2S)-2-[(4S)-4-(3-ethoxy-4-methoxyphenyl)-2-oxopyrrolidin-1-yl]-N-(3-isopropyl-1,2,4-thiadiazol-5-yl)propanamide, LC/MS (EI) $t_R$ 3.91 (Method C), m/z 433.2 (M$^+$+1)

137) (2R)-2-[(4S)-4-(3-ethoxy-4-methoxyphenyl)-2-oxopyrrolidin-1-yl]-N-(3-isopropyl-1,2,4-thiadiazol-5-yl)propanamide, LC/MS (EI) $t_R$ 3.91 (Method C), m/z 433.2 (M$^+$+1)

138) (2S)-2-[(4R)-4-(3-ethoxy-4-methoxyphenyl)-2-oxopyrrolidin-1-yl]-N-(3-isopropyl-1,2,4-thiadiazol-5-yl)propanamide, LC/MS (EI) $t_R$ 3.92 (Method C), m/z 433.2 (M$^+$+1)

139) (2R)-2-[(4R)-4-(3-ethoxy-4-methoxyphenyl)-2-oxopyrrolidin-1-yl]-N-(3-isopropyl-1,2,4-thiadiazol-5-yl)propanamide, LC/MS (EI) $t_R$ 3.95 (Method C), m/z 433.2 (M$^+$+1)

140) (2R)-2-[(4S)-4-(3-ethoxy-4-methoxyphenyl)-2-oxopyrrolidin-1-yl]-N-(4-methyl-1,3-thiazol-2-yl)propanamide, LC/MS (EI) $t_R$ 3.48 (Method C), m/z 404.1 (M$^+$+1)

141) (2S)-2-[(4S)-4-(3-ethoxy-4-methoxyphenyl)-2-oxopyrrolidin-1-yl]-N-(4-methyl-1,3-thiazol-2-yl)propanamide, LC/MS (EI) $t_R$ 3.52 (Method C), m/z 404.1 (M$^+$+1)

142) 2-{(4S)-4-[3-(cyclopropylmethoxy)-4-methoxyphenyl]-2-oxopyrrolidin-1-yl}-N-(6-methylpyridin-2-yl)acetamide LC/MS (EI) $t_R$ 3.4 (Method C), m/z 410.2 (M$^+$+1)

143) 2-{(4S)-4-[3-(cyclopropylmethoxy)-4-methoxyphenyl]-2-oxopyrrolidin-1-yl}-N-1,3-thiazol-2-ylacetamide, LC/MS (EI) $t_R$ 3.4 (Method C), m/z 402.1 (M+$^+$IX)

144) N-(4-cyclopropyl-1,3-thiazol-2-yl)-2-[(4S)-4-(3-isopropoxy-4-methoxyphenyl)-2-oxopyrrolidin-1-yl]acetamide, LC/MS (EI) $t_R$ 3.89 (Method C), m/z 430.2 (M$^+$+1)
145) N-(3-fluorophenyl)-2-[(4S)-4-(3-isopropoxy-4-methoxyphenyl)-2-oxopyrrolidin-1-yl]acetamide, [LC/MS (EI) $t_R$ 3.89 (Method C), m/z 401.2 (M$^+$+1)
146) 2-{(4S)-4-[3-(cyclopropylmethoxy)-4-methoxyphenyl]-2-oxopyrrolidin-1-yl}-N-(5-methylisoxazol-3-yl)acetamide, LC/MS (EI) $t_R$ 3.6 (Method C), m/z 400.2 (M$^+$+1)
151) 2-{(4S)-4-[4-(difluoromethoxy)-3-isopropoxyphenyl]-2-oxopyrrolidin-1-yl}-N-(3-fluorophenyl)acetamide, LC/MS (EI) $t_R$ 4.35 (Method C), m/z 437.1 (M$^+$+1)
152) 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, LC/MS (EI) $t_R$ 4.34 (Method C), m/z 469.1 (M$^+$+1)
154) N-(4-cyclopropyl-1,3-thiazol-2-yl)-2-{(4S)-4-[4-(difluoromethoxy)-3-isopropoxyphenyl]-2-oxopyrrolidin-1-yl}acetamide, LC/MS (EI) $t_R$ 4.38 (Method C), m/z 466.1 (M$^+$+1)
161) N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, LC/MS (EI) $t_R$ 3.76 (Method C), m/z 467.1 (M$^+$+1)
163) 2-{(4S)-4-[3-(cyclopropylmethoxy)-4-(difluoromethoxy)phenyl]-2-oxopyrrolidin-1-yl}-N-(5-cyclopropyl-1,3,4-thiadiazol-2-yl)acetamide, LC/MS (EI) $t_R$ 3.75 (Method C), m/z 479.1 (M$^+$+1)
165) 2-{(4S)-4-[3-(cyclopropylmethoxy)-4-(difluoromethoxy)phenyl]-2-oxopyrrolidin-1-yl}-N-(3-isopropyl-1,2,4-thiadiazol-5-yl)acetamide LC/MS (EI) $t_R$ 4.35 (Method C), m/z 481.1 (M$^+$+1)
167) 2-{(4S)-4-[3-(cyclopropylmethoxy)-4-(difluoromethoxy)phenyl]-2-oxopyrrolidin-1-yl}-N-(4-cyclopropyl-1,3-thiazol-2-yl)acetamide, LC/MS (EI) $t_R$ 4.4 (Method C), m/z 478.1 (M$^+$+1)
168) 2-{(4S)-4-[3-(cyclopropylmethoxy)-4-(difluoromethoxy)phenyl]-2-oxopyrrolidin-1-yl}-N-(3-fluorophenyl)acetamide LC/MS (EI) $t_R$ 4.36 (Method C), m/z 449.2 (M$^+$+1)
170) 2-{(4S)-4-[4-(difluoromethoxy)-3-ethoxyphenyl]-2-oxopyrrolidin-1-yl}-N-(3-methylisothiazol-5-yl)acetamide, LC/MS (EI) $t_R$ 3.73 (Method C), m/z 426.1 (M$^+$+1).

The separate enantiomers of racemic compounds listed above can be obtained through the use of optically active starting materials or by conventional resolution techniques such as chiral HPLC.

The following compounds may be made by a similar procedure using different starting materials:
171) (2S)-2-{(4S)-4-[4-(difluoromethoxy)-3-ethoxyphenyl]-2-oxopyrrolidin-1-yl}-N-(3-fluorophenyl)propanamide,
172) (2R)-2-{(4S)-4-[4-(difluoromethoxy)-3-ethoxyphenyl]-2-oxopyrrolidin-1-yl}-N-(3-fluorophenyl)propanamide,
173) (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide,
174) (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide,
175) 2-{(4S)-4-[4-(difluoromethoxy)-3-ethoxyphenyl]-2-oxopyrrolidin-1-yl}-N-(6-methylpyridin-2-yl)acetamide,
176) (2S)-2-{(4S)-4-[4-(difluoromethoxy)-3-ethoxyphenyl]-2-oxopyrrolidin-1-yl}-N-(6-methylpyridin-2-yl)propanamide, and
177) (2R)-2-{(4S)-4-[4-(difluoromethoxy)-3-ethoxyphenyl]-2-oxopyrrolidin-1-yl}-N-(6-methylpyridin-2-yl)propanamide.

Example 11

(4S)-1-[N-(4-Carboxyphenyl)aminocarbonylmethyl]-4-(4-methoxy-3-(3R)-tetrahydrofuranyloxyphenyl)-2-pyrrolidone

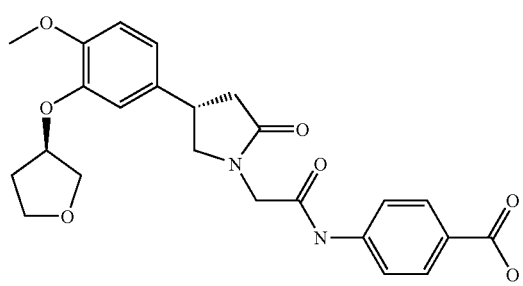

A solution of sodium hydroxide (0.5M, 148 uL) was added to a solution of (4S)-4-(4-Methoxy-3-(3R)-tetrahydrofuranyloxyphenyl)-1-[N-(4-ethoxycarbonylphenyl)aminocarbonylmethyl)]-2-pyrrolidone (18 mg, 0.037 mmol) in methanol (1 mL) and water (0.5 mL), and the resulting mixture stirred at room temperature for 7 days. The solvent was then removed and the residue was partitioned between ethyl acetate and 1M HCl (10 mL each). Evaporation of the organic solvent afforded 14 mg of crude product, which was reconstituted in 0.75 mL of 60% acetonitrile/water (containing 0.1% formic acid) and purified on a reverse phase hplc column (C18—5 um; 30×100 mm) using a 20-80% acetonitrile/water (0.1% formic acid) gradient over 6 minutes. The fraction at 3.4 minutes was collected and concentrated to afford 8.6 mg (51%) of (4S)-1-[N-(4-carboxyphenyl)aminocarbonylmethyl)]-4-(4-methoxy-3-(3R)-tetrahydrofuranyloxyphenyl)-2-pyrrolidone as a white solid. $^1$H NMR (CDCl$_3$+trace DMSO-d$_6$; 300 MHz) 9.5 (s, 1H); 7.9 (d, 2H); 7.6 (d, 2H) 6.8 (s, 2H) 4.9 (m, 1H), 3.9-4.2 (q, 2H) 3.7-3.9 (m, 5H); 3.7 (s, 3H); 3.5 (m, 2H); 2.8 (m, 1H); 2.3-2.6 (m, 3H); 2.2 (m, 2H); MS [M+H]=455; [M+Na]=477.

(4S)-1-[N-(3-Carboxyphenyl)aminocarbonylmethyl]-4-(4-methoxy-3-(3R)-tetrahydrofuranyloxyphenyl)-2-pyrrolidone was made with a similar procedure using different starting materials.

Example 12

(4S)-4-(4-Methoxy-3-(3R)-tetrahydrofuranyloxyphenyl)-1-[N-(2-methylphenyl)sulfonylaminocarbonylmethyl]-2-pyrrolidone

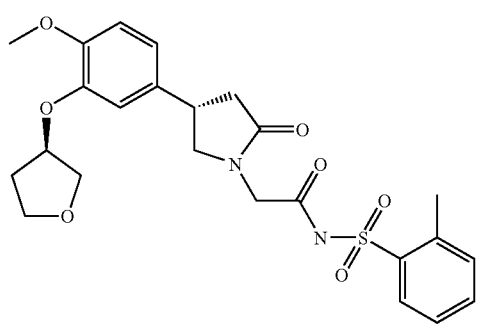

o-Tolylsulfonamide (51 mg, 0.30 mmol), DMAP (22 mg, 0.18 mmol), and EDCI (58 mg, 0.30 mmol) were added to a mixture of (4S)-4-[4-Methoxy-3-(3R)-tetrahydrofuranyloxyphenyl]-2-pyrrolidone-1-acetic acid (50 mg, 0.15 mmol) in DMF (3 mL). After stirring for 90 minutes at room temperature the reaction was diluted with ethyl acetate (60 mL) and washed with 1M HCl, water (30 mL) and brine (30 mL). The organic solvent was dried over sodium sulfate and evaporated to provide 92 mg of an amber oil. The oil was purified by HPLC using a C18 column (5 um; 30×100 mm) and a gradient of 20-80% acetonitrile/water (0.1% formic acid) over 6 minutes. The fraction at 4 minutes was collected and concentrated to afford 25 mg (35%) of (4S)-4-(4-methoxy-3-(3R)-tetrahydrofuranyloxyphenyl)-1-[N-(2-methylphenyl)sulfonylaminocarbonylmethyl]-2-pyrrolidone as a white solid. $^1$H NMR (CDCl$_3$; 300 MHz) 9.6 (br s, 1H); 8.2 (d, 1H); 7.5 (t, 1H); 7.2-7.4 (m, 2H); 6.7-6.9 (m, 3H); 5.0 (br s, 1H); 3.8-4.1 (m, 9H); 5.5-3.7 (m, 2H); 2.9 (m, 2H); 2.5-2.7 (m, 4H); 2.2 (m, 2H). MS [M+H]=489.

(4S)-4-(4-Methoxy-3-(3R)-tetrahydrofuranyloxyphenyl)-1-(N-phensulfonylaminocarbonylmethyl)-2-pyrrolidone was made by a similar procedure using different starting materials.

Example 13

(4S)-4-(4-Methoxy-3-(3R)-tetrahydrofuranyloxyphenyl)-1-[N-(3-phenpropyl)]-2-pyrrolidone

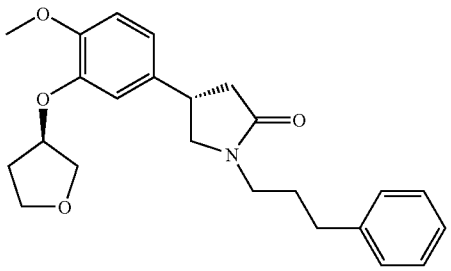

A solution of (4S)-4-(4-methoxy-3-(3R)-tetrahydrofuranyloxyphenyl)-2-pyrrolidone (100 mg, 0.36 mmol) in 2.6 mL of DMF was added to a flask containing of NaH (30 mg, 0.75 mmol, 60% dispersion in mineral oil) and 1 mL of DMF. The mixture was stirred at room temperature for 3 hours. A solution of 1-bromo-3-phenylpropane (0.16 mL, 1.08 mmol) in 1 mL DMF was then added and the resulting mixture was stirred at room temperature for 16 hours. The mixture was then poured into a mixture of ethyl acetate (15 mL) and water (15 mL), which was then washed with water (3×15 mL) and brine (1×15 mL), and dried over Na$_2$SO$_4$. Purification by HPLC afforded 101 mg (71%) of (4S)-4-(4-methoxy-3-(3R)-tetrahydrofuranyloxyphenyl)-1-[N-3-phenpropyl)]-2-pyrrolidone as a clear oil. $^1$H-NMR (CDCl$_3$) δ 7.32-7.27 (m, 2H), 7.22-7.18 (m, 3H), 6.84 (t, J=8.3 Hz, 1H), 6.80 (dd, J=1.9 Hz, J=8.3 Hz, 1H), 6.69 (d, J=1.9 Hz), 4.48 (m, 1H), 3.99-3.89 (m, 4H), 3.84 (s, 3H), 3.69 (dd, J=8 Hz, J=9 Hz, 1H), 3.43-3.28 (m, 4H), 2.78 (dd, J=8.8 Hz, J=16.8 Hz, 1H), 2.66 (m, 2H), 2.50 (dd, J=8.0 Hz, J=16.8 Hz 1H), 2.20-2.13 (m, 2H), 1.88 (m, 2H).

The following compounds were made using a similar procedure with different starting materials:
(4S)-4-(4-Methoxy-3-(3R)-tetrahydrofuranyloxyphenyl)-1-[N-(2-phenoxyethyl)]-2-pyrrolidone
(4S)-4-(4-methoxy-3-(3R)-tetrahydrofuranyloxyphenyl)-1-[N-(2-tert-butyldimethylsilyloxyethyl)-2-pyrrolidone Example 14A (4S)-4-(4-Methoxy-3-(3R)-tetrahydrofuranyloxyphenyl)-1-[N-(2-hydroxyethyl)]-2-pyrrolidone (Intermediate)

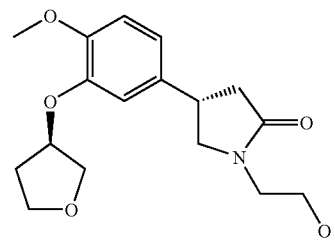

3.7 mL of TBAF (1.0M in THF, 3.7 mmol, 2.5 equivalents) was added to (4S)-4-(4-methoxy-3-(3R)-tetrahydrofuranyloxyphenyl)-1-[N-(2-tert-butyldimethylsilyloxyethyl)-2-pyrrolidone n 12 mL of THF and stirred for one hour at room temperature. The mixture was then poured into 50 mL of water and extracted 2×50 mL of CH$_2$Cl$_2$ and dried over Na$_2$SO$_4$. The solvent was removed and the residue purified by column chromatography (elution with CH$_2$Cl$_2$ to 10% MeOH:CH$_2$Cl$_2$ over 20 minutes) to yield 387 mg (78%) of (4S)-4-(4-methoxy-3-(3R)-tetrahydrofuranyloxyphenyl)-1-[N-(2-hydroxyethyl)]-2-pyrrolidone as a clear oil. $^1$H-NMR (CDCl$_3$) δ 6.80 (s, 2H), 6.72 (s, 1H), 4.96-4.91 (m, 1H), 4.02-3.81 (m, 5H), 3.79 (s, 3H), 3.53-3.41 (m, 4H), 2.98-2.92 (m, 2H), 2.78 (dd, J=8.8 Hz, J=16.8 Hz, 1H), 2.58 (bs, 1H), 2.49 (dd, J=8.1 Hz, J=16.8 Hz, 1H), 2.16 (m, 2H).

Example 14B (4S)-4-(4-Methoxy-3-(3R)-tetrahydrofuranyloxyphenyl)-1-[N-(2-phenthioethyl)]-2-pyrrolidone

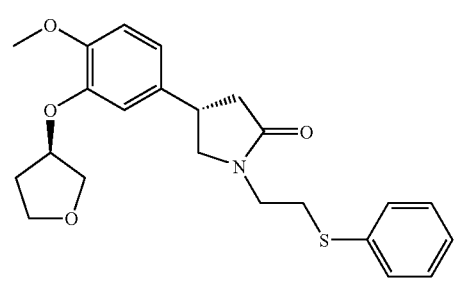

Methanesulfonyl chloride (40 μL, 0.52 mmol), and diisopropylethylamine (0.11 mL, 0.65 mmol) were added to a solution of (4S)-4-(4-methoxy-3-(3R)-tetrahydrofuranyloxyphenyl)-1-[N-(2-hydroxyethyl)]-2-pyrrolidone (83 mg, 0.26 mmol) in 3 mL of CH$_2$Cl$_2$. The mixture was stirred at room temperature for 1 hour. It was then washed with 10 mL of water and dried over Na$_2$SO$_4$, filtered and the solvent was removed. The crude (4S)-(4-methoxy-(3R)-tetrahydrofuranylphenyl)-1-[N-(2-methanesulfonylethanol)]-2-pyrrolidone was then dissolved in 3 mL of DMF with 108 mg (0.78 mmol) of K$_2$CO$_3$ and 53 μL of thiophenol and heated to 60° C. for 2 hours. The mixture was then added to a mixture of 20 mL of saturated K$_2$CO$_3$ and 20 mL of ethyl acetate. The organic layer was washed with water (2×20 mL) and brine (1×20 mL), dried over Na₂SO₄, filtered, and then the solvent was removed. Purification by column chromatography using 50% ethyl acetate to 100% ethyl acetate gradient over 20 minutes afforded 34.7 mg (32%) of (4S)-4-(4-methoxy-3-(3R)-tetrahydrofuranyloxyphenyl)-1-[N-(2-phenthioethyl)]-2-pyrrolidone as a clear oil. ¹H-NMR δ 7.41-7.2 (m, 5H), 6.73-6.86 (m, 3H), 4.95 (m, 1H), 3.87-4.05 (m, 4H), 3.84 (s, 3H), 3.76 (m, 1H), 3.58 (dt, J=2 Hz, J=6.8, 2H), 3.40 (m, 2H), 3.15 (t, J 6.6 Hz, 2H), 2.75 (dd, J=8.6 Hz, J=17 Hz, 1H), 2.47 (dd, J=8.6, J=17 Hz, 1H), 2.12 (m, 2H).

(4S)-4-(4-Methoxy-3-(3R)-tetrahydrofuranyloxyphenyl)-1-[N-(2-(4-methoxyphenyl)oxyethyl)]-2-pyrrolidone was made using a similar procedure with different starting materials.

Example 14C (4S)-1-[2-(4-Isopropylphenylthio)ethyl]-4-[4-methoxy-3-(3R)-tetrahydrofuranyloxyphenyl]-2-pyrrolidone

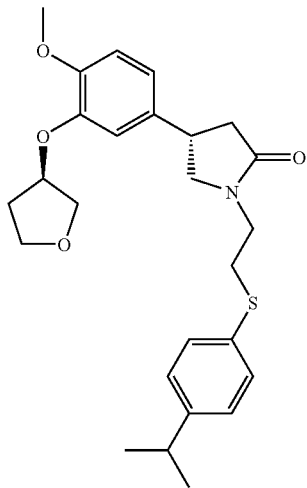

Cs₂CO₃ (111 mg, 0.34 mmol), 4-isopropylthiophenol (52 µL, 0.34 mmol) and DMF (2 mL) were added to a flask containing (4S)-4-[4-methoxy-3-(3R)-tetrahydrofuranyloxyphenyl]-(2-oxo-pyrrolidin-1-yl)ethyl methanesulfonate (0.17 mmol). The reaction mixture was heated to 60° C. overnight, then cooled to room temperature. Ethyl acetate (20 mL) was then added and the organic layer was washed with saturated K₂CO₃ (10 mL), water (10 mL), and brine (10 mL), dried over Na₂SO₄, filtered, and concentrated. Purification by silica gel column chromatography using a gradient elution from 50% to 100% ethyl acetate in hexanes yielded 55 mg of (4S)-1-[2-(4-isopropylphenylthio)ethyl]-4-[4-methoxy-3-(3R)-tetrahydrofuranyloxyphenyl]-2-pyrrolidone. ¹H-NMR δ (CDCl₃) 7.3 (d, 2H), 7.2 (d, 2H), 6.8 (m, 2H), 6.7 (s, 1H), 4.9 (m, 1H), 4.0-3.8 (M, 8H), 3.5 (m, 2H), 3.4 (m, 2H), 3.1 (t, 2H), 2.8 (m, 1H), 2.7 (dd, 1H), 2.4 (dd, 1H), 2.2 (m, 2H), 1.2 (d, 6H). [M+1]=456.0

The following compounds were made using a similar procedure with different starting materials:

(4S)-1-[2-(4-Isopropylphenoxy)ethyl]-4-[4-methoxy-3-(3R)-tetrahydrofuranyloxyphenyl]-2-pyrrolidone (4S)-1-[2-(4-Isopropylphenylthio)ethyl]-4-[4-methoxy-3-(3R)-tetrahydrofuranyloxyphenyl]-2-pyrrolidone (4S)-1-[2-(3-Chlorophenylthio)ethyl]-4-[4-methoxy-3-(3R)-tetrahydrofuranyloxyphenyl]-2-pyrrolidone (4S)-1-[2-(2,3-Difluorophenoxy)ethyl]-4-[4-methoxy-3-(3R)-tetrahydrofuranyloxyphenyl]-2-pyrrolidone (4S)-1-[2-(Benzothiazol-2-yl)oxyethyl]-4-[4-methoxy-3-(3R)-tetrahydrofuranyloxyphenyl]-2-pyrrolidone (4S)-1-[2-(6-Fluorobenzothiazol-2-yl)thioethyl]-4-[4-methoxy-3-(3R)-tetrahydrofuranyloxyphenyl]-2-pyrrolidone (4S)-1-[N-(6-Fluorobenzothiazol-2-yl)aminoethyl]-4-[4-methoxy-3-(3R)-tetrahydrofuranyloxyphenyl]-2-pyrrolidone (4S)-1-[N-(Benzothiazol-2-yl)aminoethyl]-4-[4-methoxy-3-(3R)-tetrahydrofuranyloxyphenyl]-2-pyrrolidone (4S)-4-[4-methoxy-3-(3R)-tetrahydrofuranyloxyphenyl]-1-[2-(4-trifluoromethylphenoxy)ethyl]-2-pyrrolidone (4S)-1-[2-(2-Fluorophenylthio)ethyl]-4-[4-methoxy-3-(3R)-tetrahydrofuranyloxyphenyl]-2-pyrrolidone (4S)-1-[2-(3-Flurorophenylthio)ethyl]-4-[4-methoxy-3-(3R)-tetrahydrofuranyloxyphenyl]-2-pyrrolidone (4S)-4-[4-methoxy-3-(3R)-tetrahydrofuranyloxyphenyl]-1-[2-(4-methoxyphenylthio)ethyl]-2-pyrrolidone (S)-1-(2-Azido-ethyl)-4-{4-methoxy-3-[(R)-(tetrahydro-furan-3-yl)oxy]-phenyl}-pyrrolidin-2-one Example 15

(4S)-4-(4-Methoxy-3-(3R)-tetrahydrofuranyloxyphenyl)-1-[N-(2-phenylsulfonylethyl)]-2-pyrrolidone

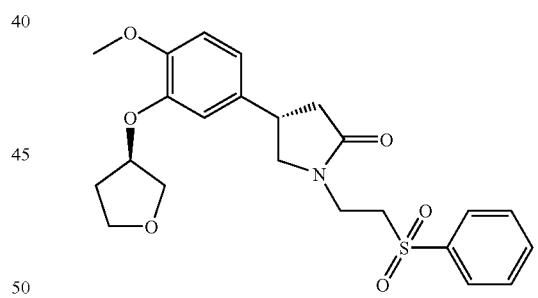

(4S)-4-(4-methoxy-3-(3R)-tetrahydrofuranyloxyphenyl)-1-[N-(2-phenthioethyl)]-2-pyrrolidone (1 equivalent) was dissolved in CH₂Cl₂ and 3 equivalents of m-CPBA were added. The reaction was stirred overnight at room temperature, then added to mixture of a saturated solution of NaHCO₃ and CH₂Cl₂, and extracted with CH₂Cl₂ (2×10 mL). The combined organics were then washed with water (1×10 mL) and brine (1×10 mL). Purification by column chromatography using a 50% ethyl acetate in hexanes to 100% ethyl acetate gradient over 10 minutes afforded 82 mg (57%) of (4S)-4-(4-methoxy-3-(3R)-tetrahydrofuranyloxyphenyl)-1-[N-(2-phenylsulfonylethyl)]-2-pyrrolidone as a clear oil. ¹H-NMR δ 7.94 (d, J=7.5 Hz, 2H), 7.75-7.59 (m, 3H), 6.83

(m, 2H), 6.73 (s, 1H), 4.97 (m, 1H), 4.05-3.87, (m, 4H), 3.85 (s, 3H), 3.83-3.73 (m, 3H), 3.5-3.38 (m, 4H), 2.72 (dd, J=9 Hz, J=17 Hz, 1H), 2.48 (dd, J=9 Hz, J=17 Hz, 1H), 2.21-2.15 (m, 2H).

Example 16

(4S)-2,3-Difluoro-4-[4-methoxy-3-(3R)tetrahydrofuranyloxyphenyl]-N-[2-(2-oxopyrrolidin-1-yl)ethyl]-benzamide

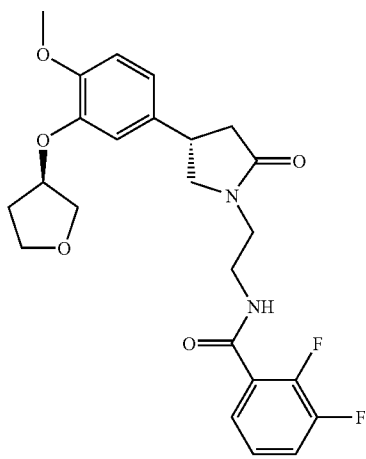

DIC (0.10 mL, 0.63 mmol) was added to 0° C. under an atmosphere of argon to a flask containing of 2,3-difluorobenzoic acid (100 mg, 0.63 mmol), HOBt (85 mg, 0.63 mmol) and THF (6.5 mL), and the mixture stirred for 30 minutes. The resulting solution was then added to a flask containing (S)-1-(2-azido-ethyl)-4-{4-methoxy-3-[(R)-(tetrahydro-furan-3-yl)oxy]-phenyl}-pyrrolidin-2-one (55 mg, 0.16 mmol) in THF (3 mL) at room temperature, followed by the addition of PBu$_3$ (0.12 mL). The reaction was stirred at room temperature overnight, then the solvent was removed under reduced pressure and the residue was dissolved in ethyl acetate (10 mL). The organic layer was washed with 10 mL each of 1N HCl, K$_2$CO$_3$, water and brine, dried over Na$_2$SO$_4$, filtered and concentrated. Purification by silica gel column chromatography using a gradient elution from 0% to 10% methanol in dichloromethane afforded 27 mg of (4S)-2,3-Difluoro-4-[4-methoxy-3-(3R)-tetrahydrofuranyloxyphenyl]-N-[2-(2-oxopyrrolidin-1-yl)ethyl]-benzamide. $^1$H-NMR δ (CDCl$_3$) 7.7 (t, 1H), 7.3 (m, 1H), 7.2 (m, 2H), 6.8 (s, 2H), 6.7 (s, 1H), 4.9 (m, 1H), 4.0 (m, 3H), 3.8 (m, 5H), 3.7 (m, 2H), 3.0 (m, 2H), 2.3 (m, 2H), 2.7 (dd, 1H), 2.5 (dd, 1H), 2.1 (m, 2H). [M+1]= 461.0

The following compounds were made using a similar procedure with different starting materials:
(4S)-4-[4-Methoxy-3-(3R)-tetrahydrofuranyloxyphenyl]-N-[2-(2-oxopyrrolidin-1-yl)ethyl]benzamide
(4S)-2,3-Difluoro-4-[4-methoxy-3-(3R)-tetrahydrofuranyloxyphenyl]-N-[2-(2-oxopyrrolidin-1-yl)ethyl]-benzamide

Example 17

(4S)-1-[N-(4-Carboxythiazol-2-yl)aminocarbonylmethyl]-4-[4-methoxy-3-(3R)-tetrahydrofuranyloxyphenyl]-2-pyrrolidone

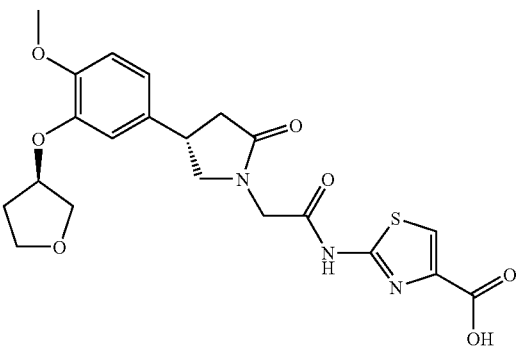

1M NaOH (0.46 mL; 0.46 mmol) was added to a stirred mixture of (4S)-1-[N-(4-Ethoxycarbonylthiazol-2-yl)aminocarbonylmethyl]-4-[4-methoxy-3-(3R)-tetrahydrofuranyloxyphenyl]-2-pyrrolidone (95 mg, 0.19 mmol) in dioxane (5 mL) and water (1 mL). The reaction was then heated to 100° C. for 2 hours. Product purification was performed by reverse phase liquid chromatography on a C18 column (30×100 mm) using a gradient of 20-80% acetonitrile/water (containing 0.1% formic acid) in 6 minutes with a flow of 45 mL/min. Ultraviolet detection at 277 nm was utilized and the combined fractions containing the target were evaporated to afford 18 mg (20%) of (4S)-1-[N-(4-Carboxythiazol-2-yl)aminocarbonylmethyl]-4-[4-methoxy-3-(3R)-tetrahydrofuranyloxyphenyl]-2-pyrrolidone as a white solid. $^1$H NMR (CDCl$_3$: 300 MHz) δ 2.2 (m, 2H); 2.6 (m, 1H); 2.9 (m, 1H); 3.5 (m, 2H); 3.8 (s, 3H); 3.9-4.1 (m, 5H); 4.2-4.4 (q, 2H); 5.0 (m, 1H); 6.85 (s, 2H); 6.9 (s, 1H); 7.8 (s, 1H). ES-MS [M+H]=462.2

The following compounds were made using a similar procedure with different starting materials:
(4S)-4-[4-Methoxy-3-(3R)-tetrahydrofuranyloxyphenyl]-N-[2-(2-oxopyrrolidin-1-yl)ethyl]-4-methoxybenzamide

Example 18

(4S)-1-[N-(4-Carboxy-3-fluorophenyl)aminocarbonylmethyl]-4-[4-methoxy-3-(3R)-tetrahydrofuranyloxyphenyl]-2-pyrrolidone

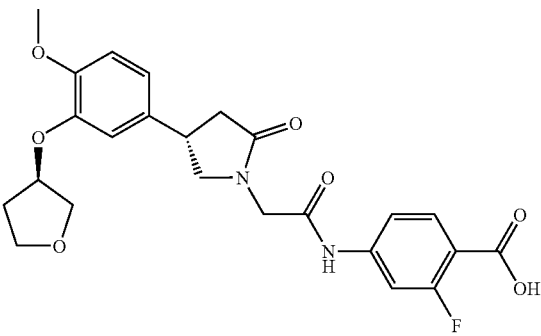

Trifluoroacetic acid (1 mL) was added to (4S)-1-[N-(4-tert-butyloxycarbonyl-3-fluorophenyl)aminocarbonylmethyl]-4-

[4-methoxy-3-(3R)-tetrahydrofuranyloxyphenyl]-2-pyrrolidone (55 mg, 0.104 mmol) in dichloromethane (1 mL) and the resulting solution was stirred at room temperature for 45 minutes. The solvent was then evaporated under reduced pressure and the residue was taken up in ethyl acetate (50 mL) and washed with water (2×10 mL each) and brine (10 mL). The organic layer was dried over sodium sulfate and evaporated to provide a tan solid. The crude product was purified by reverse phase liquid chromatography using a C18 column (30×100 mm) and a gradient of 20-80% acetonitrile/water (plus 0.1% formic acid) over six minutes at a flow rate of 45 mL/min. Ultraviolet detection at 269 nm was utilized and the combined fractions containing the target compound were evaporated to afford 3.6 mg (7%) of (4S)-1-[N-(4-Carboxy-3-fluorophenyl)aminocarbonylmethyl]-4-[4-methoxy-3-(3R)-tetrahydrofuranyloxyphenyl]-2-pyrrolidone as a white foam. ES-MS [M+H]=473.1

Example 19

In Vitro Measurement of Type 4 Phosphodiesterase

Enzyme Preparation:

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay:

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 ul) expressing hPDE-4D6 were combined with 50 ul of assay mix and 10 ul of inhibitors and incubated for 12 min at room temperature. Final concentrations of assay components were: 0.4 ug enzyme, 10 mM Tris-HCl (pH 7.5), 10 mM $MgCl_2$, 3 uM cAMP, 0.002 U 5'-nucleotidase, and $3\times10^4$ cpm of [3H]cAMP. The reaction was stopped by adding 100 µl of boiling 5 mN HCl. An aliquot of 75 µl of reaction mixture was transferred from each well to alumina columns (Multiplate; Millipore). Labeled adenosine was eluted into an OptiPlate by spinning at 2000 rpm for 2 min; 150 µl per well of scintillation fluid was added to the OptiPlate. The plate was sealed, shaken for about 30 min, and cpm of [$^3$H]adenosine was determined using a Packard Topcount 96 counter.

All test compounds are dissolved in 100% DMSO and diluted into the assay such that the final concentration of DMSO is 0.1%. DMSO does not affect enzyme activity at this concentration.

Example 20

Passive Avoidance in Rats

An In Vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198-204.). The apparatus (Model E10-16SC, Coulbourn Instruments, Allentown, Pa.) consisted of a two-compartment chamber with an illuminated compartment connected to a darkened compartment by a guillotine door. The floor of the darkened compartment consisted of stainless steel rods through which an electric foot-shock could be delivered from a constant current source. All experimental groups were first habituated to the apparatus the day before the start of the experiment. During the training, the rat (Male Sprague-Dawley (Harlan) weighing 250 to 350 g) was placed in the illuminated compartment facing away from the closed guillotine door for 1 minute before the door was raised. The latency for entering the darkened compartment was recorded. After the rat entered the darkened compartment, the door was closed and a 0.5 mA electric shock was administered for 3 seconds. Twenty-four hours later, the rat was administered 0.1 mg/kg of the test compound or saline, 30 minutes prior to the injection of saline or test compound (dosed from 0.1 to 2.5 mg/kg, i.p.), which was 30 minutes before the retention test started. The rat was again placed in the illuminated compartment with the guillotine door open. The latency for entering the darkened compartment was recorded for up to 180 seconds, at which time the trial was terminated.

All data were analyzed by analyses of variance (ANOVA); individual comparisons were made using Kewman-Keuls tests. Naïve rats required less than 30 seconds, on average, to cross from the illuminated compartment to the darkened compartment.

Example 21

Radial Arm Maze Task in Rats

An In Vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198-204.). Five days after initial housing, rats (male Sprague-Dawley (Harlan) weighing 250 to 350 g) were placed in the eight-arm radial maze (each arm was 60×10×12 cm high; the maze was elevated 70 cm above the floor) for acclimation for two days. Rats were then placed individually in the center of the maze for 5 minutes with food pellets placed close to the food wells, and then, the next day, in the wells at the end of the arms; 2 sessions a day were conducted. Next, four randomly selected arms were then baited with one pellet of food each. The rat was restricted to the center platform (26 cm in diameter) for 15 seconds and then allowed to move freely throughout the maze until it collected all pellets of food or 10 minutes passed, whichever came first. Four parameters were recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error was zero and the average reference memory error was less than one in five successive trials, the rats began the drug tests. The test compound or saline was injected 15 minutes prior to vehicle or test agent, which was given 45 minutes before the test. Experiments were performed in a lighted room, which contained several extra-maze visual cues.

All data were analyzed by analyses of variance (ANOVA); individual comparisons were made using Kewman-Keuls tests.

A decrease in adenosine concentration is indicative of inhibition of PDE activity. This procedure was used to screen compounds of the present invention for their ability to inhibit PDE4. $pIC_{50}$ values were determined by screening 6 to 12 concentrations of compound ranging from 0.1 nM to 10,000 nM and then plotting drug concentration versus $^3$H-adenosine concentration. Prism® was used to estimate $pIC_{50}$ values.

The $pIC_{50}$ values of preferred compounds according to the invention are less than 100 nM, especially less than 10 nM.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:

1. A compound selected from:

2-[4-(3-ethoxy-4-methoxyphenyl)-2-oxopyrrolidin-1-yl]-N-(5-methylisoxazol-3-yl)acetamide, 2-[4-(3-ethoxy-4-methoxyphenyl)-2-oxopyrrolidin-1-yl]-N-(4-methyl-1,3-thiazol-2-yl)acetamide, 2-[4-(3-ethoxy-4-methoxyphenyl)-2-oxopyrrolidin-1-yl]-N-(3-methylisothiazol-5-yl)acetamide, 2-[4-(3-ethoxy-4-methoxyphenyl)-2-oxopyrrolidin-1-yl]-N-(6-methylpyridin-2-yl)acetamide, 2-[(4S)-4-(3-ethoxy-4-methoxyphenyl)-2-oxopyrrolidin-1-yl]-N-(3-fluorophenyl)acetamide, 2-[(4R)-4-(3-ethoxy-4-methoxyphenyl)-2-oxopyrrolidin-1-yl]-N-(3-fluorophenyl)acetamide, 2-[(4S)-4-(3-ethoxy-4-methoxyphenyl)-2-oxopyrrolidin-1-yl]-N-methyl-N-(4-methyl-1,3-thiazol-2-yl)acetamide, 2-[(4S)-4-(3-ethoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-ethoxy-4-methoxyphenyl)-2-oxopyrrolidin-1-yl]-N-methylacetamide, N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide, 2-[(4R)-4-(3-ethoxy-4-methoxyphenyl)-2-oxopyrrolidin-1-yl]-N-(3-isopropyl-1,2,4-thiadiazol-5-yl)-N-methylacetamide, N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-methylisothiazol-5-yl)acetamide, 2-[(4R)-4-(3-ethoxy-4-methoxyphenyl)-2-oxopyrrolidin-1-yl]-N-(3-methylisothiazol-5-yl)acetamide, 2-[(4S)-4-(3-ethoxy-4-methoxyphenyl)-2-oxopyrrolidin-1-yl]-N-(3-isopropyl-1,2,4-thiadiazol-5-yl)acetamide, N-(5-cyclopropyl-1,3,4-thiadiazol-2-yl)-2-[(4S)-4-(3-ethoxy-4-methoxyphenyl)-2-oxopyrrolidin-1-yl]acetamide, N-(4-cyclopropyl-1,3-thiazol-2-yl)-2-[(4S)-4-(3-ethoxy-4-methoxyphenyl)-2-oxopyrrolidin-1-yl]acetamide, 2-[(4S)-4-(3-ethoxy-4-methoxyphenyl)-2-oxopyrrolidin-1-yl]-N-(5-pyridin-4-yl-1,3,4-thiadiazol-2-yl)acetamide, 2-[(4S)-4-(3-ethoxy-4-methoxyphenyl)-2-oxopyrrolidin-1-yl]-N-(4-methyl-1,3-benzothiazol-2-yl)acetamide, 2-[(4S)-4-(3-isopropoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]-N-methylacetamide, 2-[(4S)-4-(3-ethoxy-4-methoxyphenyl)-2-oxopyrrolidin-1-yl]-N-(3-methyl-1H-pyrazol-5-yl)acetamide, 2-[(4S)-4-(3-isopropoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-fluorophenyl)-N-methylacetamide, 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-fluorophenyl)acetamide, 2-{(4S)-4-[4-(difluoromethoxy)-3-ethoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}acetamide, 2-[(4S)-4-(3-ethoxy-4-methoxyphenyl)-2-oxopyrrolidin-1-yl]-N-[4-(trifluoromethyl)-1,3-thiazol-2-yl]acetamide, 2-[(4S)-4-(3-ethoxy-4-methoxyphenyl)-2-oxopyrrolidin-1-yl]-N-(4-methoxy-1,3-benzothiazol-2-yl)acetamide, 2-[(4S)-4-(3-ethoxy-4-methoxyphenyl)-2-oxopyrrolidin-1-yl]-N-(4-methyl-1,3-thiazol-2-yl)acetamide, 2-[(4S)-4-(3-ethoxy-4-methoxyphenyl)-2-oxopyrrolidin-1-yl]-N-methyl-N-(3-methylisothiazol-5-yl)acetamide, 2-[(4S)-4-(3-ethoxy-4-methoxyphenyl)-2-oxopyrrolidin-1-yl]-N-(5-methylisoxazol-3-yl)acetamide, (2S)-2-[(4S)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(3-isopropyl-1,2,4-thiadiazol-5-yl)propanamide, (2S)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(4-methyl-1,3-thiazol-2-yl)propanamide, (2S)-2-[(4S)-4-(3-ethoxy-4-methoxyphenyl)-2-oxopyrrolidin-1-yl]-N-(4-methyl-1,3-thiazol-2-yl)propanamide, N-(4-cyclopropyl-1,3-thiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]acetamide, N-(4-cyclopropyl-1,3-thiazol-2-yl)-2-[(4S)-4-(3-isopropoxy-4-methoxyphenyl)-2-oxopyrrolidin-1-yl]-N-methylacetamide, N-(4-cyclopropyl-1,3-thiazol-2-yl)-2-[(4S)-4-(3-ethoxy-4-methoxyphenyl)-2-oxopyrrolidin-1-yl]-N-methylacetamide, 2-{(4S)-4-[4-(difluoromethoxy)-3-isopropoxyphenyl]-2-oxopyrrolidin-1-yl}-N-(3-fluorophenyl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, N-(4-cyclopropyl-1,3-thiazol-2-yl)-2-{(4S)-4-[4-(difluoromethoxy)-3-isopropoxyphenyl]-2-oxopyrrolidin-1-yl}acetamide, N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-isopropoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-methylisothiazol-5-yl)acetamide, (2S)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, 2-{(4S)-4-[4-(difluoromethoxy)-3-ethoxyphenyl]-2-oxopyrrolidin-1-yl}-N-(6-methylpyridin-2-yl)acetamide, (2S)-2-{(4S)-4-[4-(difluoromethoxy)-3-ethoxyphenyl]-2-oxopyrrolidin-1-yl}-N-(6-methylpyridin-2-yl)propanamide, (2R)-2-{(4S)-4-[4-(difluoromethoxy)-3-ethoxyphenyl]-2-oxopyrrolidin-1-yl}-N-(6-methylpyridin-2-yl)propanamide, 2-{(4S)-4-[4-(difluoromethoxy)-3-ethoxyphenyl]-2-oxopyrrolidin-1-yl}-N-(3-fluorophenyl)acetamide, 2-[(4S)-4-(3-ethoxy-4-methoxyphenyl)-2-oxopyrrolidin-1-yl]-N-(3-isopropyl-1,2,4-thiadiazol-5-yl)acetamide, 2-{(4S)-4-[4-difluoromethoxy-3-ethoxyphenyl]-2-oxopyrrolidin-1-yl}-N-(3-isopropyl-1,2,4-thiadiazol-5-yl)acetamide, and N-(4-cyclopropyl-1,3-thiazol-2-yl)-2-{(4S)-4-[4-difluoromethoxy-3-ethoxyphenyl]-2-oxopyrrolidin-1-yl}acetamide, and pharmaceutically acceptable salts thereof, solvates thereof, and wherein if the compound exhibits chirality it can be in the form of a mixture of enantiomers such as a racemate or a mixture of diastereomers, or can be in the form of a single enantiomer or a single diastereomer.

2. A compound according to claim 1, wherein said compound is selected from:

2-[4-(3-ethoxy-4-methoxyphenyl)-2-oxopyrrolidin-1-yl]-N-(3-fluorophenyl)acetamide, 2-[4-(3-ethoxy-4-methoxyphenyl)-2-oxopyrrolidin-1-yl]-N-(3-methyl-1H-pyrazol-5-yl)acetamide, 2-[4-(3-ethoxy-4-methoxyphenyl)-2-oxopyrrolidin-1-yl]-N-(5-methylisoxazol-3-yl)acetamide, 2-[4-(3-ethoxy-4-methoxyphenyl)-2-oxopyrrolidin-1-yl]-N-(4-methyl-1,3-thiazol-2-yl)acetamide, 2-[4-(3-ethoxy-4-methoxyphenyl)-2-oxopyrrolidin-1-yl]-N-(3-methylisothiazol-5-yl)acetamide, and 2-[4-(3-ethoxy-4-methoxyphenyl)-2-oxopyrrolidin-1-yl]-N-(6-methylpyridin-2-yl)acetamide, and pharmaceutically acceptable salts thereof, and wherein if the compound exhibits chirality it can be in the form of a mixture of enantiomers such as a racemate or a mixture of diastereomers, or can be in the form of a single enantiomer or a single diastereomer.

3. A compound according to claim 1, wherein said compound is selected from:

2-[(4S)-4-(3-ethoxy-4-methoxyphenyl)-2-oxopyrrolidin-1-yl]-N-(3-fluorophenyl)acetamide, 2-[(4R)-4-(3-ethoxy-4-methoxyphenyl)-2-oxopyrrolidin-1-yl]-N-(3-fluorophenyl)acetamide, 2-[(4S)-4-(3-ethoxy-4-methoxyphenyl)-2-oxopyrrolidin-1-yl]-N-methyl-N-(4-methyl-1,3-thiazol-2-yl)acetamide, 2-[(4S)-4-(3-ethoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-ethoxy-4-methoxyphenyl)-2-oxopyrrolidin-1-yl]-N-methylacetamide, N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide, 2-[(4R)-4-(3-ethoxy-4-methoxyphenyl)-2-oxopyrrolidin-1-yl]-N-(3-isopropyl-1,2,4-thiadiazol-5-yl)-N-methylacetamide, N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-methylisothiazol-5-yl)acetamide, 2-[(4R)-4-(3-ethoxy-4-methoxyphenyl)-2-oxopyrrolidin-1-yl]-N-(3-methylisothiazol-5-yl)acetamide, 2-[(4S)-4-(3-ethoxy-4-methoxyphenyl)-2-oxopyrrolidin-1-yl]-N-(3-isopropyl-1,2,4-thiadiazol-5-yl)acetamide, N-(5-cyclopropyl-1,3,4-thiadiazol-2-yl)-2-[(4S)-4-(3-ethoxy-4-methoxyphenyl)-2-oxopyrrolidin-1-yl]acetamide, N-(4-cyclopropyl-1,3-thiazol-2-yl)-2-[(4S)-4-(3-ethoxy-4-methoxyphenyl)-2-oxopyrrolidin-1-yl]acetamide, 2-[(4S)-4-(3-ethoxy-4-methoxyphenyl)-2-oxopyrrolidin-1-yl]-N-(5-pyridin-4-yl-1,3,4-thiadiazol-2-yl)acetamide, 2-[(4S)-4-(3-ethoxy-4-methoxyphenyl)-2-oxopyrrolidin-1-yl]-N-(4-methyl-1,3-benzothiazol-2-yl)acetamide, 2-[(4S)-4-(3-isopropoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]-N-methylacetamide, 2-[(4S)-4-(3-ethoxy-4-methoxyphenyl)-2-oxopyrrolidin-1-yl]-N-(3-methyl-1H-pyrazol-5-yl)acetamide, 2-[(4S)-4-(3-isopropoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-fluorophenyl)-N-methylacetamide, 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-fluorophenyl)acetamide, 2-{(4S)-4-[4-(difluoromethoxy)-3-ethoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}acetamide, 2-[(4S)-4-(3-ethoxy-4-methoxyphenyl)-2-oxopyrrolidin-1-yl]-N-[4-(trifluoromethyl)-1,3-thiazol-2-yl]acetamide, 2-[(4S)-4-(3-ethoxy-4-methoxyphenyl)-2-oxopyrrolidin-1-yl]-N-(4-methoxy-1,3-benzothiazol-2-yl)acetamide, 2-[(4S)-4-(3-ethoxy-4-methoxyphenyl)-2-oxopyrrolidin-1-yl]-N-(4-methyl-1,3-thiazol-2-yl)acetamide, 2-[(4S)-4-(3-ethoxy-4-methoxyphenyl)-2-oxopyrrolidin-1-yl]-N-methyl-N-(3-methylisothiazol-5-yl)acetamide, 2-[(4S)-4-(3-ethoxy-4-methoxyphenyl)-2-oxopyrrolidin-1-yl]-N-(5-methylisoxazol-3-yl)acetamide, (2S)-2-[(4S)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(3-isopropyl-1,2,4-thiadiazol-5-yl)propanamide, (2S)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(4-methyl-1,3-thiazol-2-yl)propanamide, (2S)-2-[(4S)-4-(3-ethoxy-4-methoxyphenyl)-2-oxopyrrolidin-1-yl]-N-(4-methyl-1,3-thiazol-2-yl)propanamide, N-(4-cyclopropyl-1,3-thiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]acetamide, N-(4-cyclopropyl-1,3-thiazol-2-yl)-2-[(4S)-4-(3-isopropoxy-4-methoxyphenyl)-2-oxopyrrolidin-1-yl]-N-methylacetamide, N-(4-cyclopropyl-1,3-thiazol-2-yl)-2-[(4S)-4-(3-ethoxy-4-methoxyphenyl)-2-oxopyrrolidin-1-yl]-N-methylacetamide, 2-{(4S)-4-[4-(difluoromethoxy)-3-isopropoxyphenyl]-2-oxopyrrolidin-1-yl}-N-(3-fluorophenyl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, N-(4-cyclopropyl-1,3-thiazol-2-yl)-2-{(4S)-4-[4-(difluoromethoxy)-3-isopropoxyphenyl]-2-oxopyrrolidin-1-yl}acetamide, N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-isopropoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, and 2-{(4S)-4-[4-(difluoromethoxy)-3-ethoxyphenyl]-2-oxopyrrolidin-1-yl}-N-(3-methylisothiazol-5-yl)acetamide, and pharmaceutically acceptable salts thereof, solvates thereof, and wherein if the compound exhibits chirality it can be in the form of a mixture of enantiomers such as a racemate or a mixture of diastereomers, or can be in the form of a single enantiomer or a single diastereomer.

4. A compound according to claim 1, wherein said compound is selected from:

2-[(4S)-4-(3-ethoxy-4-methoxyphenyl)-2-oxopyrrolidin-1-yl]-N-(3-fluorophenyl)acetamide, 2-[(4R)-4-(3-ethoxy-4-methoxyphenyl)-2-oxopyrrolidin-1-yl]-N-(3-fluorophenyl)acetamide, 2-[(4S)-4-(3-ethoxy-4-methoxyphenyl)-2-oxopyrrolidin-1-yl]-N-methyl-N-(4-methyl-1,3-thiazol-2-yl)acetamide, 2-[(4S)-4-(3-ethoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-ethoxy-4-methoxyphenyl)-2-oxopyrrolidin-1-yl]-N-methylacetamide, N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide, 2-[(4R)-4-(3-ethoxy-4-methoxyphenyl)-2-oxopyrrolidin-1-yl]-N-(3-isopropyl-1,2,4-thiadiazol-5-yl)-N-methylacetamide, N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-methylisothiazol-5-yl)acetamide, 2-[(4S)-4-(3-ethoxy-4-methoxyphenyl)-2-oxopyrrolidin-1-yl]-N-(3-isopropyl-1,2,4-thiadiazol-5-yl)acetamide, N-(5-cyclopropyl-1,3,4-thiadiazol-2-yl)-2-[(4S)-4-(3-ethoxy-4-methoxyphenyl)-2-oxopyrrolidin-1-yl]acetamide, N-(4-cyclopropyl-1,3-thiazol-2-yl)-2-[(4S)-4-(3-ethoxy-4-methoxyphenyl)-2-oxopyrrolidin-1-yl]acetamide, 2-[(4S)-4-(3-ethoxy-4-methoxyphenyl)-2-oxopyrrolidin-1-yl]-N-(5-pyridin-4-yl-1,3,4-thiadiazol-2-yl)acetamide, 2-[(4S)-4-(3-ethoxy-4-methoxyphenyl)-2-oxopyrrolidin-1-yl]-N-(4-methyl-1,3-benzothiazol-2-yl)acetamide, 2-[(4S)-4-(3-isopropoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]-N-methylacetamide, 2-[(4S)-4-(3-ethoxy-4-methoxyphenyl)-2-oxopyrrolidin-1-yl]-N-(3-methyl-1H-pyrazol-5-yl)acetamide, 2-[(4S)-4-(3-isopropoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-fluorophenyl)-N-methylacetamide, 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-fluorophenyl)acetamide, 2-{(4S)-4-[4-(difluoromethoxy)-3-ethoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}acetamide, 2-[(4S)-4-(3-ethoxy-4-methoxyphenyl)-2-oxopyrrolidin-1-yl]-N-[4-(trifluoromethyl)-1,3-thiazol-2-yl]acetamide, 2-[(4S)-4-(3-ethoxy-4-methoxyphenyl)-2-oxopyrrolidin-1-yl]-N-(4-methoxy-1,3-benzothiazol-2-yl)acetamide, 2-[(4S)-4-(3-ethoxy-4-methoxyphenyl)-2-oxopyrrolidin-1-yl]-N-(4-methyl-1,3-thiazol-2-yl)acetamide, 2-[(4S)-4-(3-ethoxy-4-methoxyphenyl)-2-oxopyrrolidin-1-yl]-N-methyl-N-(3-methylisothiazol-5-yl)acetamide, 2-[(4S)-4-(3-ethoxy-4-methoxyphenyl)-2-oxopyrrolidin-1-yl]-N-(5-methylisoxazol-3-yl)acetamide, (2S)-2-[(4S)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(3-isopropyl-1,2,4-thiadiazol-5-yl)propanamide, (2S)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(4-methyl-1,3-thiazol-2-yl)propanamide, (2S)-2-[(4S)-4-(3-ethoxy-4-methoxyphenyl)-2-oxopyrrolidin-1-yl]-N-(4-methyl-1,3-thiazol-2-yl)propanamide, N-(4-cyclopropyl-1,3-thiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]acetamide, N-(4-cyclopropyl-1,3-thiazol-2-yl)-2-[(4S)-4-(3-isopropoxy-4-methoxyphenyl)-2-oxopyrrolidin-1-yl]-N-methylacetamide, N-(4-cyclopropyl-1,3-thiazol-2-yl)-2-[(4S)-4-(3-ethoxy-4-methoxyphenyl)-2-oxopyrrolidin-1-yl]-N-methylacetamide, 2-{(4S)-4-[4-(difluoromethoxy)-3-isopropoxyphenyl]-2-oxopyrrolidin-1-yl}-N-(3-fluorophenyl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, N-(4-cyclopropyl-1,3-thiazol-2-yl)-2-{(4S)-4-[4-(difluoromethoxy)-3-isopropoxyphenyl]-2-oxopyrrolidin-1-yl}acetamide, N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-isopropoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, (4R)-4-[4-(difluoromethoxy)-3-isopropoxyphenyl]-1-isopropylpyrrolidin-2-one, N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, and 2-{(4S)-4-[4-(difluoromethoxy)-3-ethoxyphenyl]-2-oxopyrrolidin-1-yl}-N-(3-methylisothiazol-5-yl)acetamide;

and pharmaceutically acceptable salts thereof, and wherein if the compound exhibits chirality it can be in the form of a mixture of enantiomers such as a racemate or a mixture of diastereomers, or can be in the form of a single enantiomer or a single diastereomer.

5. A pharmaceutical composition comprising a compound of claim 1 and a pharmaceutically acceptable carrier.

6. A pharmaceutical composition of claim 5, wherein the compound is provided in a unit dosage of 0.1-50 mg.

7. A compound according to claim 1, wherein said compound is selected from:

(2S)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, 2-{(4S)-4-[4-(difluoromethoxy)-3-ethoxyphenyl]-2-oxopyrrolidin-1-yl}-N-(6-methylpyridin-2-yl)acetamide, (2S)-2-{(4S)-4-[4-(difluoromethoxy)-3-ethoxyphenyl]-2-oxopyrrolidin-1-yl}-N-(6-methylpyridin-2-yl)propanamide, (2R)-2-{(4S)-4-[4-(difluoromethoxy)-3-ethoxyphenyl]-2-oxopyrrolidin-1-yl}-N-(6-methylpyridin-2-yl)propanamide, 2-{(4S)-4-[4-(difluoromethoxy)-3-ethoxyphenyl]-2-oxopyrrolidin-1-yl}-N-(3-fluorophenyl)acetamide, 2-[(4S)-4-(3-ethoxy-4-methoxyphenyl)-2-oxopyrrolidin-1-yl]-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, and N-(4-cyclopropyl-1,3-thiazol-2-yl)-2-{(4S)-4-[4-(difluoromethoxy)-3-ethoxyphenyl]-2-oxopyrrolidin-1-yl}acetamide, and pharmaceutically acceptable salts thereof, and wherein if the compound exhibits chirality it can be in the form of a mixture of enantiomers such as a racemate or a mixture of diastereomers, or can be in the form of a single enantiomer or a single diastereomer.

8. A pharmaceutical composition comprising a compound of claim 2 and a pharmaceutically acceptable carrier.

9. A pharmaceutical composition comprising a compound of claim 3 and a pharmaceutically acceptable carrier.

10. A pharmaceutical composition comprising a compound of claim 4 and a pharmaceutically acceptable carrier.

11. A pharmaceutical composition comprising a compound of claim 7 and a pharmaceutically acceptable carrier.

12. A compound according to claim 7, wherein said compound is (2S)-2-{(4S)-4-[4-(difluoromethoxy)-3-ethoxyphenyl]-2-oxopyrrolidin-1-yl}-N-(3-fluorophenyl)propanamide, or a pharmaceutically acceptable salt thereof.

13. A compound according to claim 7, wherein said compound is (2R)-2-{(4S)-4-[4-(difluoromethoxy)-3-ethoxyphenyl]-2-oxopyrrolidin-1-yl}-N-(3-fluorophenyl)propanamide, or a pharmaceutically acceptable salt thereof.

14. A compound according to claim 7, wherein said compound is (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, or a pharmaceutically acceptable salt thereof.

15. A compound according to claim 7, wherein said compound is (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, or a pharmaceutically acceptable salt thereof.

16. A compound according to claim 7, wherein said compound is 2-{(4S)-4-[4-(difluoromethoxy)-3-ethoxyphenyl]-2-oxopyrrolidin-1-yl}-N-(6-methylpyridin-2-yl)acetamide, or a pharmaceutically acceptable salt thereof.

17. A compound according to claim 7, wherein said compound is (2S)-2-{(4S)-4-[4-(difluoromethoxy)-3-ethoxyphenyl]-2-oxopyrrolidin-1-yl}-N-(6-methylpyridin-2-yl)propanamide, or a pharmaceutically acceptable salt thereof.

18. A compound according to claim 7, wherein said compound is (2R)-2-{(4S)-4-[4-(difluoromethoxy)-3-ethoxyphenyl]-2-oxopyrrolidin-1-yl}-N-(6-methylpyridin-2-yl)propanamide, or a pharmaceutically acceptable salt thereof.

19. A compound according to claim 7, wherein said compound is 2-{(4S)-4-[4-(difluoromethoxy)-3-ethoxyphenyl]-2-oxopyrrolidin-1-yl}-N-(3-fluorophenyl)acetamide, or a pharmaceutically acceptable salt thereof.

20. A compound according to claim 7, wherein said compound is 2-[(4S)-4-(3-ethoxy-4-methoxyphenyl)-2-oxopyrrolidin-1-yl]-N-(3-isopropyl-1,2,4-thiadiazol-5-yl)acetamide, or a pharmaceutically acceptable salt thereof.

21. A compound according to claim 7, wherein said compound is 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, or a pharmaceutically acceptable salt thereof.

22. A compound according to claim 7, wherein said compound is N-(4-cyclopropyl-1,3-thiazol-2-yl)-2-{(4S)-4-[4-(difluoromethoxy)-3-ethoxyphenyl]-2-oxopyrrolidin-1-yl}acetamide, or a pharmaceutically acceptable salt thereof.

23. A compound according to claim 1, wherein said compound is in the form of a pharmaceutically acceptable salt.

24. A compound according to claim 2, wherein said compound is in the form of a pharmaceutically acceptable salt.

25. A compound according to claim 3, wherein said compound is in the form of a pharmaceutically acceptable salt.

26. A compound according to claim 4, wherein said compound is in the form of a pharmaceutically acceptable salt.

27. A compound according to claim 7, wherein said compound is in the form of a pharmaceutically acceptable salt.

28. A compound according to claim 1, wherein said compound is selected from:

2-[4-(3-ethoxy-4-methoxyphenyl)-2-oxopyrrolidin-1-yl]-N-(5-methylisoxazol-3-yl)acetamide, 2-[4-(3-ethoxy-4-methoxyphenyl)-2-oxopyrrolidin-1-yl]-N-(4-methyl-1,3-thiazol-2-yl)acetamide, 2-[4-(3-ethoxy-4-methoxyphenyl)-2-oxopyrrolidin-1-yl]-N-(3-methylisothiazol-5-yl)acetamide, 2-[4-(3-ethoxy-4-methoxyphenyl)-2-oxopyrrolidin-1-yl]-N-(6-methylpyridin-2-yl)acetamide, 2-[(4S)-4-(3-ethoxy-4-methoxyphenyl)-2-oxopyrrolidin-1-yl]-N-(3-fluorophenyl)acetamide, 2-[(4R)-4-(3-ethoxy-4-methoxyphenyl)-2-oxopyrrolidin-1-yl]-N-(3-fluorophenyl)acetamide, 2-[(4S)-4-(3-ethoxy-4-methoxyphenyl)-2-oxopyrrolidin-1-yl]-N-methyl-N-(4-methyl-1,3-thiazol-2-yl)acetamide, 2-[(4S)-4-(3-ethoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-ethoxy-4-methoxyphenyl)-2-oxopyrrolidin-1-yl]-N-methylacetamide, N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide, 2-[(4R)-4-(3-ethoxy-4-methoxyphenyl)-2-oxopyrrolidin-1-yl]-N-(3-isopropyl-1,2,4-thiadiazol-5-yl)-N-methylacetamide, N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-methylisothiazol-5-yl)acetamide, 2-[(4R)-4-(3-ethoxy-4-methoxyphenyl)-2-oxopyrrolidin-1-yl]-N-(3-methylisothiazol-5-yl)acetamide, 2-[(4S)-4-(3-ethoxy-4-methoxyphenyl)-2-oxopyrrolidin-1-yl]-N-(3-isopropyl-1,2,4-thiadiazol-5-yl)acetamide, N-(5-cyclopropyl-1,3,4-thiadiazol-2-yl)-2-[(4S)-4-(3-ethoxy-4-methoxyphenyl)-2-oxopyrrolidin-1-yl]acetamide, N-(4-cyclopropyl-1,3-thiazol-2-yl)-2-[(4S)-4-(3-ethoxy-4-methoxyphenyl)-2-oxopyrrolidin-1-yl]acetamide, 2-[(4S)-4-(3-ethoxy-4-methoxyphenyl)-2-oxopyrrolidin-1-yl]-N-(5-pyridin-4-yl-1,3,4-thiadiazol-2-yl)acetamide, 2-[(4S)-4-(3-ethoxy-4-methoxyphenyl)-2-oxopyrrolidin-1-yl]-N-(4-methyl-1,3-benzothiazol-2-yl)acetamide, 2-[(4S)-4-(3-isopropoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]-N-methylacetamide, 2-[(4S)-4-(3-ethoxy-4-methoxyphenyl)-2-oxopyrrolidin-1-yl]-N-(3-methyl-1H-pyrazol-5-yl)acetamide, 2-[(4S)-4-(3-isopropoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-fluorophenyl)-N-methylacetamide, 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-fluorophenyl)acetamide, 2-{(4S)-4-[4-(difluoromethoxy)-3-ethoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}acetamide, 2-[(4S)-4-(3-ethoxy-4-methoxyphenyl)-2-oxopyrrolidin-1-yl]-N-[4-(trifluoromethyl)-1,3-thiazol-2-yl]acetamide, 2-[(4S)-4-(3-ethoxy-4-methoxyphenyl)-2-oxopyrrolidin-1-yl]-N-(4-methoxy-1,3-benzothiazol-2-yl)acetamide, 2-[(4S)-4-(3-ethoxy-4-methoxyphenyl)-2-oxopyrrolidin-1-yl]-N-(4-methyl-1,3-thiazol-2-yl)acetamide, 2-[(4S)-4-(3-ethoxy-4-methoxyphenyl)-2-oxopyrrolidin-1-yl]-N-methyl-N-(3-methylisothiazol-5-yl)acetamide, 2-[(4S)-4-(3-ethoxy-4-methoxyphenyl)-2-oxopyrrolidin-1-yl]-N-(5-methylisoxazol-3-yl)acetamide, (2S)-2-[(4S)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(3-isopropyl-1,2,4-thiadiazol-5-yl)propanamide, (2S)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(4-methyl-1,3-thiazol-2-yl)propanamide, (2S)-2-[(4S)-4-(3-ethoxy-4-methoxyphenyl)-2-oxopyrrolidin-1-yl]-N-(4-methyl-1,3-thiazol-2-yl)propanamide, N-(4-cyclopropyl-1,3-thiazol-2-yl)-2-[(4S)-4-(3-isopropoxy-4-methoxyphenyl)-2-oxopyrrolidin-1-yl]acetamide, N-(3-fluorophenyl)-2-[(4S)-4-(3-isopropoxy-4-methoxyphenyl)-2-oxopyrrolidin-1-yl]acetamide, N-(4-cyclopropyl-1,3-thiazol-2-yl)-2-[(4S)-4-(3-isopropoxy-4-methoxyphenyl)-2-oxopyrrolidin-1-yl]-N-methylacetamide, N-(4-cyclopropyl-1,3-thiazol-2-yl)-2-[(4S)-4-(3-ethoxy-4-methoxyphenyl)-2-oxopyrrolidin-1-yl]-N-methylacetamide, 2-{(4S)-4-[4-(difluoromethoxy)-3-isopropoxyphenyl]-2-oxopyrrolidin-1-yl}-N-(3-fluorophenyl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, N-(4-cyclopropyl-1,3-thiazol-2-yl)-2-{(4S)-4-[4-(difluoromethoxy)-3-isopropoxyphenyl]-2-oxopyrrolidin-1-yl}acetamide, N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-isopropoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, and 2-{(4S)-4-[4-(difluoromethoxy)-3-ethoxyphenyl]-2-oxopyrrolidin-1-yl}-N-(3-methylisothiazol-5-yl)acetamide, and pharmaceutically acceptable salts thereof, and
wherein if the compound exhibits chirality it can be in the form of a mixture of enantiomers such as a racemate or a mixture of diastereomers, or can be in the form of a single enantiomer or a single diastereomer.

29. A compound according to claim 1, wherein said compound is selected from:

2-{(4S)-4-[4-(difluoromethoxy)-3-ethoxyphenyl]-2-oxopyrrolidin-1-yl}-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-fluorophenyl)acetamide, 2-{(4S)-4-[4-(difluoromethoxy)-3-ethoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}acetamide, 2-{(4S)-4-[4-(difluoromethoxy)-3-isopropoxyphenyl]-2-oxopyrrolidin-1-yl}-N-(3-fluorophenyl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, N-(4-cyclopropyl-1,3-thiazol-2-yl)-2-{(4S)-4-[4-(difluoromethoxy)-3-isopropoxyphenyl]-2-oxopyrrolidin-1-yl}acetamide, N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-isopropoxyphenyl]-2-oxopyrrolidin-1-yl}-N-(3-fluorophenyl)-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-methylisothiazol-5-yl)acetamide, (2S)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, 2-{(4S)-4-[4-(difluoromethoxy)-3-ethoxyphenyl]-2-oxopyrrolidin-1-yl}-N-(6-methylpyridin-2-yl)acetamide, (2S)-2-{(4S)-4-[4-(difluoromethoxy)-3-ethoxyphenyl]-2-oxopyrrolidin-1-yl}-N-(6-methylpyridin-2-yl)propanamide, (2R)-2-{(4S)-4-[4-(difluoromethoxy)-3-ethoxyphenyl]-2-oxopyrrolidin-1-yl}-N-(6-methylpyridin-2-yl)propanamide, and 2-{(4S)-4-[4-(difluoromethoxy)-3-ethoxyphenyl]-2-oxopyrrolidin-1-yl}-N-(3-fluorophenyl)acetamide, and pharmaceutically acceptable salts thereof, and
wherein if the compound exhibits chirality it can be in the form of a mixture of enantiomers such as a racemate or a mixture of diastereomers, or can be in the form of a single enantiomer or a single diastereomer.

30. A compound according to claim 1, wherein said compound is selected from:

(2S)-2-[(4S)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(3-isopropyl-1,2,4-thiadiazol-5-yl)propanamide, (2S)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(4-methyl-1,3-thiazol-2-yl)propanamide, (2S)-2-[(4S)-4-(3-ethoxy-4-methoxyphenyl)-2-oxopyrrolidin-1-yl]-N-(4-methyl-1,3-thiazol-2-yl)propanamide, (2S)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-fluorophenyl)propanamide, (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, (2S)-2-{(4S)-4-[4-(difluoromethoxy)-3-ethoxyphenyl]-2-oxopyrrolidin-1-yl}-N-(6-methylpyridin-2-yl)propanamide, and (2R)-2-{(4S)-4-[4-(difluoromethoxy)-3-ethoxyphenyl]-2-oxopyrrolidin-1-yl}-N-(6-methylpyridin-2-yl)propanamide, and pharmaceutically acceptable salts thereof, and
wherein if the compound exhibits chirality it can be in the form of a mixture of enantiomers such as a racemate or a mixture of diastereomers, or can be in the form of a single enantiomer or a single diastereomer.

31. A compound according to claim 1, wherein said compound is selected from:

2-[4-(3-ethoxy-4-methoxyphenyl)-2-oxopyrrolidin-1-yl]-N-(5-methylisoxazol-3-yl)acetamide, 2-[4-(3-ethoxy-4-methoxyphenyl)-2-oxopyrrolidin-1-yl]-N-(4-methyl-1,3-thiazol-2-yl)acetamide, 2-[4-(3-ethoxy-4-methoxyphenyl)-2-oxopyrrolidin-1-yl]-N-(3-methylisothiazol-5-yl)acetamide, 2-[4-(3-ethoxy-4-methoxyphenyl)-2-oxopyrrolidin-1-yl]-N-(6-methylpyridin-2-yl)acetamide, 2-[(4S)-4-(3-ethoxy-4-methoxyphenyl)-2-oxopyrrolidin-1-yl]-N-methyl-N-(4-methyl-1,3-thiazol-2-yl)acetamide, 2-[(4S)-4-(3-ethoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-ethoxy-4-methoxyphenyl)-2-oxopyrrolidin-1-yl]-N-methylacetamide, N-(cyclopropylmethyl)-2-[(4S)-4-(3-ethoxy-4-methoxyphenyl)-2-oxopyrrolidin-1-yl]-N-(3-isopropyl-1,2,4-thiadiazol-5-yl)acetamide, 2-[(4R)-4-(3-ethoxy-4-methoxyphenyl)-2-oxopyrrolidin-1-yl]-N-(3-isopropyl-1,2,4-thiadiazol-5-yl)-N-methylacetamide, N-(cyclopropylmethyl)-N-(3-isopropyl-1,2,4-thiadiazol-5-yl)-2-((4S)-4-{4-methoxy-3-[(3R)-tetrahydrofuran-3-yloxy]phenyl}-2-oxopyrrolidin-1-yl)acetamide, N-(cyclopropylmethyl)-2-[(4R)-4-(3-ethoxy-4-methoxyphenyl)-2-oxopyrrolidin-1-yl]-N-(3-isopropyl-1,2,4-thiadiazol-5-yl)acetamide, 2-[(4S)-4-(3-ethoxy-4-methoxyphenyl)-2-oxopyrrolidin-1-yl]-N-(3-methylisothiazol-5-yl)acetamide, 2-[(4R)-4-(3-ethoxy-4-methoxyphenyl)-2-oxopyrrolidin-1-yl]-N-(3-methylisothiazol-5-yl)acetamide, 2-[(4S)-4-(3-ethoxy-4-methoxyphenyl)-2-oxopyrrolidin-1-yl]-N-(3-isopropyl-1,2,4-thiadiazol-5-yl)acetamide, N-(5-cyclopropyl-1,3,4-thiadiazol-2-yl)-2-[(4S)-4-(3-ethoxy-4-methoxyphenyl)-2-oxopyrrolidin-1-yl]acetamide, N-(4-cyclopropyl-1,3-thiazol-2-yl)-2-[(4S)-4-(3-ethoxy-4-methoxyphenyl)-2-oxopyrrolidin-1-yl]acetamide, 2-[(4S)-4-(3-ethoxy-4-methoxyphenyl)-2-oxopyrrolidin-1-yl]-N-(5-pyridin-4-yl-1,3,4-thiadiazol-2-yl)acetamide, 2-[(4S)-4-(3-ethoxy-4-methoxyphenyl)-2-oxopyrrolidin-1-yl]-N-(4-methyl-1,3-benzothiazol-2-yl)acetamide, 2-[(4S)-4-(3-isopropoxy-4-methoxyphenyl)-2-oxopyrrolidin-1-yl]-N-(3-isopropyl-1,2,4-thiadiazol-5-yl)-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]-N-methylacetamide, N-(5-cyclopropyl-1,3,4-thiadiazol-2-yl)-2-[(4S)-4-(3-isopropoxy-4-methoxyphenyl)-2-oxopyrrolidin-1-yl]acetamide, 2-[(4S)-4-(3-ethoxy-4-methoxyphenyl)-2-oxopyrrolidin-1-yl]-N-(3-methyl-1H-pyrazol-5-yl)acetamide, 2-[(4S)-4-(3-isopropoxy-4-methoxyphenyl)-2-oxopyrrolidin-1-yl]-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, 2-{(4S)-4-[4-(difluoromethoxy)-3-ethoxyphenyl]-2-oxopyrrolidin-1-yl}-N-(3-isopropyl-1,2,4-thiadiazol-5-yl)-N-methylacetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}acetamide, N-(5-cyclopropyl-1,3,4-thiadiazol-2-yl)-2-{(4S)-4-[4-(difluoromethoxy)-3-ethoxyphenyl]-2-oxopyrrolidin-1-yl}-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}acetamide, 2-[(4S)-4-(3-ethoxy-4-methoxyphenyl)-2-oxopyrrolidin-1-yl]-N-[4-(trifluoromethyl)-1,3-thiazol-2-yl]acetamide, 2-[(4S)-4-(3-ethoxy-4-methoxyphenyl)-2-oxopyrrolidin-1-yl]-N-(4-methoxy-1,3-benzothiazol-2-yl)acetamide, 2-[(4S)-4-(3-ethoxy-4-methoxyphenyl)-2-oxopyrrolidin-1-yl]-N-(4-methyl-1,3-thiazol-2-yl)acetamide, 2-[(4S)-4-(3-ethoxy-4-methoxyphenyl)-2-oxopyrrolidin-1-yl]-N-methyl-N-(3-methylisothiazol-5-yl)acetamide, 2-[(4S)-4-(3-ethoxy-4-methoxyphenyl)-2-oxopyrrolidin-1-yl]-N-(5-methylisoxazol-3-yl)acetamide, (2S)-2-[(4S)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(3-isopropyl-1,2,4-thiadiazol-5-yl)propanamide, (2S)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4R)-4-(3-ethoxy-4-methoxyphenyl)-2-oxopyrrolidin-1-yl]-N-(3-isopropyl-1,2,4-thiadiazol-5-yl)propanamide, (2R)-2-[(4S)-4-(3-ethoxy-4-methoxyphenyl)-2-oxopyrrolidin-1-yl]-N-(4-methyl-1,3-thiazol-2-yl)propanamide, (2S)-2-[(4S)-4-(3-ethoxy-4-methoxyphenyl)-2-oxopyrrolidin-1-yl]-N-(4-methyl-1,3-thiazol-2-yl)propanamide, N-(4-cyclopropyl-1,3-thiazol-2-yl)-2-[(4S)-4-(3-isopropoxy-4-methoxyphenyl)-2-oxopyrrolidin-1-yl]acetamide, N-(4-cyclopropyl-1,3-thiazol-2-yl)-2-[(4S)-4-(3-isopropoxy-4-methoxyphenyl)-2-oxopyrrolidin-1-yl]-N-methylacetamide, N-(4-cyclopropyl-1,3-thiazol-2-yl)-2-[(4S)-4-(3-ethoxy-4-methoxyphenyl)-2-oxopyrrolidin-1-yl]-N-methylacetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)acetamide, 2-{(4S)-4-[4-(difluoromethoxy)-3-isopropoxyphenyl]-2-oxopyrrolidin-1-yl}-N-(3-isopropyl-1,2,4-thiadiazol-5-yl)-N-methylacetamide, N-(4-cyclopropyl-1,3-thiazol-2-yl)-2-{(4S)-4-[4-(difluoromethoxy)-3-isopropoxyphenyl]-2-oxopyrrolidin-1-yl}acetamide, N-(4-cyclopropyl-1,3-thiazol-2-yl)-2-{(4S)-4-[4-(difluoromethoxy)-3-isopropoxyphenyl]-2-oxopyrrolidin-1-yl}-N-methylacetamide, N-(4-cyclopropyl-1,3-thiazol-2-yl)-2-{(4S)-4-[4-(difluoromethoxy)-3-ethoxyphenyl]-2-oxopyrrolidin-1-yl}-N-methylacetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}acetamide, N-(5-cyclopropyl-1,3,4-thiadiazol-2-yl)-2-{(4S)-4-[4-(difluoromethoxy)-3-isopropoxyphenyl]-2-oxopyrrolidin-1-yl}-N-methylacetamide, 2-{(4S)-4-[4-(difluoromethoxy)-3-ethoxyphenyl]-2-oxopyrrolidin-1-yl}-N-(3-methylisothiazol-5-yl)acetamide, (2R)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, (2S)-2-{(4S)-4-[4-(difluoromethoxy)-3-ethoxyphenyl]-2-oxopyrrolidin-1-yl}-N-(3-isopropyl-1,2,4-thiadiazol-5-yl)propanamide, 2-{(4S)-4-[4-(difluoromethoxy)-3-ethoxyphenyl]-2-oxopyrrolidin-1-yl}-N-(6-methylpyridin-2-yl)acetamide, (2S)-2-{(4S)-4-[4-(difluoromethoxy)-3-ethoxyphenyl]-2-oxopyrrolidin-1-yl}-N-(6-methylpyridin-2-yl)propanamide, (2R)-2-{(4S)-4-[4-(difluoromethoxy)-3-ethoxyphenyl]-2-oxopyrrolidin-1-yl}-N-(6-methylpyridin-2-yl)propanamide, 2-[(4S)-4-(3-ethoxy-4-methoxyphenyl)-2-oxopyrrolidin-1-yl]-N-(3-isopropyl-1,2,4-thiadiazol-5-yl)acetamide, and 2-{(4S)-4-[4-(difluoromethoxy)-3-ethoxyphenyl]-2-oxopyrrolidin-1-yl}-N-(3-isopropyl-1,2,4-thiadiazol-5-yl)acetamide, and pharmaceutically acceptable salts thereof, and wherein if the compound exhibits chirality it can be in the form of a mixture of enantiomers such as a racemate or a mixture of diastereomers, or can be in the form of a single enantiomer or a single diastereomer.

32. A compound according to claim 28, wherein said compound is in the form of a pharmaceutically acceptable salt.

33. A compound according to claim 29, wherein said compound is in the form of a pharmaceutically acceptable salt.

34. A compound according to claim 30, wherein said compound is in the form of a pharmaceutically acceptable salt.

35. A compound according to claim 31, wherein said compound is in the form of a pharmaceutically acceptable salt.

* * * * *